(12) United States Patent
Kasibhatla et al.

(10) Patent No.: US 11,591,313 B2
(45) Date of Patent: Feb. 28, 2023

(54) INHIBITORS OF ECTONUCLEOTIDE PYROPHOSPHATASE/PHOSPHODIESTERASE 1 (ENPP1) AND METHODS OF USE THEREOF

(71) Applicant: Stingray Therapeutics, Inc., Houston, TX (US)

(72) Inventors: Srinivas Rao Kasibhatla, San Diego, CA (US); Raman Kumar Kalakuntla, Telangana (IN); Alexis Weston, Phoenix, AZ (US); Trason Thode, Phoenix, AZ (US); Sunil Sharma, Phoenix, AZ (US); Mohan R. Kaadige, Scottsdale, AZ (US)

(73) Assignee: STINGRAY THERAPEUTICS, INC., Houston, TX (US)

( * ) Notice: Subject to any disclaimer, the term of this patent is extended or adjusted under 35 U.S.C. 154(b) by 32 days.

(21) Appl. No.: 17/168,109

(22) Filed: Feb. 4, 2021

(65) Prior Publication Data
US 2021/0253556 A1    Aug. 19, 2021

Related U.S. Application Data

(60) Provisional application No. 62/970,138, filed on Feb. 4, 2020.

(51) Int. Cl.
| | | |
|---|---|---|
| *C07D 403/04* | (2006.01) | |
| *A61P 35/00* | (2006.01) | |
| *C07D 239/88* | (2006.01) | |
| *C07D 239/94* | (2006.01) | |
| *C07D 239/74* | (2006.01) | |
| *C07D 403/14* | (2006.01) | |
| *C07D 487/08* | (2006.01) | |
| *C07D 401/14* | (2006.01) | |
| *C07D 401/04* | (2006.01) | |
| *C07D 215/54* | (2006.01) | |

(52) U.S. Cl.
CPC ............ *C07D 403/04* (2013.01); *A61P 35/00* (2018.01); *C07D 215/54* (2013.01); *C07D 239/74* (2013.01); *C07D 239/88* (2013.01); *C07D 239/94* (2013.01); *C07D 401/04* (2013.01); *C07D 401/14* (2013.01); *C07D 403/14* (2013.01); *C07D 487/08* (2013.01)

(58) Field of Classification Search
CPC .................................................... C07D 403/04
See application file for complete search history.

(56) References Cited

U.S. PATENT DOCUMENTS 11,407,729 B2 *   8/2022   Vankayalapati ..... C07D 215/46

FOREIGN PATENT DOCUMENTS

WO    WO-2019051269 A1 *   3/2019   ........... A61K 31/517

* cited by examiner

*Primary Examiner* — Golam M Shameem
(74) *Attorney, Agent, or Firm* — Wood, Phillips, Katz, Clark Mortimer

(57) ABSTRACT

Compounds and methods for their preparation and use as therapeutic or prophylactic agents, for example for treatment of cancer, bacterial or viral diseases by targeting Ectonucleotide Pyrophosphatase/Phosphodiesterase-1 (ENPP1).

45 Claims, 5 Drawing Sheets

LEGEND

| Number on X-axis | Compound Number | Number on X-axis | Compound Number | Number on X-axis | Compound Number |
|---|---|---|---|---|---|
| 1 | 047 | 8 | 054 | 15 | 061 |
| 2 | 048 | 9 | 055 | 16 | 062 |
| 3 | 049 | 10 | 056 | 17 | 015 |
| 4 | 050 | 11 | 057 | 18 | 005 |
| 5 | 051 | 12 | 058 | 19 | 063 |
| 6 | 052 | 13 | 059 | 20 | 065 |
| 7 | 053 | 14 | 060 | 21 | 064 |

FIGURE 3

Compound 015-HCl PK Profile (Rat):

%F: 28.8 (Oral Bioavailability)
$T_{1/2}$(PO): 5.49hr
$T_{1/2}$(IV): 2.1 hr
$AUC_{last}$ (IV): 496 hr*ng/mL
$AUC_{last}$(PO): 650 hr*ng/mL

INHIBITORS OF ECTONUCLEOTIDE PYROPHOSPHATASE/PHOSPHODIESTERASE 1 (ENPP1) AND METHODS OF USE THEREOF

FIELD OF THE INVENTION

The present invention generally relates to inhibitors of Ectonucleotide Pyrophophatase/Phosphodiesterase (ENPP1). The invention is directed to pharmaceutical compositions containing the Formula 1 or Formula 2 compounds and methods of using the compounds or compositions to treat various types of human cancers where the ENPP1 is overexpressed, cardiovascular, diabetes, obesity, NASH, glaucoma, antiviral, antibacterial and anti-fibrotic therapeutics. The invention is also directed to methods of making the compounds and its pharmaceuticals salts.

BACKGROUND OF THE INVENTION

Ectonucleotide Pyrophophatase/Phosphodiesterase (ENPP) family members include seven isoforms, ENPP1-7, which are type II transmembrane glycoproteins or ectoenzymes. Mass spectrometry and proteomics analysis from more than 370 protein targets led to the identification of an extracellular protein ENPP1 as one of the top hits which exhibited high hydrolytic activity. ATP is an identified substrate of ENPP1, which is hydrolyzed to AMP and PPi. CD73 converts AMP to adenosine and inorganic phosphate (Pi). The kinetic experimental data indicates that the ENPP1 is capable of hydrolyzing ATP. These ectonucleotide enzymes are involved in the hydrolysis of pyrophosphate (PPi) and phosphodiester bonds in extracellular nucleotides; such as triphosphates, oligonucleotides and that generates nucleoside 5'-monophosphates. One of the key isoforms, ENPP1 (Plasma cell membrane glycoprotein-1, PC-1), is involved in a number of physiological processes, such as development, formation and trafficking, as well as in pathophysiological conditions. Aberrant ENPP1 expression has been detected in breast cancers relative to normal mammary epithelium, an evidence of its potential in the development of bone metastasis (occurs in approximately 80% cases), Hodgkin's lymphoma, hepatocellular carcinoma, follicular lymphoma, glioblastoma and in other malignant tumor tissues.

Recent reports suggest that the cyclic dinucleotides (CDNs), a substrate for ENPP1, stimulate innate immunity via STING-dependent activation of interferon genes. ENPP1 inhibition of STING pathway activation is critical for tumor control, similar to that of checkpoint inhibitors such as anti PD-1 or PD-L1 which are promising immunotherapeutics for various cancers. In addition, mutations in ENPP1 were associated with several disorders including infantile arterial calcification (generalized arterial calcification of infancy or GACI), ossification of the posterior longitudinal ligament of the spine and insulin signaling and resistance. ENPP1 expression is high in bone and cartilage and is implicated in lung and kidney fibrosis. A correlation was also found between expression of ENPP1 and the grade of astrocytic tumor. Another study reported that ENPP1 was required to maintain the undifferentiated and proliferative state of glioblastoma stem-like cells. Therefore, ENPP1 is an attractive druggable target for the development of novel anticancer, cardiovascular, diabetes, obesity, NASH, glaucoma, and anti-fibrotic therapeutics.

Importance of ENPP1 activity was further investigated from both direct binding assay and in vitro cellular efficacy on MDA-MB231 cells. The siRNA-based knock down of ENPP1 significantly reduced its catalytic activity both in cell specific and in vivo experiments. These experiments demonstrated that the ENPP1 activity was abolished on treatment with siRNA. This further supports the validity of this target in certain diseases. It has been shown recently that the bisphosphothionate analog of endogenous cGAMP is resistant to hydrolysis by ENPP1 phosphodiesterase, and particularly the cyclic dinucleotides (CDNs) are more potent at inducing IFN-β secretion in human THP1 cells by a mechanism of inhibiting the ENPP1 activity and simultaneous STING activation responses.

There is ample evidence that ENPP1 expression is prominent in human primary breast tumors relative to normal mammary epithelium, with highest levels observed in breast-bone metastasis. These data not only support a potential role for ENPP1 in breast-bone metastasis, but also support as a potential prognostic marker for breast cancer. More recently, ENPP1 was shown to be upregulated in lung cancer. Knockdown of ENPP1 in lung cancer cell lines HCC827 and A549 resulted in suppressed colonogenic formation, anchorage-independent growth in vitro, and tumorigenicity in vivo. These results from target validation experiments clearly support the pharmacological role of ENPP1 for the development of novel immunotherapeutics for cancers.

Furthermore, ENPP1 activity has also been implicated in diseases caused by bacteria and/or viruses, and therefore modulators of ENPP1 can be used to treat bacterial and/or viral diseases and conditions.

SUMMARY OF THE INVENTION

The invention, in one aspect, relates to compounds of Formula I or Formula II as follows:

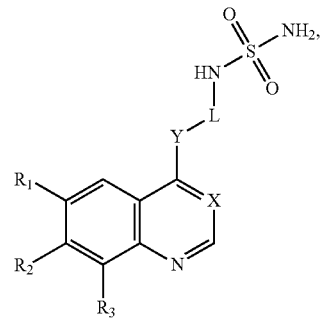

Formula I wherein
X is N or CR$_{11}$;
Y is selected from the group consisting of —CR$_4$R$_5$—, —NR$_6$—, —N(CH$_2$)$_m$O—, —O—, —S—, —S(O)—, —S(O)$_2$, aryl, and heteroaryl; wherein m is 2 or 3;
L is selected from the group consisting of an C$_1$-C$_5$ alkyl, and C$_1$-C$_5$ alkenyl;
each R$_1$, R$_2$ and R$_3$ are independently selected from the group consisting of hydrogen, halogen, CN, OR$^a$, —C(=O)NR$^b$R$^c$, —NR$^b$R$^c$, —C(=O)R$^d$, aryl, heteroaryl, cycloalkyl, and heterocycloalkyl.
each R$^a$ is independently selected from the group consisting of hydrogen, lower alkyl, —(CH$_2$)$_n$—C(=O)NR$^b$R$^c$, aralkyl, aryl, heteroaryl, heterocycloalkyl, and cycloalkyl;
wherein n is an integer between 1 and 3;

each $R^b$ and $R^c$ is independently selected from the group consisting of hydrogen, a lower alkyl, and lower aryl, heterocycloalkyl, or cycloalkyl;
each $R^d$ is independently selected from the group consisting of —$OR^e$ and lower alkyl;
each $R^e$ is independently selected from the group consisting of hydrogen, a lower alkyl, and a lower aryl;
$R_{11}$ is independently selected from the group consisting of hydrogen, halogen, COOEt, COOH, and CN;
$R_4$, $R_5$ and $R_6$ are independently selected from the group consisting of hydrogen and lower alkyl;
or an isomer, hydrate, solvate, polymorph, tautomer or a pharmaceutically acceptable salt thereof.

A compound of Formula II is as follows:

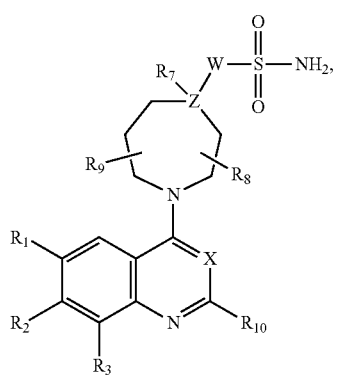

Formula II wherein
X is N or $CR_{11}$;
Z is C or N;
W is selected from the group consisting of an $C_1$-$C_5$ alkyl, —C(=O)—(CH$_2$)$_n$—, —($C_1$-$C_5$ alkyl)-N—; NH, and a direct bond as follows:

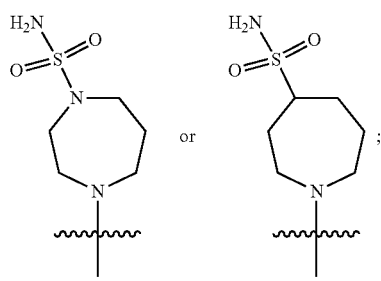 [SMILES: *N1CCCN(S(N)(=O)=O)CC1 ; *N1CCCC(S(N)(=O)=O)CC1]

each $R_1$; $R_2$ and $R_3$ are independently selected from the group consisting of hydrogen, halogen, CN, $OR^a$, —C(=O)NR$^b$R$^c$, —NR$^b$R$^c$, —C(=O)R$^d$, aryl, heteroaryl, cycloalkyl, and heterocycloalkyl.
each $R^a$ is independently selected from the group consisting of hydrogen, lower alkyl, and —(CH$_2$)$_n$—C(=O)NR$^b$R$^c$, aralkyl, aryl, heteroaryl, heterocycloalkyl, cycloalkyl; wherein n is an integer between 1 and 3;
each $R^b$ and $R^c$ is independently selected from the group consisting of hydrogen, a lower alkyl, and lower aryl, heterocycloalkyl, or cycloalkyl;
each $R^d$ is independently selected from the group consisting of —$OR^e$ and lower alkyl;
each $R^e$ is independently selected from the group consisting of hydrogen, a lower alkyl, and a lower aryl;

$R_{11}$ is independently selected from the group consisting of hydrogen, halogen, COOEt, COOH, and CN;
$R_7$, $R_8$ and $R_9$ are independently selected from the group consisting of H, halogen and lower alkyl; and $R_8$ and $R_9$ can also form a bridge across the 7-membered ring with 1 or 2 atoms, as follows:

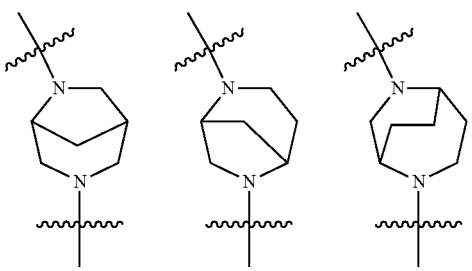 [SMILES: *N1CC2CC(C1)N(*)C2 ; *N1CCC2CC1CN2* ; *N1CCC2CCC1CN2*]

$R_{10}$ is independently selected from the group consisting of hydrogen and $CF_3$;
or an isomer, hydrate, solvate, polymorph, tautomer or a pharmaceutically acceptable salt thereof.

The invention encompasses any compounds or structures that include any combinations of the substituents as defined above.

In one preferred embodiment, Y in Formula I is pyridinyl.
In one preferred embodiment, X in Formula I or Formula II is C—CN.
In one preferred embodiment, Y in Formula I is $NR_6$.
In one preferred embodiment, in compounds of Formula I and Formula II, $R_1$, $R_2$ and $R_3$ are selected from the group consisting of $CH_3O$ and H.
In one preferred embodiment, in compounds of Formula II, Z is N.
In one preferred embodiment, in compounds of Formula II, W is selected from the group consisting of -4,5-imidazole, 2-Oxazole, 3-pyrrole; pyrazole, and thiazole.
In one preferred embodiment, in compounds of Formula II, X is N.
In one preferred embodiment, in compounds of Formula II, X is C—CN.
In one preferred embodiment, in compounds of Formula II, $R_7$, $R_8$ and $R_9$ are independently selected from the group consisting of H and halogen.
In one preferred embodiment, in compounds of Formula II, $R_7$ is a halogen, and more preferably F.
In one preferred embodiment,
the compound is of Formula I;
X is N;
Y is selected from the group consisting of pyridinyl, $C_1$-$C_5$ alkyl, O, N, and S;
L is an optionally substituted $C_1$-$C_5$ alkyl; and
$R_1$ and $R_2$ are both $CH_3O$.
In another preferred embodiment,
the compound is of Formula II;
X is N;
Z is N;
W is selected from the group consisting of an optionally substituted $C_1$-$C_5$ alkyl, —C(=O)—(CH$_2$)—, —(an optionally substituted $C_1$-$C_5$ alkyl)-N; and a direct bond; and
$R_1$ and $R_2$ are both $CH_3O$.

Examples of the provided compounds include:
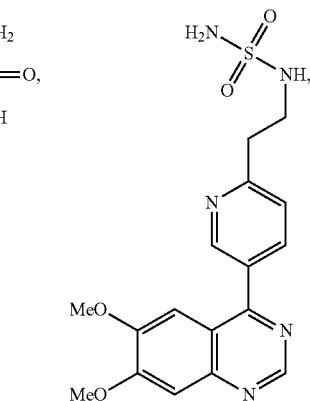
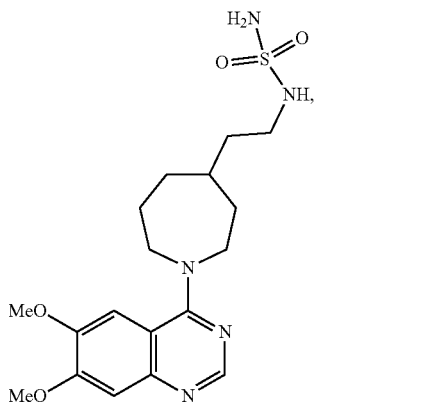
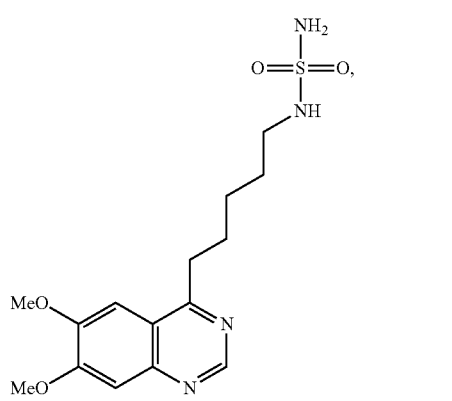
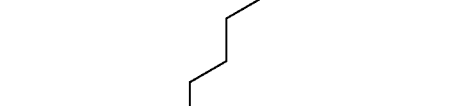
-continued
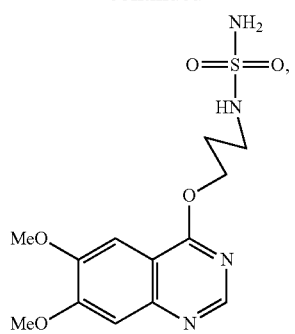
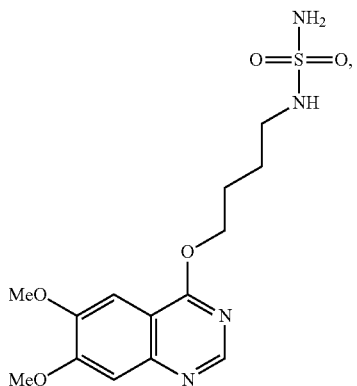
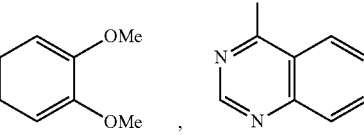

-continued
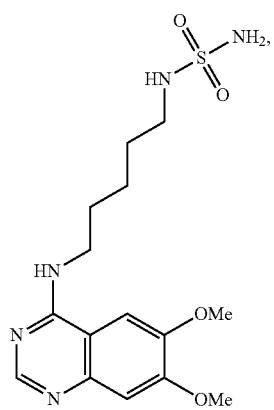
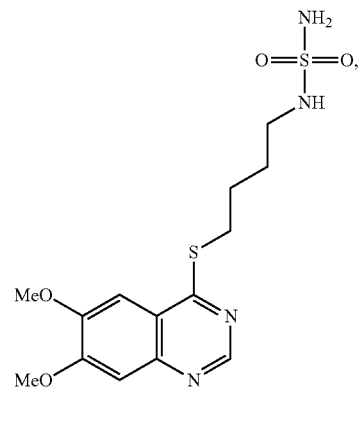
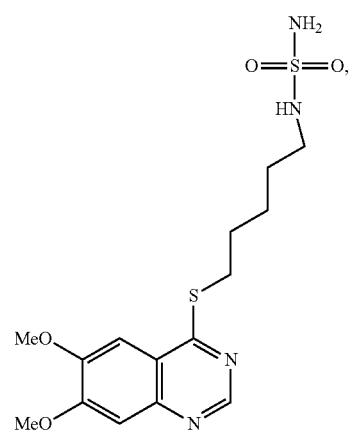
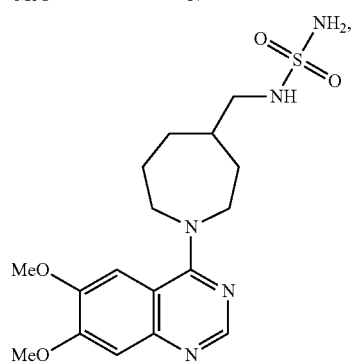
-continued
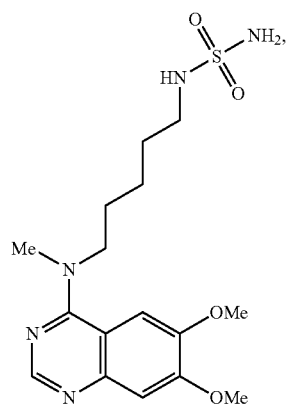
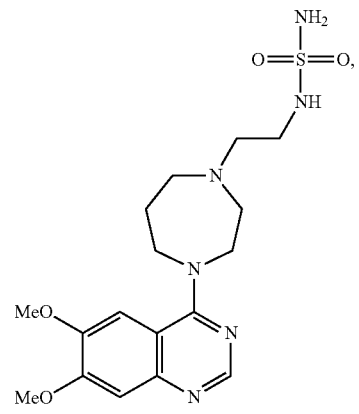
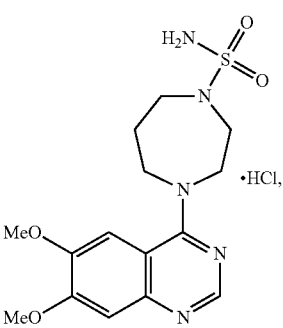
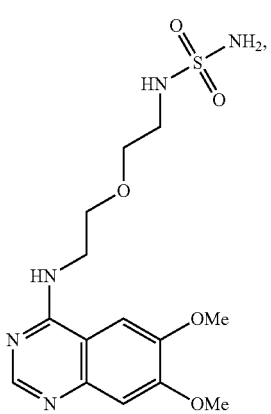

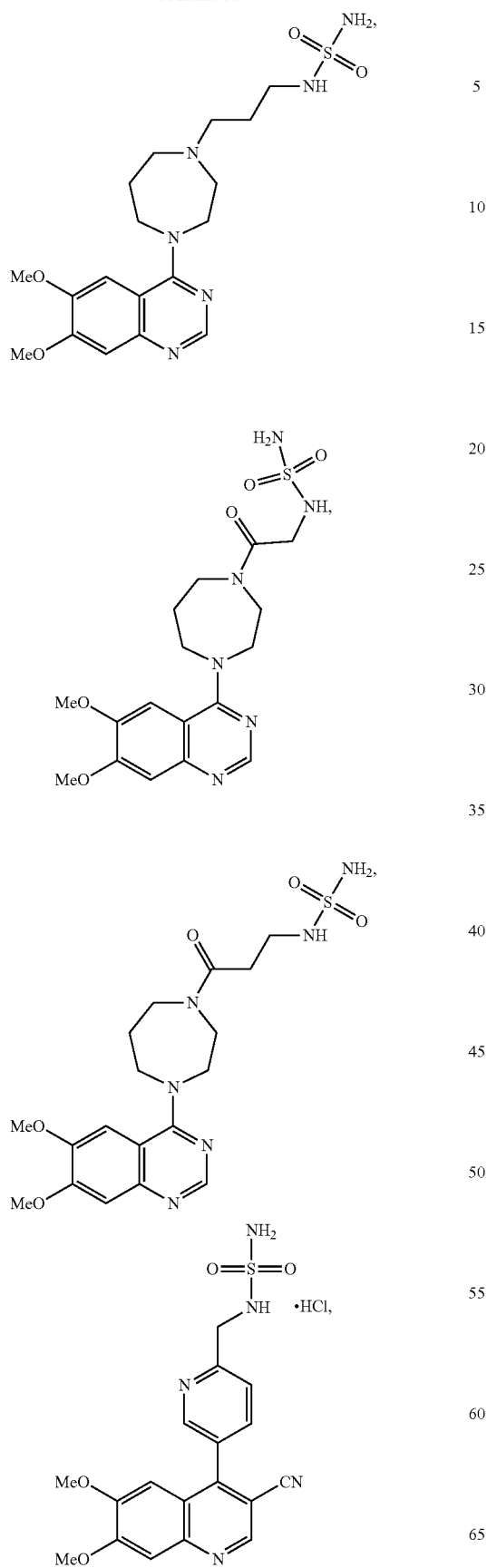
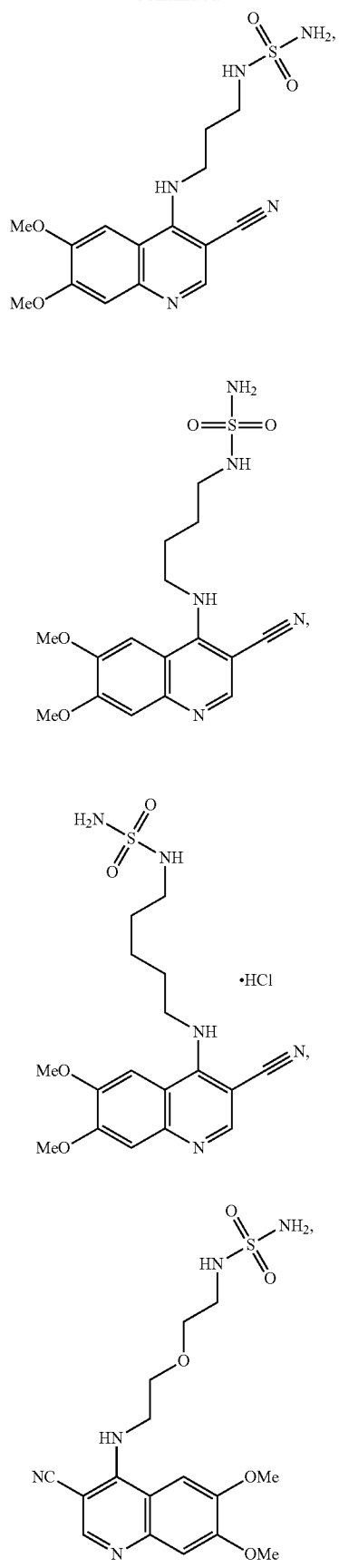

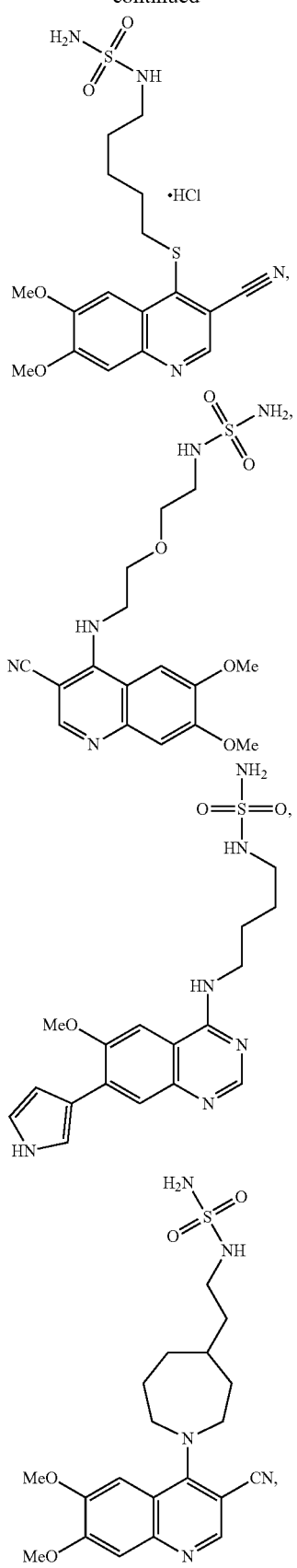
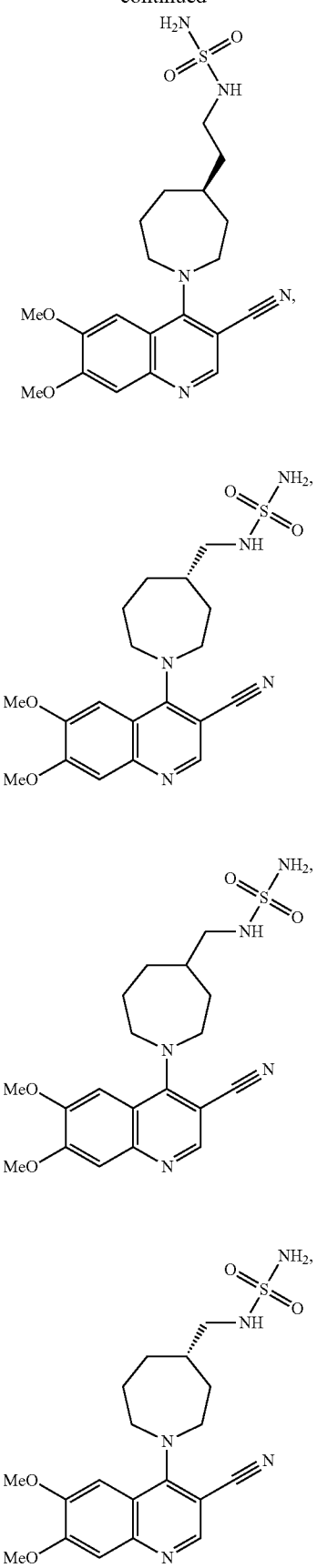

-continued
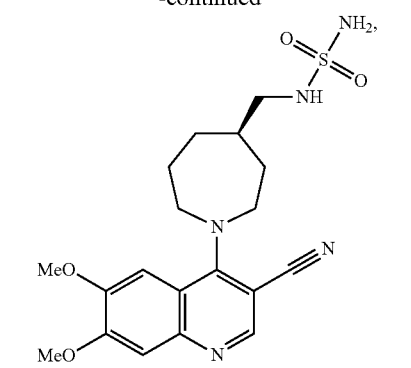
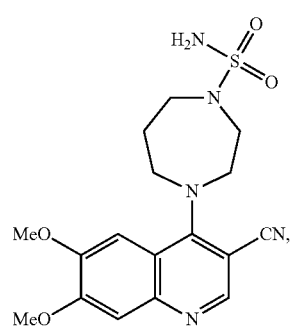
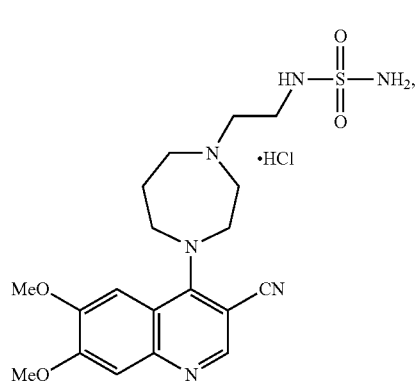
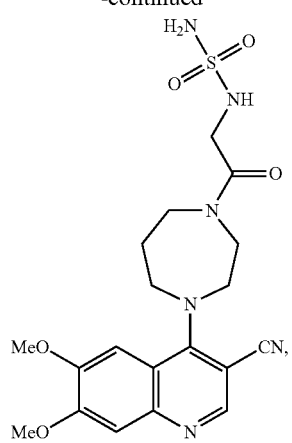
-continued
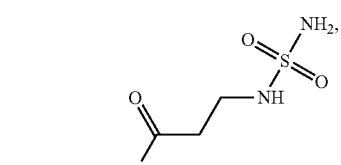
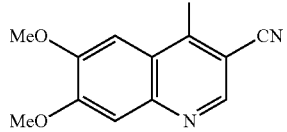
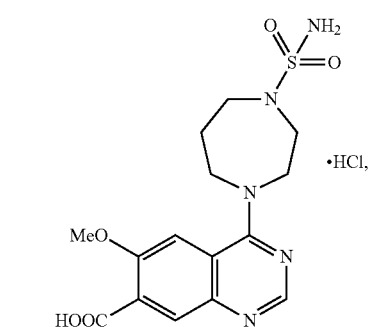
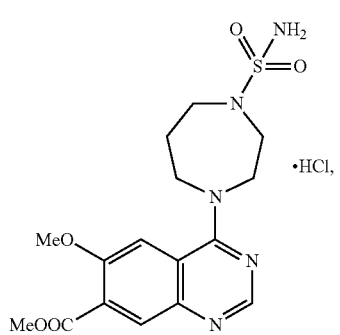

-continued
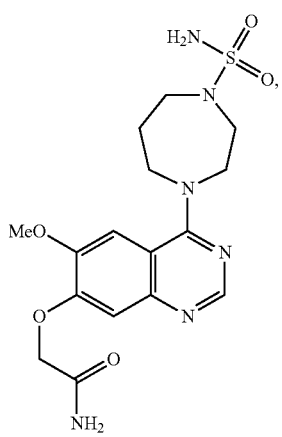
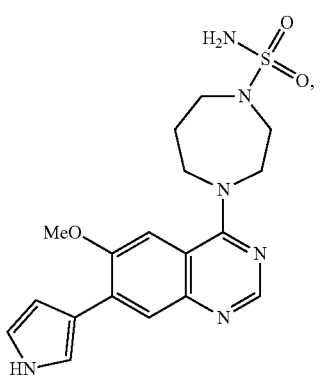
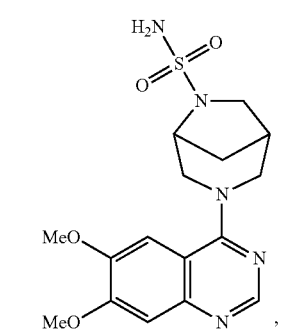
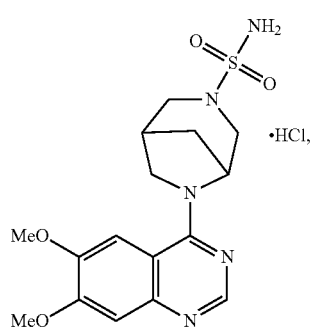
-continued
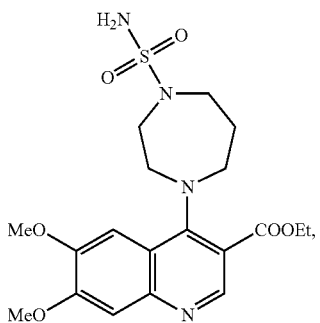
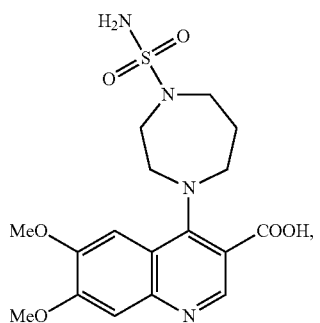
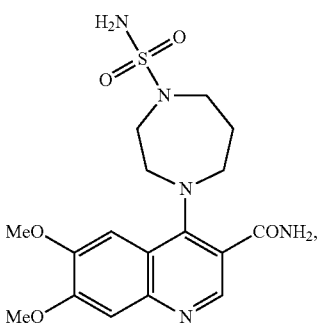
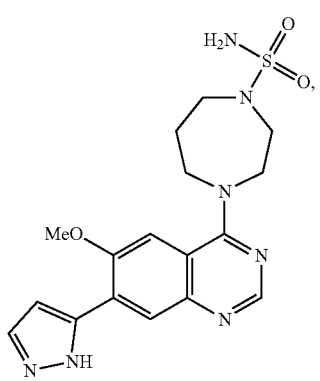
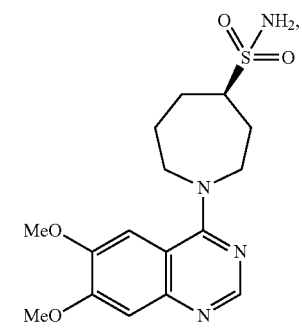

-continued
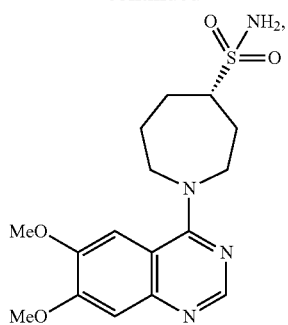
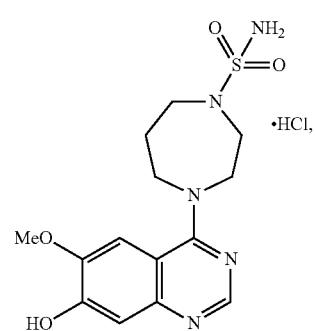
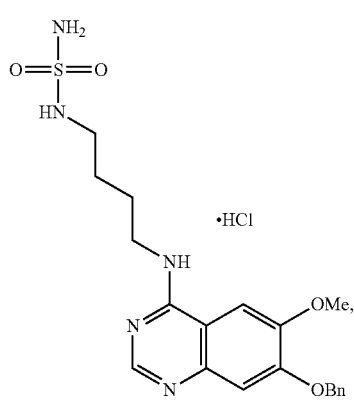
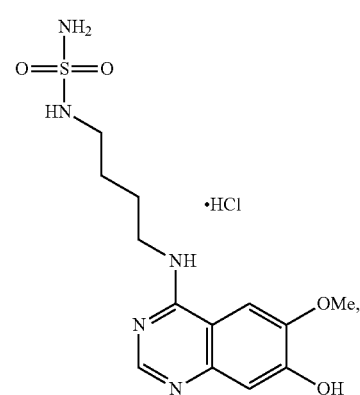
-continued
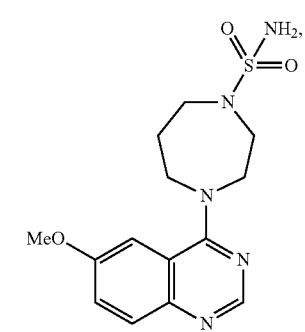
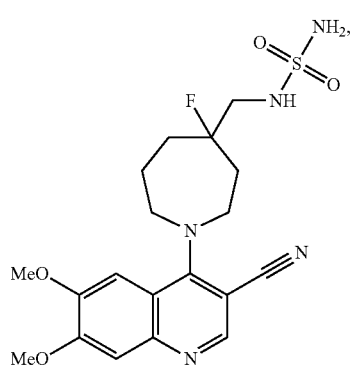
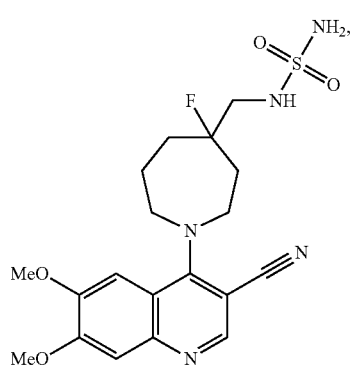
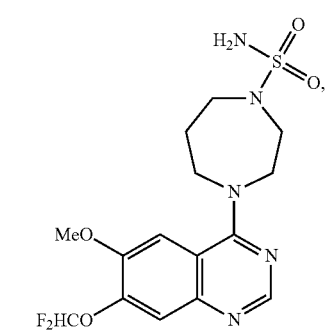

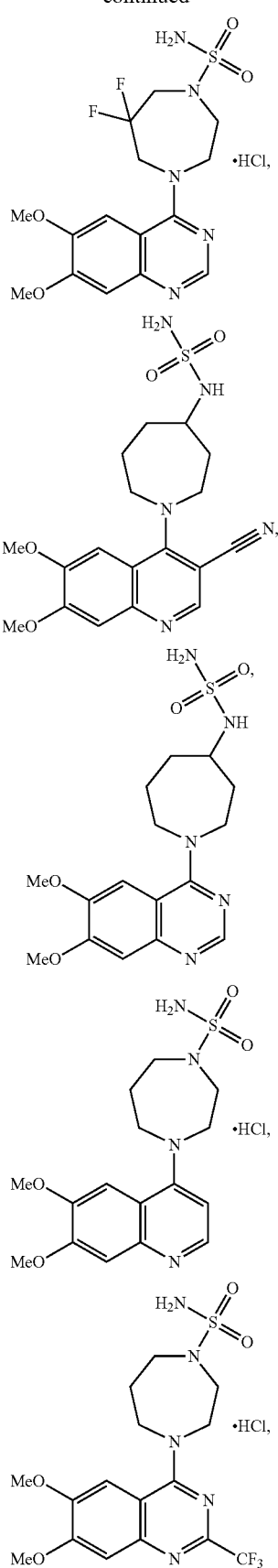

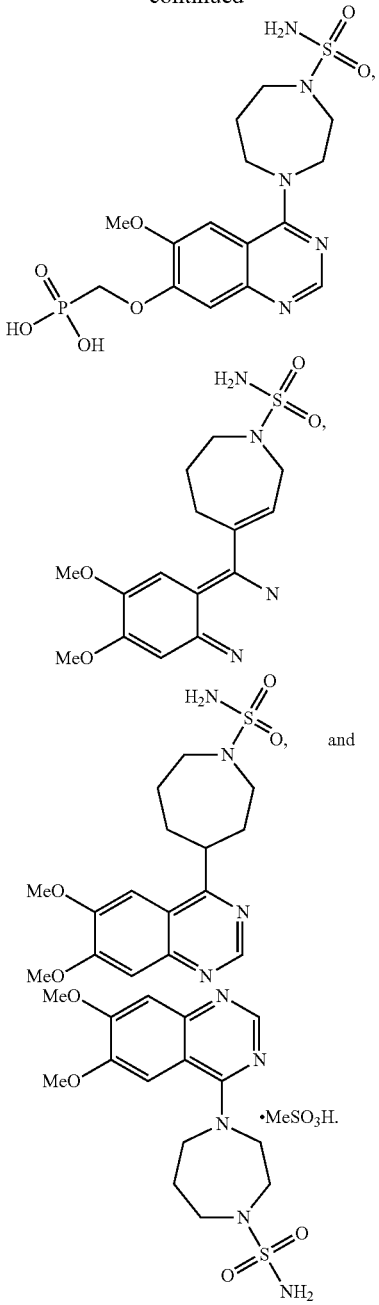

The invention also includes hydrates, solvates, polymorphs, isomers, tautomers of the compounds, pharmaceutically acceptable salts of the compounds and pharmaceutically acceptable salts of the tautomers.

The invention also provides pharmaceutical formulations, medicaments including the compounds, methods of preparing pharmaceuticals formulations, medicaments, compounds, and methods of treating patients with the provided pharmaceutical formulations and compounds.

The compounds of the invention were identified by structure-based, computational docking and binding free energies.

Also disclosed are pharmaceutical compositions comprising a therapeutically effective amount of a disclosed compound and a pharmaceutically acceptable carrier.

Also disclosed are synthetic methods for making the disclosed compounds. In a further aspect, disclosed are the products of the disclosed synthetic methods.

Also disclosed are methods for the treatment of a disorder associated with an ENPP1 activity dysfunction in a mammal comprising the step of administering to the mammal a therapeutically effective amount of a disclosed compound, or a pharmaceutically acceptable salt, tautomer, isomer, hydrate, solvate, or polymorph thereof.

Also disclosed are methods for inhibition of ENPP1 activity in a mammal comprising the step of administering to the mammal a therapeutically effective amount of least one disclosed compound, or a pharmaceutically acceptable salt, tautomer, isomer, hydrate, solvate, or polymorph thereof.

Also disclosed are methods for inhibiting ENPP1 activity in at least one cell, comprising the step of contacting the at least one cell with an effective amount of least one disclosed compound, or a pharmaceutically acceptable salt, tautomer, isomer, hydrate, solvate, or polymorph thereof.

Also disclosed are methods for treating a disorder associated with an ENPP1 activity dysfunction in a mammal through eliciting an immunotherapeutic response in the mammal, comprising administering to the mammal a therapeutically effective amount of a disclosed compound, or a pharmaceutically acceptable salt, tautomer, isomer, hydrate, solvate, or polymorph thereof, wherein this compound causes an immunotherapeutic response beneficial in the treatment of the disorder associated with an ENPP1 activity. Such disorder can be, but is not limited to, any type of cancer or any disease caused by bacteria and/or viruses wherein ENPP1 activity has been implicated. Diseases and conditions treatable by the compounds of the present invention include, but are not limited to, cancers, cardiovascular diseases, diabetes, obesity, NASH, glaucoma, fibrotic anti-viral, antibacterial and anti-fibrotic therapeutics.

Also disclosed are pharmaceutical compositions comprising a pharmaceutically acceptable carrier and an effective amount of a disclosed compound, or a pharmaceutically acceptable salt, tautomer, isomer, hydrate, solvate, or polymorph thereof.

Also disclosed are kits comprising at least one disclosed compound, or a pharmaceutically acceptable salt, tautomer, isomer, hydrate, solvate, or polymorph thereof.

Also disclosed are methods for manufacturing a medicament comprising, combining at least one disclosed compound or at least one disclosed product with a pharmaceutically acceptable carrier or diluent. In a further aspect, the invention relates to the use of a disclosed compound in the manufacture of a medicament for the treatment of a disorder associated with an ENPP1 activity dysfunction. In a further aspect, the invention relates to the uses of disclosed compounds in the manufacture of a medicament for the treatment of a disorder of uncontrolled cellular proliferation.

Also disclosed are uses of a disclosed compound or a disclosed product in the manufacture of a medicament for the treatment of a disorder associated with an ENPP1 dysfunction in a mammal.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

FIG. 3 shows a PK profile of Compound 015-HCl in rat.

DETAILED DESCRIPTION OF THE INVENTION

A. Definitions

Figure 1:
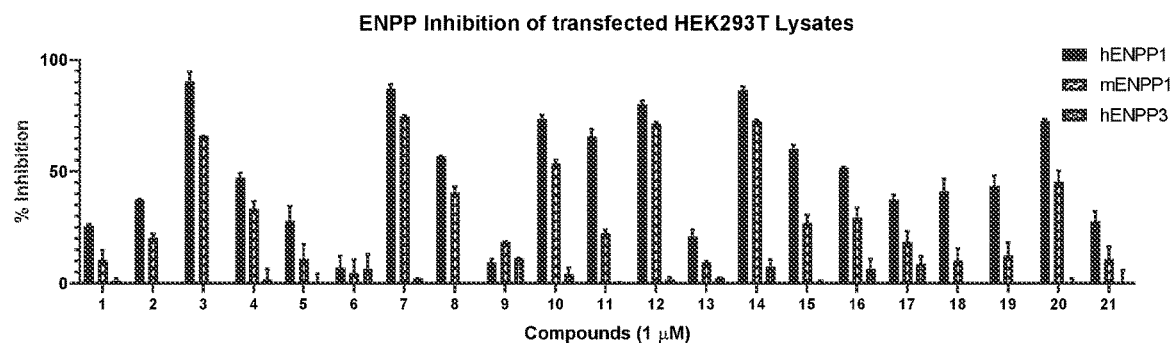
FIG. 1 shows a chart of ENPP inhibition of transfected HEK293T cells lysates by compounds of the invention.
Figure 2:
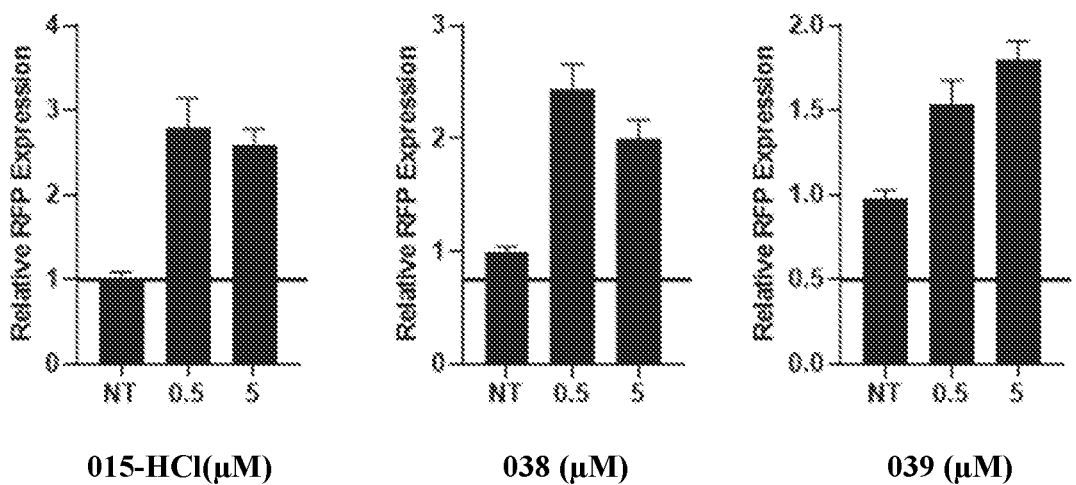
FIG. 2 shows results of Immune Infiltration Assay in HPAC cells.
Figure 4A:
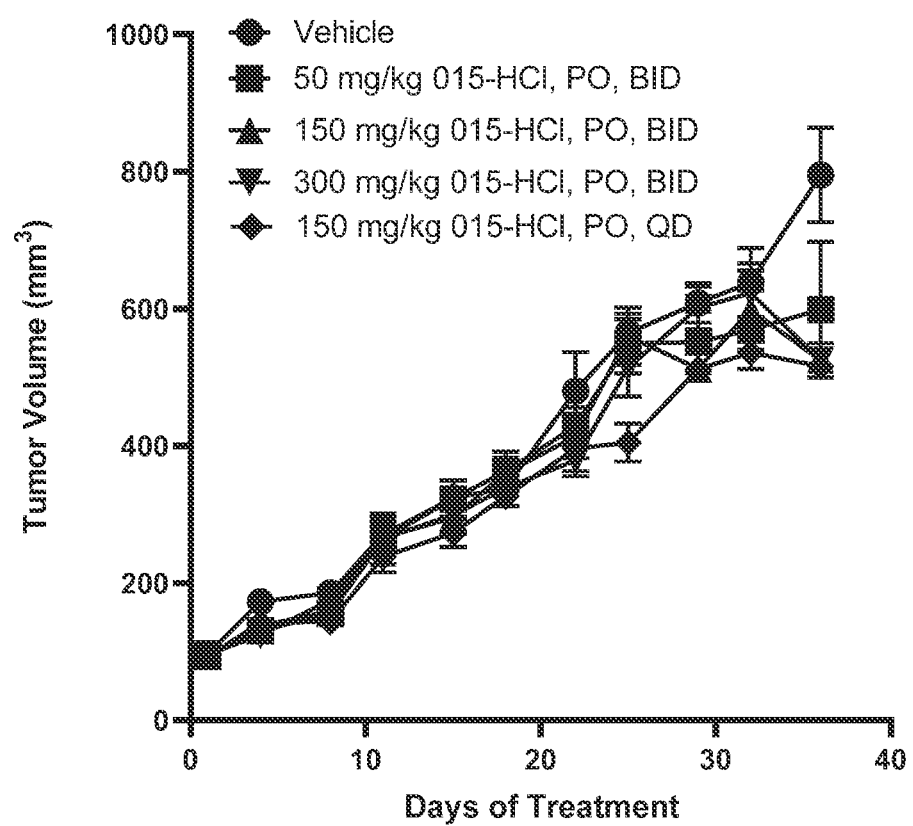
FIG. 4A shows an in vivo inhibition of tumor with Compound 015-HCl.
Figure 4B:
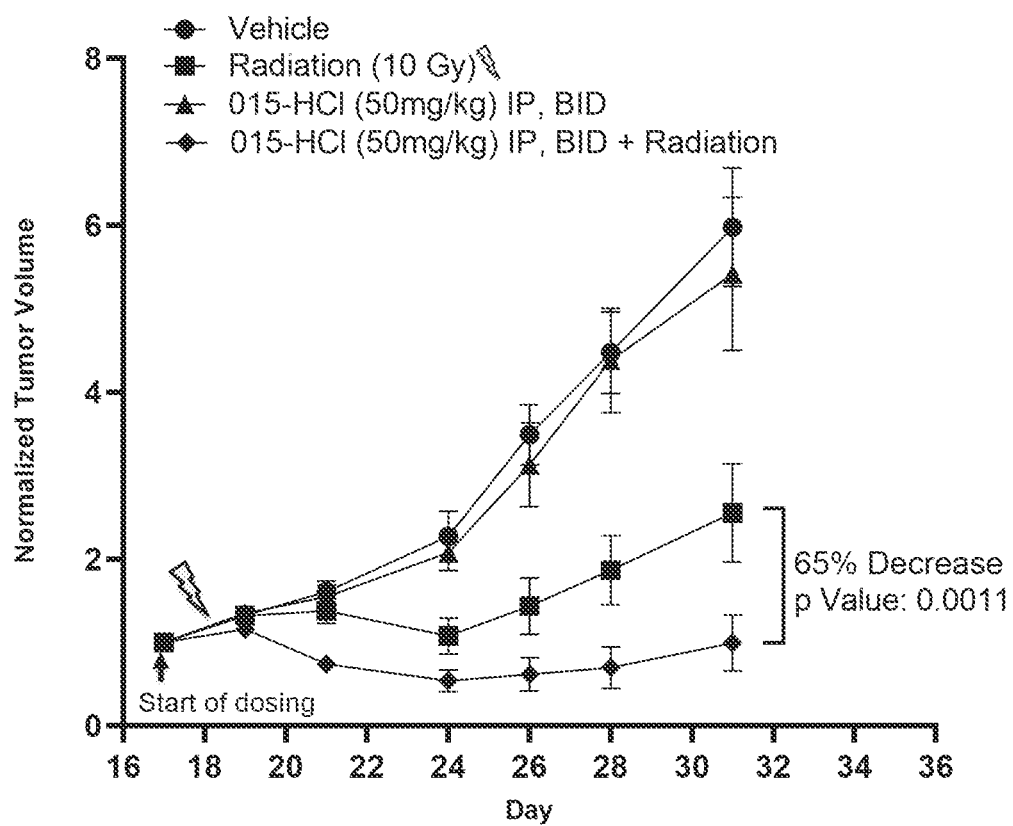
FIG. 4B shows an in vivo inhibition of tumor with Compound 015-HCl combined with radiation treatment.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as ChemDraw™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the term "ENPP1" refers to Ectonucleotide Pyrophophatase/Phosphodiesterase.

As used herein, the terms "optional" or "optionally" means that the subsequently described event or circumstance can or can not occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of a disorder of uncontrolled cellular proliferation associated with an ENPP1 dysfunction prior to the administering step. In some aspects of the disclosed method, the subject has been diagnosed with a need for inhibition of ENPP1 prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, zebra fish etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder of uncontrolled cellular proliferation" means having been subjected to a physical examination by a person of skill, for example, a physician, and found to have a condition that can be diagnosed or treated by a compound or composition that can inhibit ENPP1. As a further example, "diagnosed with a need for inhibition of ENPP1" refers to having been subjected to a physical examination by a person of skill, for example, a physician, and found to have a condition characterized by an ENPP1 dysfunction. Such a diagnosis can be in reference to a disorder, such as a disorder of uncontrolled cellular proliferation, cancer and the like, as discussed herein. For example, "diagnosed with a need for treatment of one or more disorders of uncontrolled cellular proliferation associated with an ENPP1 dysfunction" means having been subjected to a physical examination by a person of skill, for example, a physician, and found to have one or more disorders of uncontrolled cellular proliferation associated with an ENPP1 dysfunction.

As used herein, the phrase "identified to be in need of treatment for a disorder," or the like, refers to selection of a subject based upon need for treatment of the disorder. For example, a subject can be identified as having a need for treatment of a disorder (e.g., a disorder related to a dysfunction of ENPP1) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, intraurethral administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex, and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$EC_{50}$," is intended to refer to the concentration of a substance (e.g., a compound or a drug) that is required for 50% agonism or activation of a biological process, or component of a process, including a protein, subunit, organelle, ribonucleoprotein, etc. In one aspect, an $EC_{50}$ can refer to the concentration of a substance that is required for 50% agonism or activation in vivo, as further defined elsewhere herein. In a further aspect, $EC_{50}$ refers to the concentration of agonist or activator that provokes a response halfway between the baseline and maximum response.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. For example, an $IC_{50}$ can refer to the concentration of a substance that is required for 50% inhibition in vivo or the inhibition is measured in vitro, as further defined elsewhere herein. Alternatively, $IC_{50}$ refers to the half maximal (50%) inhibitory concentration (IC) of a substance. The inhibition can be measured in a cell-line such as AN3 CA, BT-20, BT-549, HCT 116, HER218, MCF7, MDA-MB-231, MDA-MB-235, MDA-MB-435S, MDA-MB-468, PANC-1, PC-3, SK-N-MC, T-47D, and U-87 MG.

The term "pharmaceutically acceptable" describes a material that is not biologically or otherwise undesirable, i.e., without causing an unacceptable level of undesirable biological effects or interacting in a deleterious manner.

The term "stable," as used herein, refers to compounds that are not substantially altered when subjected to conditions to allow for their production, detection, and, in certain aspects, their recovery, purification, and use for one or more of the purposes disclosed herein.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, $R_1$; $R_2$, $R_3$, etc and $R^a$, $R^b$, $R^c$, $R^d$, etc are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, 5-butyl, t-butyl, n-pentyl, isopentyl, 5-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

For example, a "$C_1$-$C_3$ alkyl" group can be selected from methyl, ethyl, n-propyl, i-propyl, and cyclopropyl, or from a subset thereof. In certain aspects, the "$C_1$-$C_3$ alkyl" group can be optionally further substituted. As a further example, a "$C_1$-$C_4$ alkyl" group can be selected from methyl, ethyl, n-propyl, i-propyl, cyclopropyl, n-butyl, i-butyl, s-butyl, t-butyl, and cyclobutyl, or from a subset thereof. In certain aspects, the "$C_1$-$C_4$ alkyl" group can be optionally further substituted. As a further example, a "$C_1$-$C_6$ alkyl" group can be selected from methyl, ethyl, 72-propyl, i-propyl, cyclopropyl, n-butyl, i-butyl, s-butyl, t-butyl, cyclobutyl, n-pentyl, i-pentyl, 5-pentyl, t-pentyl, neopentyl, cyclopentyl, n-hexyl, i-hexyl, 3-methylpentane, 2,3-dimethylbutane, neohexane, and cyclohexane, or from a subset thereof. In certain aspects, the "$C_1$-$C_6$ alkyl" group can be optionally further substituted. As a further example, a "$C_1$-$C_8$ alkyl" group can be selected from methyl, ethyl, n-propyl, i-propyl, cyclopropyl, n-butyl, i-butyl, s-butyl, t-butyl, cyclobutyl, n-pentyl, i-pentyl, 5-pentyl, t-pentyl, neopentyl, cyclopentyl, n-hexyl, i-hexyl, 3-methylpentane, 2,3-dimethylbutane, neohexane, cyclohexane, heptane, cycloheptane, octane, and cyclooctane, or from a subset thereof. In certain aspects, the "$C_1$-$C_8$ alkyl" group can be optionally further substituted. As a further example, a "$C_1$-$C_{12}$ alkyl" group can be selected from methyl, ethyl, n-propyl, i-propyl, cyclopropyl, n-butyl, i-butyl, s-butyl, t-butyl, cyclobutyl, n-pentyl, i-pentyl, 5-pentyl, t-pentyl, neopentyl, cyclopentyl, n-hexyl, i-hexyl, 3-methylpentane, 2,3-dimethylbutane, neohexane, cyclohexane, heptane, cycloheptane, octane, cyclooctane, nonane, cyclononane, decane, cyclodecane, undecane, cycloundecane, dodecane, and cyclododecane, or from a subset thereof. In certain aspects, the "$C_1$-$C_{12}$ alkyl" group can be optionally further substituted.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, nitrile, sulfonamide, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, nitrile, sulfonamide, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The terms "halogen," "halide," and "halo," as used herein, refer to the halogens fluorine, chlorine, bromine, and iodine. It is also contemplated that, in various aspects, halogen can be selected from fluoro, chloro, bromo, and iodo. For example, halogen can be selected from fluoro, chloro, and bromo. As a further example, halogen can be selected from fluoro and chloro. As a further example, halogen can be selected from chloro and bromo. As a further example, halogen can be selected from bromo and iodo. As a further example, halogen can be selected from chloro, bromo, and iodo. In one aspect, halogen can be fluoro. In a further aspect, halogen can be chloro. In a still further aspect, halogen is bromo. In a yet further aspect, halogen is iodo.

It is also contemplated that, in certain aspects, pseudohalogens (e.g. triflate, mesylate, tosylate, brosylate, etc.) can be used in place of halogens. For example, in certain aspects, halogen can be replaced by pseudohalogen. As a further example, pseudohalogen can be selected from triflate, mesylate, tosylate, and brosylate. In one aspect, pseudohalogen is triflate. In a further aspect, pseudohalogen is mesylate. In a further aspect, pseudohalogen is tosylate. In a further aspect, pseudohalogen is brosylate.

The term "heterocycle," as used herein refers to single and multi-cyclic aromatic or non-aromatic ring systems in which at least one of the ring members is other than carbon. Heterocycle includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, unless explicitly stated otherwise, a chemical group may be substituted, regardless whether it is explicitly stated that it is "optionally substituted". In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

All the enantiomers were separated by SFC column and the stereochemistry is tentative.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture.

Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

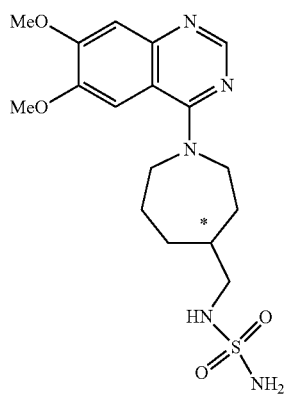 [SMILES: COc1cc2ncnc(N3CCCC(CNS(N)(=O)=O)CC3)c2cc1OC]

Such as

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{35}$S, $^{18}$F and $^{36}$Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

It is also appreciated that certain compounds described herein can be present as an equilibrium of tautomers. For example, ketones with an α-hydrogen can exist in an equilibrium of the keto form and the enol form.

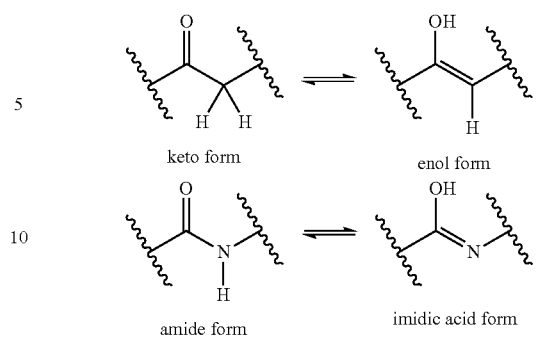

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

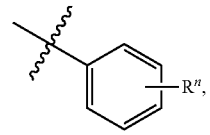

which is understood to be equivalent to a formula:

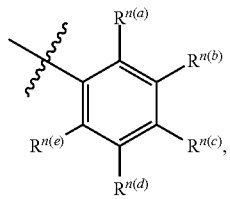

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Sigma-Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as *Fieser and Fieser's Reagents for Organic Synthesis*, Volumes 1-17 (John Wiley and Sons, 1991); *Rodd's Chemistry of Carbon Compounds*, Volumes 1-5 and Supplemental (Elsevier Science Publishers, 1989); *Organic Reactions*, Volumes 1-40 (John Wiley and Sons, 1991); March's *Advanced Organic Chemistry*, (John Wiley and Sons, 4th Edition); and Larock's *Comprehensive Organic Transformations* (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful as inhibitors of ENPP1. Moreover, in one aspect, the compounds of the invention are useful in the treatment of disorders of uncontrolled cellular proliferations. In a further aspect, the disorder of uncontrolled cellular proliferation is a cancer or a tumor. In a still further aspect, the disorder of uncontrolled cellular proliferation is associated with an ENPP1 dysfunction, as further described herein.

In another aspect, the compounds of the invention are useful in the treatment of diseases of bacterial or viral origin. Accordingly, in one aspect, the invention provides a method of treating a disease caused by bacteria or viruses, comprising administering to a subject a therapeutically effective amount of a compound of the invention.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

The invention, in one aspect, relates to compounds of Formula I or Formula II:

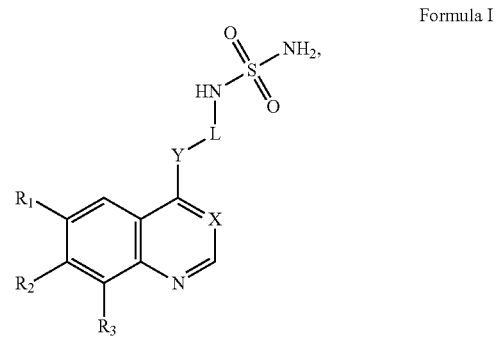

Formula I wherein

X is N or $CR_{11}$;

Y is selected from the group consisting of —$CR_4R_5$—, —$NR_6$—, —$N(CH_2)_mO$—, —O—, —S—, —S(O)—, —$S(O)_2$, aryl, and heteroaryl; wherein m is 2 or 3;

L is selected from the group consisting of an $C_1$-$C_5$ alkyl, and $C_1$-$C_5$ alkenyl;

each $R_1$, $R_2$ and $R_3$ are independently selected from the group consisting of hydrogen, halogen, CN, $OR^a$, —C(=O)$NR^bR^c$, —$NR^bR^c$, —C(=O)$R^d$, aryl, heteroaryl, cycloalkyl, and heterocycloalkyl.

each $R^a$ is independently selected from the group consisting of hydrogen, lower alkyl, —$(CH_2)_n$—C(=O)$NR^bR^c$, aralkyl, aryl, heteroaryl, heterocycloalkyl, and cycloalkyl;

wherein n is an integer between 1 and 3;

each $R^b$ and $R^c$ is independently selected from the group consisting of hydrogen, a lower alkyl, and lower aryl, heterocycloalkyl, or cycloalkyl;

each $R^d$ is independently selected from the group consisting of —$OR^e$ and lower alkyl;

each $R^e$ is independently selected from the group consisting of hydrogen, a lower alkyl, and a lower aryl;

$R_{11}$ is independently selected from the group consisting of hydrogen, halogen, COOEt, COOH, and CN;

$R_4$, $R_5$ and $R_6$ are independently selected from the group consisting of hydrogen and lower alkyl;

or an isomer, hydrate, solvate, polymorph, tautomer or a pharmaceutically acceptable salt thereof.

A compound of Formula II is as follows:

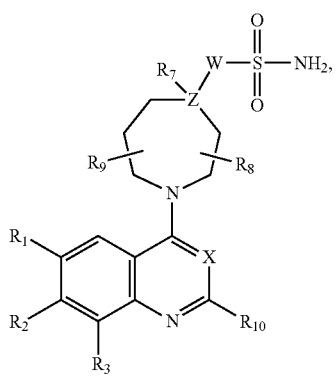

Formula II wherein

X is N or $CR_{11}$;

Z is C or N;

W is selected from the group consisting of an $C_1$-$C_5$ alkyl, —C(=O)—$(CH_2)_n$—, —($C_1$-$C_5$ alkyl)-N—; NH, and a direct bond as follows:

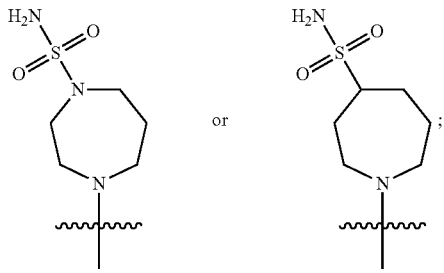 [SMILES: *N1CCCN(S(N)(=O)=O)CC1 ; *N1CCCC(S(N)(=O)=O)CC1]

each $R_1$, $R_2$ and $R_3$ are independently selected from the group consisting of hydrogen, halogen, CN, $OR^a$, —C(=O)$NR^bR^c$, —$NR^bR^c$, —C(=O)$R^d$, aryl, heteroaryl, cycloalkyl, and heterocycloalkyl.

each $R^a$ is independently selected from the group consisting of hydrogen, lower alkyl, and —$(CH_2)_n$—C(=O)$NR^bR^c$, aralkyl, aryl, heteroaryl, heterocycloalkyl, cycloalkyl;

wherein n is an integer between 1 and 3;

each $R^b$ and $R^c$ is independently selected from the group consisting of hydrogen, a lower alkyl, and lower aryl, heterocycloalkyl, or cycloalkyl;

each $R^d$ is independently selected from the group consisting of —$OR^e$ and lower alkyl;

each $R^e$ is independently selected from the group consisting of hydrogen, a lower alkyl, and a lower aryl;

$R_{11}$ is independently selected from the group consisting of hydrogen, halogen, COOEt, COOH, and CN;

$R_7$, $R_8$ and $R_9$ are independently selected from the group consisting of H, halogen and lower alkyl; and $R_8$ and $R_9$ can also form a bridge across the 7-membered ring with 1 or 2 atoms, as follows:

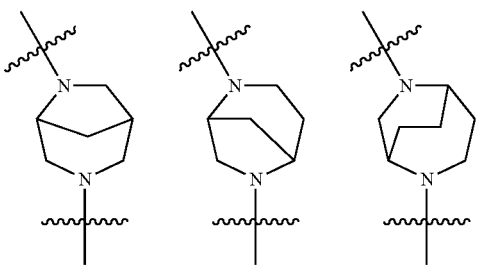 [SMILES: *N1CC2CC(C1)N(*)C2 ; *N1CCC2CC1CN2* ; *N1CCC2CCC1CN2*]

$R_{10}$ is independently selected from the group consisting of hydrogen and $CF_3$;

or an isomer, hydrate, solvate, polymorph, tautomer or a pharmaceutically acceptable salt thereof.

The invention encompasses any compounds or structures that include any combinations of the substituents as defined above.

In one preferred embodiment, Y in Formula I is pyridinyl.

In one preferred embodiment, X in Formula I or Formula II is C—CN.

In one preferred embodiment, Y in Formula I is $NR_6$.

In one preferred embodiment, in compounds of Formula I and Formula II, $R_1$, $R_2$ and $R_3$ are selected from the group consisting of $CH_3O$ and H.

In one preferred embodiment, in compounds of Formula II, Z is N.

In one preferred embodiment, in compounds of Formula II, W is selected from the group consisting of -4,5-imidazole, 2-Oxazole, 3-pyrrole; pyrazole, and thiazole.

In one preferred embodiment, in compounds of Formula II, X is N.

In one preferred embodiment, in compounds of Formula II, X is C—CN.

In one preferred embodiment, in compounds of Formula II, $R_7$, $R_8$ and $R_9$ are independently selected from the group consisting of H and halogen.

In one preferred embodiment, in compounds of Formula II, $R_7$ is a halogen, and more preferably F.

In one preferred embodiment, in compounds of Formula II, $R_8$ and $R_9$ are both halogen.

In one preferred embodiment, the compound is of Formula I;

X is N;

Y is selected from the group consisting of pyridinyl, $C_1$-$C_5$ alkyl, O, N, and S;

L is an optionally substituted $C_1$-$C_5$ alkyl; and $R_1$ and $R_2$ are both $CH_3O$.

In another preferred embodiment, the compound is of Formula II;

X is N;

Z is N;

W is selected from the group consisting of an optionally substituted $C_1$-$C_5$ alkyl, —C(=O)—$(CH_2)$—, —(an optionally substituted $C_1$-$C_5$ alkyl)-N; and a direct bond; and $R_1$ and $R_2$ are both $CH_3O$.

Examples of the provided compounds include:
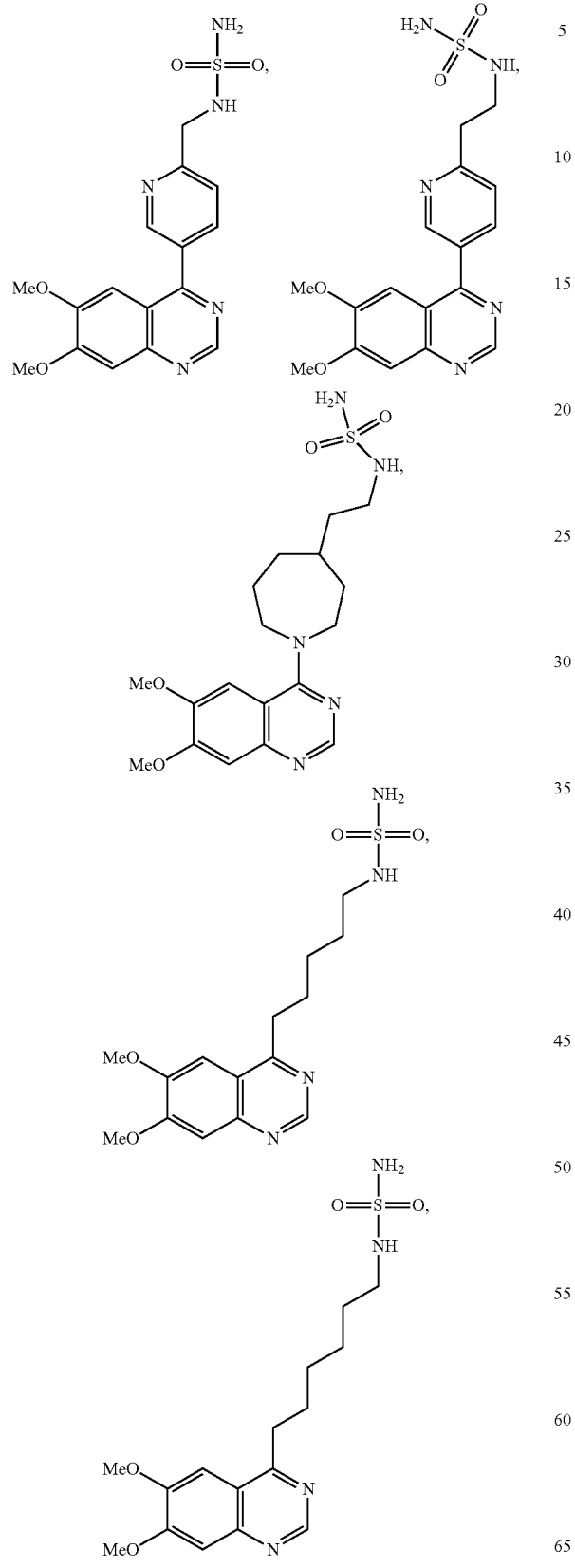
-continued
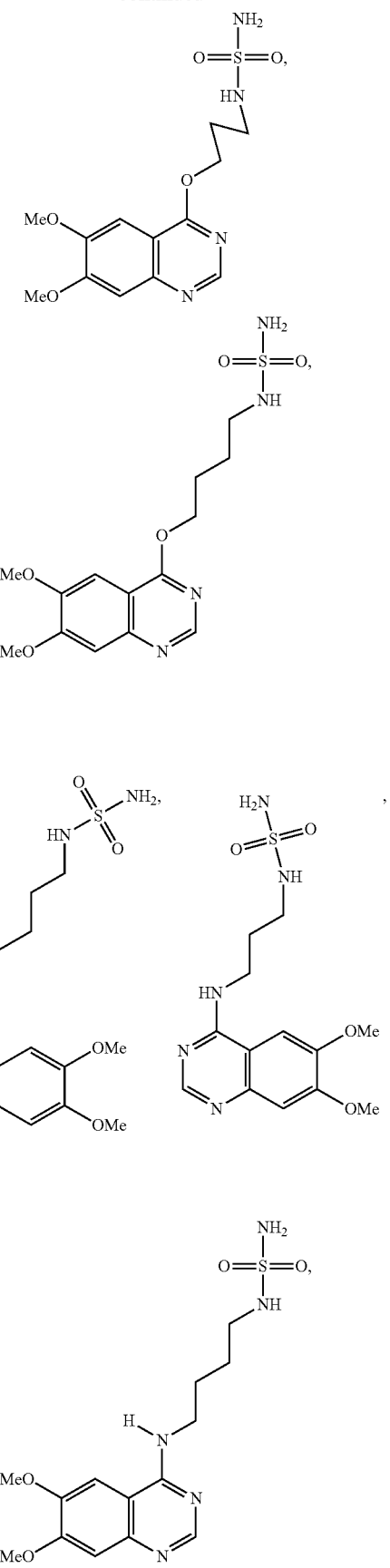

-continued
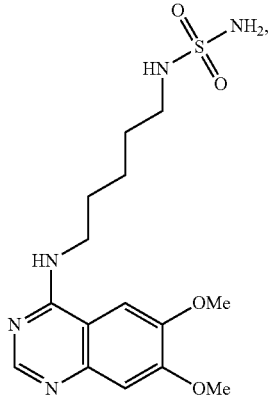
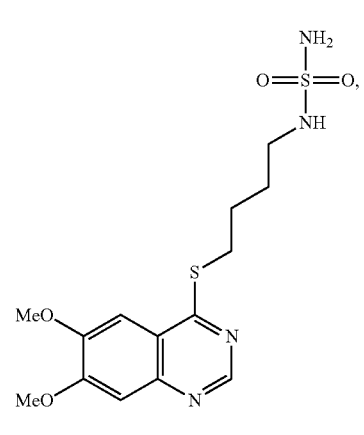
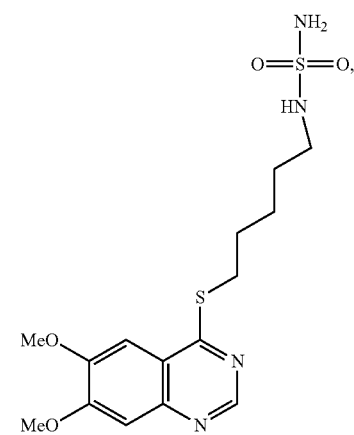
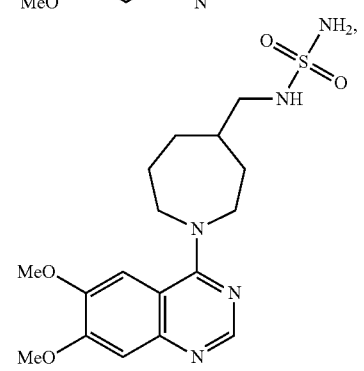
-continued
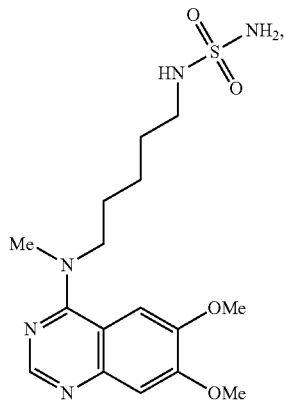
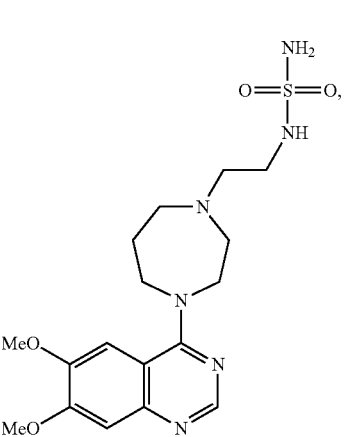
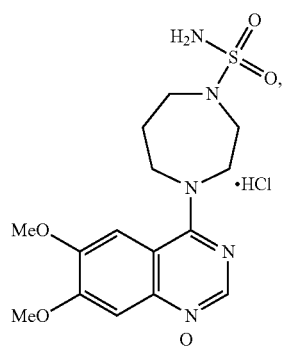
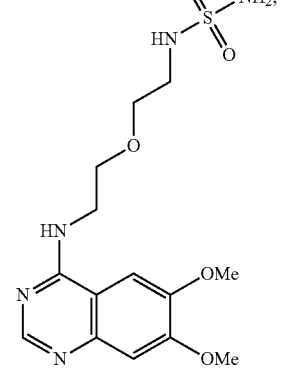

-continued
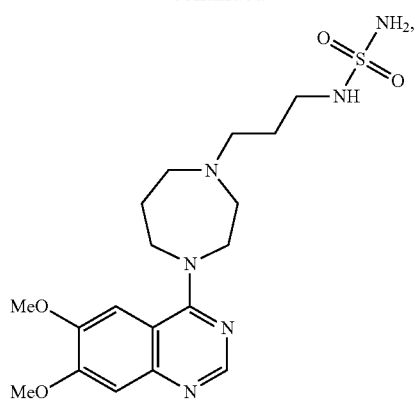
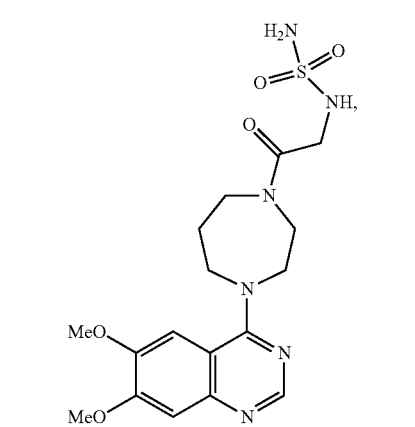
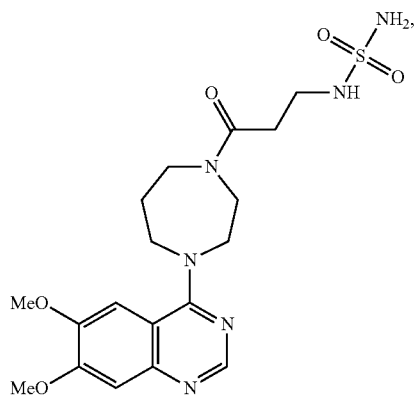
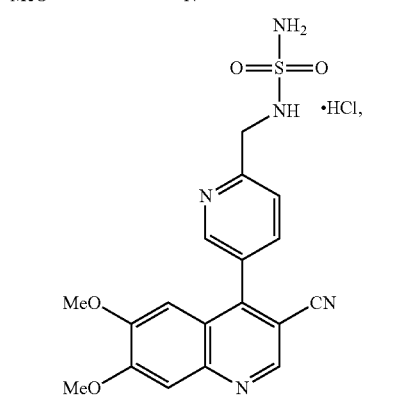
-continued
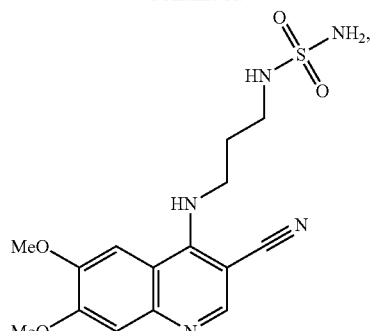
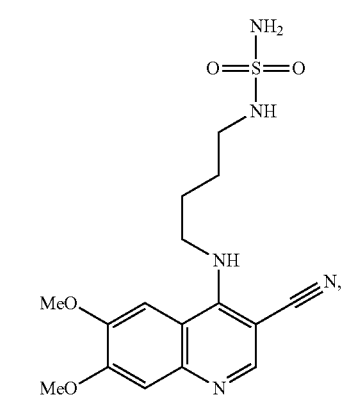
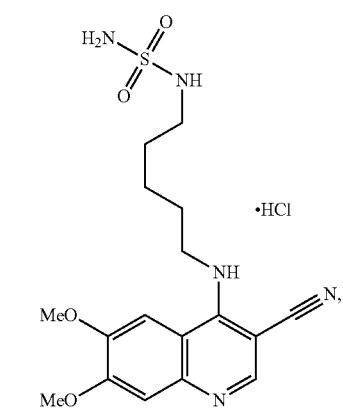
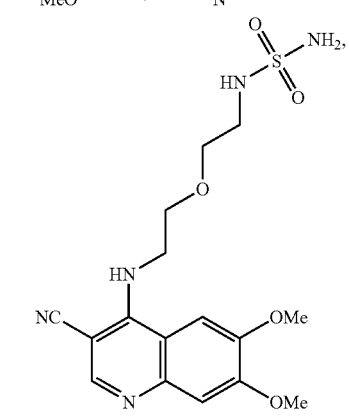

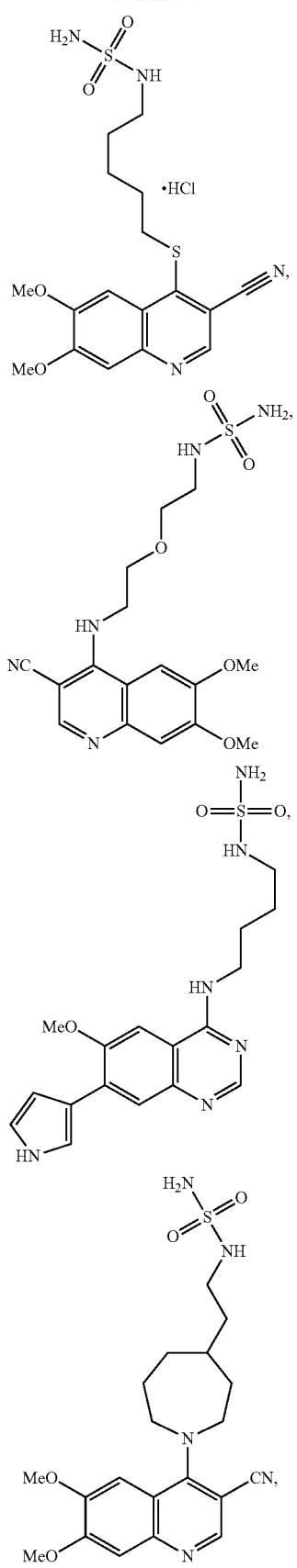
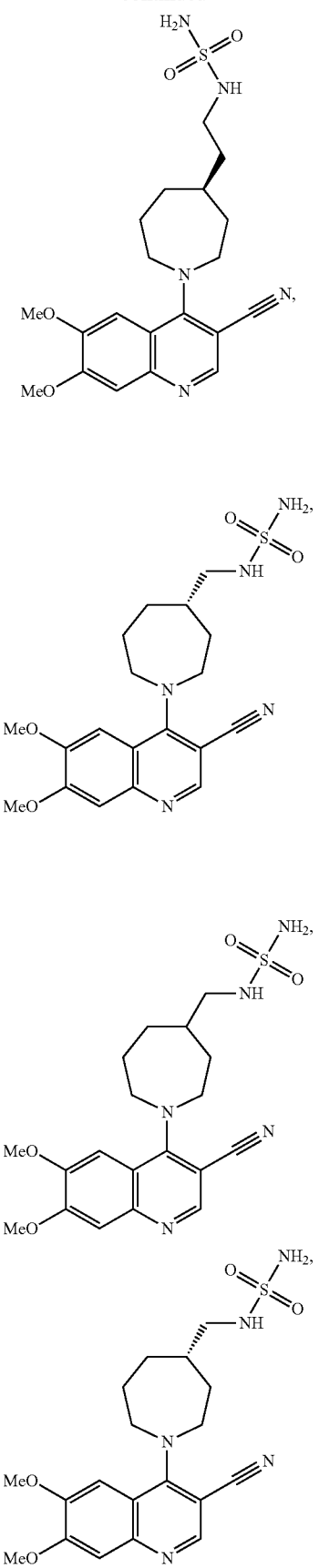

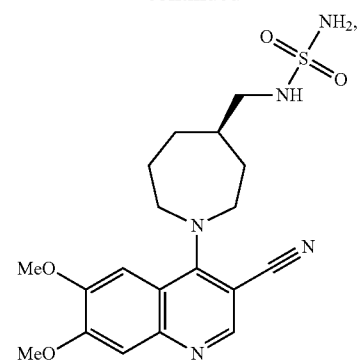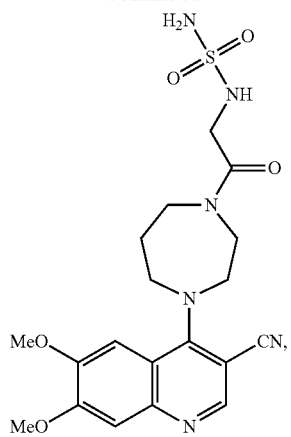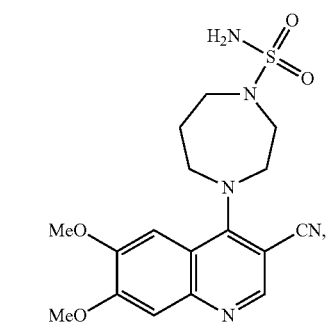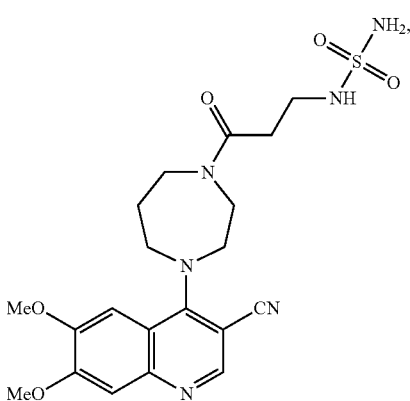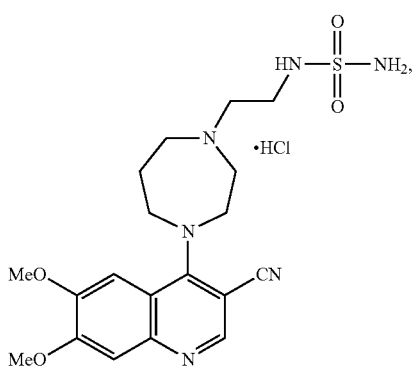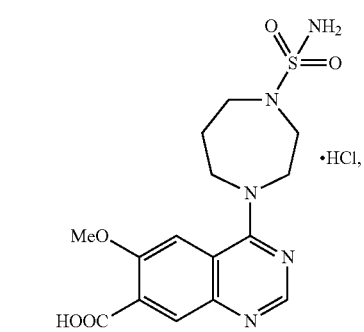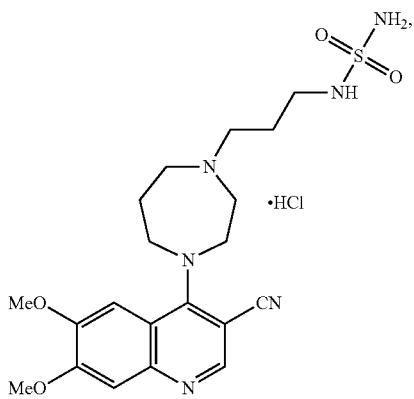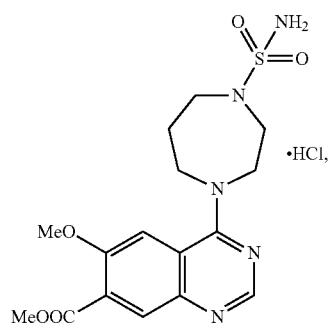

-continued
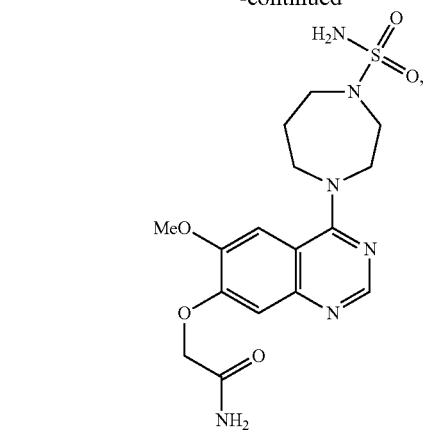
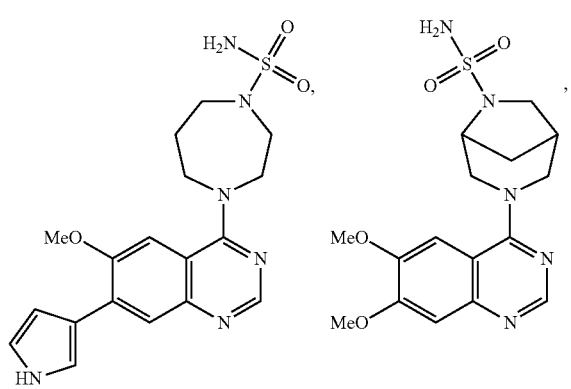
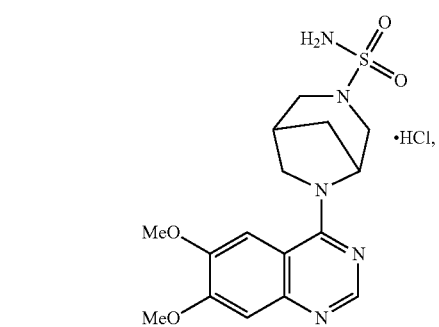
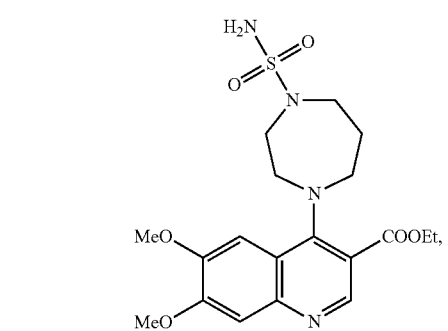
-continued
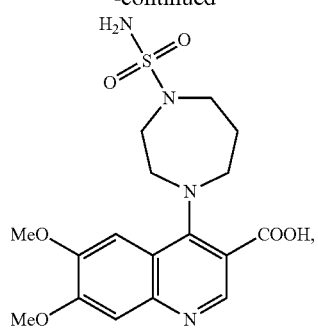
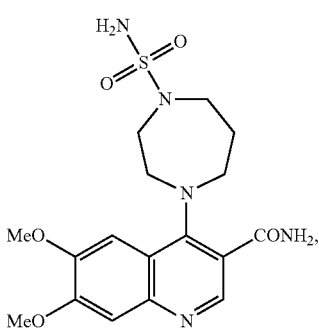
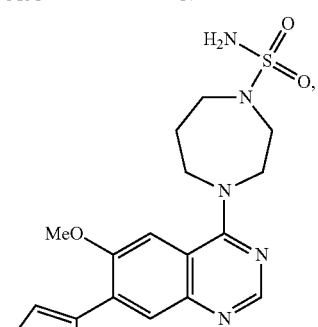
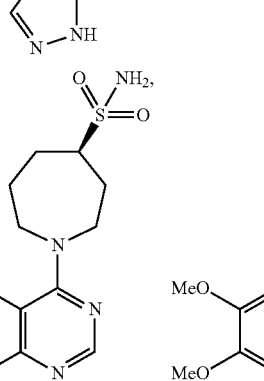
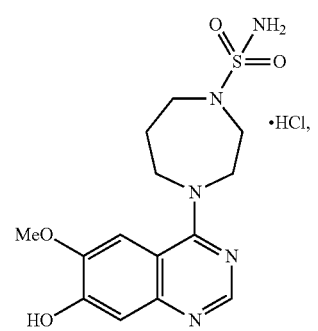

49
-continued
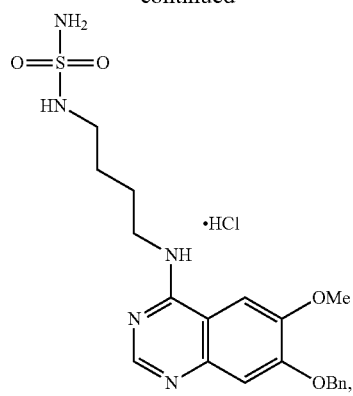
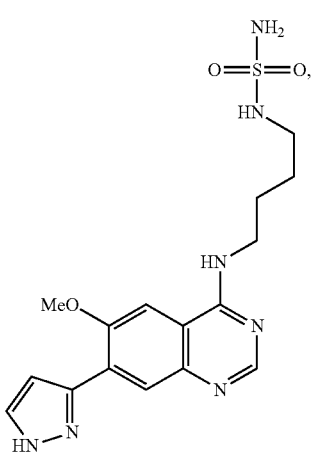
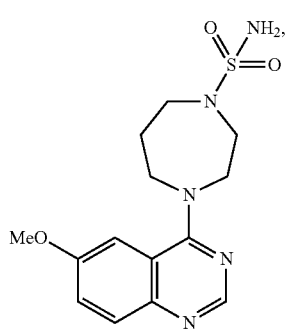
50
-continued
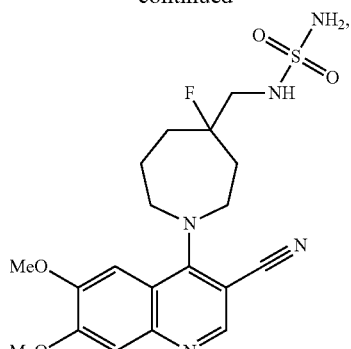

-continued

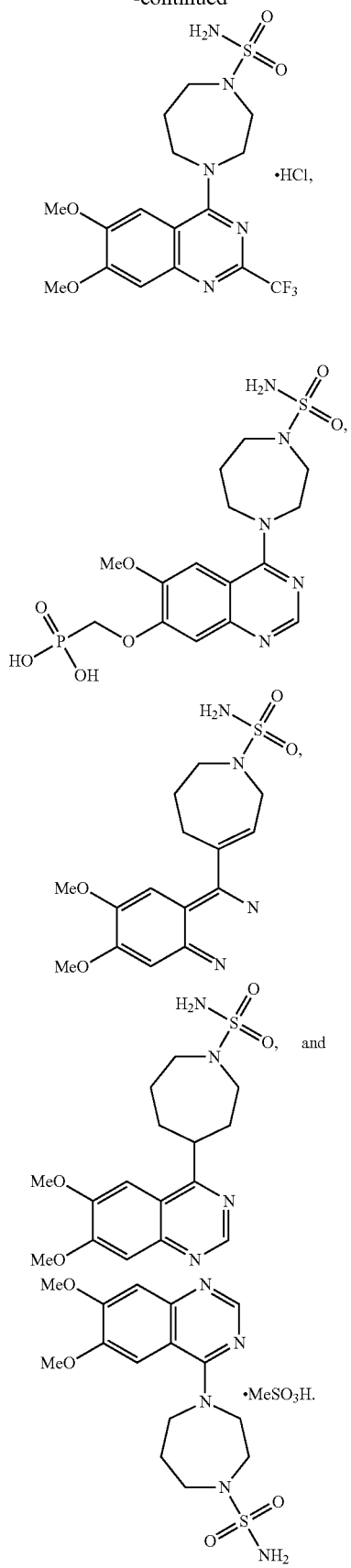

The invention also provides a pharmaceutical composition comprising a therapeutically effective amount of any of a compound of the invention and a pharmaceutically acceptable carrier.

The invention also provides a method for the treatment of a disorder of uncontrolled cellular proliferation in a mammal, the method comprising the step of administering to the mammal an effective amount of any of the compounds of the invention.

The invention also provides a method for decreasing ENPP1 activity in a mammal, the method comprising the step of administering to the mammal an effective amount of any of the compounds of the invention.

The invention also provides a method for inhibiting ENPP1 activity in a mammal, the method comprising the step of administering to the mammal an effective amount of any of the compounds of the invention.

C. Methods of Making the Compounds

In one aspect, the invention relates to methods of making compounds useful as inhibitors of ENPP1. In a further aspect, the products of disclosed methods of making are modulators of ENPP1 activity.

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, in addition to other standard manipulations known in the literature or to one skilled in the art. The following examples are provided so that the invention might be more fully understood, are illustrative only, and should not be construed as limiting.

In one aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

Where reaction conditions and amounts of ingredients are not stated, it is believed that it is within a skill in the art to determine them. It is contemplated that each disclosed methods can further comprise additional steps, manipulations, and/or components. It is also contemplated that any one or more step, manipulation, and/or component can be optionally omitted from the invention. It is understood that disclosed methods can be used to provide the disclosed compounds. It is also understood that the products of the disclosed methods can be employed in the disclosed methods of using.

D. Pharmaceutical Compositions

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In a further aspect, the invention relates to pharmaceutical compositions comprising a pharmaceutically acceptable carrier and an effective amount of the product of a disclosed synthetic method. In a further aspect, the effective amount is a therapeutically effective amount. In a further aspect, the effective amount is a prophylactically effective amount. In a further aspect, the compound is a disclosed compound.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require inhibition or negative modulation of ENPP1 protein activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for inhibiting or negatively modulating ENPP1 protein activity (e.g., treatment of a disorder of uncontrolled cellular proliferation, or one or more neurodegenerative disorders associated with ENPP1 dysfunction) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above-mentioned pathological conditions.

It is understood that the disclosed compositions can be prepared from the disclosed compounds. It is also understood that the disclosed compositions can be employed in the disclosed methods of using.

E. Methods of Using the Compounds and Compositions

The disclosed compounds can be used as single agents or in combination with one or more other drugs in the treatment, prevention, control, amelioration or reduction of risk of the aforementioned diseases, disorders and conditions for which compounds of formulas I or II or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

The pharmaceutical compositions and methods of the present invention can further comprise other therapeutically active compounds as noted herein which are usually applied in the treatment of the above-mentioned pathological conditions.

1. Treatment Methods

The compounds disclosed herein are useful for treating, preventing, ameliorating, controlling or reducing the risk of a variety of disorders wherein the patient or subject would benefit from inhibition or negative modulation of ENPP1. In one aspect, provided is a method of treating or preventing a disorder in a subject comprising the step of administering to the subject at least one disclosed compound; at least one disclosed pharmaceutical composition; and/or at least one disclosed product in a dosage and amount effective to treat the disorder in the subject.

Also provided is a method for the treatment of one or more disorders, for which ENPP1 inhibition is predicted to be beneficial, in a subject comprising the step of administering to the subject at least one disclosed compound; at least one disclosed pharmaceutical composition; and/or at least one disclosed product in a dosage and amount effective to treat the disorder in the subject.

In one aspect, provided is a method for treating a disorder of uncontrolled cellular proliferation, comprising: administering to a subject at least one disclosed compound; at least one disclosed pharmaceutical composition; and/or at least one disclosed product in a dosage and amount effective to treat the disorder in the subject. In a further aspect, provided is a method for treating or preventing a neurodegenerative disorder, comprising: administering to a subject at least one disclosed compound; at least one disclosed pharmaceutical composition; and/or at least one disclosed product in a dosage and amount effective to treat the disorder in the subject. Also provided is a method for the treatment of a disorder in a mammal comprising the step of administering to the mammal at least one disclosed compound, composition, or medicament.

The invention is directed at the use of described chemical compositions to treat diseases or disorders in patients (preferably human) wherein ENPP1 inhibition would be predicted to have a therapeutic effect, such as disorders of uncontrolled cellular proliferation (e.g. cancers) and neurodegenerative disorders such as Alzheimer's disease, Huntington's disease, and Parkinson's disease, diseases caused by bacteria and/or viruses (including DNA and RNA viruses), by administering one or more disclosed compounds or products.

The compounds of the invention can also be used for immunotherapy. In one embodiment, the compounds of the invention treat disorders of uncontrolled cellular proliferation, and/or diseases caused by bacteria and/or viruses through immunotherapy, meaning that the compounds elicit immunotherapeutic response which results in the treatment of these diseases.

The compounds disclosed herein are useful for treating, preventing, ameliorating, controlling or reducing the risk of a variety of disorders of uncontrolled cellular proliferation.

Also provided is a method of use of a disclosed compound, composition, or medicament. In one aspect, the method of use is directed to the treatment of a disorder. In a further aspect, the disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

Examples of disorders treatable with the provided compounds include a disorder of uncontrolled cellular proliferation. In a yet further aspect, the disorder of uncontrolled cellular proliferation is cancer. In a yet further aspect, the cancer is a leukemia. In an even further aspect, the cancer is a sarcoma. In a still further aspect, the cancer is a solid tumor. In a yet further aspect, the cancer is a lymphoma.

It is understood that cancer refer to or describe the physiological condition in mammals that is typically characterized by unregulated cell growth. The cancer may be multi-drug resistant (MDR) or drug-sensitive. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer.

In various aspects, further examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas In a further aspect, the cancer is a hematological cancer. In a still further aspect, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), Hodgkin lymphoma, Non-Hodgkin lymphoma, multiple myeloma, solitary myeloma, localized myeloma, and extramedullary myeloma. In a still further aspect, the cancer is selected from chronic lymphocytic leukemia, small lymphocytic lymphoma, B-cell non-Hodgkin lymphoma, and large B-cell lymphoma.

In a further aspect, the cancer is a cancer of the brain. In a still further aspect, the cancer of the brain is selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In one aspect, the cancer can be a cancer selected from cancers of the blood, brain, genitourinary tract, gastrointestinal tract, colon, rectum, breast, kidney, lymphatic system, stomach, lung, pancreas, and skin. In a further aspect, the cancer is selected from prostate cancer, glioblastoma multiforme, endometrial cancer, breast cancer, and colon cancer. In a further aspect, the cancer is selected from a cancer of the breast, ovary, prostate, head, neck, and kidney. In a still further aspect, the cancer is selected from cancers of the blood, brain, genitourinary tract, gastrointestinal tract, colon, rectum, breast, livery, kidney, lymphatic system, stomach, lung, pancreas, and skin. In a yet further aspect, the cancer is selected from a cancer of the lung and liver. In an even further aspect, the cancer is selected from a cancer of the breast, ovary, testes and prostate. In a still further aspect, the cancer is a cancer of the breast. In a yet further aspect, the cancer is a cancer of the ovary. In an even further aspect, the cancer is a cancer of the prostate. In a still further aspect, the cancer is a cancer of the testes.

In various aspects, disorders associated with an ENPP1 dysfunction include neurodegenerative disorders. In a further aspect, the neurodegenerative disease is selected from Alzheimer's disease, Parkinson's disease, and Huntington's disease.

The compounds are further useful in a method for the prevention, treatment, control, amelioration, or reducation of risk of the diseases, disorders and conditions noted herein. The compounds are further useful in a method for the prevention, treatment, control, amelioration, or reduction of risk of the aforementioned diseases, disorders and conditions in combination with other agents.

The present invention is further directed to administration of an ENPP1 inhibitor for improving treatment outcomes in the context of disorders of uncontrolled cellular proliferation, including cancer. That is, in one aspect, the invention relates to a cotherapeutic method comprising the step of administering to a mammal an effective amount and dosage of at least one compound of the invention in connection with cancer therapy.

In a further aspect, administration improves treatment outcomes in the context of cancer therapy. Administration in connection with cancer therapy can be continuous or intermittent. Administration need not be simultaneous with therapy and can be before, during, and/or after therapy. For example, cancer therapy can be provided within 1, 2, 3, 4, 5, 6, 7 days before or after administration of the compound. As a further example, cancer therapy can be provided within 1, 2, 3, or 4 weeks before or after administration of the compound. As a still further example, cognitive or behavioral therapy can be provided before or after administration within a period of time of 1, 2, 3, 4, 5, 6, 7, 8, 9, or 10 half-lives of the administered compound.

In one aspect, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly. In one embodiment, the invention is directed to a combination therapy wherein a compound of Formula I or Formula II is used together with radiation therapy. Radiation therapy can be conducted simultaneously, prior or after administering a compound of the present invention.

Accordingly, the pharmaceutical compositions include those that contain one or more other active ingredients, in addition to a compound of the present invention.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present invention. When a compound of the present invention is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present invention.

The weight ratio of a disclosed compound to the second active ingredient can be varied and will depend upon the effective dose of each ingredient. Generally, an effective dose of each will be used. Thus, for example, when a compound of the present invention is combined with another agent, the weight ratio of a disclosed compound to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

In one aspect, the compound can be employed in combination with anti-cancer therapeutic agents or other known therapeutic agents.

In the treatment of conditions which require inhibition or negative modulation of ENPP1, an appropriate dosage level will generally be about 0.01 to 1000 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in one aspect, the invention relates to methods for inhibiting or negatively modulating ENPP1 in at least one cell, comprising the step of contacting the at least one cell with at least one compound of the invention, in an amount effective to modulate or activate ENPP1 activity response, e.g. in the at least one cell. In a further aspect, the cell is mammalian, for example human. In a further aspect, the cell has been isolated from a subject prior to the contacting step. In a further aspect, contacting is via administration to a subject.

a. Treatment of a Disorder of Uncontrolled Cellular Proliferation

In one aspect, the invention relates to a method for the treatment of a disorder of uncontrolled cellular proliferation in a mammal, the method comprising the step of administering to the mammal an effective amount of at least one disclosed compound or a product of a disclosed method of making a compound, or a pharmaceutically acceptable salt, hydrate, solvate, or polymorph thereof, thereby treating the disorder of uncontrolled cellular proliferation.

In a still further aspect, the effective amount is a therapeutically effective amount. In a yet still further aspect, the effective amount is a prophylactically effective amount.

In a further aspect, the mammal is a human. In a yet further aspect, the method further comprises the step of identifying a mammal in need of treatment of a disorder of uncontrolled cellular proliferation. In a still further aspect, the mammal has been diagnosed with a need for treatment of a disorder of uncontrolled cellular proliferation prior to the administering step.

In a further aspect, the disorder of uncontrolled cellular proliferation is a cancer. In a yet further aspect, the cancer is a leukemia. In an even further aspect, the cancer is a sarcoma. In a still further aspect, the cancer is a solid tumor. In a yet further aspect, the cancer is a lymphoma. In an even further aspect, the cancer is selected from chronic lymphocytic leukemia, small lymphocytic lymphoma, B-cell non-Hodgkin lymphoma, and large B-cell lymphoma. In a still further aspect, the cancer is selected from cancers of the blood, brain, genitourinary tract, gastrointestinal tract, colon, rectum, breast, livery, kidney, lymphatic system, stomach, lung, pancreas, and skin. In a yet further aspect, the cancer is selected from a cancer of the lung and liver. In an even further aspect, the cancer is selected from a cancer of the breast, ovary, testes and prostate. In a still further aspect, the cancer is a cancer of the breast. In a yet further aspect, the cancer is a cancer of the ovary. In an even further aspect, the cancer is a cancer of the prostate. In a still further aspect, the cancer is a cancer of the testes.

EXAMPLES

F. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein.

The following exemplary compounds of the invention were synthesized. The Examples are provided herein to illustrate the invention, and should not be construed as limiting the invention in any way. The Examples are typically depicted in free base form, according to the IUPAC naming convention. However, some of the Examples were obtained or isolated in salt form.

Some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

Experimental Chemistry

Synthesis Schemes, Methods and Procedures

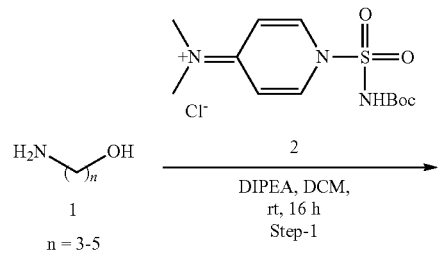

General scheme 1

Example 1: Synthesis of (N-(3-((6, 7-dimethoxyquinazolin-4-yl) oxy) propyl) sulfamide)

Step 1: Synthesis of Tert-butyl (N-(3-hydroxypropyl) sulfamoyl) carbamate

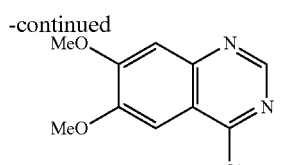

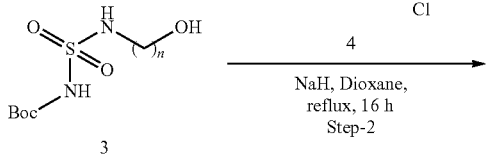

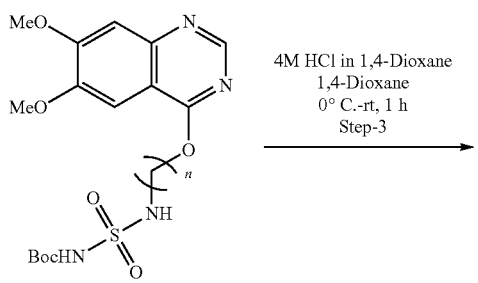

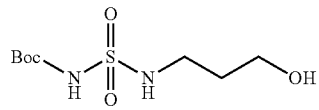

3

To a stirred solution of 3-aminopropan-1-ol 1 (500 mg, 6.666 mmol) in dichloromethane (20 ml) were added diisopropylethylamine (1.9 mL, 9.999 mmol) and N-(1-(N-(tert-butoxycarbonyl)sulfamoyl)pyridin-4(1H)-ylidene)-N-methylmethanaminium 2 (2.25 g, 7.385 mmol) at 0° C. then stirred at room temperature for 16 h. The progress of the reaction was monitored by TLC. After completion of the reaction, organic solvents completely distilled off under reduced pressure to afford crude compound. Crude compound was purified through 100-200 silica gel column chromatography by eluting 3% methanol in dichloromethane to afford semi pure compound. This semi pure was washed with 50% ethyl acetate in pet ether to afford tert-butyl (N-(3-hydroxypropyl) sulfamoyl) carbamate 3 (650 mg, 2.559 mmol, 38% yield) as an off-white solid.

1H NMR (400 MHz, DMSO) δ 10.77 (s, 1H), 7.45 (t, 1H), 4.44 (t, 1H), 3.40 (d, 2H), 2.91 (d, 2H), 1.60-1.57 (t, 2H), 1.41 (s, 9H)

The following compounds were synthesized by using the above general procedure.

| Structure | Yield (%) | 1HNMR |
|---|---|---|
| 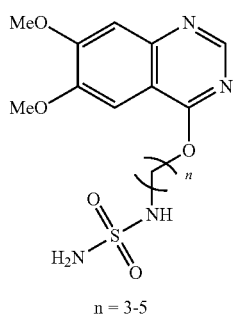 | 14 | (400 MHz, DMSO) δ 10.75 (s, 1H), 7.52 (t, 1H), 4.38 (t, 1H), 3.35 (m, 2H), 2.85 (m, 2H), 1.46 (m, 4H), 1.41 (s, 9H). |
| 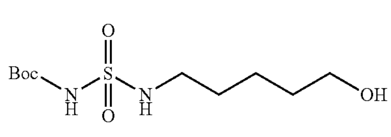 [SMILES: CC(C)(C)OC(=O)NS(=O)(=O)NCCCCCO] | 53 | (400 MHz, DMSO) δ 10.76 (s, 1H), 7.51 (t, 1H), 4.34 (t, 1H), 3.35 (m, 2H), 2.84 (m, 2H), 1.45-1.35 (m, 11H), 1.26 (m, 4H). |

Step 2: Synthesis of Tert-butyl (N-(3-((6, 7-dimethoxyquinazolin-4-yl) oxy) propyl) sulfamoyl) carbamate

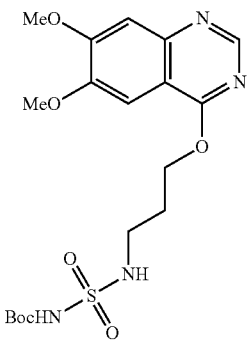 [SMILES: COc1cc2ncnc(OCCCNS(=O)(=O)NC(=O)OC(C)(C)C)c2cc1OC]

To a stirred solution of tert-butyl (N-(3-hydroxypropyl) sulfamoyl) carbamate 4 (900 mg, 3.897 mmol) in dichloromethane (20 ml) was added 60% NaH (212 mg, 5.314 mmol) and then stirred at reflux for 30 minutes. Then added 4-chloro-6, 7-dimethoxyquinazoline 3 (795 mg, 3.542 mmol) at room temperature again stirred at reflux for 16 h. The progress of the reaction was monitored by TLC. After completion of the reaction, to the reaction mixture was added water (200 mL) and extracted with ethyl acetate (2×100 mL). Combined organic layers were washed with brine solution (100 mL), dried over sodium sulfate and concentrated under reduced pressure. Crude compound was purified through 100-200 silica gel column chromatography by eluting 100% ethyl acetate to afford tert-butyl (N-(3-((6, 7-dimethoxyquinazolin-4-yl) oxy) propyl) sulfamoyl) carbamate 5 (700 mg, 1.583 mmol, 44% yield) as a pale yellow solid. 1H NMR (400 MHz, DMSO) δ 10.85 (s, 1H), 8.60 (s, 1H), 7.71 (s, 1H), 7.31 (d, 2H), 4.55 (t, 2H), 3.92 (d, 6H), 3.12 (d, 2H), 2.01 (m, 2H), 1.37 (s, 9H). LC-MS: M/Z: 442.9 (M+1)

The following compounds were synthesized by using the above general procedure.

| Structure | 1HNMR |
|---|---|
| MeO-quinazoline-O-(CH2)4-NH-S(O)2-NHBoc | (400 MHz, DMSO) δ 10.79 (s, 1H), 8.60 (s, 1H), 7.63 (bs, 1H), 7.30 (d, 2H), 4.50 (t, 2H), 3.92 (d, 6H), 2.97 (d, 2H), 1.86 (d, 2H), 1.65 (d, 2H), 1.37 (s, 9H). MS 456.9 |
| MeO-quinazoline-O-(CH2)5-NH-S(O)2-NHBoc | (400 MHz, DMSO) δ 10.86-10.67 (bs, 1H), 8.60 (s, 1H), 7.51 (bs, 1H), 7.30 (s, 1H), 7.29 (s, 1H) 4.50 (t, 2H), 3.91 (s, 3H), 3.94 (s, 3H) 2.89 (d, 2H), 1.83-1.79 (m, 2H), 1.54-1.47 (m, 4H), 1.38 (s, 9H). MS 471.2 |

Step 3: Synthesis of (N-(3-((6,7-dimethoxyquinazolin-4-yl)oxy)propyl)sulfamide)

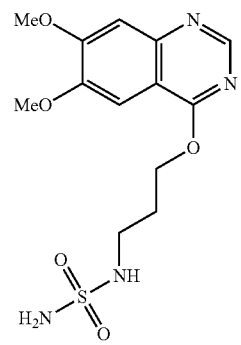 [SMILES: COc1cc2ncnc(OCCCNS(N)(=O)=O)c2cc1OC]

To a stirred solution of tert-butyl (N-(3-((6,7-dimethoxyquinazolin-4-yl)oxy)propyl)sulfamoyl)carbamate (200 mg, 0.452 mmol) in 1,4-dioxane (2 ml) was added 4M HCl in Dioxane (8 mL) at 0° C. then stirred at room temperature for 3 h. The progress of the reaction was monitored by TLC. After completion of the reaction, organic solvents completely distilled off under reduced pressure to afford crude compound. Crude compound was purified through prep HPLC method to afford pure compound of (N-(3-((6,7-dimethoxyquinazolin-4-yl)oxy)propyl)sulfamide) (Target-12) (120 mg, 0.35 mmol, 78% yield) as a pale yellow solid. 1H NMR (400 MHz, DMSO) δ 8.93 (s, 1H), 7.42 (d, 2H), 6.57 (bs, 2H), 4.67 (t, 2H), 3.96 (d, 6H), 3.10 (t, 2H), 2.06 (t, 2H).

The following compounds were synthesized by using the above general procedure.

| Compound Number | Structure | 1HNMR |
|---|---|---|
| 053 | 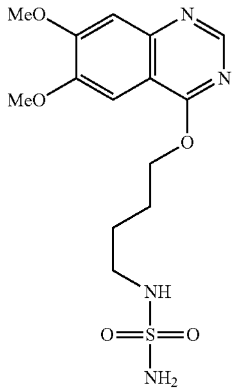 [SMILES: COc1cc2ncnc(OCCCCNS(N)(=O)=O)c2cc1OC] | (400 MHz, DMSO) δ 8.60 (s, 1H), 7.30 (d, 2H), 6.48-6.38 (m, 3H), 4.51 (t, 2H), 3.92 (d, 6H), 2.89 (t, 2H), 1.87-1.78 (m, 2H), 1.59-1.44 (m, 4H). |
| 054 | 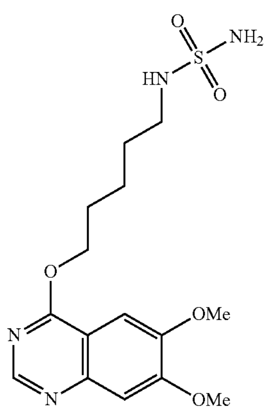 [SMILES: COc1cc2ncnc(OCCCCCNS(N)(=O)=O)c2cc1OC] | (400 MHz, DMSO) δ 8.61 (s, 1H), 7.31 (d, 2H), 6.48 (s, 2H), 6.53 (t, 1H) 4.52 (t, 2H), 3.91 (s, 3H), 3.94 (s, 3H) 2.95 (m, 2H), 1.90-1.85 (t, 2H), 1.67 (t, 2H). |
Compound 052 was also prepared based on the general procedure of Example 1.
052
1H NMR (400 MHz, DMSO) δ 8.93 (s, 1H), 7.42 (d, 2H), 6.57 (bs, 2H), 4.67 (t, 2H), 3.96 (d, 6H), 3.10 (t, 2H), 2.06 (t, 2H). LCMS 342.9; MW 378.83.
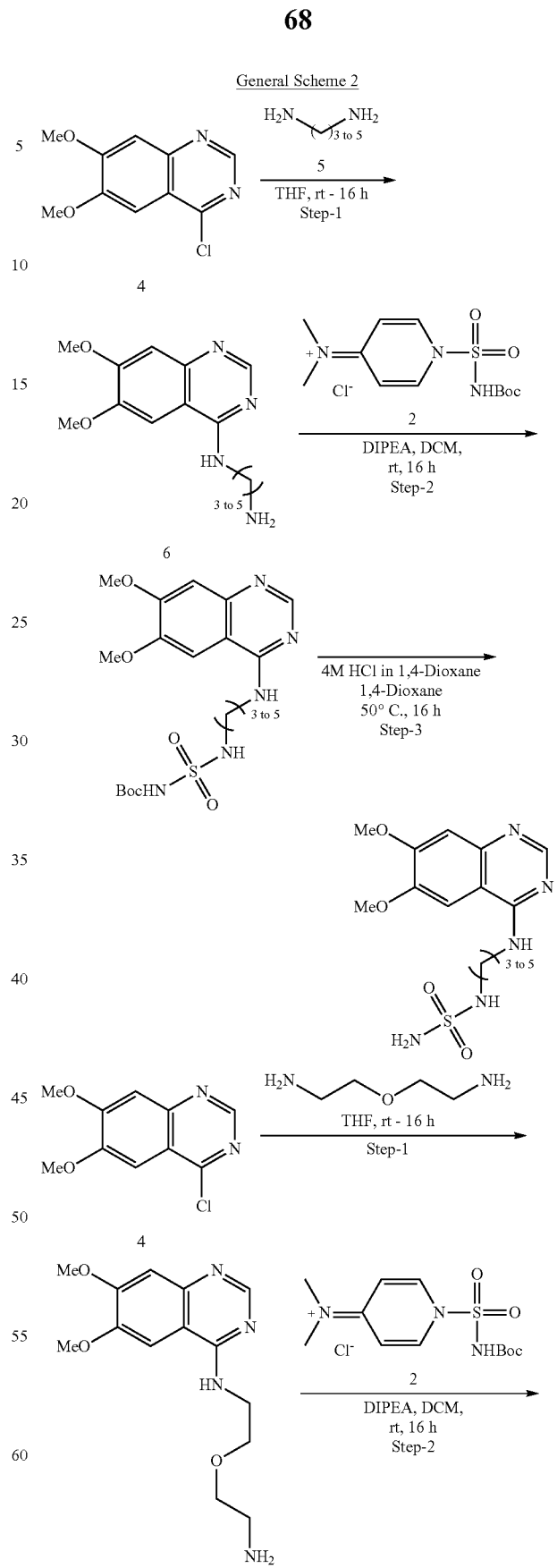
General Scheme 2

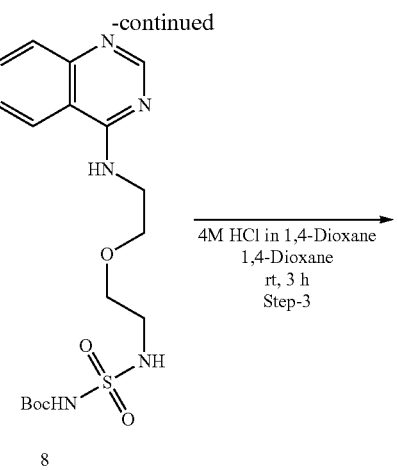

ture for 16 h. The progress of the reaction was monitored by TLC. After completion of the reaction, organic solvents completely distilled off under reduced pressure to afford crude compound. Crude compound was purified through Grace reverse phase chromatography by eluting 40% acetonitrile in water to afford pure compound of N1-(6, 7-dimethoxyquinazolin-4-yl) propane-1, 3-diamine (500 mg, 1.908 mmol, 21% yield) as a light brown solid. 1H NMR (400 MHz, DMSO) 8.3 (s, 1H), 8.0 (brs, 1H), 7.57 (s, 1H), 7.05 (s, 1H), 3.86 (s, 6H), 3.55-3.46 (m, 2H), 2.64 (t, 3H), 1.75-1.68 (m, 2H).

1.98 (s, 2H), 1.15 (d, 9H).

The following compounds were synthesized by using the above general procedures.

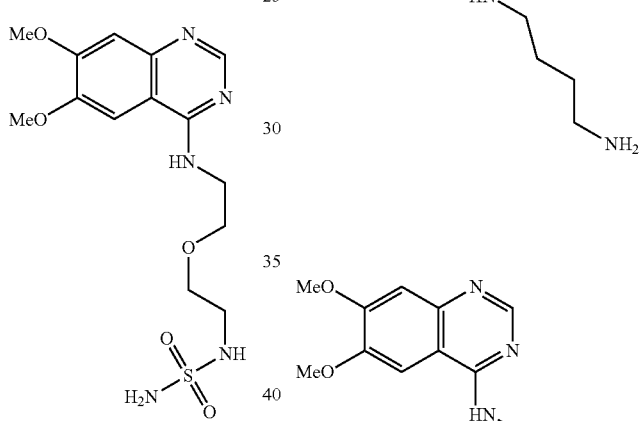

| Structure | 1HNMR |
| --- | --- |
| 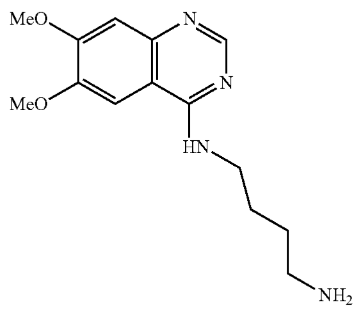 [SMILES: COc1cc2ncnc(NCCCCN)c2cc1OC] | (400 MHz, DMSO) 8.3 (s, 1H), 7.95 (s, 1H), 7.56 (s, 1H), 7.05 (s, 1H), 3.86 (s, 6H), 3.49-3.48 (m, 2H), 2.56 (t, 2H), 1.65-1.62 (m, 2H), 1.44-1.40 (m, 2H). MS 277.1 |
| 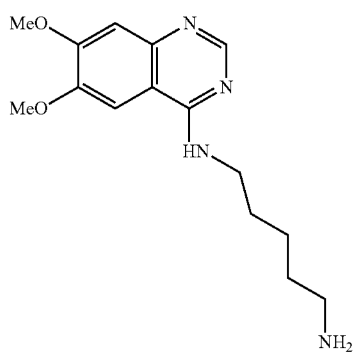 [SMILES: COc1cc2ncnc(NCCCCCN)c2cc1OC] | (400 MHz, DMSO) 8.3 (s, 1H), 7.89 (brs, 1H), 7.57 (s, 1H), 7.05 (s, 1H), 3.86 (s, 6H), 3.49-3.47 (m, 2H), 2.53 (m, 2H), 1.63-1.62 (m, 2H), 1.37-1.31 (m, 4H). |
| 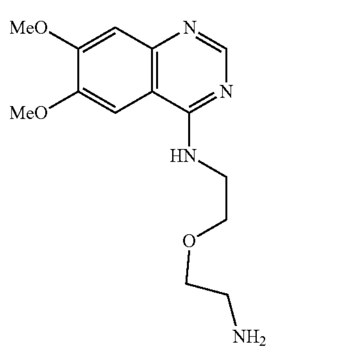 [SMILES: COc1cc2ncnc(NCCOCCN)c2cc1OC] | (400 MHz, DMSO) δ 8.31 (s, 1H), 8.00 (t, 1H), 7.59 (s, 1H), 7.06 (s, 1H), 3.87 (d, 6H), 3.70-3.66 (m, 2H), 3.60 (t, 2H), 3.38 (m, 2H), 2.64 (t, 2H). |

Example 2: N-(3-((6, 7-dimethoxyquinazolin-4-yl) amino) propyl sulfamide hydrochloride Step 1: N1-(6, 7-dimethoxyquinazolin-4-yl) propane-1, 3-diamine

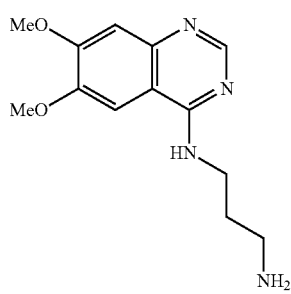

To a stirred solution of 4-chloro-6, 7-dimethoxyquinazoline (2 g, 8.9 mmol) in tetrahydrofuran (20 ml) was added propane-1, 3-diamine (3.7 mL, 44.50 mmol) at room temperature and stirred the reaction mixture at room tempera-

Step 2: Synthesis of Tert-butyl (N-(3-((6, 7-dimethoxyquinazolin-4-yl) amino) propyl) sulfamoyl) carbamate

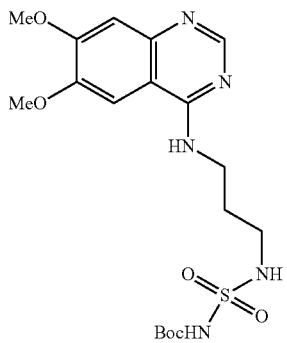 [SMILES: COc1cc2ncnc(NCCCNS(=O)(=O)NC(=O)OC(C)(C)C)c2cc1OC]

To a stirred solution of N1-(6,7-dimethoxyquinazolin-4-yl)propane-1,3-diamine (500 mg, 1.90 mmol) in dichloromethane (40 ml) were added diisopropylethylamine (1.65 mL, 9.50 mmol) and N-(1-(N-(tert-butoxycarbonyl)sulfamoyl)pyridin-4(1H)-ylidene)-N-methylmethanaminium chloride (640 mg, 1.90 mmol) at RT, then stirred at room temperature for 16 h. The progress of the reaction was monitored by TLC. After completion of the reaction, organic solvents completely distilled off under reduced pressure to afford crude compound. Crude compound was purified combi flash column chromatography by eluting 2% methanol in dichloromethane to afford tert-butyl (N-(3-((6, 7-dimethoxyquinazolin-4-yl) amino) propyl) sulfamoyl) carbamate (600 mg, 1.36 mmol, 71% yield) as a yellow solid. 1H NMR (400 MHz, DMSO) 10.83 (s, 1H), 8.31 (s, 1H), 7.89 (t, 1H), 7.60 (s, 1H), 7.54 (s, 1H), 7.06 (s, 1H) 3.87 (s, 6H), 3.55-3.50 (m, 2H), 2.98-2.93 (m, 2H), 1.82 (t, 2H), 1.36 (s, 9H). LCMS: (M+H+): m/Z: 441.9

The following compounds were synthesized by the above general procedure

| Structure | 1HNMR |
|---|---|
| MeO-quinazoline-NH-(CH2)4-NH-SO2-NHBoc | (400 MHz, DMSO) 10.79 (s, 1H), 8.3 (s, 1H), 7.88 (s, 1H), 7.57-7.56 (s, 2H), 7.05 (s, 1H), 3.87 (s, 6H), 3.49-3.48 (m, 2H), 2.92 (t, 2H), 1.64-1.62 (m, 2H), 1.54-1.50 (m, 2H), 1.38 (s, 6H). MS 455.9 |
| MeO-quinazoline-NH-(CH2)5-NH-SO2-NHBoc | (400 MHz, DMSO) 10.79 (brs, 1H), 8.3 (s, 1H), 7.88 (brs, 1H), 7.56-7.53 (m, 2H), 7.05 (s, 1H), 3.86 (s, 6H), 3.48-3.47 (m, 2H), 2.88-2.86 (m, 2H), 1.62-1.59 (m, 2H), 1.39-1.35 (m, 11H). 469.9 |
| MeO-quinazoline-NH-(CH2)2-O-(CH2)2-NH-SO2-NHBoc | (400 MHz, DMSO) δ 10.99-10.73 (m, 1H), 8.72-8.55 (m, 1H), 8.34 (s, 1H), 8.06 (s, 1H), 7.62 (s, 1H), 7.54 (t, 1H), 7.07 (s, 1H), 3.88 (s, 6H), 3.72-3.66 (m, 2H), 3.65-3.55 (m, 4H), 3.50 (t, 2H), 3.14 (m, 2H), 3.05 (m, 2H), 1.37 (s, 8H). MS 472.2 |

Step 3: Synthesis of N-(3-((6, 7-dimethoxyquinazolin-4-yl) amino) propyl) sulfamide hydrochloride To a stirred solution of tert-butyl (N-(3-((6,7-dimethoxyquinazolin-4-yl)amino)propyl)sulfamoyl)carbamate (200 mg, 0.453 mmol) in 1,4-dioxane (0.5 ml) was added 4M HCl in dioxane (2 mL) at RT, then stirred at 50° C. for 16 h. The progress of the reaction was monitored by TLC. After completion of the reaction, organic solvents completely distilled off under reduced pressure to afford crude compound. Crude compound was purified through prep HPLC to afford pure compound of (N-(3-((6,7-dimethoxyquinazolin-4-yl)amino)propyl)sulfamide hydrochloride (100 mg, 0.293 mmol, 65% yield) as an off white solid. 1H NMR (400 MHz, DMSO) 14.42 (brs, 1H), 9.99 (s, 1H), 8.79 (s, 1H), 8.02 (s, 1H), 7.23 (s, 1H), 6.61 (s, 1H), 6.53 (s, 1H), 3.94 (s, 6H), 3.73-3.71 (m, 2H), 2.97-2.96 (m, 2H), 1.90-1.86 (m, 2H). LCMS: (M+H+): m/Z: 341.9

The following compounds were synthesized by the above general procedure:

| Compound Number | Structure | 1HNMR |
|---|---|---|
| 056 | 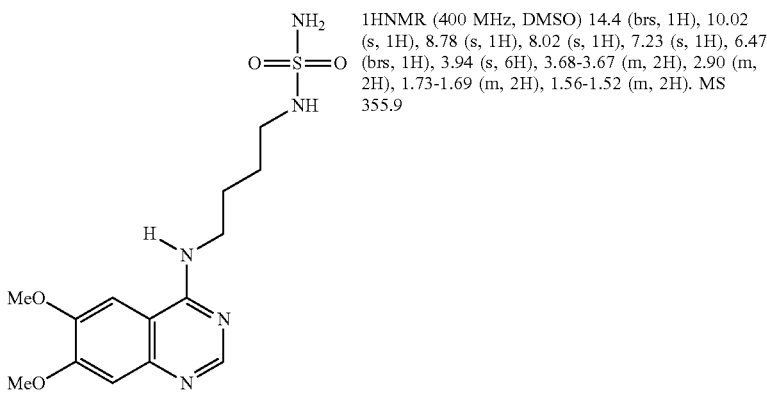 | 1HNMR (400 MHz, DMSO) 14.4 (brs, 1H), 10.02 (s, 1H), 8.78 (s, 1H), 8.02 (s, 1H), 7.23 (s, 1H), 6.47 (brs, 1H), 3.94 (s, 6H), 3.68-3.67 (m, 2H), 2.90 (m, 2H), 1.73-1.69 (m, 2H), 1.56-1.52 (m, 2H). MS 355.9 |
| 057 | 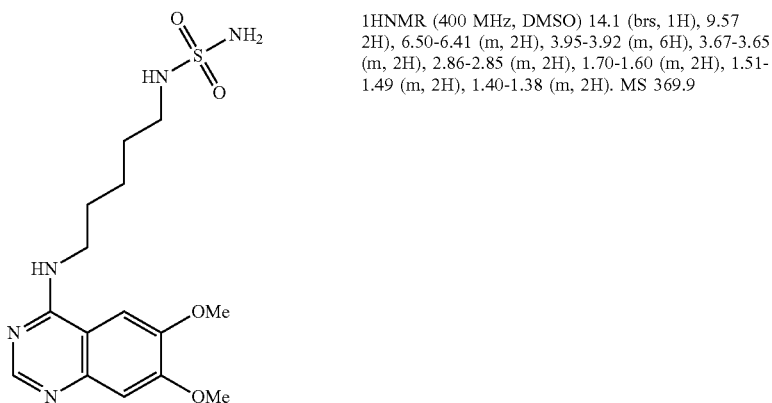 | 1HNMR (400 MHz, DMSO) 14.1 (brs, 1H), 9.57 2H), 6.50-6.41 (m, 2H), 3.95-3.92 (m, 6H), 3.67-3.65 (m, 2H), 2.86-2.85 (m, 2H), 1.70-1.60 (m, 2H), 1.51-1.49 (m, 2H), 1.40-1.38 (m, 2H). MS 369.9 |
| 005 | 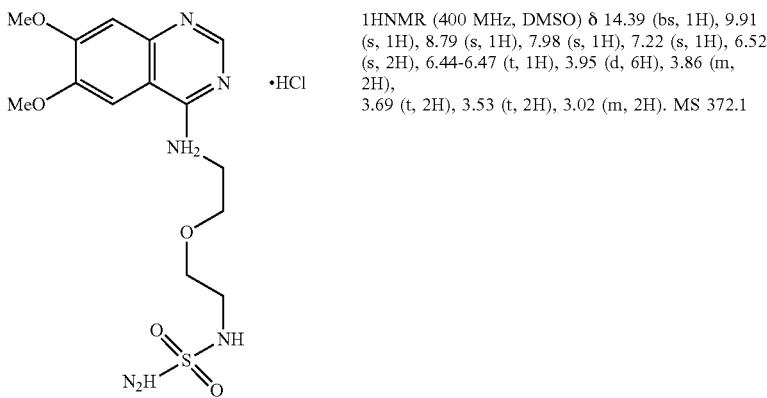 | 1HNMR (400 MHz, DMSO) δ 14.39 (bs, 1H), 9.91 (s, 1H), 8.79 (s, 1H), 7.98 (s, 1H), 7.22 (s, 1H), 6.52 (s, 2H), 6.44-6.47 (t, 1H), 3.95 (d, 6H), 3.86 (m, 2H), 3.69 (t, 2H), 3.53 (t, 2H), 3.02 (m, 2H). MS 372.1 |

Compound 055 was also synthesized by the above general procedure:

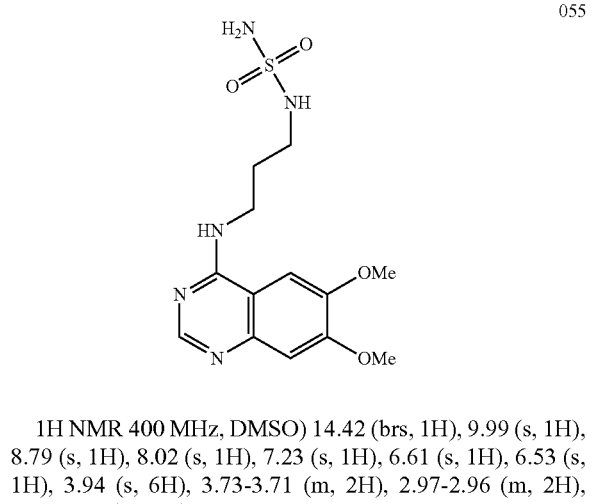

055

1H NMR 400 MHz, DMSO) 14.42 (brs, 1H), 9.99 (s, 1H), 8.79 (s, 1H), 8.02 (s, 1H), 7.23 (s, 1H), 6.61 (s, 1H), 6.53 (s, 1H), 3.94 (s, 6H), 3.73-3.71 (m, 2H), 2.97-2.96 (m, 2H), 1.90-1.86 (m, 2H). LCMS 341.9. MW. 377.84

Synthesis of Compound 006

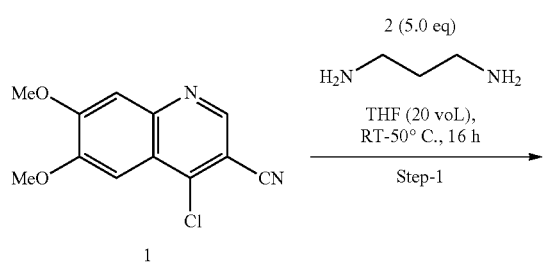

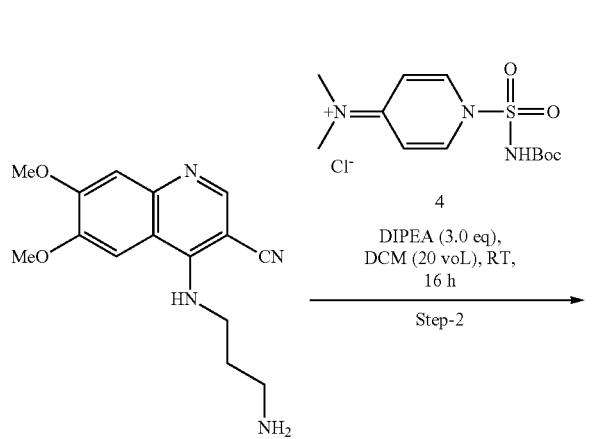

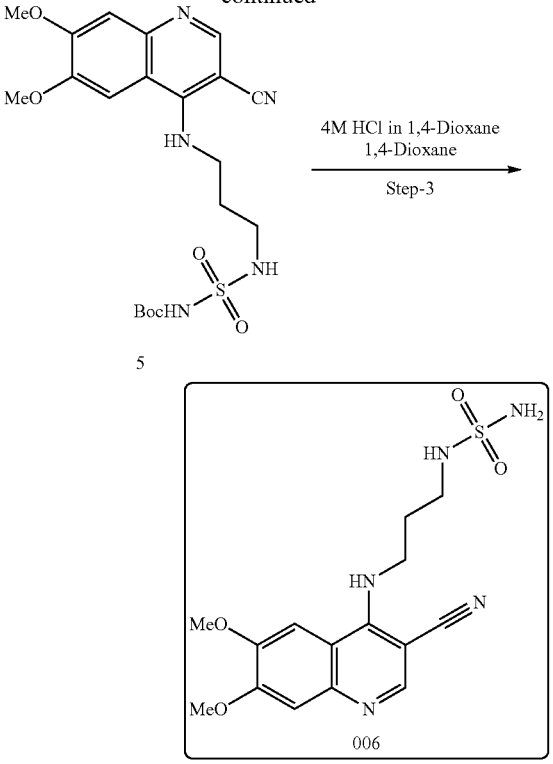

Step-1: Synthesis of 4-((3-aminopropyl) amino)-6, 7-dimethoxyquinoline-3-carbonitrile (3)

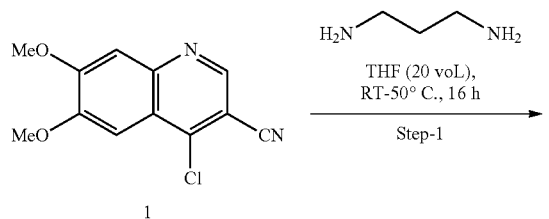

To a stirred solution of 4-chloro-6,7-dimethoxyquinoline-3-carbonitrile 1 (150 mg, 0.60 mmol) in THF (15 mL) was added propane-1,3-diamine 2 (223 mg, 3.02 mmol) then stirred the reaction mixture at 50° C. for 20 h. The progress of the reaction was monitored by TLC. After completion of the reaction, reaction mixture completely distilled off and absorbed onto celite and reverse phase grace performed using ACN/Water system to afford 4-((3-aminopropyl)amino)-6,7-dimethoxyquinoline-3-carbonitrile (250 mg) as a white solid.

Analytical Data: ¹H NMR (400 MHz, DMSO): δ 8.37 (s, 1H), 8.19 (brs, 1H), 7.9 (brs, 1H), 7.78 (s, 1H), 7.22 (s, 1H), 3.99-3.89 (m, 7H), 3.83 (q, 2H), 2.87 (t, 2H), 1.99 (t, 2H).

Step-2: Synthesis of tert-butyl (N-(3-((3-cyano-6,7-dimethoxyquinolin-4-yl)amino)propyl)sulfamoyl)carbamate (5)

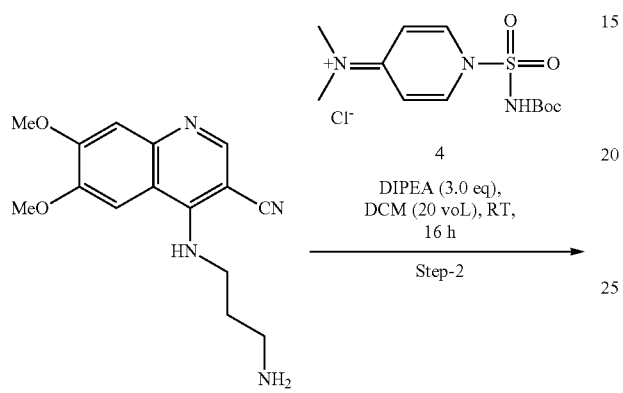

To a stirred solution of 4-((3-aminopropyl)amino)-6,7-dimethoxyquinoline-3-carbonitrile 3 (150 mg, 0.52 mmol) in DCM (10 mL) was added N-(1-(N-(tert-butoxycarbonyl)sulfamoyl)pyridin-4(1H)-ylidene)-N-methylmethanaminium chloride 4 (193 mg, 0.57 mmol) slowly and then added DIPEA (0.3 ml, 0.78 mmol) at same temperature. Then stirred the reaction mixture at room temperature for 16 h. The progress of the reaction was monitored by TLC. Reaction mixture was directly absorbed on to silica and converted into slurry. Crude was purified through combi-flash chromatography by eluting 2-3% MeOH in DCM to afford tert-butyl (N-(3-((3-cyano-6,7-dimethoxyquinolin-4-yl)amino)propyl)sulfamoyl)carbamate 5 (100 mg) as a white solid.

Analytical Data: LCMS: (M+H)⁺: m/Z: 466.2

Step-3: Synthesis of Compound 006

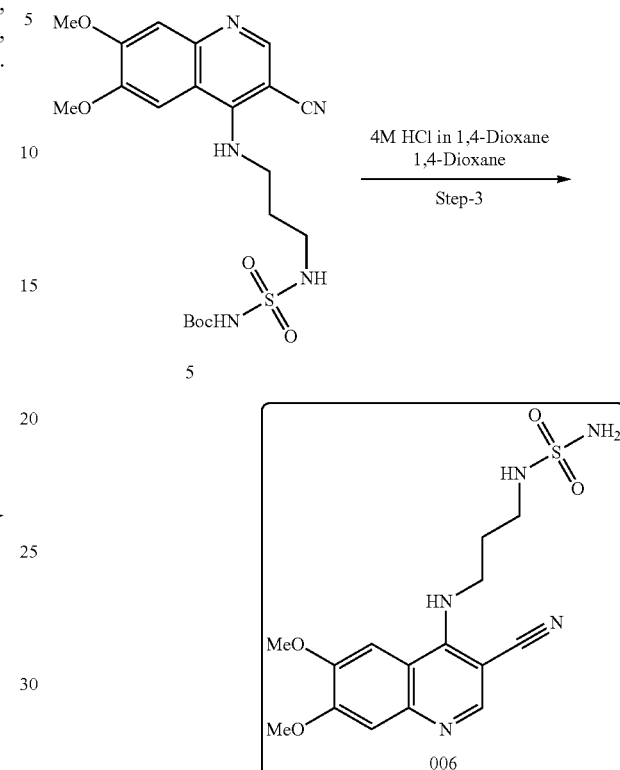

To a stirred solution of tert-butyl (N-(3-((3-cyano-6,7-dimethoxyquinolin-4-yl)amino)propyl)sulfamoyl)carbamate 5 (95 mg, 0.40 mmol) in dichloromethane (3 ml) was added 4M HCl in dioxane (2 mL) at 0° C. then stirred at room temperature for 16 h. The progress of the reaction was monitored by TLC. After completion of reaction, organic solvents completely distilled off under reduced pressure. Crude compound was purified by prep-HPLC to give Compound 006 (10 mg) as white solid.

Analytical Data: ¹H NMR (400 MHz, DMSO) δ: 8.33 (s, 1H), 7.79 (t, 1H), 7.59 (s, 1H), 7.21 (s, 1H), 6.60 (brs, 2H), 6.53 (brs, 2H), 3.90-3.89 (m, 6H), 3.78 (q, 2H), 2.99 (q, 2H), 1.92 (p, 2H).

LCMS: (M+H)⁺: m/Z: 366.2.

Synthesis of Compound 007

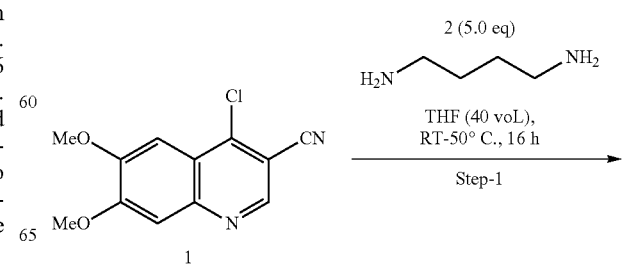

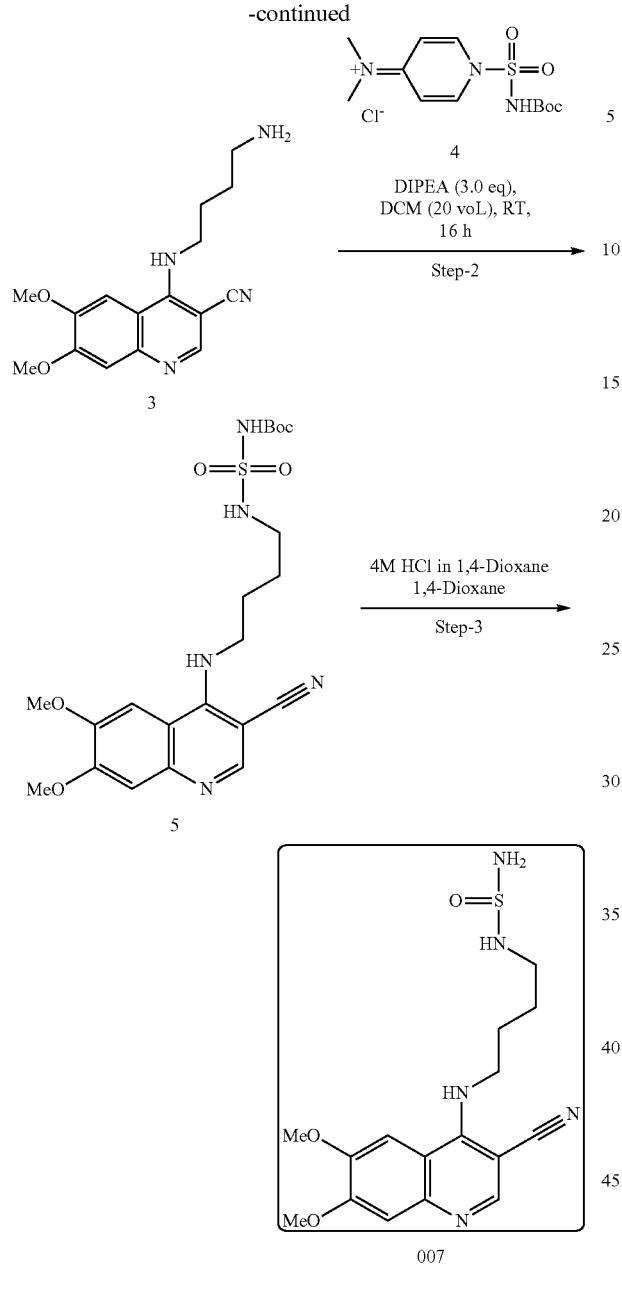

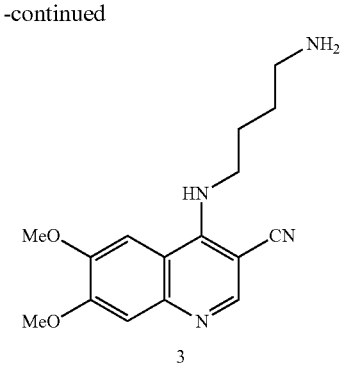

To a stirred solution of 4-chloro-6,7-dimethoxyquinoline-3-carbonitrile 1 (200 mg, 0.80 mmol) in THF (8 mL) was added butane-1,4-diamine 2 (411 mg, 4.03 mmol) then stirred the reaction mixture at 50° C. for 20 h. The progress of the reaction was monitored by TLC. After completion of the reaction, reaction mixture completely distilled off and absorbed onto celite and reverse phase grace performed using ACN/Water system to afford 4-((4-aminobutyl)amino)-6,7-dimethoxyquinoline-3-carbonitrile 3 (220 mg) as a white solid.

Analytical Data: $^1$H NMR (400 MHz, DMSO): δ 8.37 (s, 2H), 8.32 (s, 1H), 7.67 (s, 1H), 7.21 (s, 1H), 3.90-3.89 (m, 7H), 3.76 (t, 2H), 2.79 (t, 2H), 1.78-1.73 (m, 2H), 1.67-1.64 (m, 2H).

Step-2: Synthesis of tert-butyl (N-(4-((3-cyano-6,7-dimethoxyquinolin-4-yl)amino)butyl)sulfamoyl) carbamate 5

Step-1: Synthesis of 4-((4-aminobutyl)amino)-6,7-dimethoxyquinoline-3-carbonitrile 3

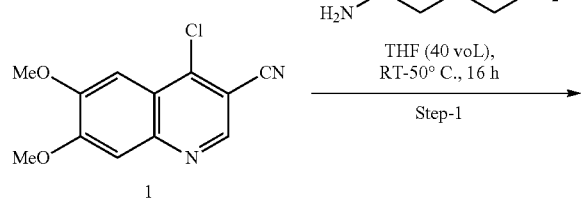

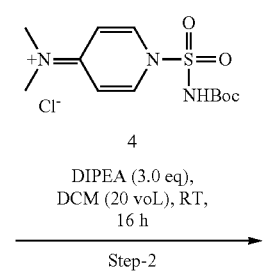

81

-continued

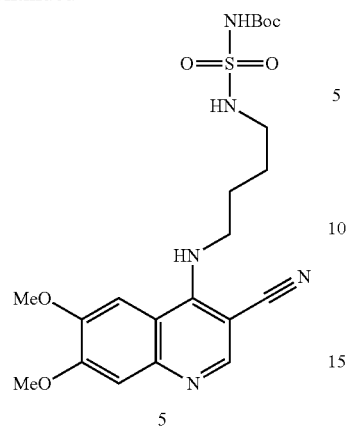

5

To a stirred solution of 4-((4-aminobutyl)amino)-6,7-dimethoxyquinoline-3-carbonitrile 3 (220 mg, 0.73 mmol) in DCM (10 mL) was added N-(1-(N-(tert-butoxycarbonyl)sulfamoyl)pyridin-4(1H)-ylidene)-N-methylmethanaminium chloride 4 (296 mg, 0.88 mmol) slowly and then added DIPEA (0.4 ml, 2.19 mmol) at same temperature. Then stirred the reaction mixture at room temperature for 16 h. The progress of the reaction was monitored by TLC. Reaction mixture was directly absorbed on to silica and converted into slurry. Crude was purified through combiflash chromatography by eluting 2-3% MeOH in DCM to afford tert-butyl (N-(4-((3-cyano-6,7-dimethoxyquinolin-4-yl)amino)butyl)sulfamoyl)carbamate 5 (100 mg) as a white solid.

Analytical Data: $^1$H NMR (400 MHz, DMSO): δ 8.46-8.44 (m, 1H), 8.31 (s, 1H), 7.82 (t, 1H), 7.60-7.57 (m, 2H), 7.20 (s, 1H), 3.90-3.89 (m, 6H), 3.72 (q, 2H), 2.92-2.91 (m, 2H), 1.73-1.70 (m, 2H), 1.58-1.54 (m, 2H).

LCMS: (M+H)$^+$: m/Z: 480

Step-3: Synthesis of Compound 007

82

-continued

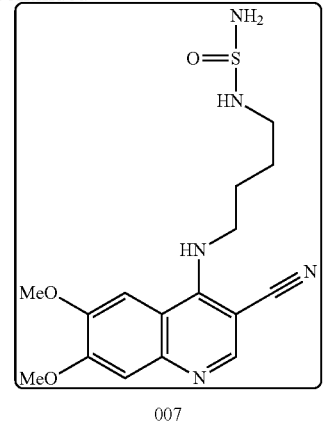

007

To a stirred solution of tert-butyl (N-(4-((3-cyano-6,7-dimethoxyquinolin-4-yl)amino)butyl)sulfamoyl)carbamate 5 (100 mg, 0.20 mmol) in dichloromethane (3 ml) was added 4M HCl in dioxane (1 mL) at 0° C. then stirred at room temperature for 16 h. The progress of the reaction was monitored by TLC. After completion of reaction, organic solvents completely distilled off under reduced pressure. Crude compound was purified by prep-HPLC to give Compound 007 (10 mg) as white solid.

Analytical Data: $^1$H NMR (400 MHz, DMSO) δ: 8.35-8.31 (m, 2H), 7.86 (t, 1H), 7.60 (s, 1H), 7.20 (s, 1H), 6.50 (t, 2H), 6.46 (s, 1H), 3.90-3.89 (m, 6H), 3.73 (q, 2H), 2.90 (q, 2H), 1.75-1.71 (m, 2H), 1.61-1.53 (m, 2H).

LCMS: (M+H)$^+$: m/Z: 380.24.

Synthetic Scheme of Compound 008

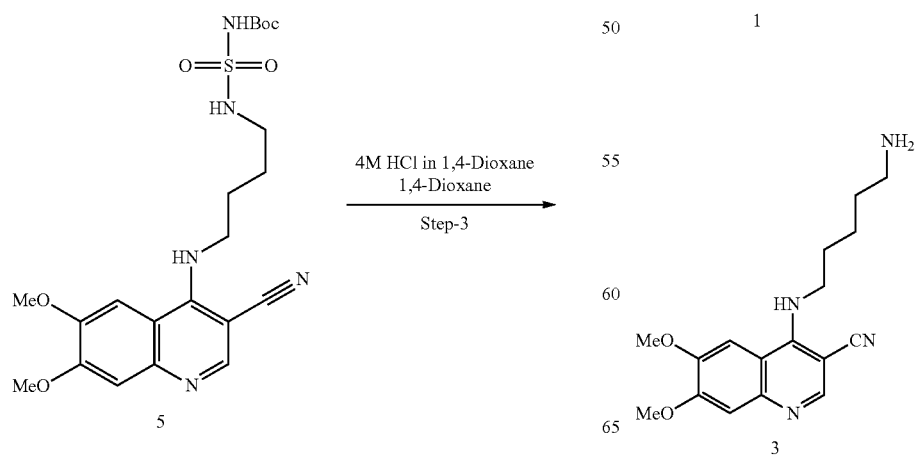

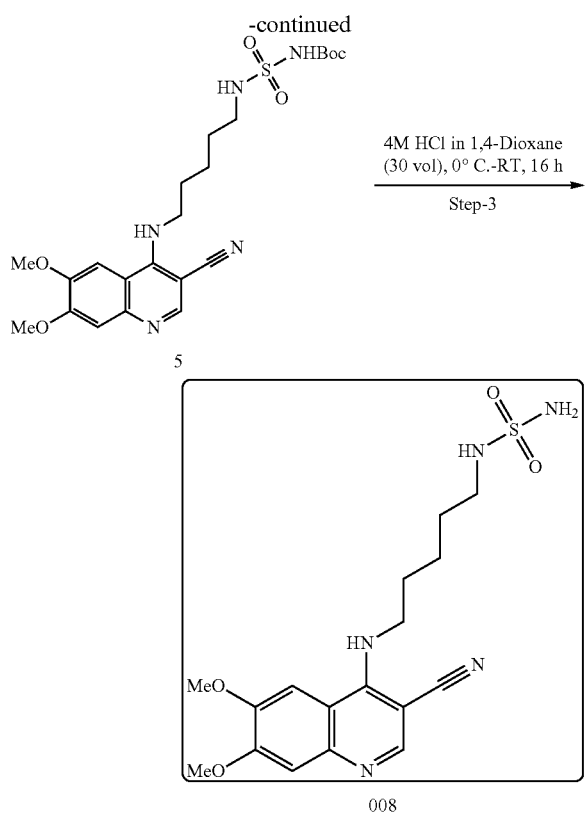

Step-1: Synthesis of 4-((5-aminopentyl)amino)-6,7-dimethoxyquinoline-3-carbonitrile 3

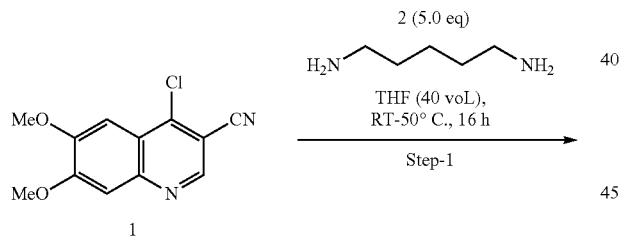

To a stirred solution of 4-chloro-6,7-dimethoxyquinoline-3-carbonitrile 1 (200 mg, 0.80 mmol) in THF (8 mL) was added butane-1,4-diamine 2 (411.2 mg, 4.03 mmol) then stirred the reaction mixture at 50° C. for 20 h. The progress of the reaction was monitored by TLC. After completion of the reaction, reaction mixture completely distilled off and absorbed onto celite and reverse phase grace performed using ACN/Water system to afford 4-((5-aminopentyl)amino)-6,7-dimethoxyquinoline-3-carbonitrile 3 (200 mg) as a white solid.

Analytical Data: $^1$H NMR (400 MHz, DMSO): δ 8.48 (s, 1H), 8.30 (s, 1H), 7.98 (brs, 1H), 7.66 (s, 1H), 7.19 (s, 1H), 3.90-3.89 (m, 6H), 3.72-3.71 (m, 2H), 2.60-2.56 (m, 2H), 1.73-1.66 (m, 2H), 1.48-1.21 (m, 4H).

LCMS: (M+H)$^+$: m/Z: 315.23

Step-2: Synthesis of tert-butyl (N-(5-((3-cyano-6,7-dimethoxyquinolin-4-yl)amino)pentyl)sulfamoyl) carbamate 5

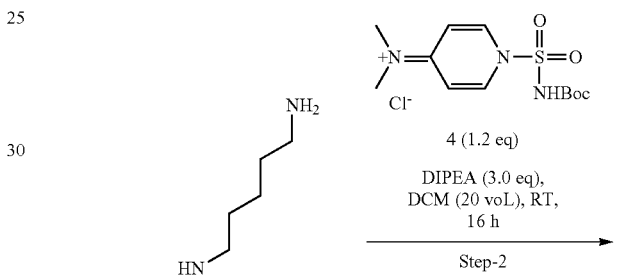

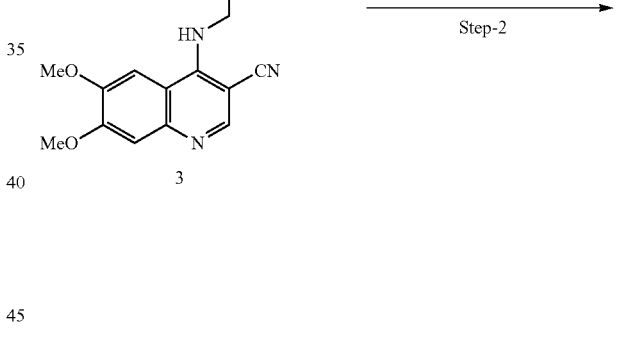

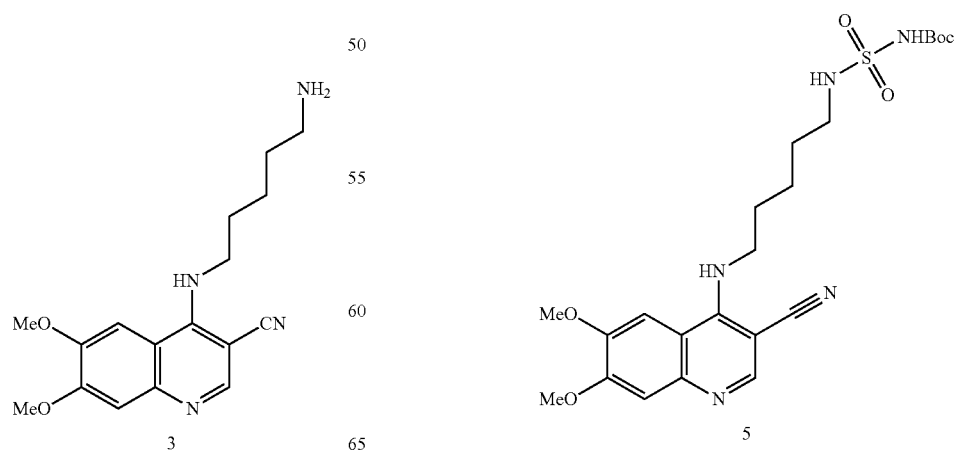

To a stirred solution of 4-((5-aminopentyl)amino)-6,7-dimethoxyquinoline-3-carbonitrile 3 (220 mg, 0.63 mmol) in DCM (10 mL) was added N-(1-(N-(tert-butoxycarbonyl)sulfamoyl)pyridin-4(1H)-ylidene)-N-methylmethanaminium chloride 4 (266 mg, 0.76 mmol) slowly and then added DIPEA (0.17 ml, 0.95 mmol) at same temperature. Then stirred the reaction mixture at room temperature for 16 h. The progress of the reaction was monitored by TLC. Reaction mixture was directly absorbed on to silica and converted into slurry. Crude was purified through combi-flash chromatography by eluting 2-3% MeOH in DCM to afford tert-butyl (N-(5-((3-cyano-6,7-dimethoxyquinolin-4-yl)amino)pentyl)sulfamoyl)carbamate 5 (130 mg) as a white solid.

Analytical Data: $^1$H NMR (400 MHz, DMSO): δ 10.75 (s, 1 h), 8.31 (s, 1H), 7.82 (t, 1H), 7.60 (s, 1H), 7.51 (brs, 1H), 7.20 (s, 1H), 3.90-3.89 (m, 6H), 3.71 (q, 2H), 2.87 (q, 2H), 1.72-1.64 (m, 2H), 1.58-1.47 (m, 2H), 1.22 (m, 2H).

LCMS: (M+H)$^+$: m/Z: 494.2

Step-3: Synthesis of Compound 008

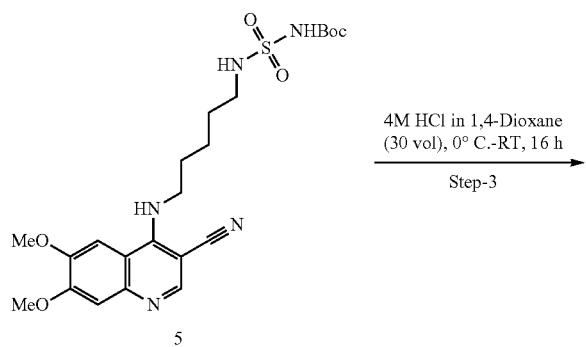

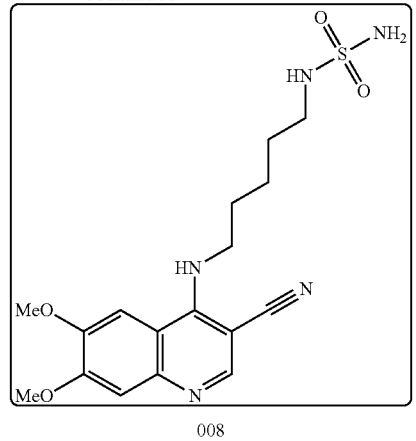

008

To a stirred solution of tert-butyl (N-(5-((3-cyano-6,7-dimethoxyquinolin-4-yl)amino)pentyl)sulfamoyl)carbamate 5 (130 mg, 0.20 mmol) in dichloromethane (4 ml) was added 4M HCl in dioxane (1.5 mL) at 0° C. then stirred at room temperature for 16 h. The progress of the reaction was monitored by TLC. After completion of reaction, organic solvents completely distilled off under reduced pressure. Crude compound was purified by prep-HPLC to give Compound 008 (10 mg) as white solid.

Analytical Data: $^1$H NMR (400 MHz, DMSO) δ: 8.31 (s, 1H), 8.12 (s, 1H), 7.84 (t, 1H), 7.60 (s, 1H), 7.20 (s, 1H), 6.45-6.44 (m, 3H), 3.90-3.89 (m, 6H), 3.72 (q, 2H), 2.86 (q, 2H), 3.01 (t, 2H), 1.73-1.65 (m, 2H), 1.55-1.48 (m, 2H), 1.43-1.40 (m, 2H).

LCMS: (M+H)$^+$: m/Z: 394.2.

Synthetic Scheme for Compounds 009 and 010

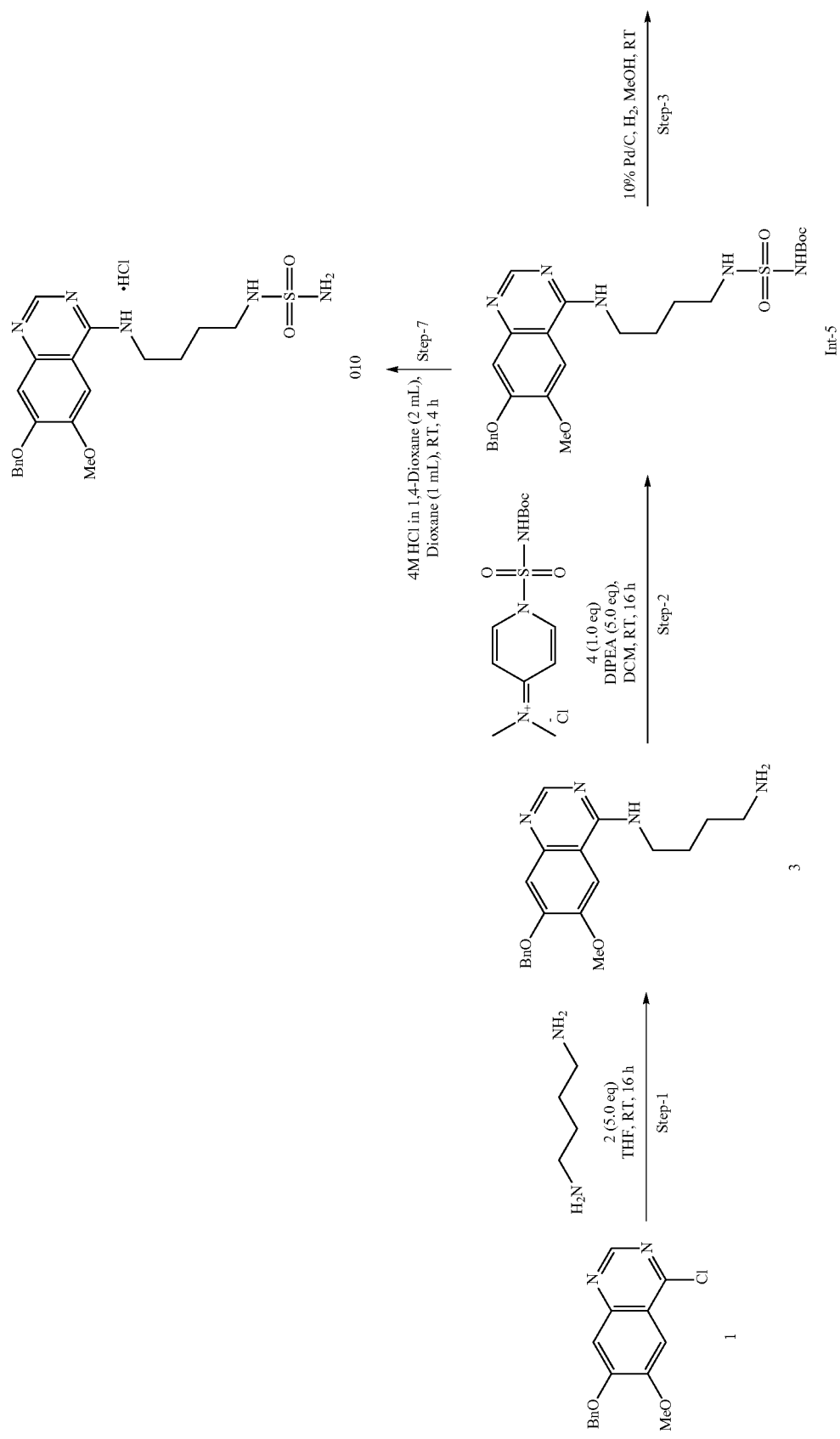

-continued
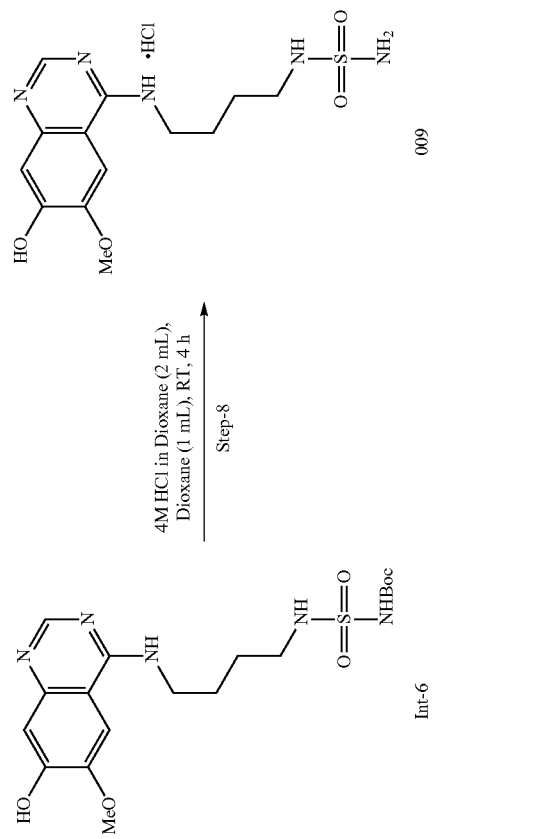

Synthesis of N1-(7-(benzyloxy)-6-methoxyquinazo-lin-4-yl)butane-1,4-diamine (3)

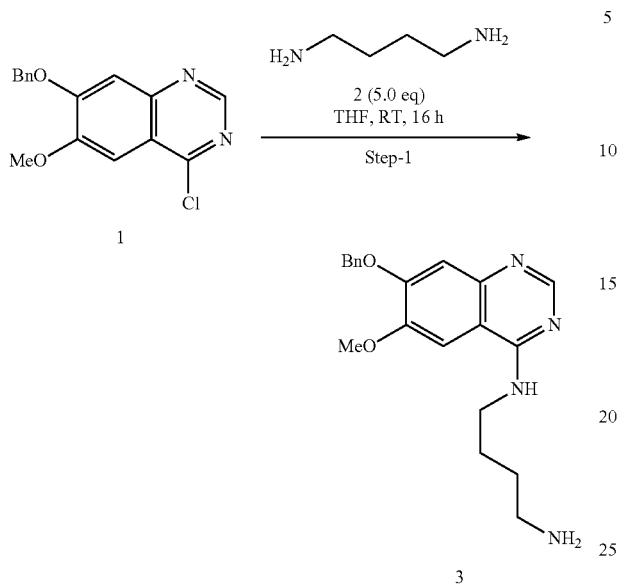

To a stirred solution of 7-(benzyloxy)-4-chloro-6-methoxyquinazoline (1) (1 g, 3.33 mmol) in tetrahydrofuran (20 mL) was added butane-1,4-diamine 2 (1.5 g, 16.66 mmol) at RT and stirred the reaction mixture at room temperature for 16 h. The progress of the reaction was monitored by TLC. After completion of the reaction, organic solvents completely distilled off under reduced pressure to afford crude compound. Crude compound was purified through Grace reverse phase chromatography by eluting 40% acetonitrile in water to afford pure compound of N1-(7-(benzyloxy)-6-methoxyquinazolin-4-yl) butane-1,4-diamine (3) (1 g, 0.284 mmol, 85% yield) as a light brown thick liquid.

Analytical Data: $^1$H NMR (400 MHz, DMSO) δ 8.29 (s, 1H), 7.95-7.98 (m, 1H), 7.59 (s, 1H), 7.32-7.48 (m, 5H), 7.15 (s, 1H), 5.22 (s, 2H), 3.87 (s, 3H), 3.47-3.51 (m, 2H), 2.56-2.59 (m, 2H), 1.62-1.66 (m, 2H), 1.41-1.44 (m, 2H).

LCMS: (M+H$^+$): m/z: 353.2

Synthesis of tert-butyl (N-(4-((7-(benzyloxy)-6-methoxyquinazolin-4-yl)amino)butyl)sulfamoyl)carbamate (Int-5)

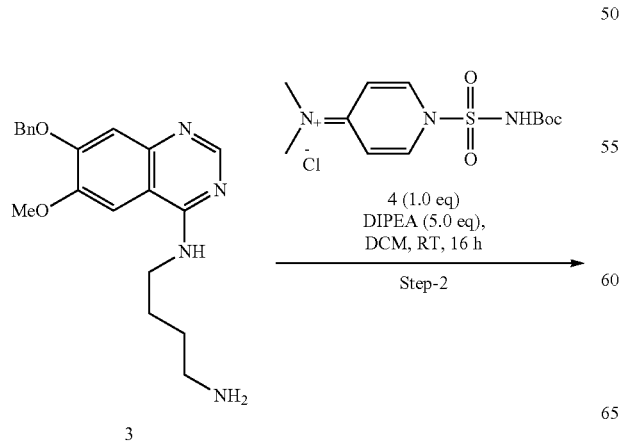

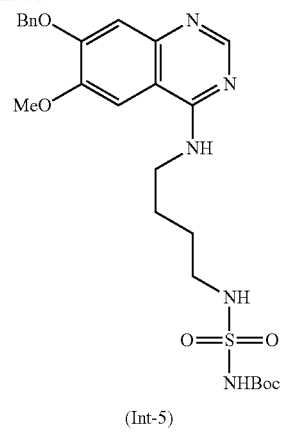

To a stirred solution of N1-(7-(benzyloxy)-6-methoxyqui-nazolin-4-yl)butane-1,4-diamine (3) (1.0 g, 2.84 mmol) in dichloromethane (20 mL) was added diisopropylethylamine (1.5 mL, 8.52 mmol) and N-(1-(N-(tert-butoxycarbonyl)sulfamoyl)pyridin-4(1H)-ylidene)-N-methylmeth-anaminium 4 (957 mg, 2.84 mmol) at RT, then stirred at room temperature for 16 h. The progress of the reaction was monitored by TLC. After completion of the reaction, organic solvents completely distilled off under reduced pressure to afford crude compound. Crude compound was purified combi flash column chromatography by eluting 10% MeOH in DCM to afford (Int-5) (1.1 g, 2.07 mmol, 73% yield) as a pale yellow solid.

Analytical Data: $^1$H NMR (400 MHz, DMSO) δ 10.83 (br s, 1H), 8.3 (s, 1H), 7.93 (brs, 1H), 7.59-7.561 (m, 2H), 7.46-7.61 (d, 2H), 7.32-7.42 (m, 3H), 7.16 (s, 1H), 5.226 (s, 2H), 4.03 (s, 1H), 3.88 (s, 3H), 3.46-3.50 (m, 2H), 2.89-2.93 (m, 2H), 1.62-1.66 (m, 2H), 1.52-1.54 (m, 2H), 1.38 (s, 9H).

LCMS: (M+H)$^+$: m/z: 532.2

Synthesis of tert-butyl (N-(4-((7-hydroxy-6-methoxyquinazolin-4-yl)amino)butyl)sulfamoyl)carbamate (Int-6)

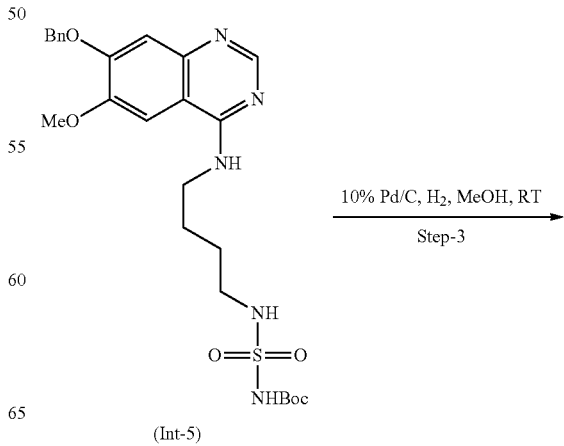

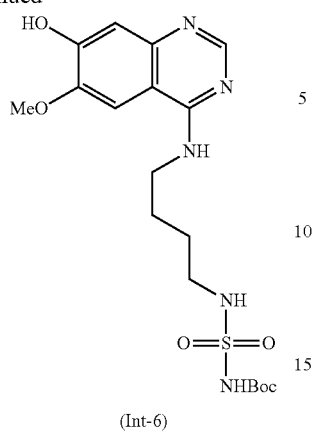

(Int-6)

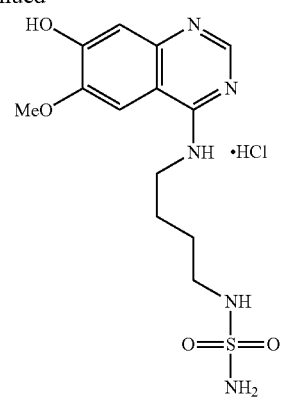

009

To a stirred solution of tert-butyl (N-(4-((7-(benzyloxy)-6-methoxyquinazolin-4-yl)amino)butyl)sulfamoyl)carbamate (5) (1 g, 1.88 mmol) in methanol (15 mL) and EtOAc (2.5 mL) was added 10% Pd/C (100 mg) and stirred the reaction mixture under balloon hydrogen atmosphere at room temperature for 6 h. The progress of the reaction was monitored by TLC. After completion of the reaction, reaction mixture filtered through celite and washed the celite bed with 5% methanol in dichloromethane (100 mL). Filtrate was concentrated under reduced pressure to afford tert-butyl (N-(4-((7-hydroxy-6-methoxyquinazolin-4-yl)amino)butyl) sulfamoyl)carbamate (6) (800 mg, 1.81 mmol, 96% yield) as a pale yellow solid.

Analytical Data: $^1$H NMR (400 MHz, DMSO) δ 10.13 (br s, 1H), 8.24 (s, 1H), 7.83 (brs, 1H), 7.54-7.57 (m, 2H), 6.92 (s, 1H), 3.87 (s, 3H), 3.45-3.50 (m, 2H), 2.88-2.93 (m, 2H), 1.59-1.65 (m, 2H), 1.50-1.53 (m, 2H), 1.38 (s, 9H).

LCMS: (M+H$^+$): m/Z: 442.2

Preparation of Compound 009

To a stirred solution of Int-6 (100 mg, 0.226 mmol) in 1,4-dioxane (1.0 mL) was added 4M HCl in dioxane (2.0 mL) at RT. Reaction mixture was stirred at RT for 6 h. The progress of the reaction was monitored by TLC. After completion of the reaction, organic solvents completely distilled off under reduced pressure to afford crude compound. Crude compound was purified through prep HPLC method to afford pure compound of Compound 009 (50 mg, 0.146 mmol, 64% yield) as an Off-white solid.

Analytical Data: $^1$H NMR (400 MHz, DMSO-d$_6$) δ 14.27 (brs, 1H), 11.41 (s, 1H), 9.80 (s, 1H), 8.70 (s, 1H), 7.94 (s, 1H), 7.19 (s, 1H), 6.47-6.51 (m, 3H), 3.93 (s, 3H), 3.61-3.68 (m, 2H), 2.87-2.92 (m, 2H), 1.66-1.71 (m, 2H), 1.49-1.57 (m, 2H), 1.23-1.28 (m, 2H).

LCMS: (M+H)$^+$: m/Z: 342.1

Preparation of Compound 010

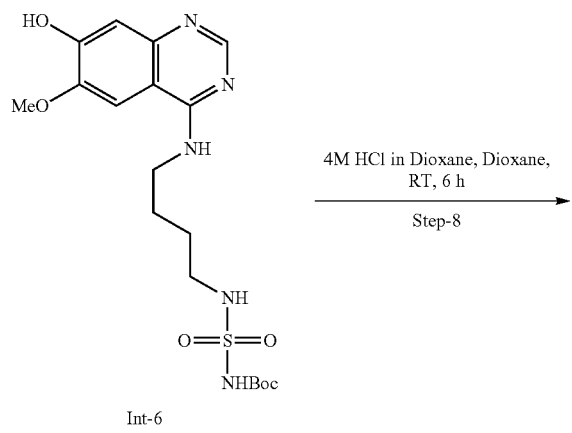

Int-6

4M HCl in Dioxane, Dioxane, RT, 6 h

Step-8

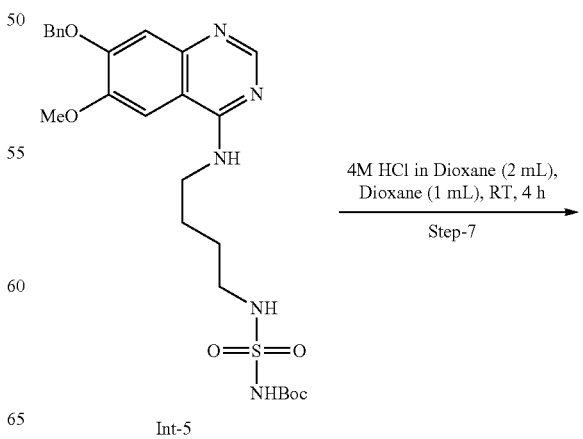

Int-5

4M HCl in Dioxane (2 mL), Dioxane (1 mL), RT, 4 h

Step-7

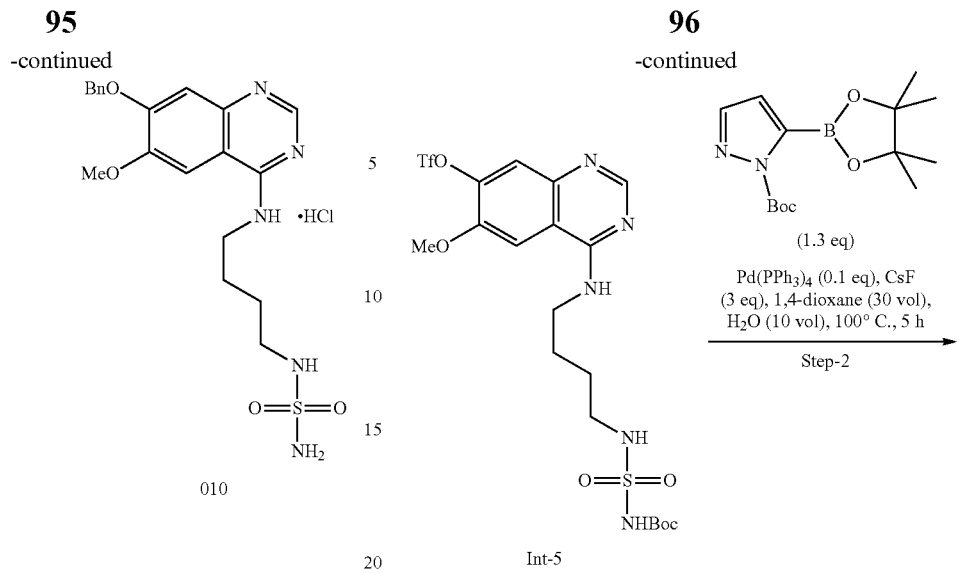

To a stirred solution of Int-5 (100 mg, 0.188 mmol) in 1,4-dioxane (1.0 mL) was added 4M HCl in dioxane (2.0 mL) at RT. Reaction mixture was stirred at RT for 6 h. The progress of the reaction was monitored by TLC. After completion of the reaction, organic solvents completely distilled off under reduced pressure to afford crude compound. Crude compound was purified through prep HPLC method to afford pure compound of Int-5 (50 mg, 1.16 mmol, 61% yield) as an Off-white solid.

Analytical Data: $^1$H NMR (400 MHz, DMSO) δ 8.3 (s, 1H), 8.14 (s, 2H), 7.92 (m, 1H), 7.6 (s, 1H), 7.47-7.49 (d, 2H), 7.39-7.41 (t, 2H), 7.35-7.37 (m, 1H), 7.17 (s, 1H), 6.45 (s, 1H), 5.23 (s, 2H), 3.89 (s, 3H), 3.50-3.51 (m, 2H), 2.89-2.94 (m, 2H), 1.66-1.70 (m, 2H), 1.54-1.56 (m, 2H).

LCMS: (M+H)$^+$: m/Z: 432.2

Synthetic Scheme for Compound 011

4-((4-((N-(tert-butoxycarbonyl)sulfamoyl)amino)butyl)amino)-6-methoxyquinazolin-7-yl trifluoromethanesulfonate (Int-5)

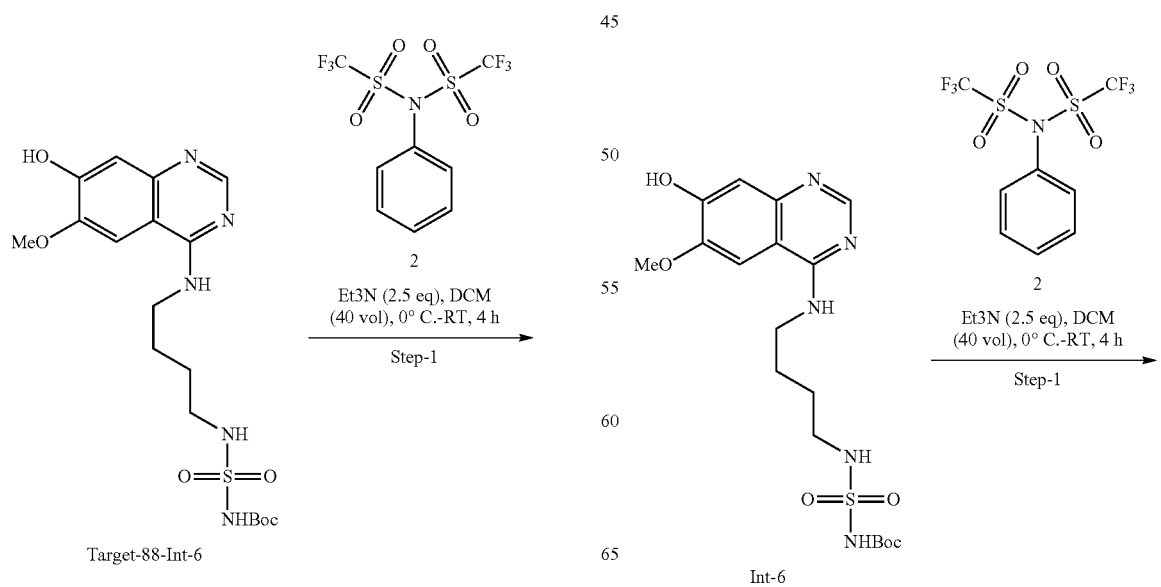

-continued

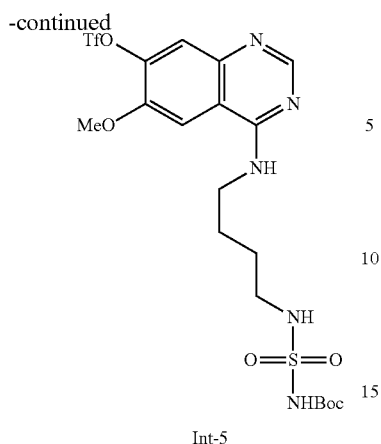

Int-5

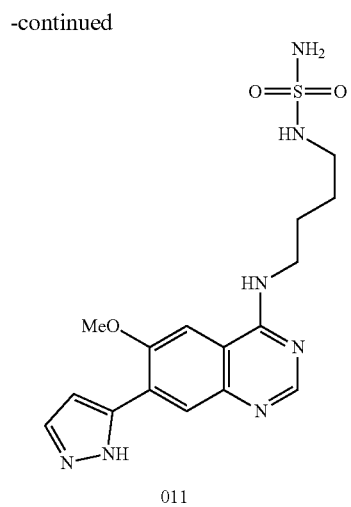

011

To a stirred solution of Int-6 (500 mg, 1.13 mmol) in dichloromethane (20 mL) were added triethylamine (0.475 mL, 3.39 mmol) and 1,1,1-trifluoro-N-phenyl-N-((trifluoromethyl)sulfonyl)methanesulfonamide 2 (445 mg, 1.24 mmol) at 0° C. then stirred at room temperature 4 h. The progress of the reaction was monitored by TLC. After completion of the reaction, organic solvents completely distilled off under reduced pressure and water (200 mL) was added to the crude and partitioned with dichloromethane (2×200 mL). Combined organic layers were washed with brine solution (200 mL), dried over sodium sulfate and concentrated under reduced pressure. Crude was purified by combi-flash chromatography by eluting 70% ethyl acetate in pet ether to afford 4-((4-((N-(tert-butoxycarbonyl)sulfamoyl)amino)butyl)amino)-6-methoxyquinazolin-7-yl trifluoromethanesulfonate Int-5 (450 mg, 0.785 mmol, 69% yield over two steps) as a pale yellow solid.

LCMS: (M+H⁺): m/Z: 574.1

Preparation of Compound 011

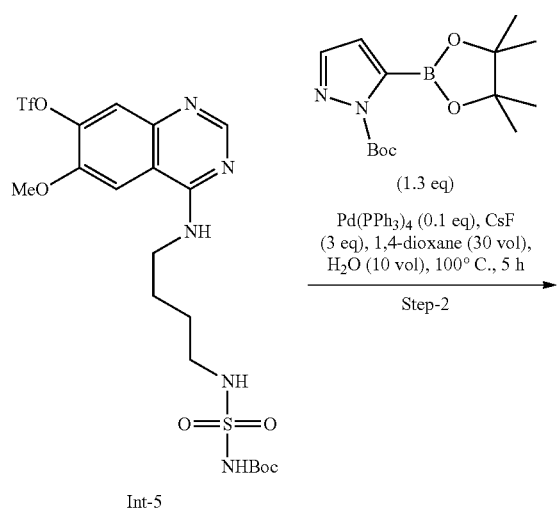

Int-5

In a sealed tube, to the stirred solution of 4-((4-((N-(tert-butoxycarbonyl)sulfamoyl)amino)butyl)amino)-6-methoxyquinazolin-7-yl trifluoromethanesulfonate Int-5 (50 mg, 0.349 mmol) in dioxane (2 mL) and water (05 mL) were added tert-butyl 5-(4,4,5,5-tetramethyl-1,3,2-dioxaborolan-2-yl)-1H-pyrazole-1-carboxylate (33 mg, 0.113 mmol) and cesium fluoride (40 mg, 0.26 mmol) was then degassed the reaction mixture for 30 minutes. Then tetrakis(triphenylphosphine)palladium(0) (100 mg, 0.0087 mmol) was added again degassed for 5 minutes and stirred the reaction mixture at 100° C. for 5 h. The progress of the reaction was monitored by TLC. After completion of the reaction, reaction mixture was poured into water (100 mL) and filtered through celite. Washed the celite bed with 10% methanol in dichloromethane (100 mL) and separated the two layers. Organic layer washed with brine solution (200 mL), dried over sodium sulfate and concentrated under reduced pressure. Crude was purified prep HPLC method to afford (Compound 011) (10 mg, 0.127 mmol, 29%) as a Off-white solid.

Analytical Data: ¹H NMR (400 MHz, DMSO) δ 12.96 (brs, 1H), 8.39 (s, 1H), 8.23 (brs, 1H), 8.13 (s, 2H), 7.74 (s, 2H), 6.88 (d, 1H), 6.495 (t, 1H), 6.46 (s, 2H), 4.0 (s, 3H), 3.53-3.58 (q, 2H), 2.90-2.95 (q, 2H), 1.66-1.72 (m, 2H), 1.55-1.59 (m, 2H).

LCMS: (M+H⁺): m/Z: 392.1

General scheme 3

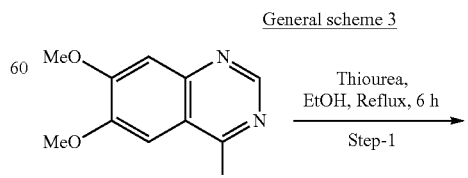

-continued

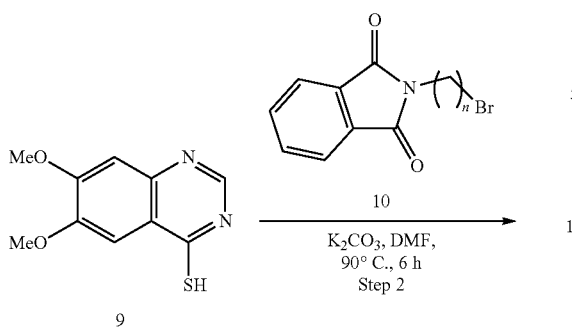

9

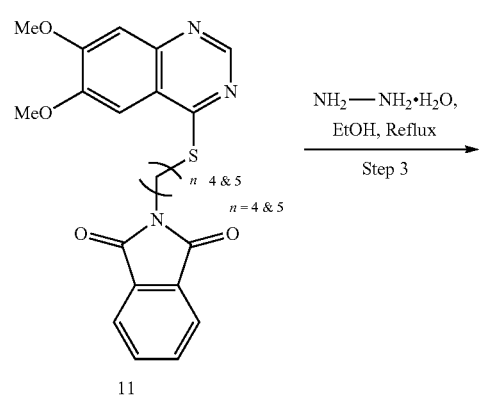

11

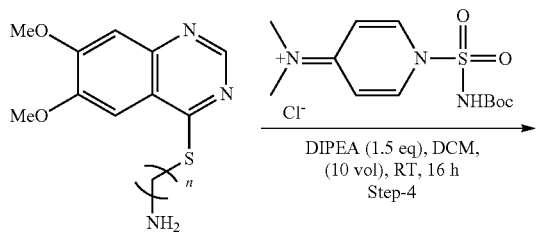

12

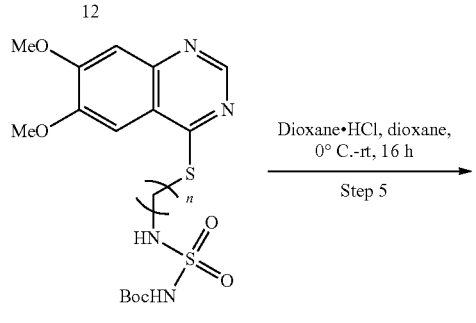

13

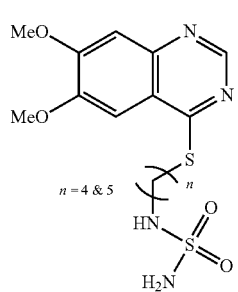

Example 3: N-(4-((6, 7-dimethoxyquinazolin-4-yl) thio) butyl) sulfamide hydrochloride

Step 1: Synthesis of 6, 7-dimethoxyquinazoline-4-thiol

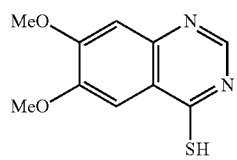 [SMILES: COc1cc2ncnc(S)c2cc1OC]

To a stirred solution of 4-chloro-6, 7-dimethoxyquinazoline (500 mg, 2.2 mmol) in ethanol (5 ml) was added thio urea (338 mg, 4.44 mmol) at RT and stirred the reaction mixture at reflux for 4 h. The progress of the reaction was monitored by TLC. After completion of the reaction, reaction mixture was allowed to settle at RT. Solid formed was collected by filtration which is the desired compound 6, 7-dimethoxyquinazoline-4-thiol (400 mg, 1.801 mmol, 80% yield) as a light brown solid. 1H NMR (400 MHz, DMSO) δ 13.67 (s, 1H), 8.09-8.10 (s, 1H), 7.90 (s, 1H), 7.16 (s, 1H), 3.93 (s, 3H), 3.89 (s, 3H). LCMS: (M+H)+: m/Z: 222.9

Step 2: Synthesis of 2-(4-((6, 7-dimethoxyquinazolin-4-yl) thio) butyl) isoindoline-1, 3-dione

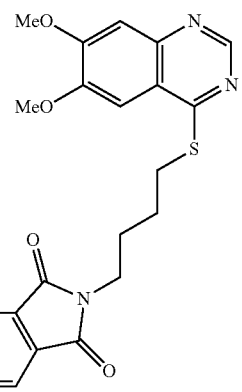

To a stirred solution of 6,7-dimethoxyquinazoline-4-thiol (1 g, 4.5 mmol) in DMF (10 ml) were added potassium carbonate (684 mg, 4.95 mmol) and 2-(4-bromobutyl)isoindoline-1,3-dione (1.27 g, 4.5 mmol) then stirred at 90° C. for 6 h. The progress of the reaction was monitored by TLC. After completion of the reaction, reaction mixture was poured on water and extracted with ethyl acetate. Organic layer was separated was washed with water and was concentrated under reduced pressure to afford the pure compound of 2-(4-((6, 7-dimethoxyquinazolin-4-yl) thio) butyl) isoindoline-1, 3-dione (800 mg, 1.891 mmol, 42% yield) as a light brown solid. 1H NMR (400 MHz, DMSO) δ 8.75 (s, 1H), 7.81-7.82 (m, 4H), 7.26 (s, 1H), 7.13 (s, 1H), 3.95 (s, 3H), 3.91 (s, 3H), 3.61 (t, 2H), 3.30-3.36 (m, 2H), 1.75 (m, 4H). LCMS: (M+H)+: m/Z: 424.2.

101

The following compound was synthesized by the above procedure

| Structure | 1HNMR |
|---|---|
| 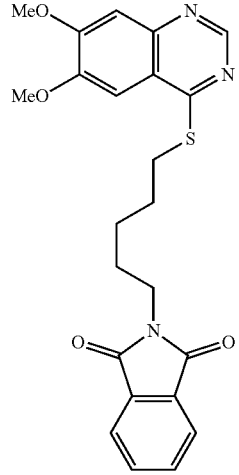 [SMILES: COc1cc2ncnc(SCCCCCN3C(=O)c4ccccc4C3=O)c2cc1OC] | (400 MHz, DMSO) δ 8.79 (s, 1H), 7.83-7.78 (m, 4H), 7.28 (s, 1H), 7.13 (s, 1H), 3.95 (s, 3H), 3.91 (s, 3H), 3.58-3.55 (t, 2H), 3.37-3.30 (t, 2H), 1.75-1.70 (m, 2H), 1.68-1.61 (m, 2H), 1.47-1.43 (m, 2H). MS 437.9 |

102

The following compound was synthesized by the above procedure

| Structure | 1HNMR |
|---|---|
| 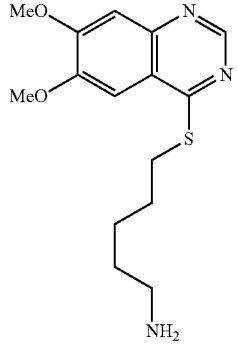 [SMILES: COc1cc2ncnc(SCCCCCN)c2cc1OC] | MS 308.1 |

Step-4: Tert-butyl (N-(4-((6, 7-dimethoxyquinazolin-4-yl) thio) butyl) sulfamoyl) carbamate

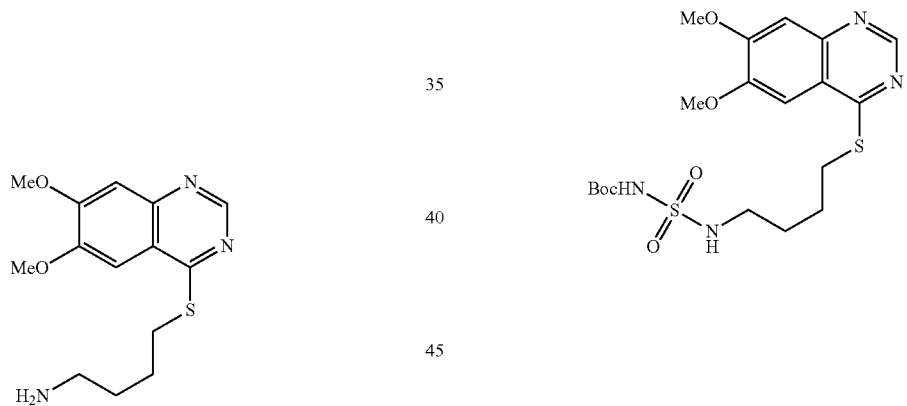

To a stirred solution of 4-((6,7-dimethoxyquinazolin-4-yl)thio)butan-1-amine 5 (550 mg, 1.87 mmol) in dichloromethane (20 ml) were added diisopropylethylamine (1.6 mL, 9.38 mmol) and N-(1-(N-(tert-butoxycarbonyl)sulfamoyl)pyridin-4(1H)-ylidene)-N-methylmethanaminium chloride 4 (337 mg, 1.87 mmol) at RT, then stirred at room temperature for 16 h. The progress of the reaction was monitored by TLC. After completion of the reaction, organic solvents completely distilled off under reduced pressure to afford crude compound. Crude compound was purified using combi flash column chromatography by eluting 60% ethyl acetate in pet-ether to afforded tert-butyl (N-(4-((6, 7-dimethoxyquinazolin-4-yl) thio) butyl) sulfamoyl) carbamate 6 (150 mg, 0.317 mmol, 17% yield) as a white solid.

Analytical Data: 1H NMR (400 MHz, DMSO) δ: 10.79 (s, H), 8.82 (s, 1H), 7.62-7.59 (t, 1H), 7.30 (s, 1H), 7.17 (s, 1H), 3.95 (s, 3H), 3.93 (s, 3H), 3.34 (t, 2H), 2.94-2.90 (m, 2H), 1.77-1.70 (m, 2H), 1.64-1.59 (m, 2H), 1.39 (s, 9H).

LCMS: (M+H)+: m/Z: 473.2

Step 3: Synthesis of 4-((6,7-dimethoxyquinazolin-4-yl)thio)butan-1-amine

To a stirred solution of 2-(4-((6,7-dimethoxyquinazolin-4-yl)thio)butyl)isoindoline-1,3-dione (1.1 g, 2.60 mmol) in ethanol (30 ml) were added 90% of hydrazine hydrate (0.163 mL, 5.2 mmol) at RT, then reaction mixture was stirred at reflux for 2 h. The progress of the reaction was monitored by TLC. After completion of the reaction, reaction mixture was cooled to RT, precipitate formed. Solid was collected through filtration affording 4-((6, 7-dimethoxyquinazolin-4-yl) thio) butan-1-amine (700 mg, 2.389 mmol, 92% yield) as a light brown solid. 1H NMR (400 MHz, DMSO) δ 8.81 (s, 1H), 7.29 (s, 1H), 7.16 (s, 1H), 3.95 (s, 3H), 3.92 (s, 3H), 3.35 (t, 2H), 2.67 (t, 2H), 1.77-1.71 (m, 2H), 1.62-1.56 (m, 2H). LCMS: (M+H)+: m/Z: 294.1

| Structure | 1HNMR |
|---|---|
| 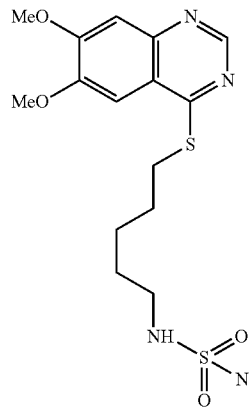 | 1H NMR (400 MHz, DMSO) δ 10.72 (bs, 1H), 8.81 (s, 1H), 7.50 (bs, 1H), 7.29 (bs, 1H), 7.16 (s, 1H), 3.95 (s, 3H), 3.93 (s, 3H), 3.35 (t, 2H), 2.86 (t, 2H), 1.75 (t, 2H), 1.50-1.44 (m, 4H), 1.39 (s, 9H). MS 487.2 | in dioxane (2 mL) at RT. Reaction mixture was stirred at RT for 16 h. The progress of the reaction was monitored by TLC. After completion of the reaction, organic solvents completely distilled off under reduced pressure to afford crude compound. Crude compound was purified through preparative HPLC method to afford pure compound of N-(4-((6, 7-dimethoxyquinazolin-4-yl) thio) butyl) sulfamide hydrochloride (30 mg, 0.08 mmol, 25% yield) as an off white solid.

Analytical Data: 1H NMR (400 MHz, DMSO) δ 8.83 (s, 1H), 7.30 (s, 1H), 7.18 (s, 1H), 6.53-6.47 (m, 3H), 3.95 (s, 3H), 3.93 (s, 3H), 3.37-3.32 (m, 2H), 2.93-2.88 (m, 2H), 1.77-1.72 (m, 2H), 1.66-1.60 (m, 2H).
LCMS: (M+H)+: m/Z: 373.23

The following compound was synthesized by the above general procedure

| Compound Number | Structure | 1HNMR |
|---|---|---|
| 012 | 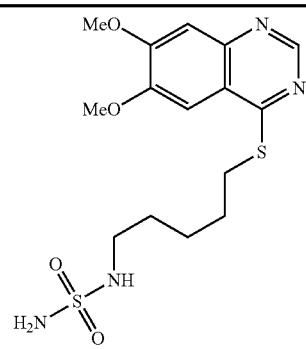 | 1HNMR (400 MHz, DMSO) δ 8.82 (s, 1H), 7.30 (s, 1H), 7.18 (s, 1H), 6.45 (s, 3H), 3.95 (s, 3H), 3.93 (s, 3H), 3.34 (t, 2H), 2.86 (d, 2H), 1.72 (t, 2H), 1.48 (brs, 4H). MS 387.1 |

Step-5: N-(4-((6, 7-dimethoxyquinazolin-4-yl) thio) butyl) sulfamide hydrochloride

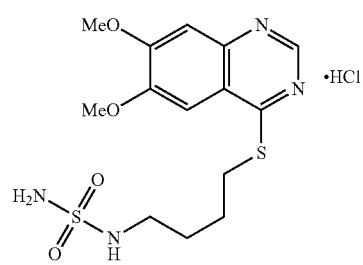 [SMILES: COc1cc2ncnc(SCCCCNS(N)(=O)=O)c2cc1OC ; Cl]

To a stirred solution of tert-butyl (N-(4-((6,7-dimethoxy-quinazolin-4-yl)thio)butyl)sulfamoyl)carbamate (6) (100 mg, 0.211 mmol) in 1,4-dioxane (1.0 ml) was added 4M HCl Compound 058 was also synthesized by the above general procedure.

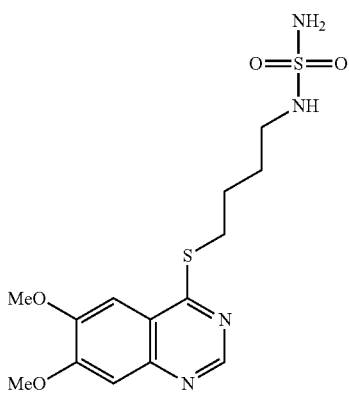

058

1H NMR (400 MHz, DMSO) δ 8.83 (s, 1H), 7.30 (s, 1H), 7.18 (s, 1H), 6.53-6.47 (m, 3H), 3.95 (s, 3H), 3.93 (s, 3H), 3.37-3.32 (m, 2H), 2.93-2.88 (m, 2H), 1.77-1.72 (m, 2H), 1.66-1.60 (m, 2H). LCMS 373.23. MW. 408.92

Compound 059 was also synthesized by the above general procedure.
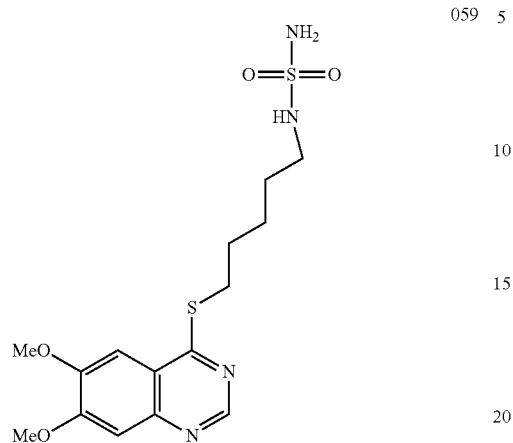
059
1H NMR (400 MHz, DMSO) δ 8.82 (s, 1H), 7.30 (s, 1H), 7.18 (s, 1H), 6.45 (s, 3H), 3.95 (s, 3H), 3.93 (s, 3H), 3.34 (t, 2H), 2.86 (d, 2H), 1.72 (t, 2H), 1.48 (brs, 4H). LCMS 387.1. MW. 422.94
Synthetic Scheme of Compounds 013 and 014

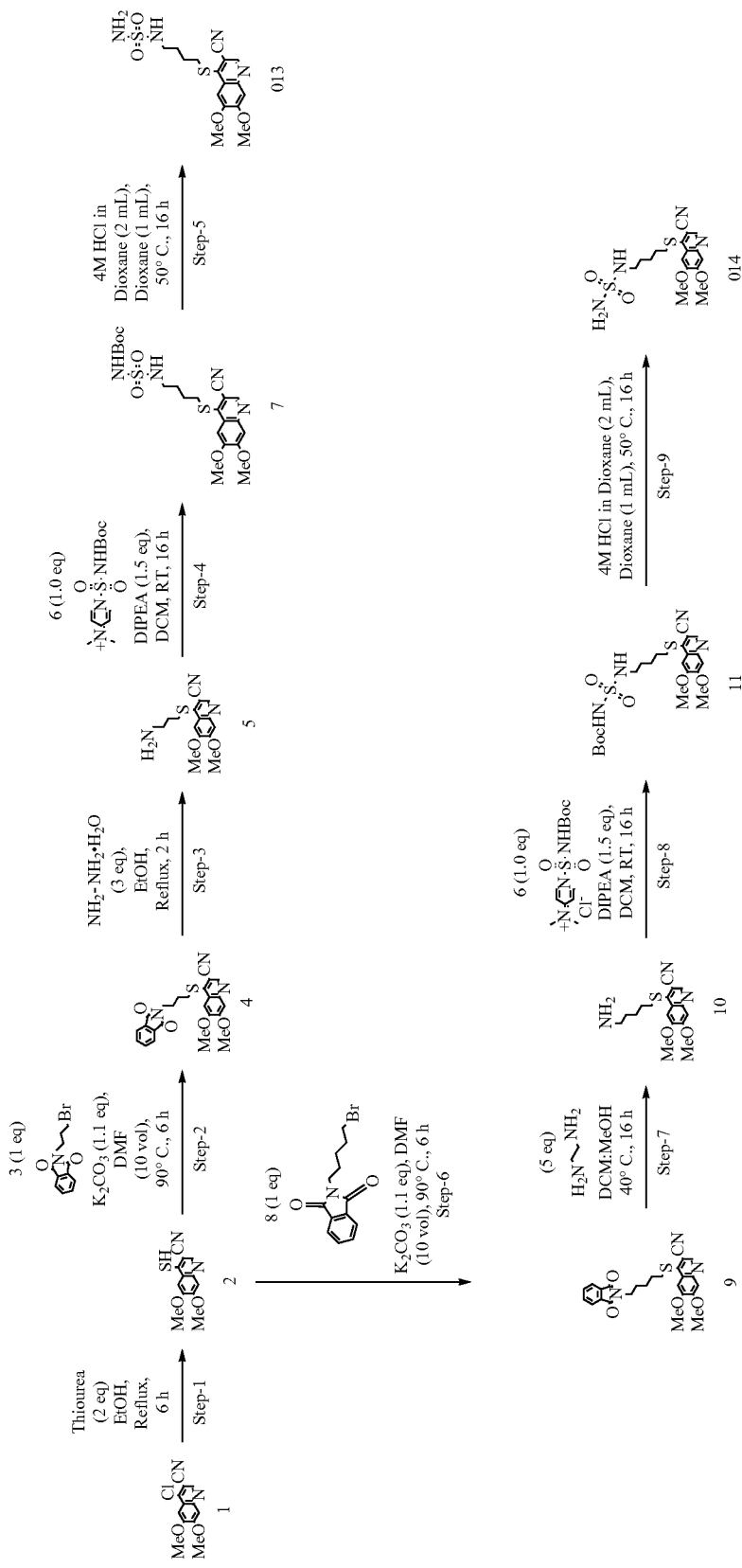

Step-1: Synthesis of 4-mercapto-6,7-dimethoxyquinoline-3-carbonitrile 2

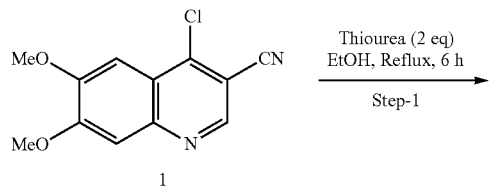

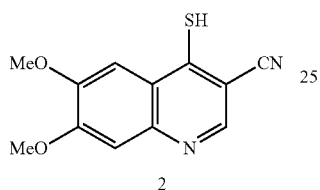

To a stirred solution of 4-chloro-6,7-dimethoxyquinoline-3-carbonitrile 1 (2000 mg, 8.06 mmol) in Ethanol (30 mL) was added thiourea (920 mg, 12.08 mmol) then refluxed for 6 h. The progress of the reaction was monitored by TLC. After completion of the reaction, reaction mixture completely distilled off and absorbed onto silica and grace column chromatography was performed using methanol/DCM to afford 4-mercapto-6,7-dimethoxyquinoline-3-carbonitrile 2 (1300 mg) as pale pink solid.

Analytical Data: $^1$H NMR (400 MHz, DMSO): δ 13.51 (brs, 1H), 8.57 (s, 1H), 8.05 (s, 1H), 7.09 (s, 1H), 3.91-3.88 (m, 6H).

LCMS: (M+H)$^+$: m/Z: 247.1

Step-2: Synthesis of 4-((4-(1,3-dioxoisoindolin-2-yl)butyl)thio)-6,7-dimethoxyquinoline-3-carbonitrile 4

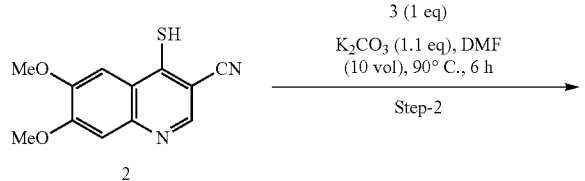

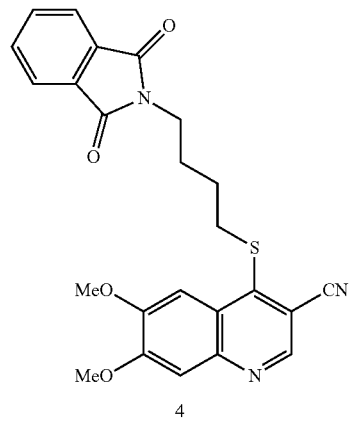

To a stirred solution of 4-mercapto-6,7-dimethoxyquinoline-3-carbonitrile 2 (450 mg, 1.8 mmol) in DMF (10 mL) was added 2-(4-bromobutyl)isoindoline-1,3-dione 3 (513 mg, 1.8 mmol) slowly and then K$_2$CO$_3$ (277 mg, 2.01 mmol) at RT. After addition, the reaction mixture heated to 90° C. for 6 h. The progress of the reaction was monitored by TLC. After completion of reaction, reaction mixture was directly poured on to ice cold water and stirred. Solid precipitated out was filtered and washed again with water and dried without necessity of any further purification to afford 4-((4-(1,3-dioxoisoindolin-2-yl)butyl)thio)-6,7-dimethoxyquinoline-3-carbonitrile 4 (600 mg) as a light brown solid.

Analytical Data: $^1$H NMR (400 MHz, DMSO) δ: 8.86 (s, 1H), 7.81-7.75 (m, 4H), 7.66 (s, 1H), 7.41 (s, 1H), 3.97-3.96 (m, 6H), 3.49 (t, 2H), 3.21 (t, 2H), 1.72-1.65 (m, 2H), 1.50-1.43 (m, 2H).

LCMS: (M+H)$^+$: m/Z: 448.26

Step-3: Synthesis of 4-((4-aminobutyl)thio)-6,7-dimethoxyquinoline-3-carbonitrile 5

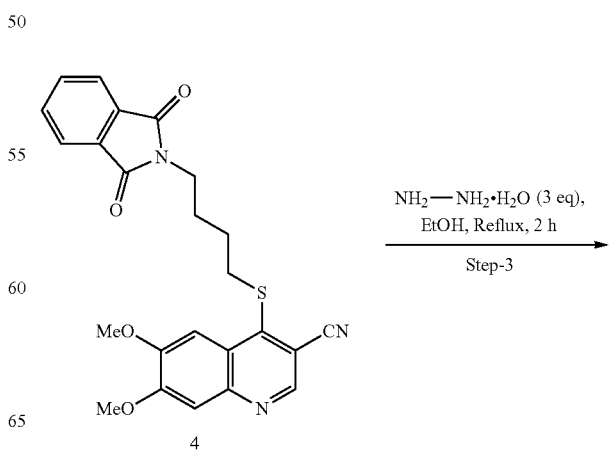

-continued

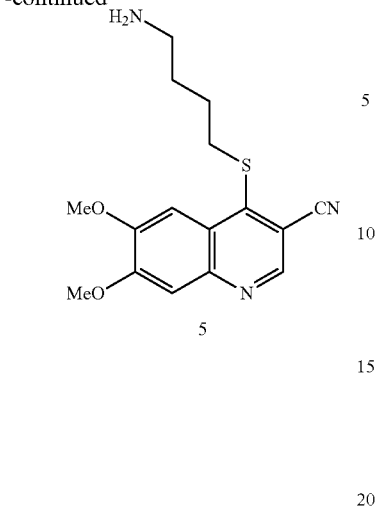

5

-continued

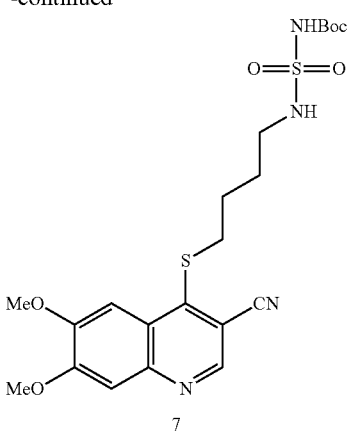

7

To a stirred solution of 4-((4-(1,3-dioxoisoindolin-2-yl)butyl)thio)-6,7-dimethoxyquinoline-3-carbonitrile 4 (550 mg, 1.2 mmol) in EtOH (10 mL) was added Hydrazine hydrate (0.19 ml, 3.7 mmol) was added and then refluxed for 2 h. The progress of the reaction was monitored by TLC. After completion, reaction mixture was directly absorbed on to celite and converted into slurry. Crude was purified through reverse-phase grace column chromatography by eluting 40% ACN/water system to afford 4-((4-aminobutyl)thio)-6,7-dimethoxyquinoline-3-carbonitrile 5 (80 mg) as a pale yellow liquid.

Analytical Data: $^1$H NMR (400 MHz, DMSO) δ: 8.91 (s, 1H), 7.71 (s, 1H), 7.50 (s, 1H), 3.99-3.96 (m, 6H), 3.20-3.15 (m, 2H), 2.45-2.44 (m, 2H), 1.53-1.41 (m, 4H).

LCMS: (M+H)$^+$: m/Z: 318.2

Step-4: Synthesis of tert-butyl (N-(4-((3-cyano-6,7-dimethoxyquinolin-4-yl)thio)butyl)sulfamoyl)carbamate 7

To a stirred solution of 4-((4-aminobutyl)thio)-6,7-dimethoxyquinoline-3-carbonitrile 5 (80 mg, 0.25 mmol) in DCM (10 mL) was added N-(1-(N-(tert-butoxycarbonyl)sulfamoyl)pyridin-4(1H)-ylidene)-N-methylmethanaminium chloride 4 (85 mg, 0.25 mmol) slowly and then added DIPEA (0.07 ml, 0.375 mmol) at same temperature. Then stirred the reaction mixture at room temperature for 16 h. The progress of the reaction was monitored by TLC. Reaction mixture was directly absorbed on to silica and converted into slurry. Crude was purified through combi-flash chromatography by eluting 70% EtOAc in Hexane to afford tert-butyl (N-(4-((3-cyano-6,7-dimethoxyquinolin-4-yl)thio)butyl)sulfamoyl)carbamate 5 (90 mg) as a white solid.

Analytical Data: $^1$H NMR (400 MHz, DMSO) δ: 10.73 (s, 1H), 8.92 (s, 1H), 7.71 (s, 1H), 7.55-7.50 (m, 2H), 3.99-3.98 (m, 6H), 3.19-3.17 (m, 2H), 2.82-2.81 (m, 2H), 1.53-1.52 (m, 4H), 1.37 (s, 9H).

LCMS: (M+H)$^+$: m/Z: 497.2

Step-5: Synthesis of Compound 013

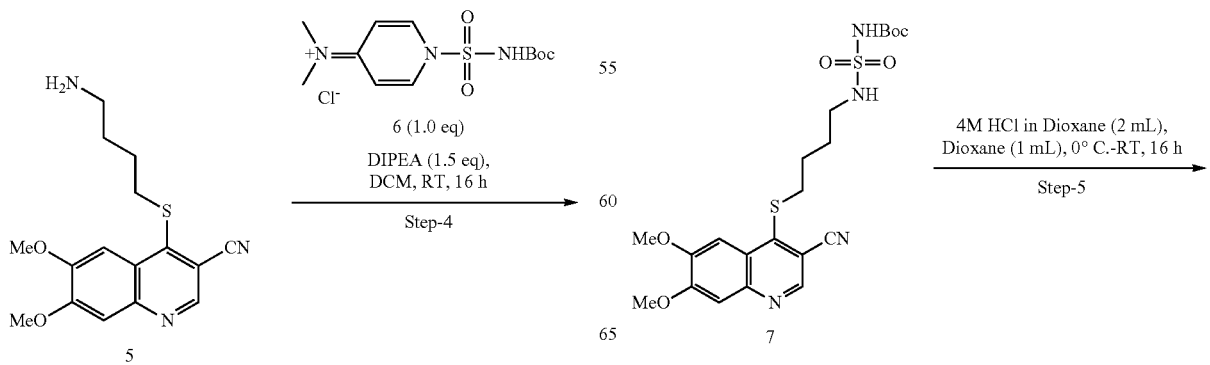

113

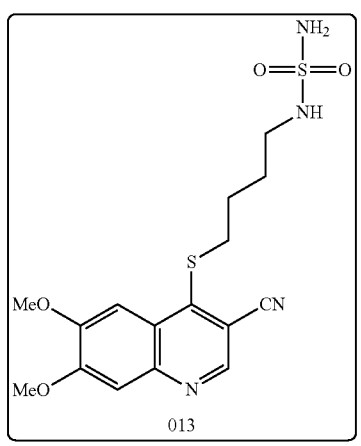

To a stirred solution of tert-butyl (1V-(4-((3-cyano-6,7-dimethoxyquinolin-4-yl)thio)butyl)sulfamoyl)carbamate 7 (90 mg, 0.18 mmol) in dichloromethane (3 ml) was added 4M HCl in dioxane (1 mL) at 0° C. then stirred at room temperature for 16 h. The progress of the reaction was monitored by TLC. After completion of reaction, organic solvents completely distilled off under reduced pressure. Crude compound was purified by prep-HPLC to give Compound 013 (25 mg) as off-white fluffy solid.

Analytical Data: $^1$H NMR (400 MHz, DMSO) δ: 8.92 (s, 1H), 7.72 (s, 1H), 7.51 (s, 1H), 6.45-6.42 (m, 3H), 6.45 (t, 1H) 3.99-3.98 (m, 6H), 3.21-3.17 (m, 2H), 2.82-2.77 (m, 2H), 1.55-1.53 (m, 4H).

LCMS: (M+H)$^+$: m/Z: 397.1.

Step-6: Synthesis of 4-((5-(1,3-dioxoisoindolin-2-yl)pentyl)thio)-6,7-dimethoxyquinoline-3-carbonitrile 9

114

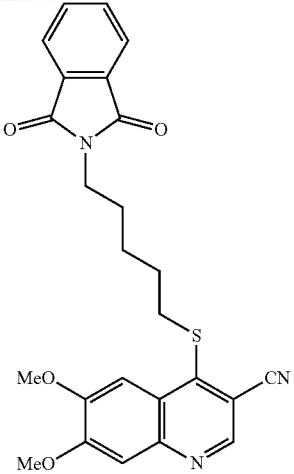

To a stirred solution of 4-mercapto-6,7-dimethoxyquinoline-3-carbonitrile 2 (450 mg, 1.8 mmol) in DMF (10 mL) was added 2-(5-bromopentyl)isoindoline-1,3-dione 8 (540 mg, 1.8 mmol) slowly and then K$_2$CO$_3$ (273 mg, 1.98 mmol) at RT. After addition, the reaction mixture heated to 90° C. for 6 h. The progress of the reaction was monitored by TLC. After completion of reaction, reaction mixture was directly poured on to ice cold water and stirred. Solid precipitated out was filtered and washed again with water and dried without necessity of any further purification to afford 4-((5-(1,3-dioxoisoindolin-2-yl)pentyl)thio)-6,7-dimethoxyquinoline-3-carbonitrile 9 (600 mg) as a light brown solid.

Analytical Data: $^1$H NMR (400 MHz, DMSO) δ: 8.89 (s, 1H), 7.81-7.75 (m, 4H), 7.69 (s, 1H), 7.48 (s, 1H), 3.98-3.96 (m, 6H), 3.49 (t, 2H), 3.17 (t, 2H), 1.56-1.46 (m, 4H), 1.40-1.36 (m, 2H).

LCMS: (M+H)$^+$: m/Z: 462.1

Step-7: Synthesis of 4-((5-aminopentyl)thio)-6,7-dimethoxyquinoline-3-carbonitrile 10

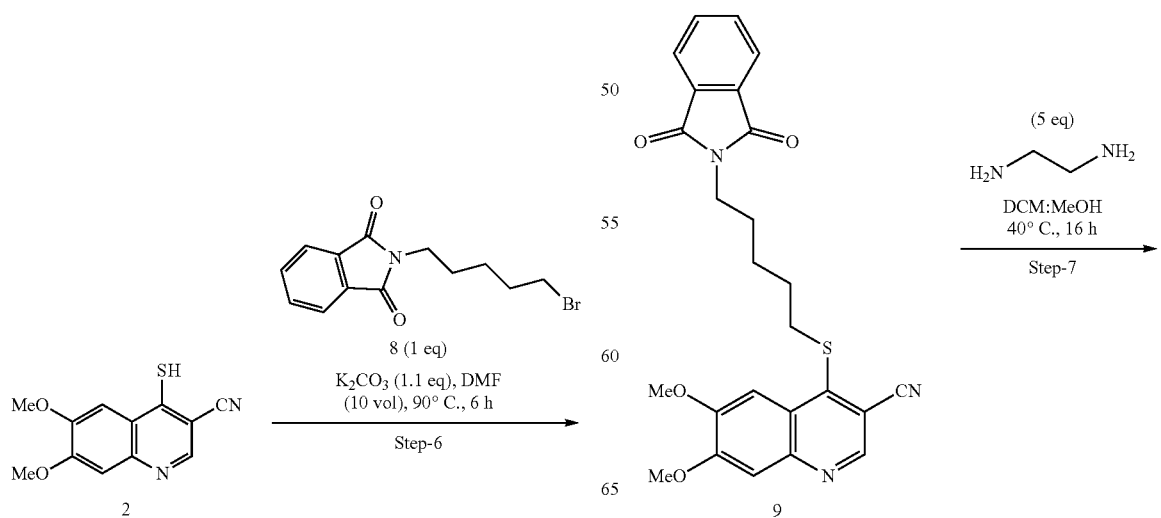

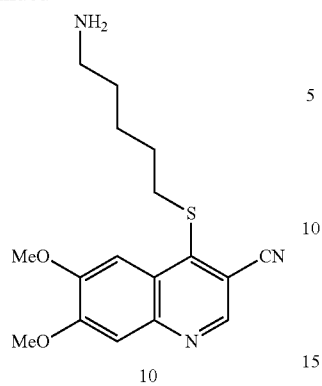

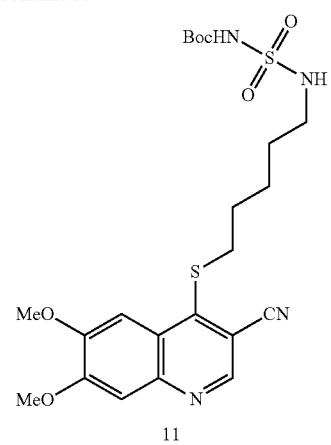

To a stirred solution of 4-((5-(1,3-dioxoisoindolin-2-yl)pentyl)thio)-6,7-dimethoxyquinoline-3-carbonitrile 9 (600 mg, 1.3 mmol) in DCM:MeOH (1:1) (10 mL) was added 1,2 Diethylamine (0.43 ml, 6.5 mmol) then heated at 40° C. for 16 h. The progress of the reaction was monitored by TLC. After completion, reaction mixture was directly absorbed on to celite and converted into slurry. Crude was purified through reverse-phase grace column chromatography by eluting 30-40% ACN/water system to afford 4-((5-aminopentyl)thio)-6,7-dimethoxyquinoline-3-carbonitrile 10 (200 mg) as a pale yellow liquid.

Analytical Data: LCMS: (M+H)$^+$: m/Z: 332.2

To a stirred solution of 4-((5-aminopentyl)thio)-6,7-dimethoxyquinoline-3-carbonitrile 10 (200 mg, 0.60 mmol) in DCM (10 mL) was added N-(1-(N-(tert-butoxycarbonyl)sulfamoyl)pyridin-4(1H)-ylidene)-N-methylmethanaminium chloride 4 (338 mg, 0.6 mmol) slowly and then added DIPEA (0.16 ml, 0.9 mmol) at same temperature. Then stirred the reaction mixture at room temperature for 16 h. The progress of the reaction was monitored by TLC. Reaction mixture was directly absorbed on to silica and converted into slurry. Crude was purified through combi-flash chromatography by eluting 70-80% EtOAc in Hexane to afford tert-butyl (N-(5-((3-cyano-6,7-dimethoxyquinolin-4-yl)thio)pentyl)sulfamoyl)carbamate 11 (90 mg) as a white solid.

Analytical Data: $^1$H NMR (400 MHz, DMSO) δ: 10.73 (s, 1H), 8.92 (s, 1H), 7.71 (s, 1H), 7.55-7.50 (m, 2H), 4.00-3.98 (m, 6H), 3.18-3.14 (m, 2H), 2.80-2.79 (m, 2H), 1.45-1.41 (m, 2H), 1.37 (m, 13H).

LCMS: (M+H)$^+$: m/Z: 511.2

Step-8: Synthesis of tert-butyl (N-(5-((3-cyano-6,7-dimethoxyquinolin-4-yl)thio)pentyl)sulfamoyl)carbamate 11

Step-9: Synthesis of Compound 014

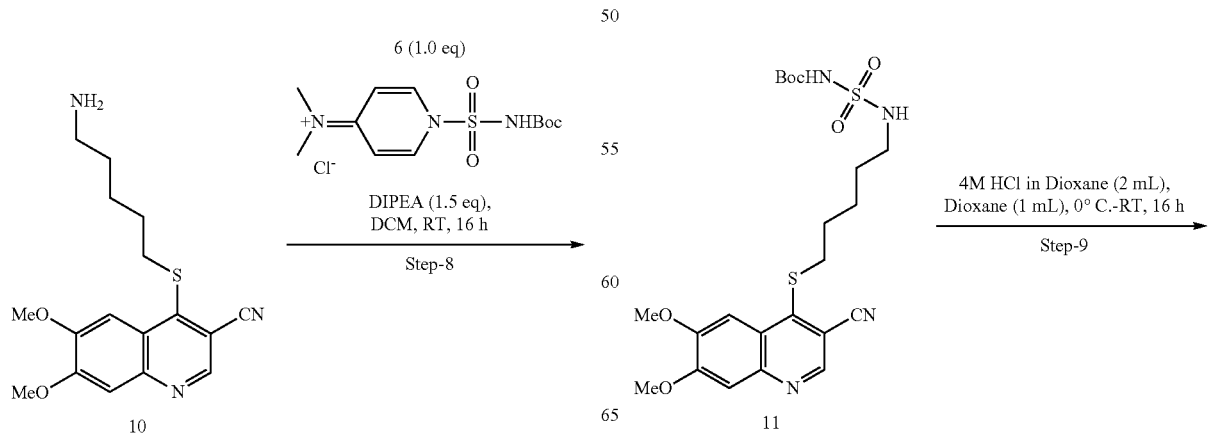

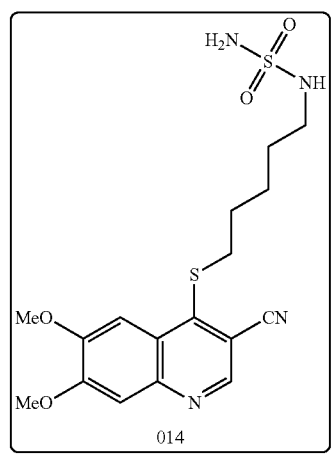

014

To a stirred solution of tert-butyl (N-(5-((3-cyano-6,7-dimethoxyquinolin-4-yl)thio)pentyl)sulfamoyl)carbamate 11 (90 mg, 0.176 mmol) in dichloromethane (2 ml) was added 4M HCl in dioxane (1 mL) at 0° C. then stirred at room temperature for 16 h. The progress of the reaction was monitored by TLC. After completion of reaction, organic solvents completely distilled off under reduced pressure. Crude compound was purified by prep-HPLC to give Compound 014 (29 mg) as off-white fluffy solid.

Analytical Data: $^1$H NMR (400 MHz, DMSO) δ: 8.93 (s, 1H), 7.73 (s, 1H), 7.51 (s, 1H), 6.41-6.39 (m, 3H), 4.09-3.99 (m, 6H), 3.19 (t, 2H), 2.80-2.78 (m, 2H), 1.51-1.49 (m, 2H), 1.48-1.40 (m, 4H).

LCMS: (M+H)$^+$: m/Z: 411.1.

General Scheme 4

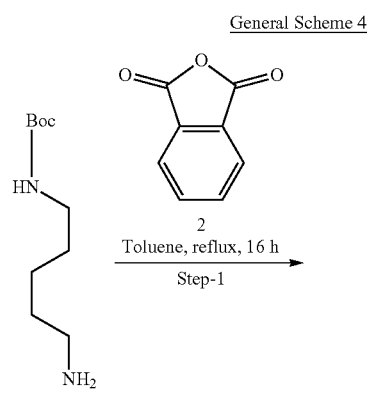

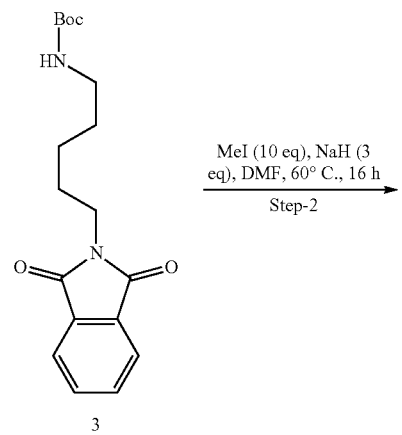

3

MeI (10 eq), NaH (3 eq), DMF, 60° C., 16 h
Step-2

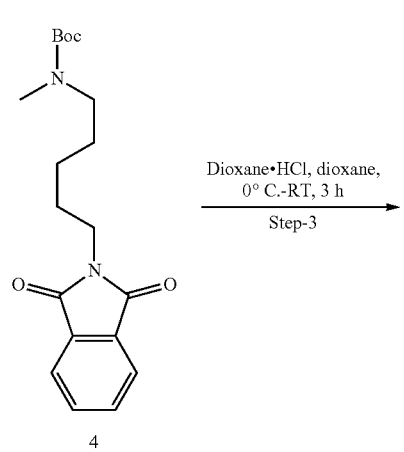

4

Dioxane•HCl, dioxane,
0° C.-RT, 3 h
Step-3

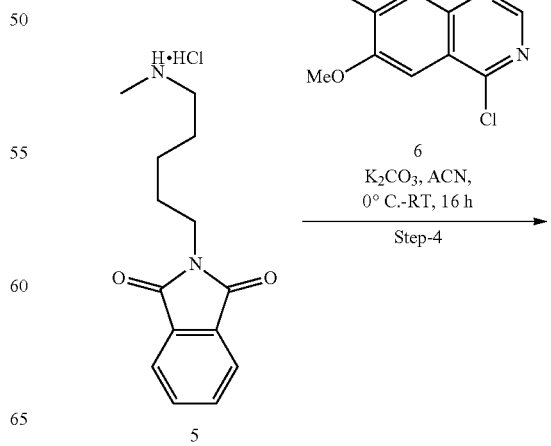

5

K$_2$CO$_3$, ACN,
0° C.-RT, 16 h
Step-4

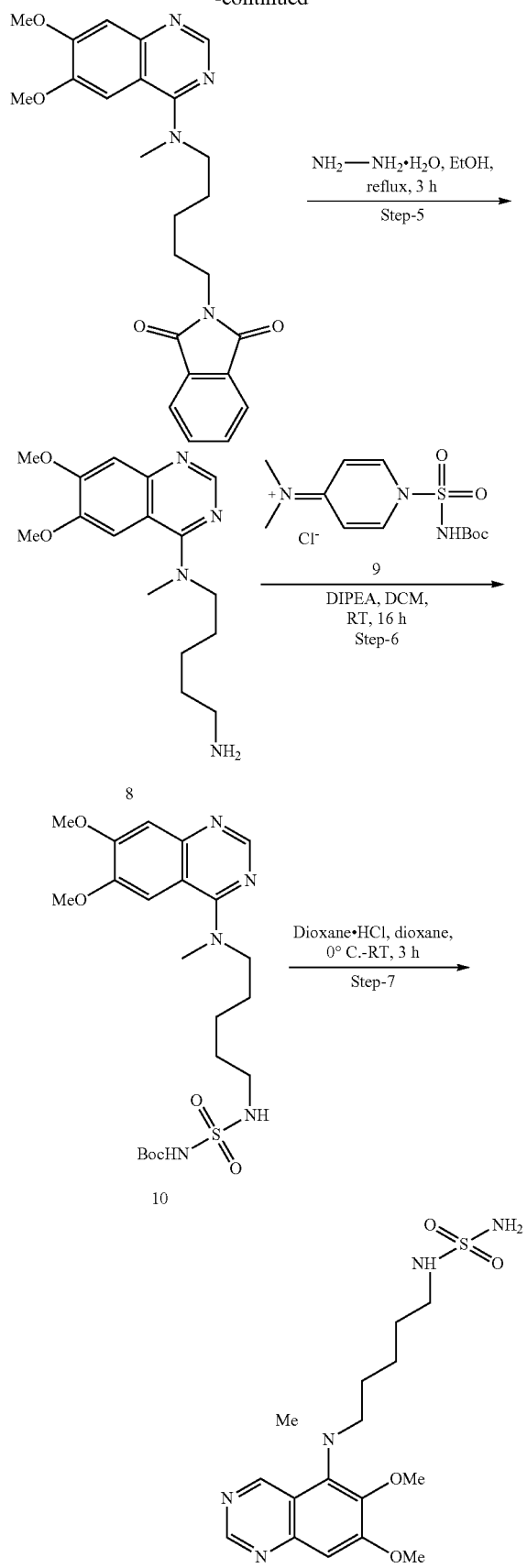

Example 4: N-(5-((6, 7-dimethoxyquinazolin-4-yl)(methyl) amino) pentyl) sulfamide

Step-1: Tert-butyl (5-(1, 3-dioxoisoindolin-2-yl) pentyl) carbamate

3

To a stirred solution of tert-butyl (5-aminopentyl) carbamate 1 (500 mg, 2.47 mmol) in toluene (10 mL) was added isobenzofuran-1, 3-dione 2 (366 mg, 2.47 mmol) then stirred the reaction mixture at reflux for 16 h. The progress of the reaction was monitored by TLC. After completion of the reaction, reaction mixture completely distilled off under reduced pressure to afford crude compound. Crude was purified through combi-flash column chromatography by eluting 20% ethyl acetate in pet ether to afford tert-butyl (5-(1, 3-dioxoisoindolin-2-yl) pentyl) carbamate (500 mg, 1.506 mmol, 61% yield) as a white solid.

Analytical Data: 1H NMR (400 MHz, DMSO) δ 7.86-7.80 (m, 4H), 6.74 (t, 1H), 3.56-3.52 (t, 2H), 2.88-2.83 (m, 2H), 1.58-1.54 (m, 2H), 1.38-1.32 (m, 11H), 1.23-1.20 (m, 2H).

LCMS: (M+Na)+: m/Z: 355.41

Step-2: Tert-butyl (5-(1, 3-dioxoisoindolin-2-yl) pentyl) (methyl) carbamate

4

To a stirred solution of tert-butyl (5-(1,3-dioxoisoindolin-2-yl)pentyl)carbamate 3 (2 g, 6.024 mmol) in N,N'-dimethylformamide (20 mL) was added 60% NaH (723 mg, 30.12 mmol) slowly at 0° C. and then added methyl iodide (8.5 g, 60.24 mmol) at same temperature. Then stirred the reaction mixture at room temperature for 16 h. The progress of the reaction was monitored by TLC. Reaction mixture was poured into ice cold water (500 mL) and extracted with ethyl acetate (2×400 mL). Combined organic layers were washed with brine solution (400 mL), dried over sodium sulfate and concentrated under reduced pressure. Crude was purified through combi-flash chromatography by eluting 20% ethyl acetate in pet ether to afford mixture of tert-butyl (5-(1, 3-dioxoisoindolin-2-yl) pentyl) (methyl) carbamate 4 (1.44 g, 4.161 mmol, 69% yield) as a white solid.

Analytical Data: 1H NMR (400 MHz, DMSO) δ 7.86-7.80 (m, 4H), 3.57-3.54 (t, 2H), 3.12-3.08 (t, 2H), 2.71 (s, 3H), 1.63-1.56 (m, 2H), 1.48-1.43 (m, 2H), 1.32 (s, 9H), 1.20-1.17 (m, 2H).

LCMS: (M−Boc)+: m/Z: 247.2

Step-3: 2-(5-(methyl amino) pentyl) isoindoline-1,3-dione hydrochloride

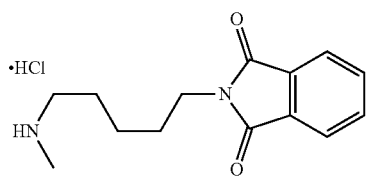 [SMILES: Cl ; CNCCCCCN1C(=O)c2ccccc2C1=O]

To a stirred solution of tert-butyl 4-(2-((N-(tert-butoxycarbonyl)sulfamoyl)amino)ethyl)-3,4-dihydroquinoline-1(2H)-carboxylate 4 (1.8 g, 5.202 mmol) in dichloromethane (15 ml) was added 4M HCl in dioxane (6.75 mL) at 0° C. then stirred at room temperature for 2 h. The progress of the reaction was monitored by TLC. After completion of reaction, organic solvents completely distilled off under reduced pressure. Crude compound was purified by trituration with diethyl ether (100 mL) to afford 2-(5-(methyl amino) pentyl) isoindoline-1, 3-dione hydrochloride 5 (1.3 g, 4.609 mmol, 89% yield) as a white solid.

Analytical Data: 1H NMR (400 MHz, DMSO) δ 8.32 (brs, 2H), 7.87-7.82 (m, 4H), 3.58-3.55 (t, 2H), 2.83 (m, 2H), 1.63-1.53 (m, 4H), 1.33-1.28 (m, 2H).

LCMS: (M+H)+: m/Z: 247.2

Step-4: 2-(5-((6, 7-dimethoxyquinazolin-4-yl)(methyl) amino) pentyl) isoindoline-1, 3-dione

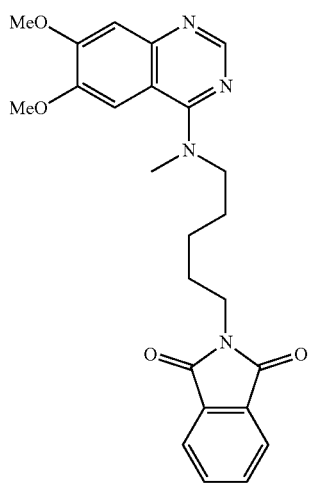 [SMILES: COc1cc2ncnc(N(C)CCCCCN3C(=O)c4ccccc4C3=O)c2cc1OC]

To a stirred solution of 2-(5-(methyl amino) pentyl) isoindoline-1, 3-dione hydrochloride 5 (1.2 g, 4.25 mmol) in acetonitrile (15 ml) were added potassium carbonate (1.76 g, 13.5 mmol) and 4-chloro-6, 7-dimethoxyquinazoline 6 (953 mg, 4.25 mmol) then stirred at room temperature for 16 h. The progress of the reaction was monitored by TLC. After completion of the reaction, added water (200 mL) and extracted with ethyl acetate (2×150 mL). Combined organic layers were washed with brine solution (100 mL), dried over sodium sulfate and concentrated under reduced pressure. Crude was purified through combi-flash column chromatography by eluting 40% ethyl acetate in hexane to afford 2-(5-((6, 7-dimethoxyquinazolin-4-yl) (methyl) amino) pentyl) isoindoline-1, 3-dione 7 (650 mg, 1.497 mmol, 44% yield) as a white solid.

Analytical Data: 1H NMR (400 MHz, DMSO) δ 8.35 (s, 1H), 7.84-7.79 (m, 4H), 7.21 (s, 1H), 7.11 (s, 1H), 3.89 (s, 3H), 3.82 (s, 3H), 3.60-3.54 (m, 2H), 3.21 (s, 3H), 1.78-1.75 (m, 2H), 1.65-1.59 (m, 2H), 1.34-1.28 (m, 2H).

LCMS: (M+H)+: m/Z: 435.2

Step-5: N1-(6, 7-dimethoxyquinazolin-4-yl)-N1-methylpentane-1, 5-diamine

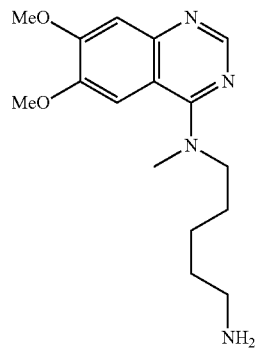 [SMILES: COc1cc2ncnc(N(C)CCCCCN)c2cc1OC]

To a stirred solution of 2-(5-((6,7-dimethoxyquinazolin-4-yl)(methyl)amino)pentyl)isoindoline-1,3-dione 7 (545 mg, 1.126 mmol) in ethanol (15 ml) was added hydrazine hydrate (0.18 mL, 3.378 mmol) then stirred the reaction mixture at 80° C. for 2 h. The progress of the reaction was monitored by TLC. After completion of reaction, precipitated solid was filtered off, washed the residue with ethanol (20 mL) and concentrated the filtrate to afford crude compound. Crude compound was purified through Grace reverse phase method by eluting 14% acetonitrile in 0.1% formic acid in water to afford N1-(6, 7-dimethoxyquinazolin-4-yl)-N1-methylpentane-1, 5-diamine 8 (330 mg, 1.085 mmol, 86% yield) as a colorless gummy liquid.

Analytical Data: 1H NMR (400 MHz, DMSO) δ 8.38 (s, 1H), 7.25 (s, 1H), 7.14 (s, 1H), 3.90 (s, 3H), 3.90 (s, 3H), 3.60-3.56 (t, 2H), 3.22-3.21 (s, 3H), 1.76-1.72 (m, 2H), 1.38-1.30 (m, 4H).

LCMS: (M+H)+: m/Z: 305.2

Step-6: Tert-butyl (N-(5-((6, 7-dimethoxyquinazolin-4-yl) (methyl) amino) pentyl) sulfamoyl) carbamate

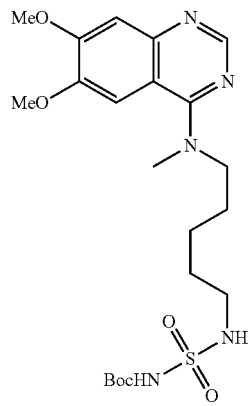

To a stirred solution of N1-(6,7-dimethoxyquinazolin-4-yl)-N1-methylpentane-1,5-diamine 8 (360 mg, 1.2 mmol) in dichloromethane (10 ml) were added diisopropylethylamine (0.3 mL, 1.81 mmol) and N-(1-(N-(tert-butoxycarbonyl)sulfamoyl)pyridin-4(1H)-ylidene)-N-methylmethanaminium chloride 9 (491 mg, 1.45 mmol) at 0° C. then stirred at room temperature for 16 h. The progress of the reaction was monitored by TLC. After completion of the reaction, organic solvents completely distilled off under reduced pressure to afford crude compound. Crude was purified through 60-120 silica gel column chromatography by eluting 2% methanol in dichloromethane to afford tert-butyl (N-(5-((6, 7-dimethoxyquinazolin-4-yl) (methyl) amino) pentyl) sulfamoyl) carbamate 10 (200 mg, 0.414 mmol, 35% yield) as a brown solid.

Analytical Data: 1H NMR (400 MHz, DMSO) δ 11.0-10.0 (brs, 1H), 8.38 (s, 1H), 7.25 (s, 1H), 7.22 (m, 1H), 7.14 (s, 1H), 3.90 (s, 3H), 3.87 (s, 3H), 3.59-3.55 (t, 2H), 3.22-3.21 (s, 3H), 1.75-1.71 (m, 2H), 1.50-1.45 (m, 2H), 1.38 (s, 9H), 1.31-1.24 (m, 1H). LCMS: (M+H)+: m/Z: 484.2

Step 7: N-(5-((6, 7-dimethoxyquinazolin-4-yl) (methyl) amino) pentyl) sulfamide (Compound 061)

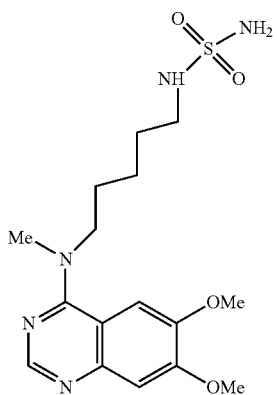 [SMILES: COc1cc2ncnc(N(C)CCCCCNS(N)(=O)=O)c2cc1OC]

To a stirred solution of tert-butyl (N-(5-((6,7-dimethoxyquinazolin-4-yl)(methyl)amino)pentyl)sulfamoyl)carbamate 10 (200 mg, 0.414 mmol) in dichloromethane (6 ml) was added 4M HCl in dioxane (4 mL) at 0° C. then stirred at room temperature for 3 h. The progress of the reaction was monitored by TLC. After completion, organic solvents completely distilled off under reduced pressure to afford crude compound. Crude was purified through prep HPLC method to afford N-(5-((6, 7-dimethoxyquinazolin-4-yl) (methyl) amino) pentyl) sulfamide (90 mg, 0.235 mmol, 57% yield) (Compound 061) as an off white solid.

Analytical Data: 1H NMR (400 MHz, DMSO) δ 8.39 (s, 1H), 8.14 (s, 1H), 7.26 (s, 1H), 7.14 (s, 1H), 6.44 (m, 3H), 3.90 (s, 3H), 3.88 (s, 3H), 3.60-3.56 (t, 2H), 2.88-2.83 (m, 2H), 1.77-1.71 (m, 2H), 1.52-1.46 (m, 2H), 1.37-1.31 (m, 2H). LCMS: (M+H)+: m/Z: 384.2

General scheme 5

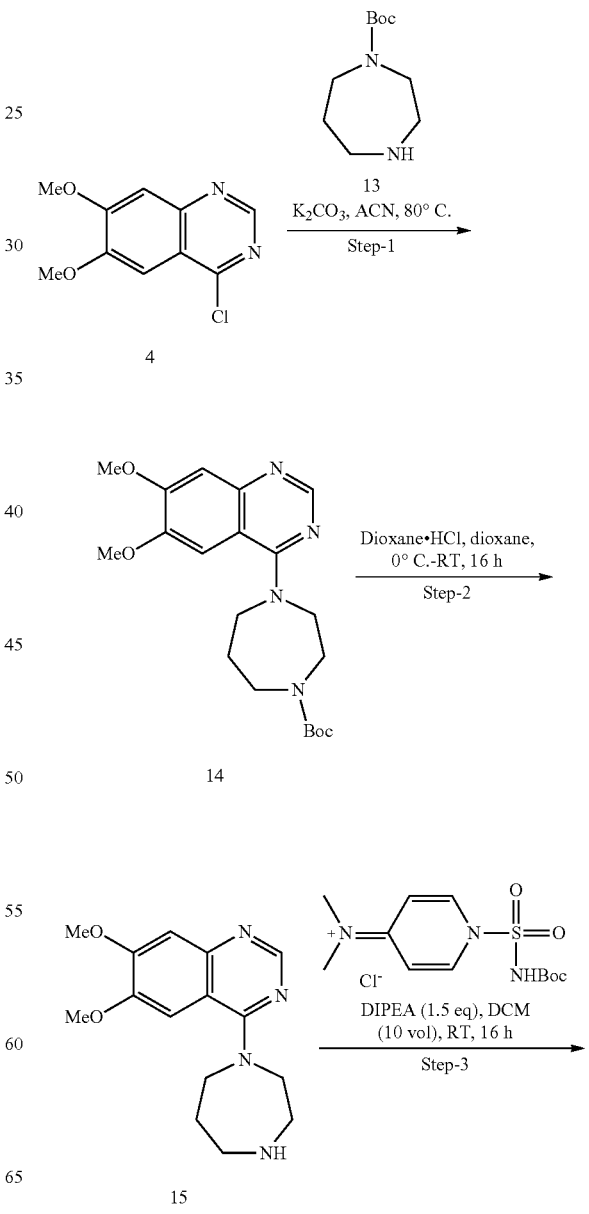

125

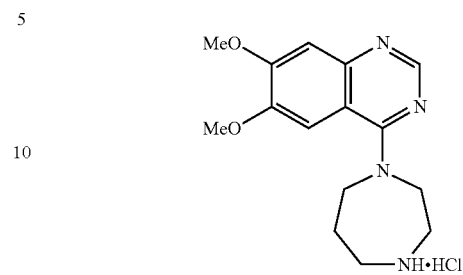

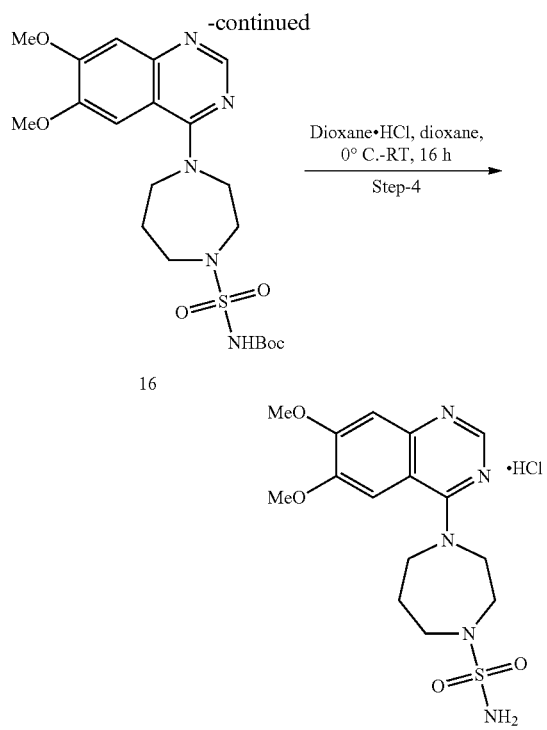

Example 5: 4-(6,7-dimethoxyquinazolin-4-yl)-1,4-diazepane-1-sulfonamide hydrochloride Salt (Compound 015)

Step-1: Tert-butyl 4-(6, 7-dimethoxyquinazolin-4-yl)-1, 4-diazepane-1-carboxylate

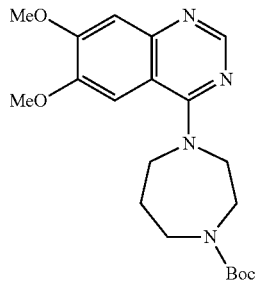 [SMILES: COc1cc2ncnc(N3CCCN(C(=O)OC(C)(C)C)CC3)c2cc1OC]

To a stirred solution of 4-chloro-6, 7-dimethoxyquinazoline 1 (2 g, 8.904 mmol) in acetonitrile (25 ml) were added potassium carbonate (2.4 g, 17.809 mmol) and tert-butyl 1,4-diazepane-1-carboxylate 2 (1.96 g, 9.795 mmol) then stirred at 80° C. for 16 h. The progress of the reaction was monitored by TLC. After completion of the reaction, reaction mixture completely distilled off under reduced pressure. Crude was purified through combi-flash chromatography by eluting 5% methanol in dichloromethane to afford tert-butyl 4-(6, 7-dimethoxyquinazolin-4-yl)-1, 4-diazepane-1-carboxylate 3 (2.7 g, 6.958 mmol, 78% yield) as a pale yellow solid.

Analytical Data: 1H NMR (400 MHz, DMSO) δ 8.38 (s, 1H), 7.14 (s, 1H), 7.25 (s, 1H), 3.97-3.94 (t, 2H), 3.89-3.84 (m, 8H), 3.59 (d, 2H), 3.41 (s, 2H), 1.98 (s, 2H), 1.15 (d, 9H).

126

Step-2: 4-(1, 4-diazepan-1-yl)-6, 7-dimethoxyquinazoline hydrochloride

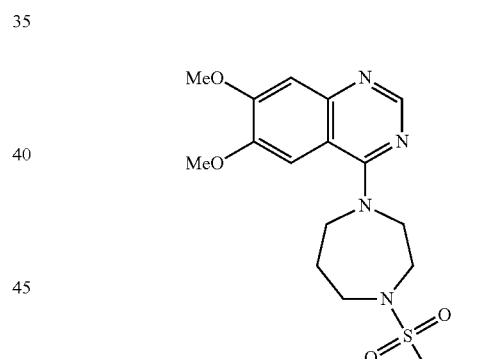

To a stirred solution of tert-butyl 4-(6,7-dimethoxyquinazolin-4-yl)-1,4-diazepane-1-carboxylate 3 (200 mg, 0.742 mmol) in dioxane (2 ml) was added 4M HCl in dioxane (8 mL) at 0° C. then stirred at room temperature for 16 h. The progress of the reaction was monitored by TLC. After completion of the reaction, organic solvents completely distilled off under reduced pressure. Crude was purified by trituration with diethyl ether (20 mL) to afford 4-(1, 4-diazepan-1-yl)-6, 7-dimethoxyquinazoline hydrochloride 4 (115 mg, 0.355 mmol, 68% yield) as a yellow solid.

Analytical Data: 1H NMR (400 MHz, DMSO) δ 9.33 (s, 2H), 8.79 (s, 1H), 7.43 (s, 1H), 7.35 (s, 1H), 4.19 (s, 2H), 4.29 (s, 2H), 3.97-3.93 (m, 6H), 3.17 (d, 2H), 2.77-2.31 (m, 2H).

Step-3: Tert-butyl ((4-(6, 7-dimethoxyquinazolin-4-yl)-1, 4-diazepan-1-yl) sulfonyl) carbamate To a stirred solution of 4-(1,4-diazepan-1-yl)-6,7-dimethoxyquinazoline hydrochloride 4 (500 mg, 1.508 mmol) in dichloromethane (10 ml) were added diisopropylethylamine (0.5 mL, 2.262 mmol) and N-(1-(N-(tert-butoxycarbonyl)sulfamoyl)pyridin-4(1H)-ylidene)-N-methylmethanaminium 5 (508 mg, 1.508 mmol) at 0° C. then stirred at room temperature for 16 h. The progress of the reaction was monitored by TLC. After completion of the reaction, reaction mixture completely distilled off under reduced pressure to afford crude compound. Crude was purified through 100-200 silica gel column chromatography by eluting 5% methanol in dichloromethane to afford semi pure compound. This semi pure was again purified by trituration with 50% ethyl acetate in pet ether to afford tert-butyl ((4-(6, 7-dimethoxyquinazolin-4-yl)-1, 4-diazepan-1-yl) sulfonyl) carbamate 6 (350 mg, 0.686 mmol, 44% yield) as an off white solid.

Analytical Data: 1H NMR (400 MHz, DMSO) δ 11.07 (brs, 1H), 8.18 (s, 1H), 7.21 (s, 1H), 3.88-3.95 (m, 10H), 3.65-3.68 (t, 2H), 3.42-3.45 (t, 2H), 2.06 (d, 2H), 1.33-1.36 (s, 9H). LCMS: (M+H+): m/Z: 468.15

Step-4: 4-(6,7-dimethoxyquinazolin-4-yl)-1,4-diazepane-1-sulfonamide hydrochloride salt (Compound 015-HCl)

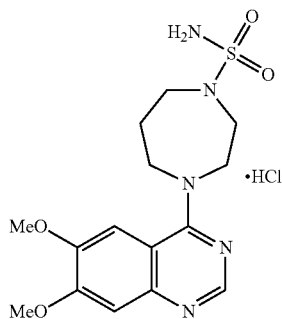 [SMILES: COc1cc2ncnc(N3CCCN(S(N)(=O)=O)CC3)c2cc1OC ; Cl]

To a stirred solution of tert-butyl ((4-(6,7-dimethoxyquinazolin-4-yl)-1,4-diazepan-1-yl)sulfonyl)carbamate 6 (300 mg, 0.646 mmol) in dioxane (2 ml) was added 4M HCl in dioxane (8 mL) at 0° C. then stirred at room temperature for 6 h. The progress of the reaction was monitored by TLC. After completion of the reaction, organic solvents completely distilled off under reduced pressure. Crude was purified by trituration with 5% methanol in dichloromethane (50 mL) to afford 4-(6,7-dimethoxyquinazolin-4-yl)-1,4-diazepane-1-sulfonamide hydrochloride salt (120 mg, 0.327 mmol, 51% yield) as an off white solid.

Analytical Data: 1H NMR (400 MHz, DMSO) δ 8.75 (s, 1H), 7.43 (s, 1H), 7.34 (s, 1H), 6.84 (s, 1H), 4.18-4.22 (m, 4H), 3.94 (s, 3H), 3.96 (s, 3H), 3.59 (m, 2H), 3.28-3.31 (t, 2H), 2.08 (brs, 2H).

LCMS: (M+H+): m/Z: 368.1

Synthetic Scheme of Compound 015-MES 4-(6,7-dimethoxyquinazolin-4-yl)-1,4-diazepane-1-sulfonamide methanesulfonate (015-MES)

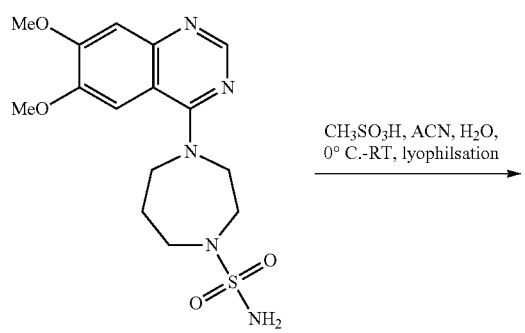

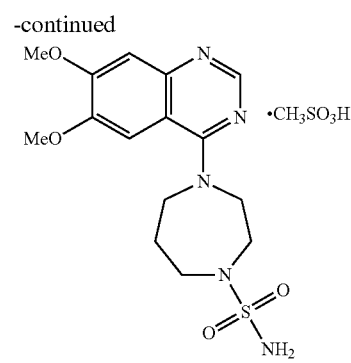

To a stirred solution of 4-(6,7-dimethoxyquinazolin-4-yl)-1,4-diazepane-1-sulfonamide (100 mg, 0.272 mmol) (Compound 015 free base was prepared from the HCl salt by stirring with triethylamine for two hours) in acetonitrile (2 ml) and water was added methane sulfonic acid (26 mg, 0.272 mmol) then reaction mixture kept under lyophilisation for 16 h to afford 4-(6, 7-dimethoxyquinazolin-4-yl)-1, 4-diazepane-1-sulfonamide methane sulfonate (Compound 015-MES) (115 mg, 0.248 mmol, 91% yield) as an off white solid.

Analytical Data: $^1$H NMR (400 MHz, DMSO) δ 14.150 (bs, 1H), 8.699 (s, 1H), 7.401 (s, 1H), 7.183 (s, 1H), 6.819 (s, 1H), 4.141-4.166 (m, 4H), 3.961 (s, 3H), 3.930 (s, 3H), 3.559-3.591 (m, 2H), 3.320 (m, 2H), 2.279 (s, 3H), 2.061-2.103 (m, 2H).

LCMS: (M+H$^+$): m/Z: 368.16.

Synthetic Scheme for Compound 016

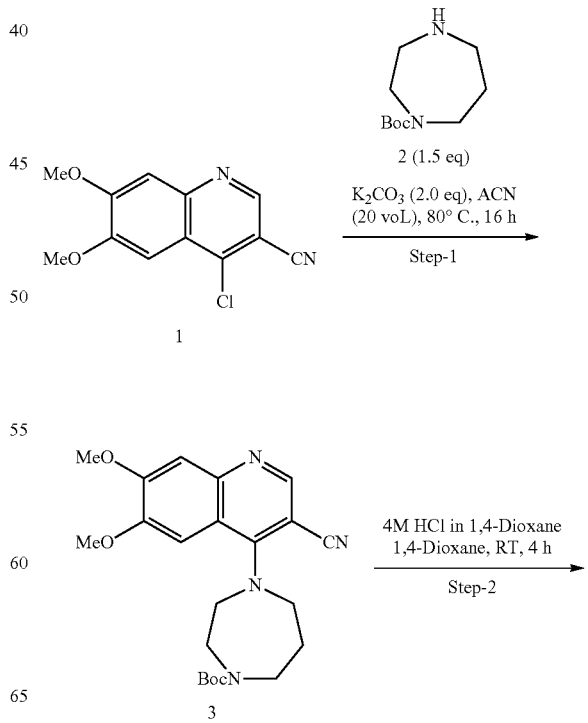

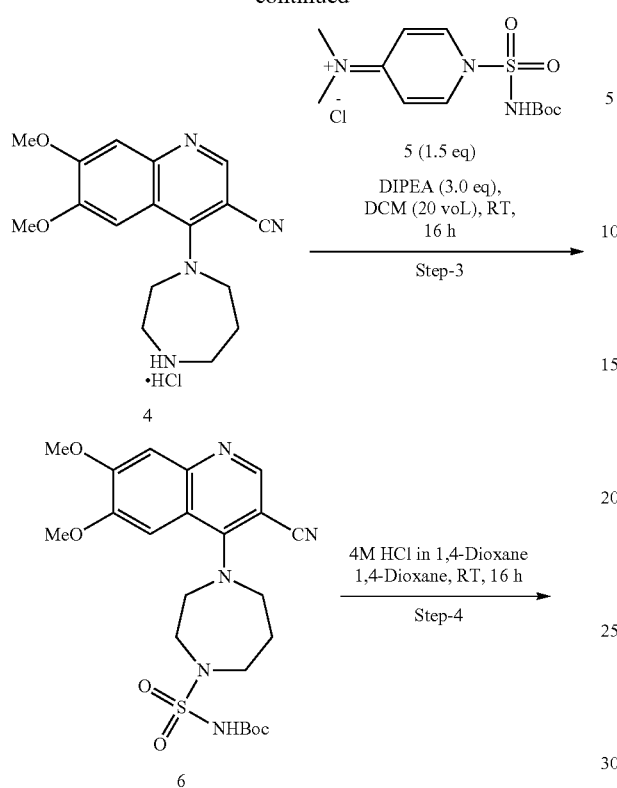

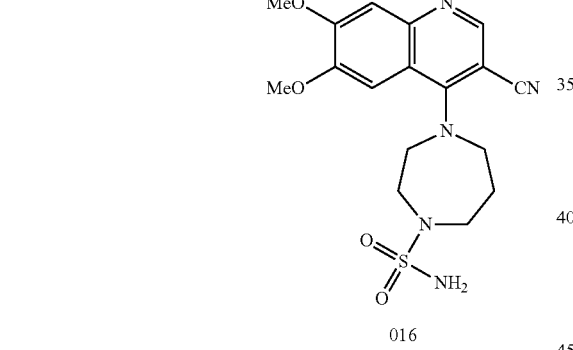

Synthesis of Tert-butyl 4-(3-cyano-6,7-dimethoxy-quinolin-4-yl)-1,4-diazepane-1-carboxylate (3)

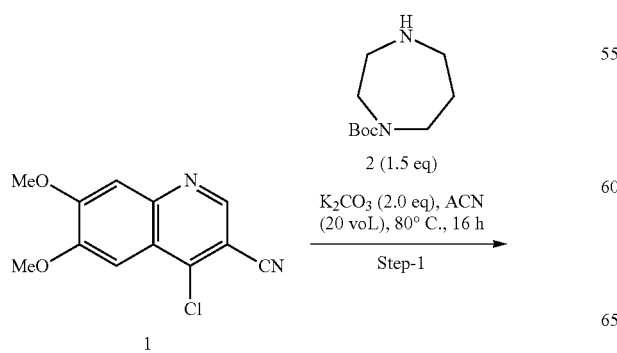

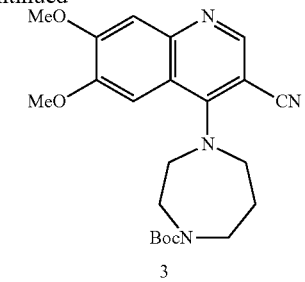

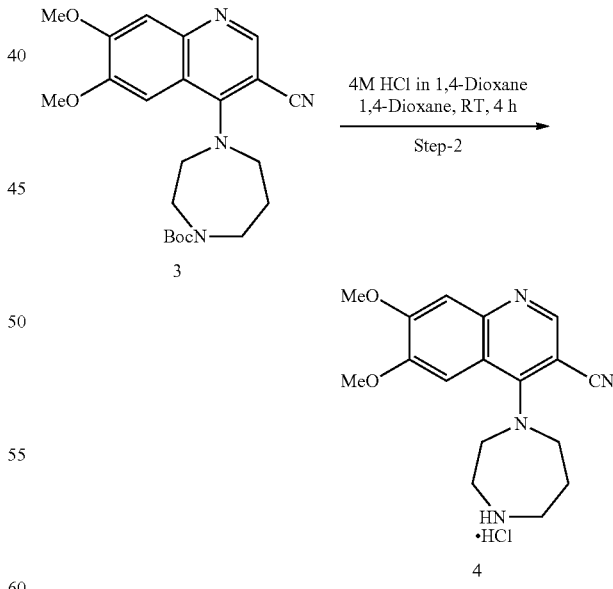

To a stirred solution of 4-chloro-6,7-dimethoxyquinoline-3-carbonitrile 1 (750 mg, 3.0 mmol) in acetonitrile (15 ml) was added potassium carbonate (834 mg, 6.0 mmol) and tert-butyl 1,4-diazepane-1-carboxylate 2 (904 mg, 4.5 mmol) then stirred at 80° C. for 16 h. The progress of the reaction was monitored by TLC. After completion of the reaction, to the reaction mixture added water (100 mL) and extracted with ethyl acetate (2×100 mL). Combined organic layers were washed with brine solution (100 mL), dried over sodium sulfate and concentrated under reduced pressure. Crude compound was purified through combi flash chromatography to afford pure compound of tert-butyl 4-(3-cyano-6,7-dimethoxyquinolin-4-yl)-1,4-diazepane-1-carboxylate (450 mg, 1.09 mmol, 38% yield) as a light yellow solid.

Analytical Data: $^1$H NMR (400 MHz, DMSO) δ 8.67 (s, 1H), 7.39 (s, 1H), 7.31 (s, 1H), 3.94 (s, 6H), 3.59-3.62 (m, 6H), 3.46-3.3.53 (m, 2H), 2.05 (s, 2H), 1.43 (s, 9H).

LCMS: (M+H)$^+$: m/Z: 413.2

Synthesis of 4-(1,4-diazepan-1-yl)-6,7-dimethoxy-quinoline-3-carbonitrile hydrochloride (4)

To a stirred solution of tert-butyl 4-(3-cyano-6,7-dimethoxyquinolin-4-yl)-1,4-diazepane-1-carboxylate 3 (450 mg, 1.09 mmol) in dioxane (2 ml) was added 4M HCl in dioxane (3 mL) at 0° C. then stirred at room temperature for 4 h. The progress of the reaction was monitored by TLC. After completion of the reaction, organic solvents completely distilled off under reduced pressure. To the crude residue was washed with ether to afford 4-(1,4-diazepan-1-yl)-6,7-dimethoxyquinoline-3-carbonitrile hydrochloride 4 (400 mg, 1.28 mmol, 92% yield) as a yellow solid.

LCMS: (M+H)$^+$: m/Z: 313.31

Synthesis of Tert-butyl ((4-(3-cyano-6,7-dimethoxy-quinolin-4-yl)-1,4-diazepan-1-yl)sulfonyl)carbamate (6)

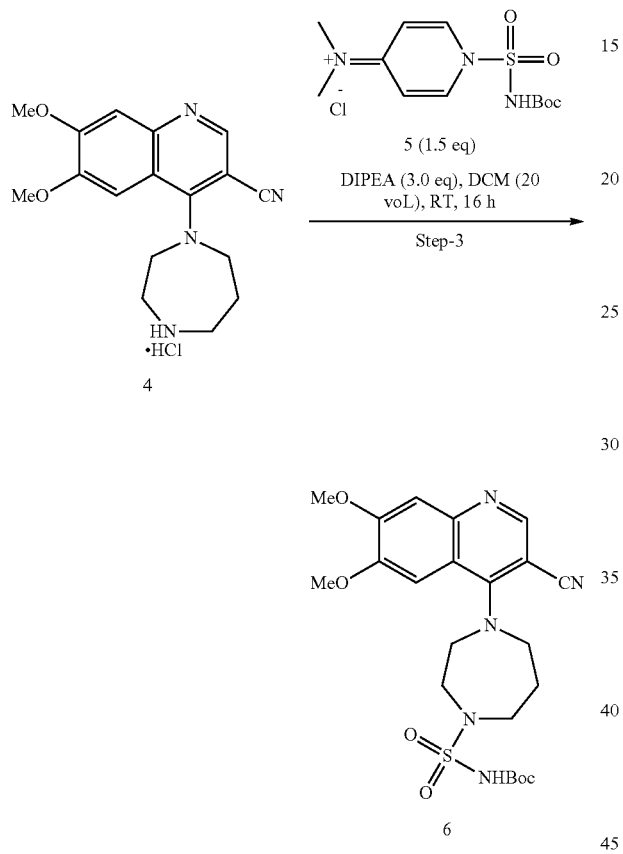

To a stirred solution of 4-(1,4-diazepan-1-yl)-6,7-dimethoxyquinoline-3-carbonitrile hydrochloride (4) (150 mg, 0.48 mmol) in dichloromethane (3 mL) were added diisopropylethylamine (0.25 mL, 1.44 mmol) and N-(1-(N-(tert-butoxycarbonyl)sulfamoyl)pyridin-4(1H)-ylidene)-N-methylmethanaminium 5 (243 mg, 0.72 mmol) at RT, then stirred at room temperature for 16 h. The progress of the reaction was monitored by TLC. After completion of the reaction, organic solvents completely distilled off under reduced pressure to afford crude compound. Crude compound was purified combi flash column chromatography by eluting 60% ethyl acetate in pet-ether to afforded tert-butyl ((4-(3-cyano-6,7-dimethoxyquinolin-4-yl)-1,4-diazepan-1-yl)sulfonyl)carbamate (6) (100 mg, 0.203 mmol, 42% yield) as a yellow solid.

Analytical Data: $^1$HNMR (400 MHz, DMSO) δ 11.07 (s, 1H), 8.69 (S, 1H), 7.39 (s, 1H), 7.34 (s, 1H), 3.92-3.94 (s, 6H), 3.58-3.68 (m, 8H), 2.08 (m, 2H), 1.43 (s, 9H).

LCMS: (M+H)$^+$: m/Z: 492.24

Preparation of Compound 016

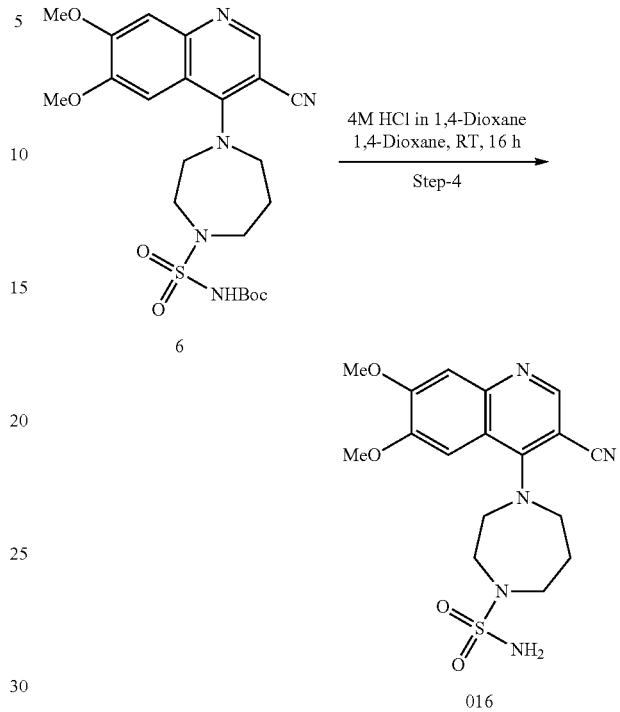

To a stirred solution of tert-butyl ((4-(3-cyano-6,7-dimethoxyquinolin-4-yl)-1,4-diazepan-1-yl)sulfonyl)carbamate (6) (100 mg, 0.203 mmol) in 1,4-dioxane (2.0 mL) was added 4M HCl in dioxane (2.0 mL) at RT. Reaction mixture was stirred at RT for 16 h. The progress of the reaction was monitored by TLC. After completion of the reaction, organic solvents completely distilled off under reduced pressure to afford crude compound. Crude compound was purified through prep HPLC method to afford pure compound of Compound 016 (35 mg, 0.089 mmol, 41% yield) as a pale yellow solid.

Analytical Data: $^1$H NMR (400 MHz, DMSO) δ 8.67 (s, 1H), 7.37 (d, 2H), 6.83 (s, 2H), 3.94 (s, 6H), 3.63-3.67 (m, 4H), 3.44-3.51 (m, 4H), 2.08 (m, 2H).

LCMS: (M+H)$^+$: m/Z: 392.2

Synthetic Scheme for Compound 017

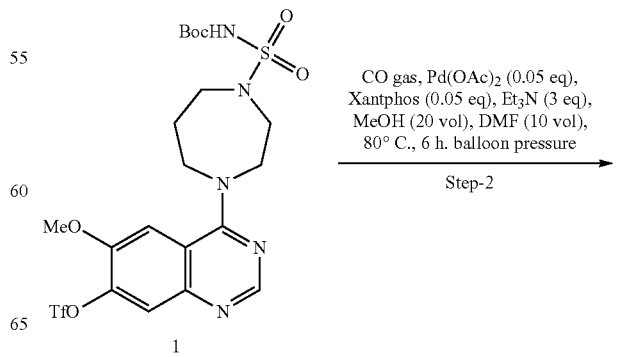

133
-continued

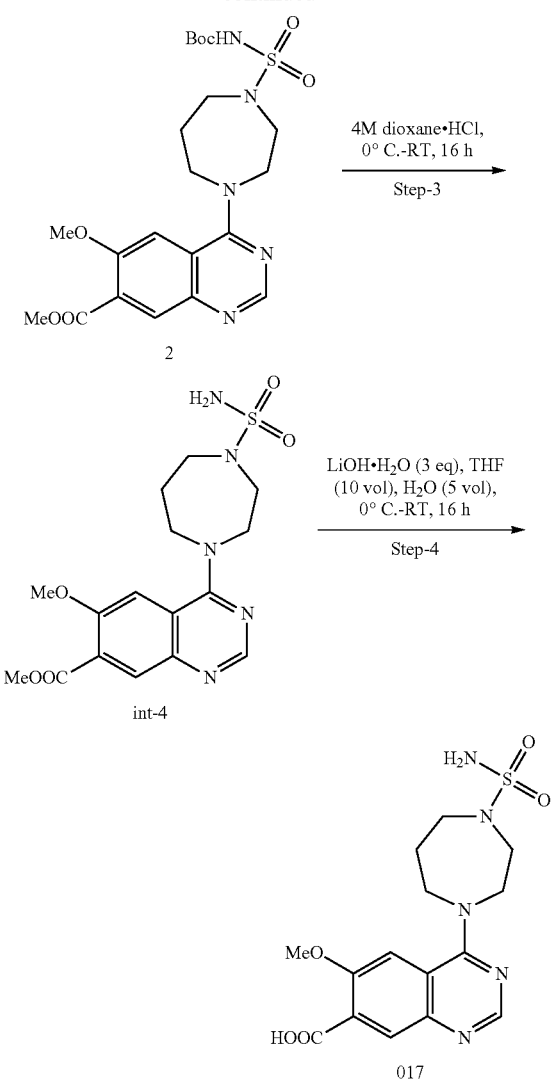

Synthesis of Methyl 4-(4-(N-(tert-butoxycarbonyl) sulfamoyl)-1, 4-diazepan-1-yl)-6-methoxyquinazoline-7-carboxylate (2)

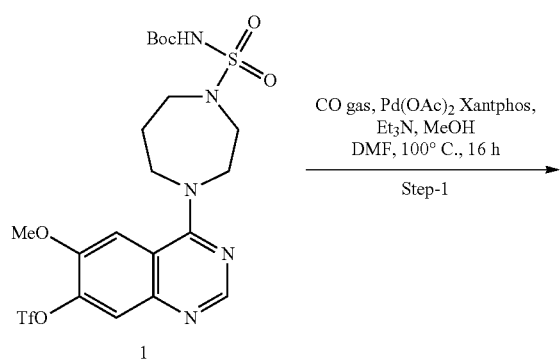

134
-continued

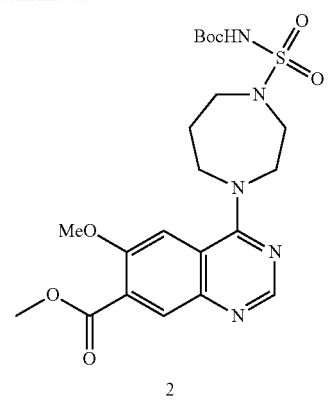

To a stirred solution of 4-(4-(N-(tert-butoxycarbonyl) sulfamoyl)-1, 4-diazepan-1-yl)-6-methoxyquinazolin-7-yl trifluoromethanesulfonate 1 (200 mg, 0.342 mmol) in N, N'-dimethylformamide (2 mL) and methanol (10 mL) were added triethylamine (103.6 mg, 1.026 mmol) was then degassed the reaction mixture for 30 minutes. Then palladium (II) acetate (3.8 mg, 0.017 mmol) and Xantphos (10 mg, 0.017 mmol) were added again degassed for 5 minutes and stirred the reaction mixture under CO gas balloon pressure at 80° C. for 6 h. The progress of the reaction was monitored by TLC. After completion of the reaction, reaction mixture completely distilled off under reduced pressure, to the crude added ethyl acetate (50 mL) and filtered through celite. Washed the celite bed with excess ethyl acetate (50 mL). Then added water (100 mL) and extracted. Organic layer washed with brine solution (100 mL), dried over sodium sulfate and concentrated under reduced pressure. Crude was purified prep HPLC method to afford methyl 4-(4-(N-(tert-butoxycarbonyl) sulfamoyl)-1, 4-diazepan-1-yl)-6-methoxyquinazoline-7-carboxylate (2) (70 mg, 0.141 mmol, 41%) as a brown solid.

Analytical Data: $^1$H NMR (400 MHz, DMSO) δ 8.493 (s, 1H), 7.952 (s, 1H), 7.392 (s, 1H), 4.008-4.024 (m, 4H), 3.938 (s, 3H), 3.865 (s, 3H), 3.691-3.718 (t, 2H), 3.446-3.476 (t, 2H), 2.099 (m, 2H), 1.363 (s, 9H).

Synthesis of Methyl 6-methoxy-4-(4-sulfamoyl-1,4-diazepan-1-yl)quinazoline-7-carboxylate hydrochloride (Int-4)

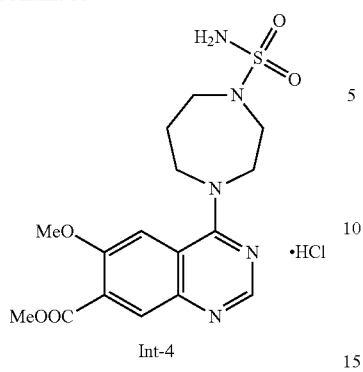

Int-4

A stirred solution of methyl 4-(4-(N-(tert-butoxycarbonyl) sulfamoyl)-1, 4-diazepan-1-yl)-6-methoxyquinazoline-7-carboxylate 2 (70 mg, 0.545 mmol) and 4M HCl in dioxane (4 mL) was stirred at room temperature for 16 h. The progress of the reaction was monitored by TLC. After completion of the reaction, organic solvents completely distilled off under reduced pressure. Crude was purified by trituration with 5% methanol in dichloromethane (5 mL) to afford methyl 6-methoxy-4-(4-sulfamoyl-1, 4-diazepan-1-yl) quinazoline-7-carboxylate hydrochloride Int-4 (55 mg, 0.127 mmol, 90% yield) as an off white solid.

Analytical Data: $^1$H NMR (400 MHz, DMSO) δ 8.486 (s, 1H), 7.948 (s, 1H), 7.406 (s, 1H), 3.990-4.040 (m, 4H), 3.937 (s, 3H), 3.865 (s, 3H), 3.523-3.548 (t, 2H), 3.274-3.293 (t, 2H), 2.103 (m, 2H).

LCMS: (M+H$^+$): m/Z: 396.1

Synthesis of 6-methoxy-4-(4-sulfamoyl-1,4-diazepan-1-yl)quinazoline-7-carboxylic Acid (Compound 017)

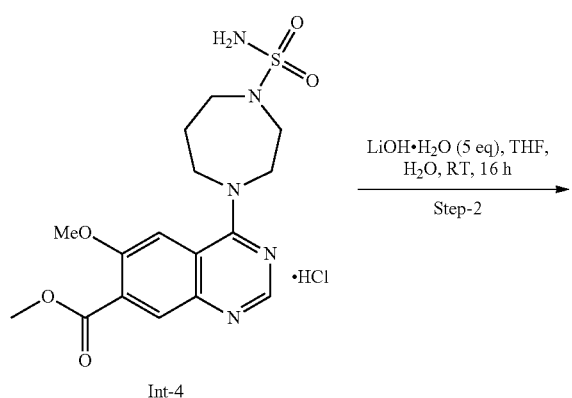

Int-4

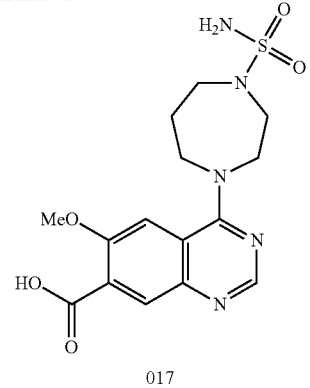

017

To a stirred solution of methyl 6-methoxy-4-(4-sulfamoyl-1,4-diazepan-1-yl)quinazoline-7-carboxylate hydrochloride (Int-4) (55 mg, 0.139 mmol) in tetrahydrofuran (3 ml) and water (1 mL) was added lithium hydroxide monohydrate (29 mg, 0.696 mmol) at 0° C. then stirred at room temperature for 16 h. After completion of the reaction organic solvents distilled off under reduced pressure. To the crude residue added water (20 mL) and acidified with 30% of citric acid solution (10 mL). Then extracted with 10% methanol in dichloromethane (50 mL) and concentrated under reduced pressure to afford crude compound. Crude compound was purified through Prep HPLC method to afford pure compound 6-methoxy-4-(4-sulfamoyl-1,4-diazepan-1-yl)quinazoline-7-carboxylic acid Compound 017 (10 mg, 0.03 mmol, 11% yield) as an off white solid.

Analytical Data: $^1$H NMR (400 MHz, DMSO) δ 13.237 (bs, 1H), 8.470 (s, 1H), 7.848 (bs, 1H), 7.363 (s, 1H), 6.787 (s, 1H), 3.980-4.033 (m, 4H), 3.923 (s, 3H), 3.522-3.547 (t, 2H), 3.280 (t, 2H), 2.072-2.102 (m, 2H).

LCMS: (M+H$^+$): m/Z: 382

Synthetic Scheme for Compound 018

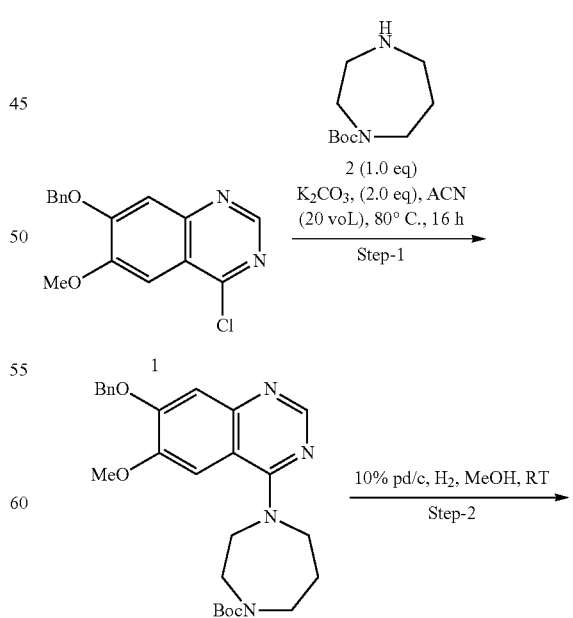

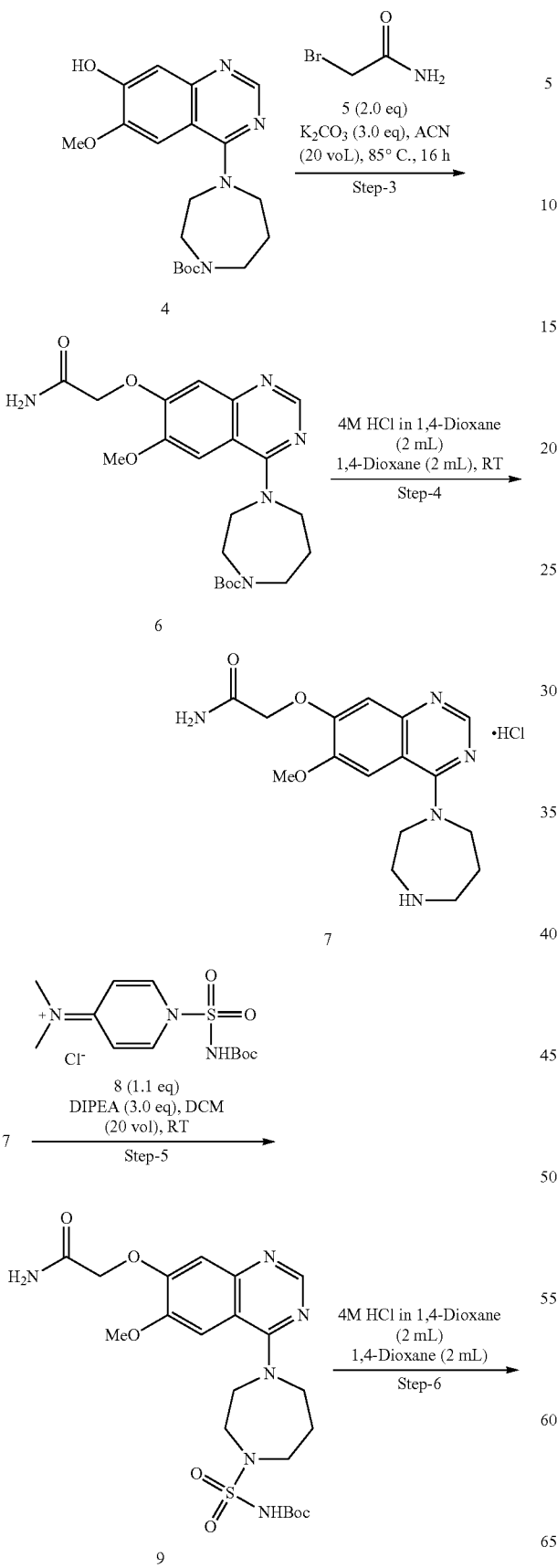
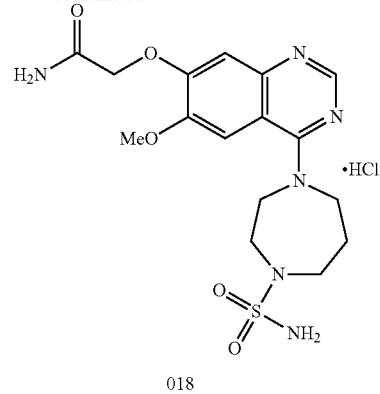
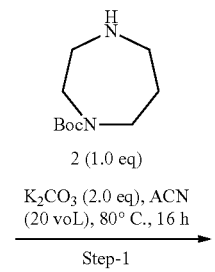
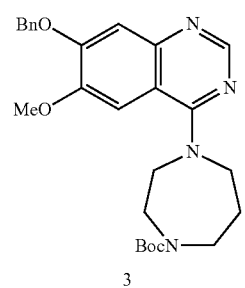

Synthesis of Tert-butyl 4-(7-(benzyloxy)-6-methoxyquinazolin-4-yl)-1,4-diazepane-1-carboxylate (3)

To a stirred solution of 7-(benzyloxy)-4-chloro-6-methoxyquinazoline 1 (250 mg, 0.831 mmol) in acetonitrile (5 ml) were added potassium carbonate (229 mg, 1.66 mmol) and tert-butyl 1,4-diazepane-1-carboxylate 2 (249 mg, 1.24 mmol) then stirred at 80° C. for 16 h. The progress of the reaction was monitored by TLC. After completion of the reaction, to the reaction mixture added water and solid formed. Collect the solid by filtration to afford pure compound of tert-butyl 4-(7-(benzyloxy)-6-methoxyquinazolin-4-yl)-1,4-diazepane-1-carboxylate (3) (380 mg, 0.818 mmol, 98%) as a white solid.

LCMS: (M+H)$^+$: m/Z: 465.3

Tert-butyl 4-(7-hydroxy-6-methoxyquinazolin-4-yl)-1,4-diazepane-1-carboxylate (4)

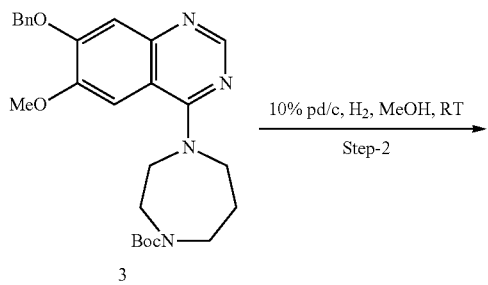

To a stirred solution of tert-butyl 4-(7-(benzyloxy)-6-methoxyquinazolin-4-yl)-1,4-diazepane-1-carboxylate (3) (400 mg, 0.862 mmol) in Methanol (3 mL) and EtOAc (2 mL) were added 10% Pd/C (40 mg) and stirred the reaction mixture under balloon hydrogen atmosphere at room temperature for 6 h. The progress of the reaction was monitored by TLC. After completion of the reaction, reaction mixture filtered through celite and washed the celite bed with 5% methanol in dichloromethane (50 mL). Filtrate was concentrated under reduced pressure to afforded tert-butyl 4-(7-hydroxy-6-methoxyquinazolin-4-yl)-1,4-diazepane-1-carboxylate (4) (300 mg, 0.802 mmol, 98% yield) as a light blue solid.

LCMS: (M+H$^+$): m/Z: 375.2

Synthesis of Tert-butyl 4-(7-(2-amino-2-oxoethoxy)-6-methoxyquinazolin-4-yl)-1,4-diazepane-1-carboxylate (6)

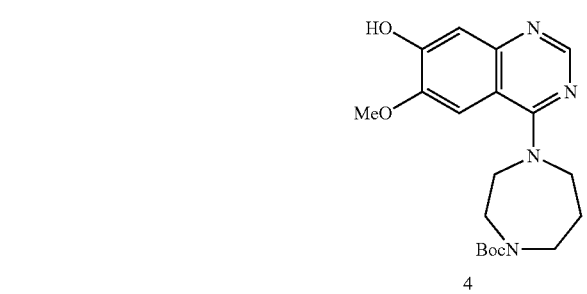

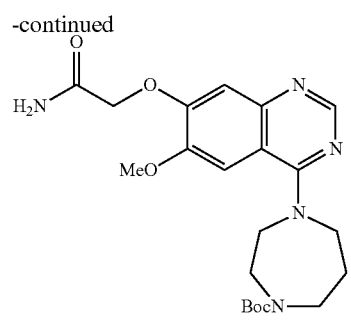

To a stirred solution of tert-butyl 4-(7-hydroxy-6-methoxyquinazolin-4-yl)-1,4-diazepane-1-carboxylate 4 (250 mg, 0.668 mmol) in acetonitrile (5 mL) were added potassium carbonate (276 mg, 2.0 mmol) and 2-bromoacetamide 5 (184 mg, 1.33 mmol) then stirred at 80° C. for 16 h. The progress of the reaction was monitored by TLC. After completion of the reaction, to the reaction mixture added water (100 mL) and extracted with ethyl acetate (2×100 mL). Combined organic layers were washed with brine solution (100 mL), dried over sodium sulfate and concentrated under reduced pressure. Crude compound was purified through combi flash chromatography to afford pure compound of tert-butyl 4-(7-(2-amino-2-oxoethoxy)-6-methoxyquinazolin-4-yl)-1,4-diazepane-1-carboxylate 6 (200 mg, 0.462 mmol, 71% yield) as a light brown syrup.

LCMS: (M+H$^+$): m/Z: 432.3

Synthesis of 2-((4-(1,4-diazepan-1-yl)-6-methoxyquinazolin-7-yl)oxy)acetamide hydrochloride (7)

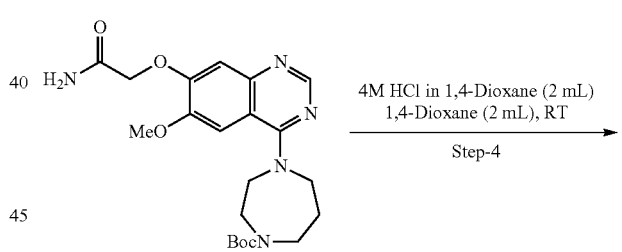

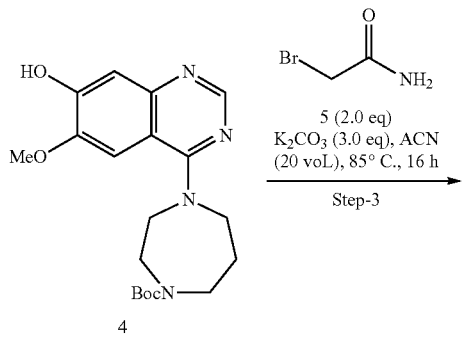

To a stirred solution of tert-butyl 4-(7-(2-amino-2-oxoethoxy)-6-methoxyquinazolin-4-yl)-1,4-diazepane-1-carboxylate 6 (200 mg, 0.462 mmol) in dioxane (1 ml) was added 4M HCl in dioxane (2 mL) at 0° C. then stirred at room temperature for 2 h. The progress of the reaction was monitored by TLC. After completion of the reaction, organic solvents completely distilled off under reduced pressure. To the crude residue was washed with ether to afford 2-((4-(1,4-diazepan-1-yl)-6-methoxyquinazolin-7-yl)oxy)acetamide hydrochloride 7 (150 mg, 0.451 mmol, 88% yield) as a yellow solid.

Analytical Data: $^1$H NMR (400 MHz, DMSO) δ 9.23 (br s, 1H), 8.77 (s, 1H), 7.46-7.47 (m, 1H), 7.01-7.26 (m, 2H), 4.74 (s, 3H), 4.19-4.26 (m, 4H), 3.94 (s, 3H), 3.71 (d, 2H), 3.45 (m, 2H), 3.18-3.3.19 (m, 2H), 2.24 (m, 2H).

Synthesis of Tert-butyl ((4-(7-(2-amino-2-oxoethoxy)-6-methoxyquinazolin-4-yl)-1,4-diazepan-1-yl)sulfonyl)carbamate (8)

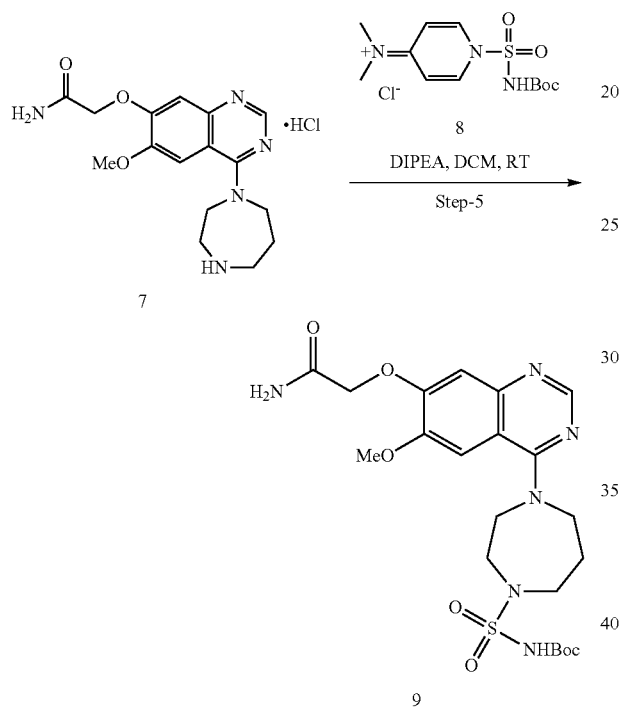

To a stirred solution of 2-((4-(1,4-diazepan-1-yl)-6-methoxyquinazolin-7-yl)oxy)acetamide hydrochloride (7) (150 mg, 0.451 mmol) in dichloromethane (3 mL) was added diisopropylethylamine (0.24 mL, 1.36 mmol) and N-(1-(N-(tert-butoxycarbonyl)sulfamoyl)pyridin-4(1H)-ylidene)-N-methylmethanaminium 5 (168 mg, 0.49 mmol) at RT, then stirred at room temperature for 16 h. The progress of the reaction was monitored by TLC. After completion of the reaction, organic solvents completely distilled off under reduced pressure to afford crude compound. Crude compound was purified combi flash column chromatography by eluting 60% ethyl acetate in pet-ether to afford tert-butyl ((4-(7-(2-amino-2-oxoethoxy)-6-methoxyquinazolin-4-yl)-1,4-diazepan-1-yl)sulfonyl)carbamate (9) (150 mg, 0.294 mmol, 65% yield) as a yellow solid.

LCMS: (M+H)$^+$: m/Z: 511.2

Synthesis of Compound 018

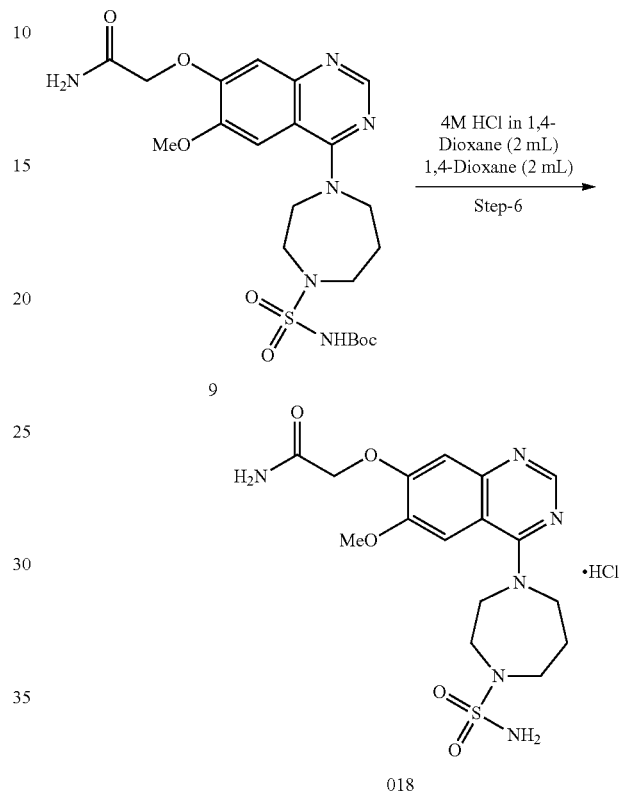

To a stirred solution of tert-butyl ((4-(7-(2-amino-2-oxoethoxy)-6-methoxyquinazolin-4-yl)-1,4-diazepan-1-yl)sulfonyl)carbamate (9) (150 mg, 0.294 mmol) in 1,4-dioxane (1.0 mL) was added 4M HCl in dioxane (2.0 mL) at RT. Reaction mixture was stirred at RT for 16 h. The progress of the reaction was monitored by TLC. After completion of the reaction, organic solvents completely distilled off under reduced pressure to afford crude compound. Crude compound was purified through prep HPLC method to afford pure compound of Compound 018 (15 mg, 0.036 mmol, 12% yield) as an Off-white solid.

Analytical Data: $^1$H NMR (400 MHz, DMSO) δ 8.39 (s, 1H), 7.42-7.47 (dd, 2H), 7.26 (s, 1H), 7.03 (s, 1H), 6.77 (s, 1H), 4.63 (s, 2H), 3.91-3.97 (m, 7H), 3.48-3.51 (m, 2H), 3.24-3.27 (m, 3H), 2.05-2.08 (m, 2H).

LCMS: (M+H)$^+$: m/Z: 411.1

Synthetic Scheme for Compounds 019, 020, 021, and 022

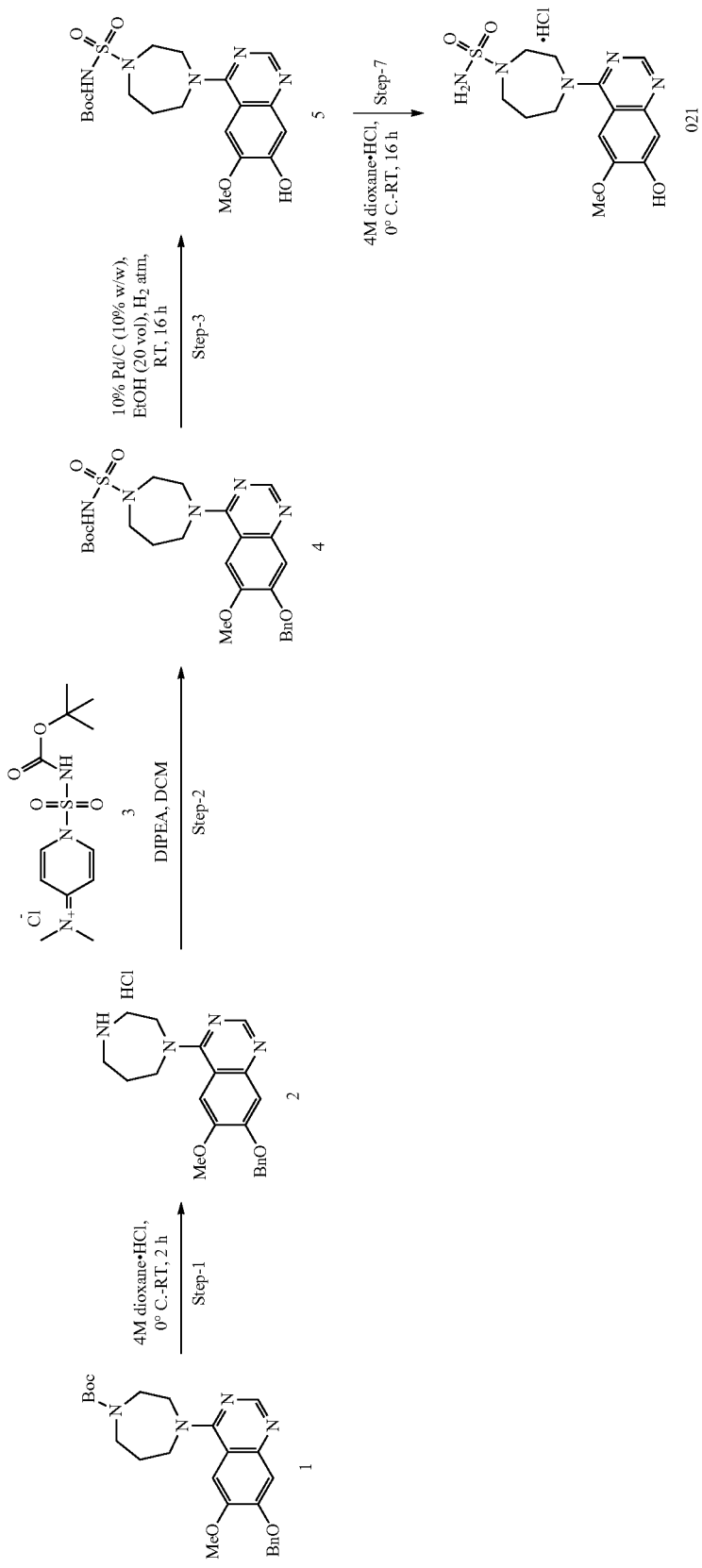

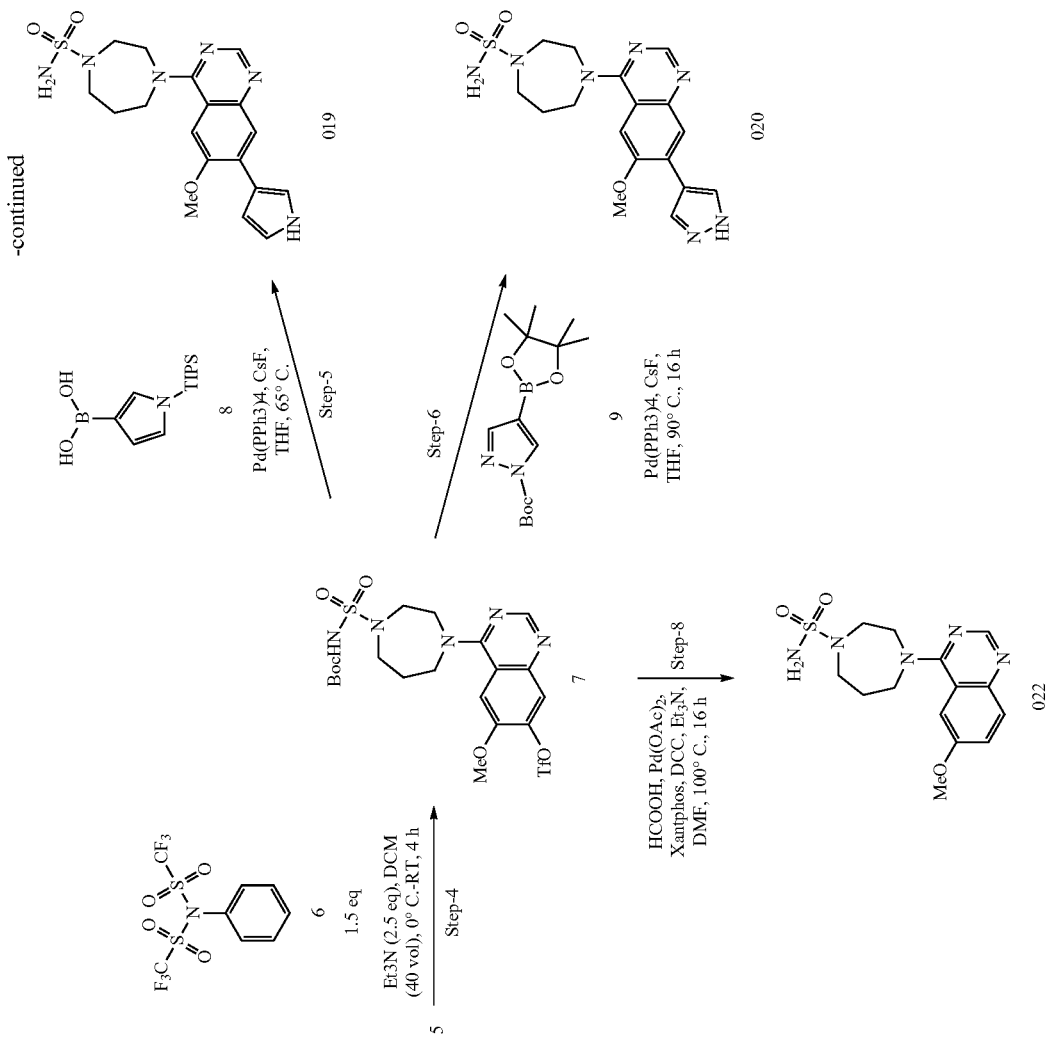

Synthesis of 7-(benzyloxy)-4-(1,4-diazepan-1-yl)-6-methoxyquinazoline hydrochloride (2)

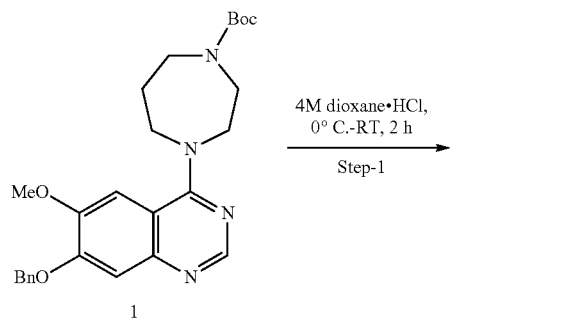

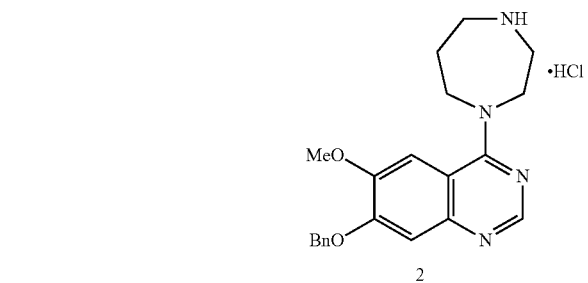

A stirred solution of tert-butyl 4-(7-(benzyloxy)-6-methoxyquinazolin-4-yl)-1,4-diazepane-1-carboxylate 1 (1 g, 2.155 mmol) and 4M HCl in dioxane (10 mL) was stirred at room temperature for 1 h. The progress of the reaction was monitored by TLC. After completion of the reaction, organic solvents completely distilled off under reduced pressure. Crude was purified by trituration with pentane (50 mL) to afford 7-(benzyloxy)-4-(1,4-diazepan-1-yl)-6-methoxyquinazoline hydrochloride 2 (600 mg, 1.5 mmol, 70% yield) as an off white solid.

Analytical Data:

LCMS: (M+H$^+$): m/Z: 365.2

Synthesis of Tert-butyl ((4-(7-(benzyloxy)-6-methoxyquinazolin-4-yl)-1,4-diazepan-1-yl)sulfonyl)carbamate (6)

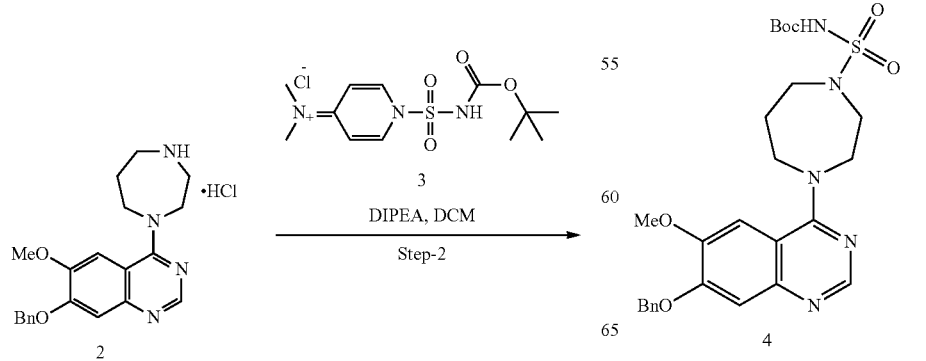

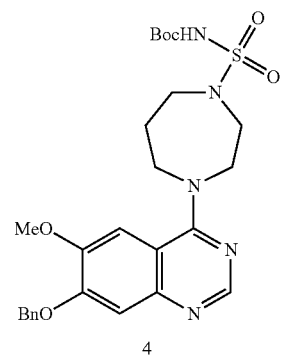

To a stirred solution of 7-(benzyloxy)-4-(1,4-diazepan-1-yl)-6-methoxyquinazoline hydrochloride 2 (1 g, 2.497 mmol) in dichloromethane (20 mL) was added diisopropylethylamine (805 mg, 6.242 mmol) and N-(1-(N-(tert-butoxycarbonyl)sulfamoyl)pyridin-4(1H)-ylidene)-N-methylmethanaminium 3 (841 mg, 2.497 mmol) at 0° C. then stirred at room temperature for 16 h. The progress of the reaction was monitored by TLC. After completion of the reaction, reaction mixture completely distilled off under reduced pressure to afford crude compound. Crude was purified through 100-200 silica gel column chromatography by eluting 5% methanol in dichloromethane to afford semi pure compound. This semi pure was again purified by trituration with 50% ethyl acetate in pet ether to afford tert-butyl ((4-(7-(benzyloxy)-6-methoxyquinazolin-4-yl)-1,4-diazepan-1-yl)sulfonyl)carbamate 4 (1.2 g, 2.21 mmol, 89% yield) as an off white solid.

Analytical Data: LCMS: (M+H$^+$): m/Z: 544.15

Synthesis of Tert-butyl ((4-(7-hydroxy-6-methoxyquinazolin-4-yl)-1,4-diazepan-1-yl)sulfonyl)carbamate (5)

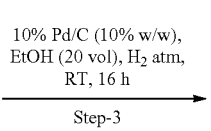

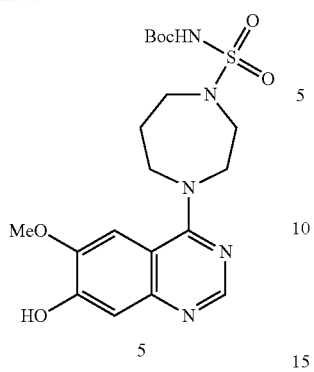
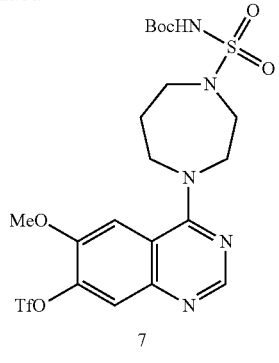

To a stirred solution of tert-butyl ((4-(7-(benzyloxy)-6-methoxyquinazolin-4-yl)-1,4-diazepan-1-yl)sulfonyl)carbamate 4 (1.2 g, 2.21 mmol) in ethanol (30 mL) was added 10% Pd/C (200 mg) and stirred the reaction mixture under balloon hydrogen atmosphere at room temperature for 16 h. The progress of the reaction was monitored by TLC. After completion, reaction mixture filtered through celite and washed the celite bed with 5% methanol in dichloromethane (100 mL). Filtrate was concentrated under reduced pressure to afford semi pure compound of tert-butyl ((4-(7-hydroxy-6-methoxyquinazolin-4-yl)-1,4-diazepan-1-yl)sulfonyl)carbamate (5) (1.1 g, crude) as an off white solid.

Analytical Data: $^1$H NMR (400 MHz, DMSO) δ 10.341 (bs, 1H), 8.345 (s, 1H), 7.205 (s, 1H), 7.027 (s, 1H), 4.330-4.356 (t, 2H), 3.890-3.924 (m, 5H), 3.661 (t, 2H), 2.054-2.061 (m, 1H), 1.247-1.366 (m, 9H).

Synthesis of 4-(4-(N-(tert-butoxycarbonyl) sulfamoyl)-1, 4-diazepan-1-yl)-6-methoxyquinazolin-7-yl trifluoromethanesulfonate (7)

To a stirred solution of tert-butyl ((4-(7-hydroxy-6-methoxyquinazolin-4-yl)-1,4-diazepan-1-yl)sulfonyl)carbamate 5 (1.1 g, 2.428 mmol) in dichloromethane (15 mL) was added triethylamine (0.85 mL, 6.07 mmol) and 1,1,1-trifluoro-N-phenyl-N-((trifluoromethyl)sulfonyl)methanesulfonamide 6 (1.3 g, 3.642 mmol) at 0° C. then stirred at room temperature 4 h. The progress of the reaction was monitored by TLC. After completion of the reaction, organic solvents completely distilled off under reduced pressure and water (200 mL) was added to the crude and partitioned with dichloromethane (2×200 mL). Combined organic layers were washed with brine solution (200 mL), dried over sodium sulfate and concentrated under reduced pressure. Crude was purified by combi-flash chromatography by eluting 70% ethyl acetate in pet ether to afford 4-(4-(N-(tert-butoxycarbonyl) sulfamoyl)-1, 4-diazepan-1-yl)-6-methoxyquinazolin-7-yl trifluoromethanesulfonate 7 (750 mg, 1.282 mmol, 58% yield over two steps) as an off white solid.

Analytical Data: $^1$H NMR (400 MHz, DMSO) δ 11.021 (s, 1H), 8.514 (s, 1H), 7.847 (s, 1H), 7.566 (s, 1H), 3.990-4.031 (m, 8H), 3.707 (s, 2H), 3.443 (s, 2H), 2.080 (bs, 2H), 1.342 (s, 9H).

Synthesis of 4-(6-methoxy-7-(1H-pyrrol-3-yl)quinazolin-4-yl)-1,4-diazepane-1-sulfonamide (Compound 019)

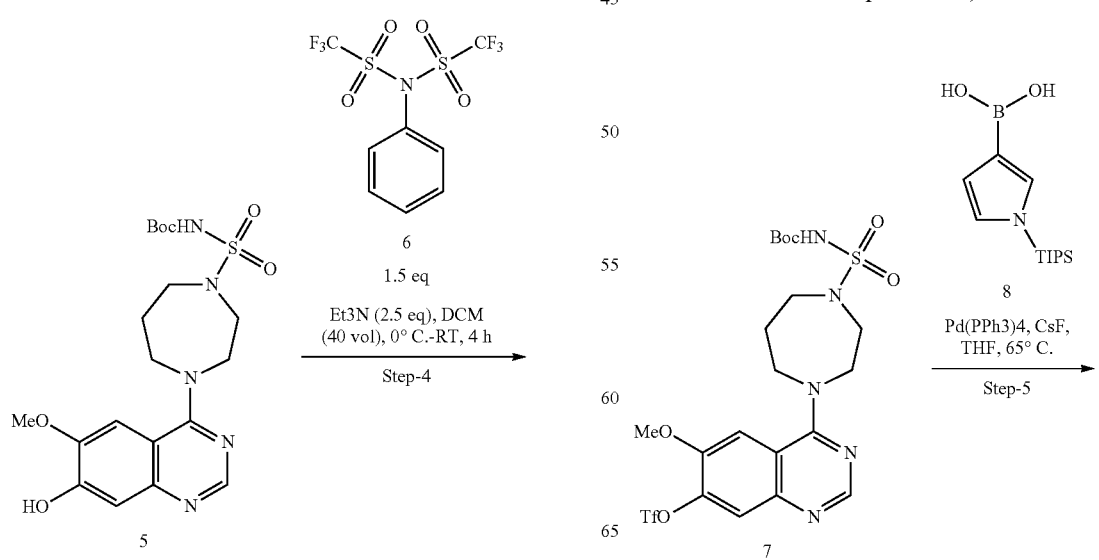

-continued

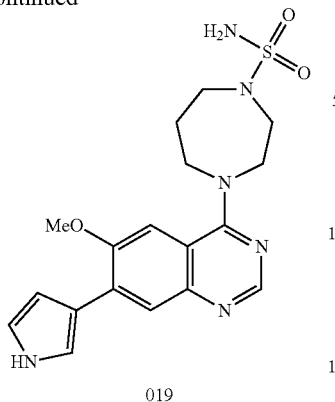

019

In a sealed tube, to the stirred solution of 4-(4-(N-(tert-butoxycarbonyl) sulfamoyl)-1, 4-diazepan-1-yl)-6-methoxyquinazolin-7-yl trifluoromethanesulfonate 7 (200 mg, 0.342 mmol) in dioxane (7 mL) and water (2 mL) were added (1-(triisopropylsilyl)-1H-pyrrol-3-yl)boronic acid (119 mg, 0.446 mmol) and cesium fluoride (104 mg, 0.684 mmol) was then degassed the reaction mixture for 30 minutes. Then tetrakis(triphenylphosphine)palladium(0) (20 mg, 0.0017 mmol) was added again degassed for 5 minutes and stirred the reaction mixture at 65° C. for 3 h. The progress of the reaction was monitored by TLC. After completion of the reaction, reaction mixture was poured into water (100 mL) and filtered through celite. Washed the celite bed with 10% methanol in dichloromethane (100 mL) and separated the two layers. Organic layer washed with brine solution (200 mL), dried over sodium sulfate and concentrated under reduced pressure. Crude was purified prep HPLC method to afford 4-(6-methoxy-7-(1H-pyrrol-3-yl)quinazolin-4-yl)-1,4-diazepane-1-sulfonamide (Compound 019) (30 mg, 0.074 mmol, 22%) as a brown solid.

Analytical Data: $^1$H NMR (400 MHz, DMSO) δ 10.984 (s, 1H), 8.332 (s, 1H), 8.180 (s, 1H), 7.832 (s, 1H), 7.493 (s, 1H), 7.288 (s, 1H), 6.833 (s, 1H), 6.650 (s, 1H), 3.838 (m, 8H), 3.499 (t, 2H), 3.251-3.277 (t, 2H), 2.068 (m, 2H).

LCMS: (M+H$^+$): m/Z: 403.1

Synthetic Scheme for Compounds 023, 024 and 025

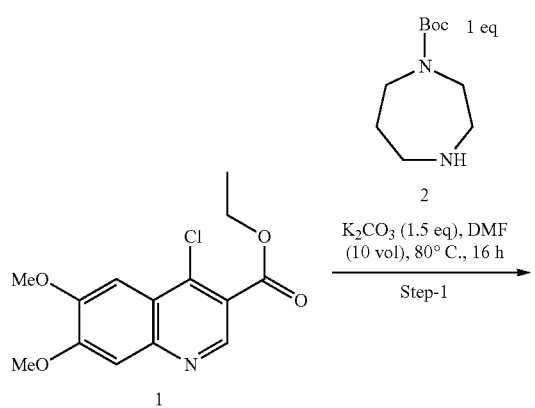

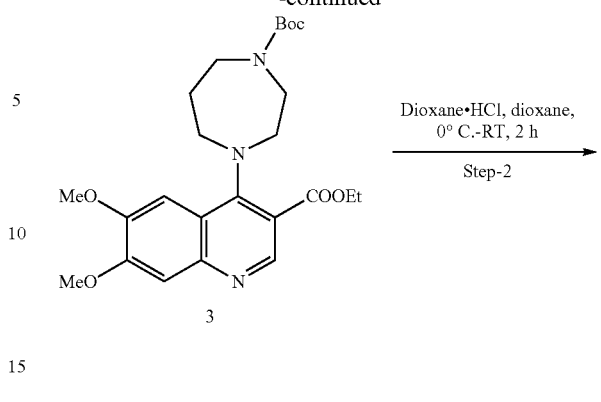

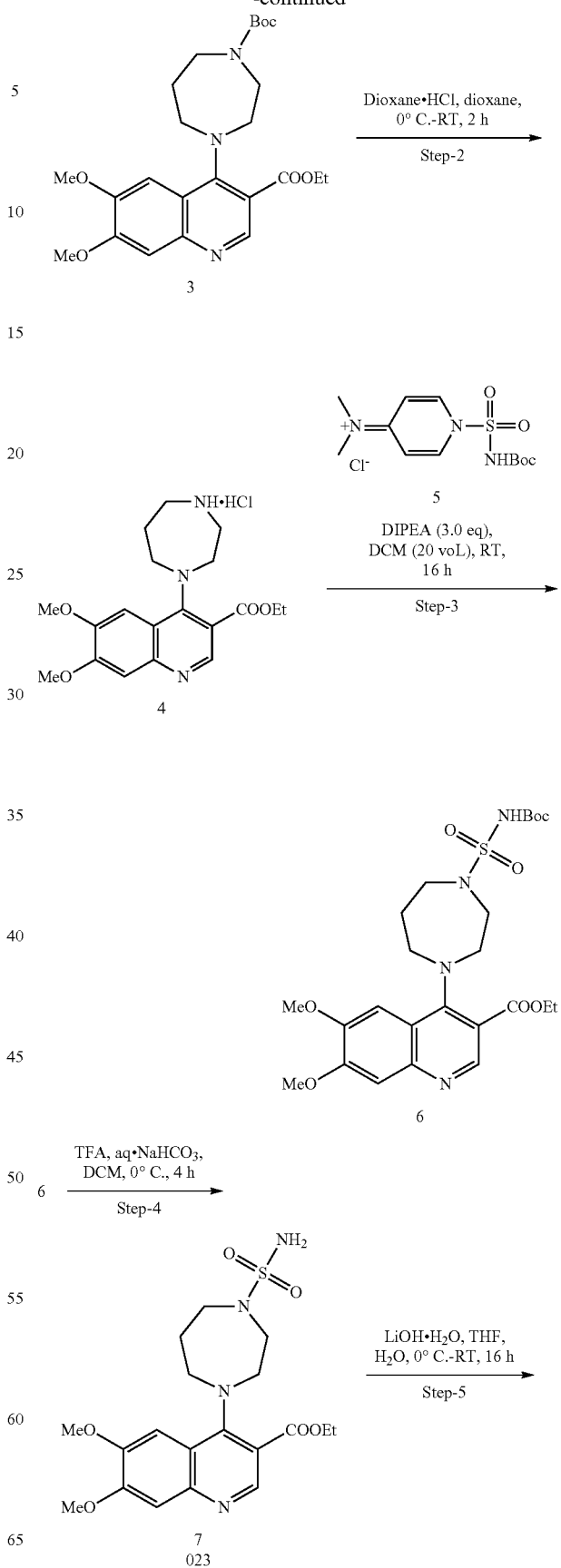

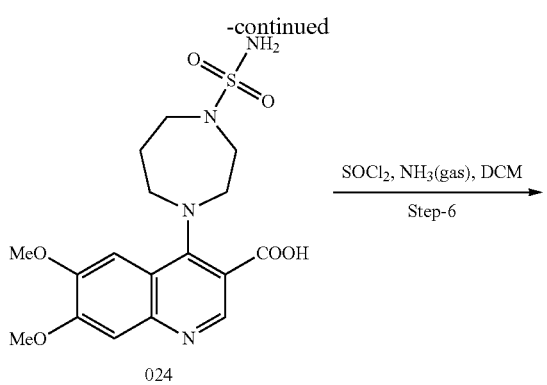

024

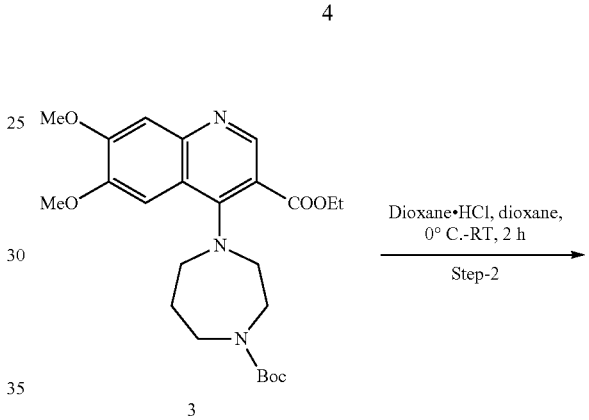

025

Step-1: Synthesis of ethyl 4-(4-(tert-butoxycarbonyl)-1,4-diazepan-1-yl)-6,7-dimethoxyquinoline-3-carboxylate 3

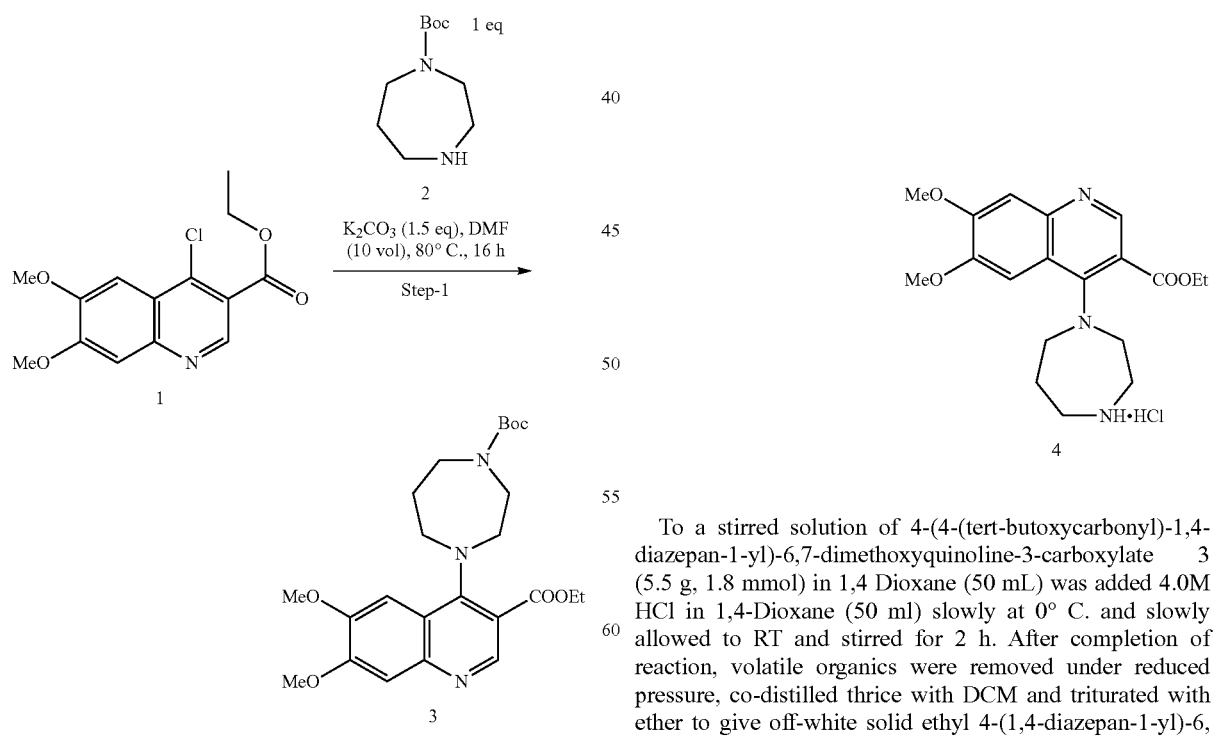

To a stirred solution of ethyl 4-chloro-6,7-dimethoxyquinoline-3-carboxylate 1 (4.2 g, 4.2 mmol) in DMF (40 mL) was added tert-butyl 1,4-diazepane-1-carboxylate (4.2 ml, 4.2 mmol) and K₂CO₃ (3.9 g, 28 mmol) then heated to 80° C. for refluxed for 16 h. The progress of the reaction was monitored by TLC. After completion of reaction, reaction mixture was directly poured on to ice cold water and stirred. Solid precipitated out was filtered and washed again with water and dried without necessity of any further purification to afford ethyl 4-(4-(tert-butoxycarbonyl)-1,4-diazepan-1-yl)-6,7-dimethoxyquinoline-3-carboxylate 3 (5.5 g) as a light yellow solid.

Analytical Data: $^1$H NMR (400 MHz, DMSO): 8.68 (s, 1H), 7.43 (s, 1H), 7.37 (s, 1H), 4.34 (q, 2H), 3.93 (s, 6H), 3.59-3.54 (m, 4H), 3.26-3.19 (m, 4H), 1.97-1.92 (m, 2H), 1.43-1.32 (m, 11H).

LCMS: (M+H)$^+$: m/Z: 247.1

Step-2: Synthesis of ethyl 4-(1,4-diazepan-1-yl)-6,7-dimethoxyquinoline-3-carboxylate hydrochloride 4

To a stirred solution of 4-(4-(tert-butoxycarbonyl)-1,4-diazepan-1-yl)-6,7-dimethoxyquinoline-3-carboxylate 3 (5.5 g, 1.8 mmol) in 1,4 Dioxane (50 mL) was added 4.0M HCl in 1,4-Dioxane (50 ml) slowly at 0° C. and slowly allowed to RT and stirred for 2 h. After completion of reaction, volatile organics were removed under reduced pressure, co-distilled thrice with DCM and triturated with ether to give off-white solid ethyl 4-(1,4-diazepan-1-yl)-6,7-dimethoxyquinoline-3-carboxylate hydrochloride 4 (4.2 g). The progress of the reaction was monitored by TLC.

Analytical Data: LCMS: (M+H)$^+$: m/Z: 360

Step-3: ethyl 4-(4-(N-(tert-butoxycarbonyl)sulfamoyl)-1,4-diazepan-1-yl)-6,7-dimethoxyquinoline-3-carboxylate 6

Step-4: Synthesis of ethyl 6,7-dimethoxy-4-(4-sulfamoyl-1,4-diazepan-1-yl)quinoline-3-carboxylate 7 (compound 023)

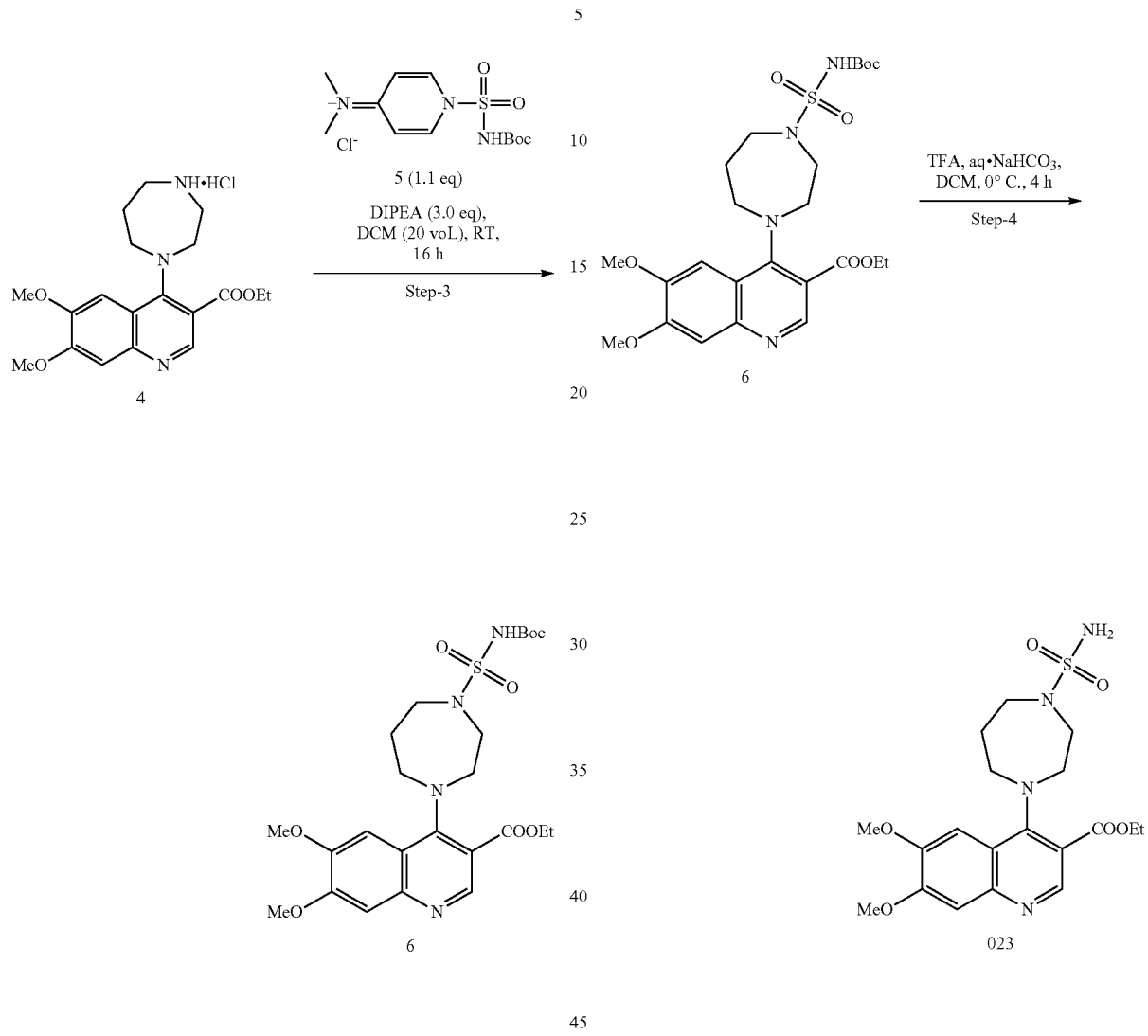

To a stirred solution of 4-((4-aminobutyl)thio)-6,7-dimethoxyquinoline-3-carbonitrile 4 (2 g, 5.56 mmol) in DCM (30 mL) was added N-(1-(N-(tert-butoxycarbonyl)sulfamoyl)pyridin-4(1H)-ylidene)-N-methylmethanaminium chloride 5 (2.06 g, 6.1 mmol) slowly and then added DIPEA (2.68 ml, 0.375 mmol) at same temperature. Then stirred the reaction mixture at room temperature for 16 h. The progress of the reaction was monitored by TLC. Reaction mixture was directly absorbed on to silica and converted into slurry. Crude was purified through combi-flash chromatography by eluting 90% EtOAc in Hexane to afford ethyl 4-(4-(N-(tert-butoxycarbonyl)sulfamoyl)-1,4-diazepan-1-yl)-6,7-dimethoxyquinoline-3-carboxylate 6 (1.1 g) as a white solid.

Analytical Data: $^1$H NMR (400 MHz, DMSO): 8.72 (s, 1H), 7.49 (s, 1H), 7.37 (s, 1H), 4.36 (q, 2H), 3.93 (s, 6H), 3.59-3.52 (m, 4H), 3.22-3.09 (m, 4H), 1.97-1.96 (m, 2H), 1.47 (s, 9H), 1.36 (t, 3H).

LCMS: (M+H)$^+$: m/Z: 539.2

To a stirred solution of ethyl 4-(4-(N-(tert-butoxycarbonyl)sulfamoyl)-1,4-diazepan-1-yl)-6,7-dimethoxyquinoline-3-carboxylate 7 (300 mg, 0.56 mmol) in dichloromethane (3 ml) was added TFA (3 mL) at 0° C., then stirred at same temperature for 4 h. The progress of the reaction was monitored by TLC. After completion of reaction, TFA was neutralized by using aq.NaHCO$_3$, and extracted with 10% MeOH/DCM and dried and concentrated. Obtained solid was triturated to give ethyl 6,7-dimethoxy-4-(4-sulfamoyl-1,4-diazepan-1-yl)quinoline-3-carboxylate 7 Compound 023 (250 mg) as pale yellow solid.

Analytical Data: $^1$H NMR (400 MHz, DMSO) δ: 8.72 (s, 1H), 7.54 (s, 1H), 7.37 (s, 1H), 6.79 (s, 2H), 4.36 (q, 2H), 3.93 (s, 6H), 3.44-3.43 (m, 4H), 3.42-3.33 (m, 4H), 1.97-1.96 (m, 2H), 1.36 (t, 3H).

LCMS: (M+H)$^+$: m/Z: 439.2

Step-5: Synthesis of 6,7-dimethoxy-4-(4-sulfamoyl-1,4-diazepan-1-yl)quinoline-3-carboxylic acid Compound 024

Step-6: Synthesis of 6,7-dimethoxy-4-(4-sulfamoyl-1,4-diazepan-1-yl)quinoline-3-carboxamide Compound 025

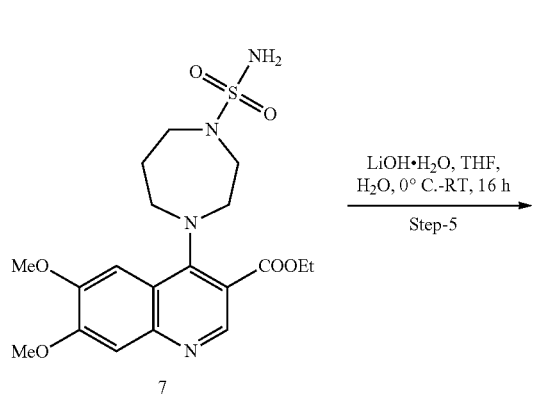
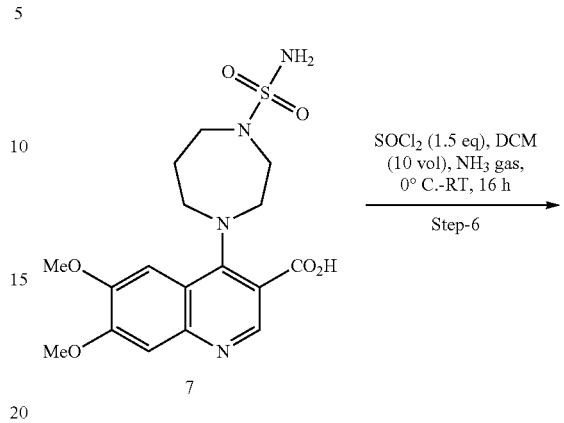
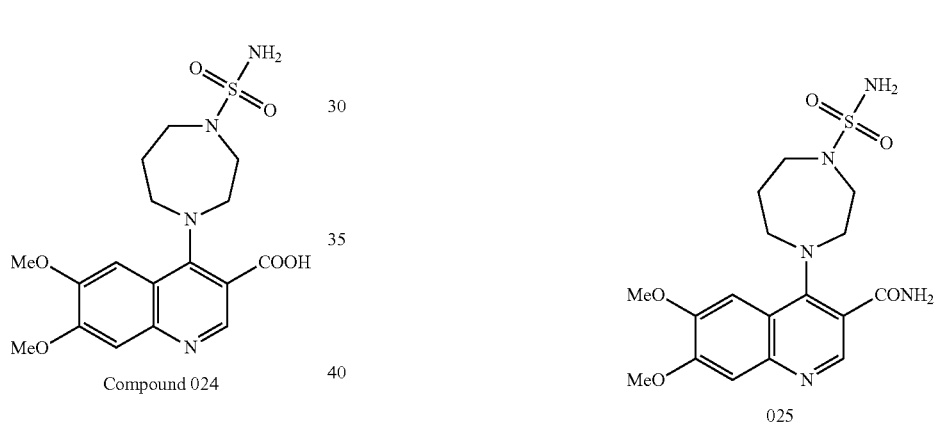

To a stirred solution of ethyl 6,7-dimethoxy-4-(4-sulfamoyl-1,4-diazepan-1-yl)quinoline-3-carboxylate 1 (250 mg, 0.57 mmol) in THF:H$_2$O (3:1) was added LiOH (119 mg, 2.85 mmol) at RT. After addition, the reaction mixture was allowed to stir at RT for 16 h. The progress of the reaction was monitored by TLC. After completion of reaction, volatile organics were evaporated and triturated with ether to give 169 mg of 6,7-dimethoxy-4-(4-sulfamoyl-1,4-diazepan-1-yl)quinoline-3-carboxylic acid 7. 69 mg of 7 was submitted for prep-HPLC. After HPLC purification, 6,7-dimethoxy-4-(4-sulfamoyl-1,4-diazepan-1-yl)quinoline-3-carboxylic acid Compound 024 (26 mg) was obtained as a pale yellow solid.

Analytical Data: $^1$H NMR (400 MHz, DMSO) δ: 13.36 (brs, 1H), 8.74 (s, 1H), 7.53 (s, 1H), 7.35 (s, 1H), 6.79 (s, 1H), 3.93 (s, 6H), 3.45-3.38 (m, 8H), 1.95 (brs, 2H).
LCMS: (M+H)$^+$: m/Z: 411.2

To a stirred solution of 6,7-dimethoxy-4-(4-sulfamoyl-1,4-diazepan-1-yl)quinoline-3-carboxylic acid 1 (100 mg, 0.24 mmol) in THF (3 ml) was added SOCl$_2$ (0.026 ml, 0.36 mmol) at 0° C. After 1 h, the reaction mixture was purged with NH$_3$ (gas) at same temperature for 10 min and allowed to stir at RT for 16 h. The progress of the reaction was monitored by TLC. After completion of reaction, Precipitate in the in the reaction mixture was washed with 10% MeOH/DCM and filtrate was dried and reduced to give crude about 85 mg. After HPLC purification, 6,7-dimethoxy-4-(4-sulfamoyl-1,4-diazepan-1-yl)quinoline-3-carboxamide Compound 025 (9 mg) was obtained as a pale yellow solid.

Analytical Data: $^1$H NMR (400 MHz, DMSO) d: 8.50 (s, 1H), 7.99 (brs, 1H), 7.57 (brs, 1H), 7.46 (s, 1H), 7.33 (s, 1H), 6.77 (s, 2H), 3.93-3.91 (m, 6H), 3.45-3.42 (m, 4H), 3.37-3.35 (m, 4H), 1.95 (brs, 2H).

Synthesis of 4-(6-methoxy-7-(1H-pyrazol-4-yl)quinazolin-4-yl)-1,4-diazepane-1-sulfonamide (Compound 020)

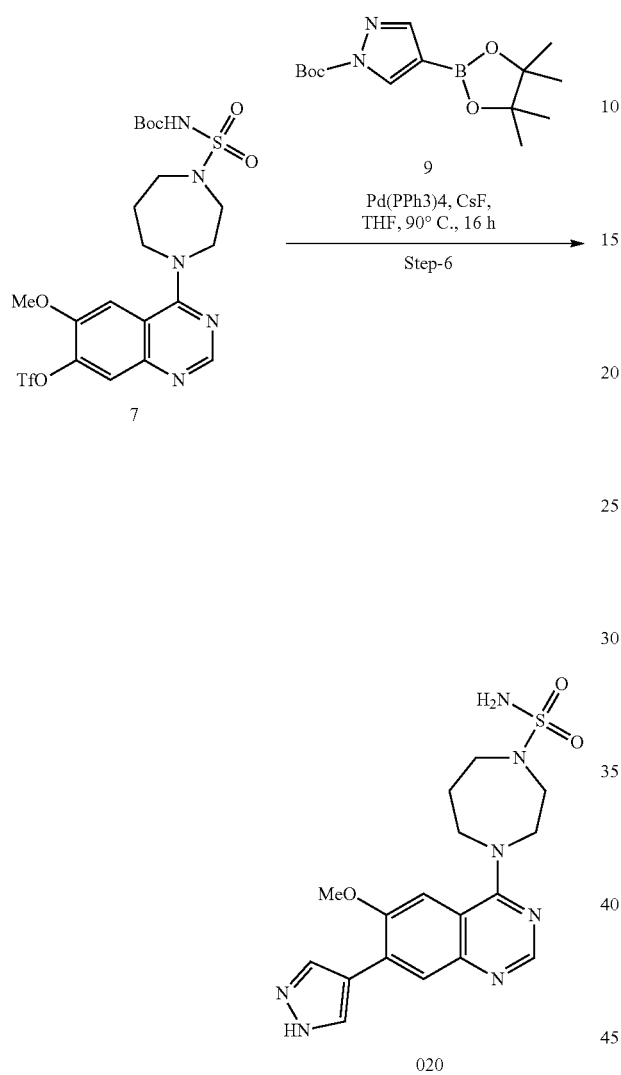

In a sealed tube, to the stirred solution of 4-(4-(N-(tert-butoxycarbonyl) sulfamoyl)-1, 4-diazepan-1-yl)-6-methoxyquinazolin-7-yl trifluoromethanesulfonate 7 (100 mg, 0.171 mmol) in dioxane (5 mL) and water (1.5 mL) were added tert-butyl 4-(4,4,5,5-tetramethyl-1,3,2-dioxaborolan-2-yl)-1H-pyrazole-1-carboxylate 9 (65 mg, 0.222 mmol) and cesium fluoride (78 mg, 0.513 mmol) was then degassed the reaction mixture for 30 minutes. Then tetrakis (triphenylphosphine)palladium(0) (20 mg, 0.0017 mmol) was added again degassed for 5 minutes and stirred the reaction mixture at 90° C. for 6 h. The progress of the reaction was monitored by TLC. After completion of the reaction, reaction mixture filtered through celite. Washed the celite bed with ethyl acetate (100 mL). Then added water (100 mL) and extracted with excess ethyl acetate (100 mL). Organic layer washed with brine solution (100 mL), dried over sodium sulfate and concentrated under reduced pressure. Crude was purified prep HPLC method to afford 4-(6-methoxy-7-(1H-pyrazol-4-yl)quinazolin-4-yl)-1,4-diazepane-1-sulfonamide (Compound 020) (10 mg, 0.024 mmol, 15%) as a brown solid.

Analytical Data: $^1$H NMR (400 MHz, DMSO) δ 13.134 (s, 1H), 8.457 (s, 1H), 8.273 (s, 1H), 8.233 (s, 1H), 7.751 (bs, 1H), 7.405 (s, 1H), 6.916 (s, 1H), 6.799 (s, 1H), 3.996-4.042 (m, 8H), 3.534-3.555 (t, 2H), 2.097-2.141 (t, 2H), 2.068 (m, 2H).

LCMS: (M+H$^+$): m/Z: 404.2.

Synthesis of 4-(7-hydroxy-6-methoxyquinazolin-4-yl)-1,4-diazepane-1-sulfonamide hydrochloride (Compound 021)

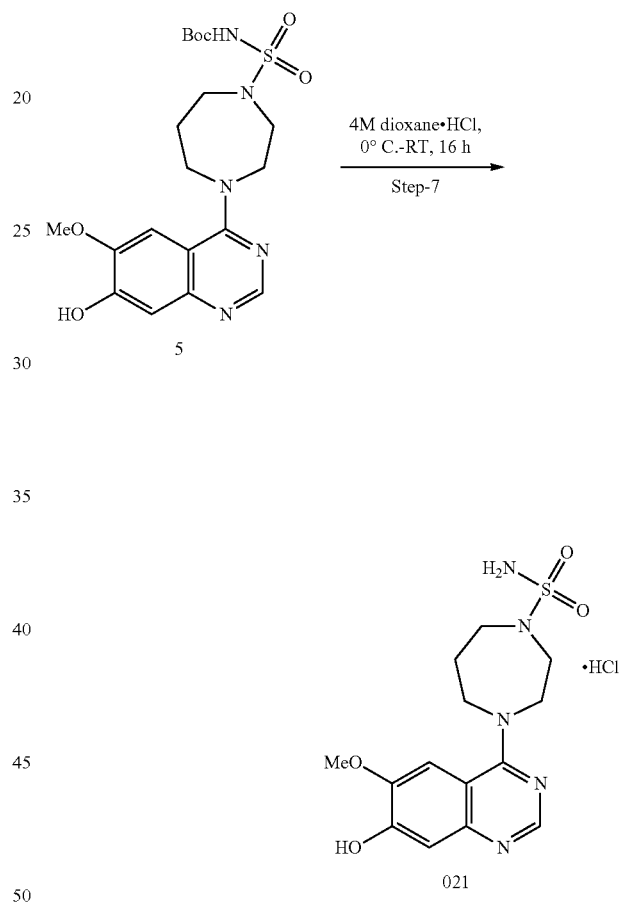

A stirred solution of tert-butyl ((4-(7-hydroxy-6-methoxyquinazolin-4-yl)-1,4-diazepan-1-yl)sulfonyl)carbamate 5 (100 mg, 0.221 mmol) and 4M HCl in dioxane (3 mL) was stirred at room temperature for 16 h. The progress of the reaction was monitored by TLC. After completion of the reaction, organic solvents completely distilled off under reduced pressure. Crude was purified through prep HPLC method to afford 4-(7-hydroxy-6-methoxyquinazolin-4-yl)-1,4-diazepane-1-sulfonamide hydrochloride (Compound 021) (600 mg, 1.5 mmol, 70% yield) as an off white solid.

Analytical Data: $^1$H NMR (400 MHz, DMSO) δ 14.348 (bs, 1H), 11.608 (s, 1H), 8.693 (s, 1H), 7.415 (s, 1H), 7.245 (s, 1H), 6.842 (s, 2H), 4.176-4.200 (m, 4H), 3.933 (s, 3H), 3.555-3.580 (m, 2H), 3.275-3.301 (t, 2H), 2.078 (m, 2H).

LCMS: (M+H$^+$): m/Z: 354.1.

Synthesis of 4-(6-methoxyquinazolin-4-yl)-1,4-diazepane-1-sulfonamide (Compound 022)

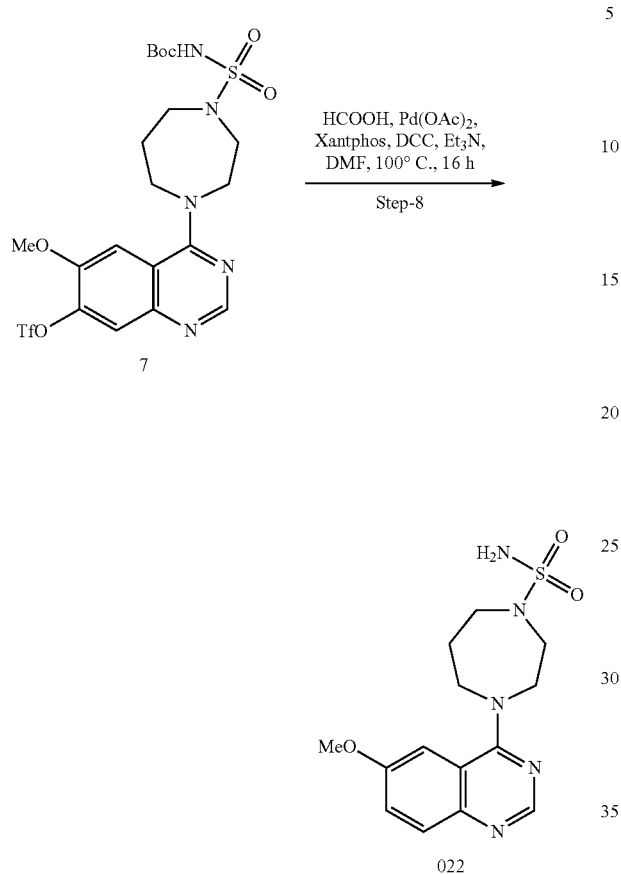

In a sealed tube, to the stirred solution of 4-(4-(N-(tert-butoxycarbonyl) sulfamoyl)-1, 4-diazepan-1-yl)-6-methoxyquinazolin-7-yl trifluoromethanesulfonate 7 (100 mg, 0.171 mmol) in N, N'-dimethylformamide (2 mL) were added formic acid 9 (0.064 mL, 1.196 mmol), triethylamine (34 mg, 0.342 mmol) was then degassed the reaction mixture for 30 minutes. Then palladium (II) acetate (2 mg, 0.0085 mmol) and Xantphos (5 mg, 0.0085 mmol) were added again degassed for 5 minutes and stirred the reaction mixture at 100° C. for 16 h. The progress of the reaction was monitored by TLC. After completion of the reaction, reaction mixture filtered through celite. Washed the celite bed with ethyl acetate (100 mL). Then added water (100 mL) and extracted with excess ethyl acetate (100 mL). Organic layer washed with brine solution (100 mL), dried over sodium sulfate and concentrated under reduced pressure. Crude was purified prep HPLC method to afford 4-(6-methoxyquinazolin-4-yl)-1,4-diazepane-1-sulfonamide (Compound 022) (10 mg, 0.024 mmol, 15%) as a brown solid.

Analytical Data: $^1$H NMR (400 MHz, DMSO) δ 8.444 (s, 1H), 7.704-7.727 (d, 1H), 7.447-7.477 (dd, 1H), 7.310-7.316 (d, 1H), 6.789 (s, 2H), 3.953-4.013 (m, 4H), 3.891 (s, 3H), 3.521-3.534 (t, 2H), 3.268-3.296 (t, 2H), 2.088-2.096 (m, 2H).

LCMS: (M+H$^+$): m/Z: 338

Synthetic Scheme of Compounds 026 and 027

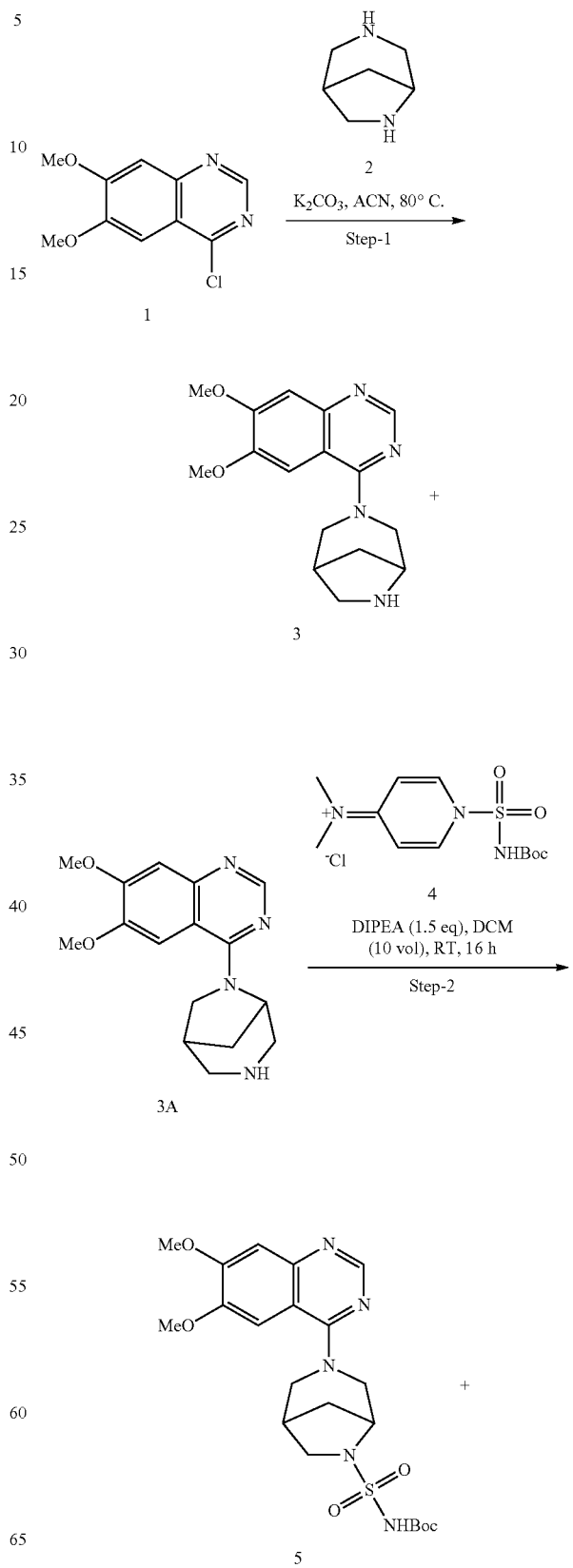

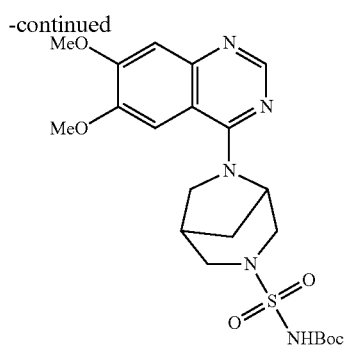

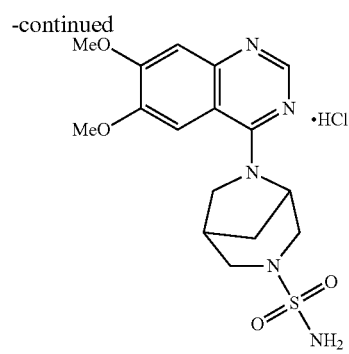

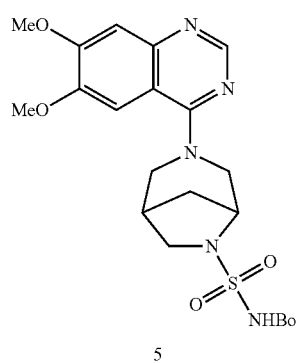

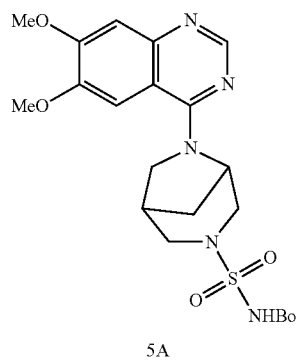

Synthesis of 4-(3,6-diazabicyclo[3.2.1]octan-3-yl)-6,7-dimethoxyquinazoline compound with 4-(3,6-diazabicyclo[3.2.1]octan-6-yl)-6,7-dimethoxyquinazoline (3 & 3A)

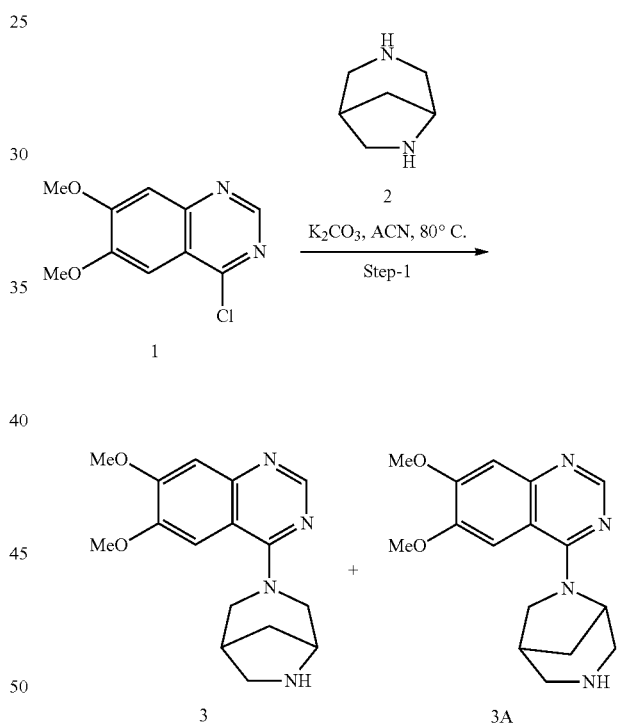

To a stirred solution of 4-chloro-6, 7-dimethoxyquinazoline 1 (1 g, 4.891 mmol) in t-BuOH (120 mL) were added cesium carbonate (5.6 g, 17.119 mmol) and 3, 6-diazabicyclo [3.2.1]octane 2 (900 mg, 4.891 mmol) then stirred at room temperature for 16 h. The progress of the reaction was monitored by TLC. After completion of the reaction, to the reaction mixture completely distilled off under reduced pressure. Crude was purified by trituration with diethyl ether to afford 4-(3,6-diazabicyclo[3.2.1]octan-3-yl)-6,7-dimethoxyquinazoline compound with 4-(3,6-diazabicyclo [3.2.1]octan-6-yl)-6,7-dimethoxyquinazoline (3 & 3A) (1.1 g crude) as a white solid.

LCMS: (M+H$^+$): m/Z: 301.2

Synthesis of Tert-butyl ((3-(6,7-dimethoxyquinazolin-4-yl)-3,6-diazabicyclo[3.2.1]octan-6-yl)sulfonyl)carbamate (5) & Tert-butyl ((6-(6,7-dimethoxyquinazolin-4-yl)-3,6-diazabicyclo[3.2.1]octan-3-yl)sulfonyl)carbamate (5A)

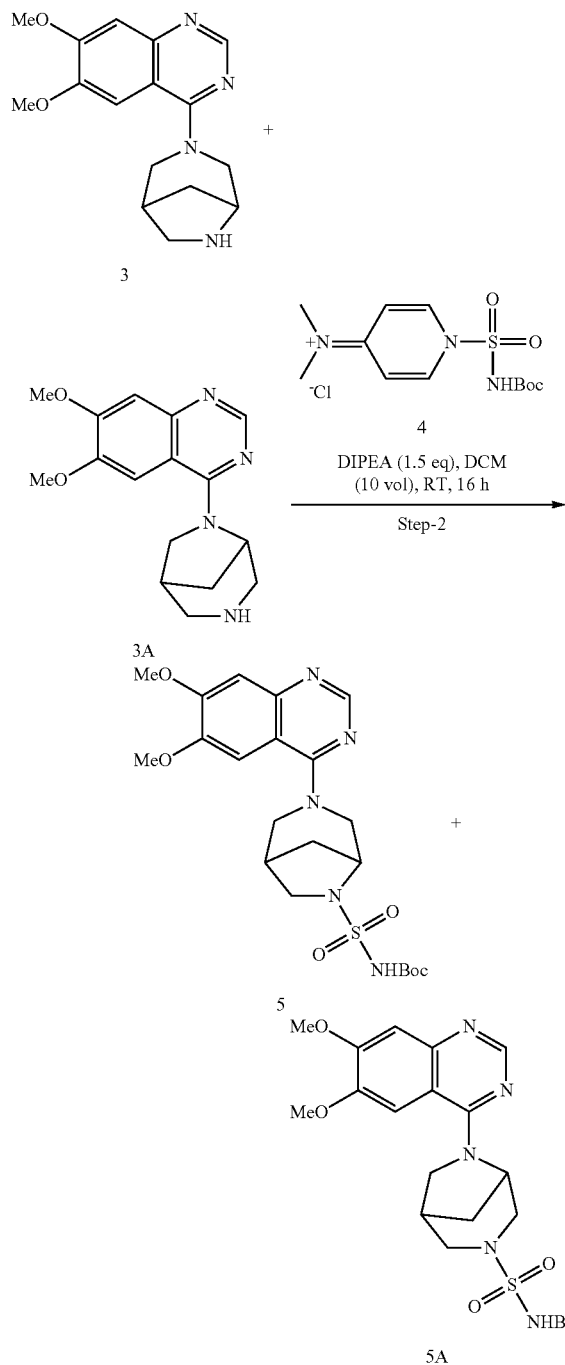

To a stirred solution of 4-(3,6-diazabicyclo[3.2.1]octan-3-yl)-6,7-dimethoxyquinazoline compound with 4-(3,6-diazabicyclo[3.2.1]octan-6-yl)-6,7-dimethoxyquinazoline (3 & 3A) (1.1 g, 3.666 mmol) in dichloromethane (20 mL) was added diisopropylethylamine (0.95 mL, 5.499 mmol) and N-(1-(N-(tert-butoxycarbonyl)sulfamoyl)pyridin-4(1H)-ylidene)-N-methylmethanaminium 4 (1.23 g, 3.66 mmol) at 0° C. then stirred at room temperature for 16 h. The progress of the reaction was monitored by TLC. After completion of the reaction, reaction mixture completely distilled off under reduced pressure to afford crude compound. Crude was purified through 100-200 silica gel column chromatography by eluting 3% methanol in dichloromethane to afford pure compounds of isomers tert-butyl ((3-(6,7-dimethoxyquinazolin-4-yl)-3,6-diazabicyclo[3.2.1]octan-6-yl)sulfonyl)carbamate (5) (500 mg, 1.041 mmol, 28% yield) & tert-butyl ((6-(6,7-dimethoxyquinazolin-4-yl)-3,6-diazabicyclo[3.2.1]octan-3-yl)sulfonyl)carbamate (5A) (150 mg, 0.312 mmol, 8% yield) as an off white solids.

Analytical Data

Cpd-5: $^1$H NMR (400 MHz, DMSO) δ 8.324 (s, 1H), 8.144 (s, 1H), 6.732-7.616 (m, 3H), 4.853-4.920 (dt, 1H), 4.287-4.351 (m, 1H), 4.127-4.155 (d, 1H), 3.961-3.989 (d, 1H), 3.896 (s, 7H), 3.588-3.616 (d, 1H), 3.413-3.439 (d, 1H), 3.174-3.199 (d, 1H), 2.886-3.012 (dd, 1H), 2.713-2.771 (m, 2H), 2.004 (m, 2H), 1.650-1.785 (dd, 1H), 1.117-1.287 (d, 8H).

LCMS: (M+H$^+$): m/Z: 480.2

Cpd-5B: $^1$H NMR (400 MHz, DMSO) δ 10.965-10.971 (brs, 1H), 8.700-8.718 (d, 1H), 7.680-7.725 (d, 1H), 7.211 (s, 1H), 6.793 (s, 1H), 5.027-5.102 (d, 1H), 4.515-4.526 (m, 1H), 4.026-4.120 (d, 1H), 3.944-3.959 (d, 6H), 3.439-3.575 (d, 1H), 3.102-3.251 (m, 3H), 2.844-2.942 (m, 2H), 2.045-2.072 (m, 1H), 1.757-1.912 (s, 1H), 1.232 (s, 5H).

LCMS: (M+H$^+$): m/Z: 480.2

Synthesis of 3-(6,7-dimethoxyquinazolin-4-yl)-3,6-diazabicyclo[3.2.1]octane-6-sulfonamide hydrochloride (Compound 026)

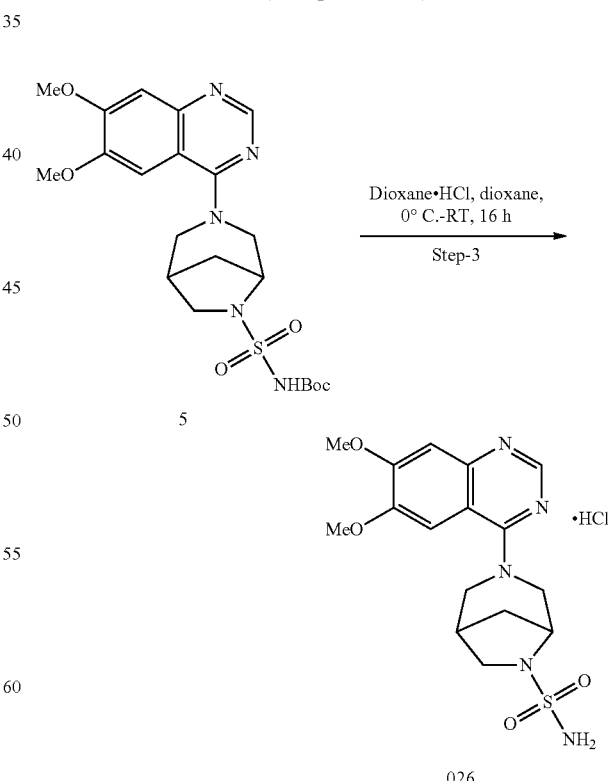

A stirred solution of tert-butyl ((3-(6,7-dimethoxyquinazolin-4-yl)-3,6-diazabicyclo[3.2.1]octan-6-yl)sulfonyl)

carbamate 5 (100 mg, 0.208 mmol) and 4M HCl in dioxane (4 mL) was stirred at room temperature for 16 h. The progress of the reaction was monitored by TLC. After completion of the reaction, organic solvents completely distilled off under reduced pressure. Crude was purified by trituration with 5% methanol in dichloromethane (50 mL) to afford 3-(6,7-dimethoxyquinazolin-4-yl)-3,6-diazabicyclo[3.2.1]octane-6-sulfonamide hydrochloride Compound 026 (70 mg, 0.168 mmol, 81% yield) as an off white solid.

Analytical Data: $^1$H NMR (400 MHz, DMSO) δ 14.287 (bs, 1H), 8.743 (s, 1H), 7.740 (s, 1H), 7.26 (s, 1H), 6.812 (s, 2H), 5.118 (s, 1H), 4.483-4.536 (bs, 1H), 4.148 (s, 1H), 3.966 (s, 3H), 3.971 (s, 3H), 3.826-3.847 (d, 1H), 3.441-3.470 (d, 1H), 2.919-2.947 (d, 1H), 2.856 (brs, 2H), 2.050-2.077 (m, 1H), 1.768-1.797 (d, 1H).

LCMS: (M+H$^+$): m/Z: 380.2

Synthesis of 6-(6,7-dimethoxyquinazolin-4-yl)-3,6-diazabicyclo[3.2.1]octane-3-sulfonamide hydrochloride (Compound 027)

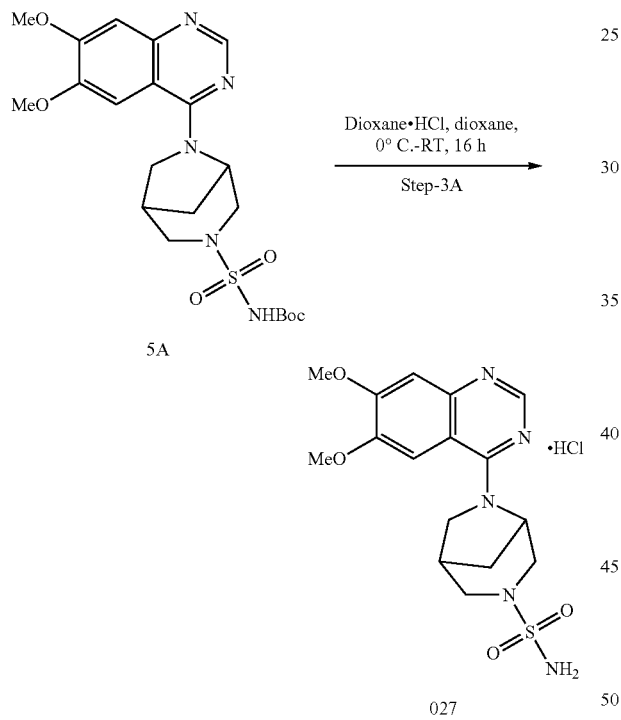

A stirred solution of tert-butyl ((6-(6,7-dimethoxyquinazolin-4-yl)-3,6-diazabicyclo[3.2.1]octan-3-yl)sulfonyl)carbamate 5A (100 mg, 0.208 mmol) and 4M HCl in dioxane (4 mL) was stirred at room temperature for 16 h. The progress of the reaction was monitored by TLC. After completion of the reaction, organic solvents completely distilled off under reduced pressure. Crude was purified by trituration with 5% methanol in dichloromethane (50 mL) to afford 6-(6,7-dimethoxyquinazolin-4-yl)-3,6-diazabicyclo[3.2.1]octane-3-sulfonamide hydrochloride Compound 027 (70 mg, 0.168 mmol, 81% yield) as an off white solid.

Analytical Data: $^1$H NMR (400 MHz, DMSO) δ 14.229 (bs, 1H), 8.724 (s, 1H), 7.733 (s, 1H), 7.243 (s, 1H), 6.802 (s, 2H), 5.111 (s, 1H), 4.498 (bs, 1H), 4.113-4.116 (d, 1H), 3.971 (s, 6H), 3.832-3.854 (d, 1H), 3.444-3.469 (d, 1H), 2.919-2.946 (d, 1H), 2.825-2.853 (brs, 2H), 2.046-2.074 (m, 1H), 1.764-1.793 (d, 1H).

LCMS: (M+H$^+$): m/Z: 380.1

Synthetic Scheme for Compound 028

Synthesis of 4-(6,7-dimethoxyquinazolin-4-yl)-1,4-diazepane-1-sulfonamide (Compound 028)

To a stirred solution of tert-butyl ((4-(7-hydroxy-6-methoxyquinazolin-4-yl)-1,4-diazepan-1-yl)sulfonyl)carbamate 1 (200 mg, 0.441 mmol) in N, N'-dimethylformamide (5 mL) and water (5 mL) were added 2-chloro-2,2-difluoroacetic acid, sodium salt (335 mg, 2.207 mmol) and cesium carbonate (719 mg, 2.205 mmol) then stirred the reaction mixture at 100° C. for 16 h. The progress of the reaction was monitored by TLC. After completion of the reaction, to the reaction mixture added water (100 mL), and extracted with ethyl acetate (2×50 mL). Combined organic layers was washed with brine solution (100 mL), dried over sodium sulfate and concentrated under reduced pressure. Crude was purified prep HPLC method to afford 4-(6,7-dimethoxyquinazolin-4-yl)-1,4-diazepane-1-sulfonamide (Compound 028) (10 mg, 0.027 mmol, 5%) as an off white solid.

Analytical Data: $^1$H NMR (400 MHz, DMSO) δ 8.460 (s, 1H), 7.425-7.470 (m, 3H), 6.796 (s, 2H), 3.979-4.001 (m, 4H), 3.959 (s, 3H), 3.509-3.535 (t, 2H), 3.261-3.289 (t, 2H), 2.084 (m, 2H).

LCMS: (M+H$^+$): m/Z: 404.1

169
Synthetic Scheme of Compound 029

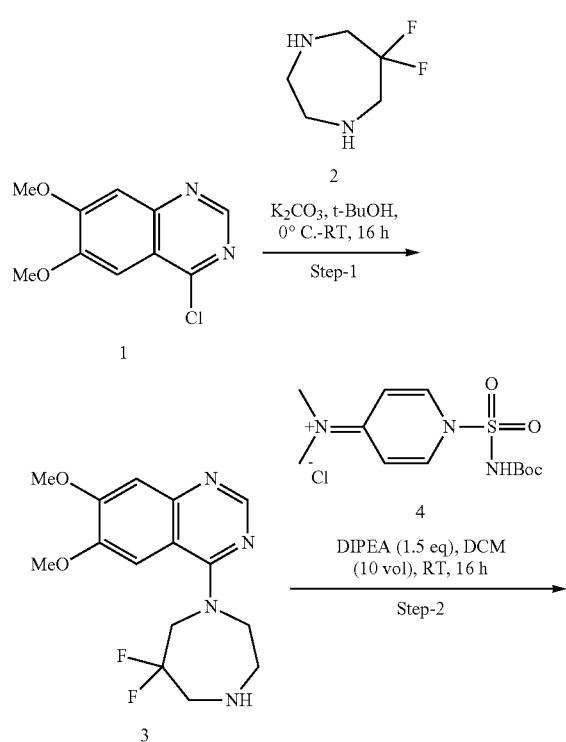

170
Synthesis of 4-(6,6-difluoro-1,4-diazepan-1-yl)-6,7-dimethoxyquinazoline (3)

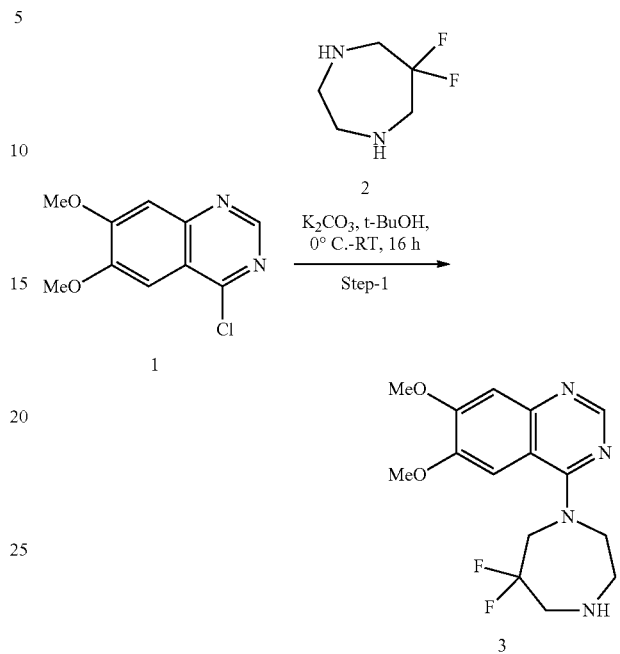

To a stirred solution of 4-chloro-6, 7-dimethoxyquinazoline 1 (160 mg, 0.695 mmol) in t-butanol (25 mL) were added potassium carbonate (288 mg, 2.085 mmol) and 6,6-difluoro-1,4-diazepane 2 (218 mg, 1.043 mmol) then stirred at room temperature for 16 h. The progress of the reaction was monitored by TLC. After completion of the reaction, the reaction mixture completely distilled off under reduced pressure. To the crude added 10% methanol in dichloromethane and filtered. Filtrate was concentrated under reduced pressure to afford 4-(6,6-difluoro-1,4-diazepan-1-yl)-6,7-dimethoxyquinazoline (3) (180 mg, crude) as an off white solid.

LCMS: (M+H$^+$): m/Z: 325.2

Synthesis of tert-butyl ((4-(6,7-dimethoxyquinazolin-4-yl)-6,6-difluoro-1,4-diazepan-1-yl)sulfonyl)carbamate (5)

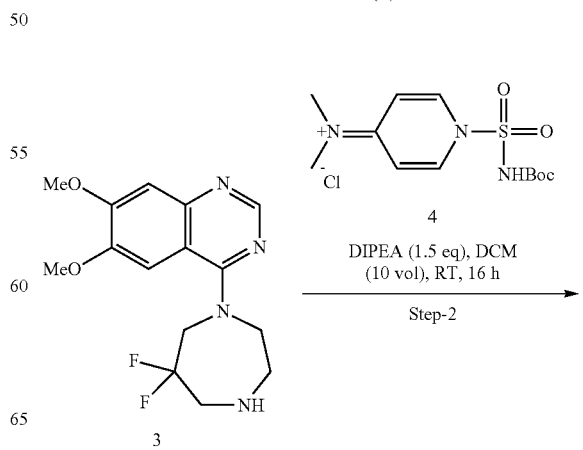

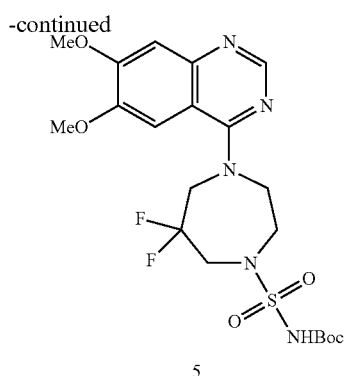

To a stirred solution of 4-(6,6-difluoro-1,4-diazepan-1-yl)-6,7-dimethoxyquinazoline (3) (150 mg, 0.463 mmol) in dichloromethane (5 ml) were added diisopropylethylamine (90 mg, 0.694 mmol) and N-(1-(N-(tert-butoxycarbonyl)sulfamoyl)pyridin-4(1H)-ylidene)-N-methylmethanaminium 4 (171 mg, 0.509 mmol) at 0° C. then stirred at room temperature for 16 h. The progress of the reaction was monitored by TLC. After completion of the reaction, reaction mixture completely distilled off under reduced pressure to afford crude compound. Crude was purified through 100-200 combi-flash chromatography by eluting 3% methanol in dichloromethane to afford tert-butyl ((4-(6,7-dimethoxyquinazolin-4-yl)-6,6-difluoro-1,4-diazepan-1-yl)sulfonyl)carbamate (5) (200 mg, 0.397 mmol, 86% yield) as an off white solid.

LCMS: (M+H⁺): m/Z: 504.2

Synthesis of 4-(6,7-dimethoxyquinazolin-4-yl)-6,6-difluoro-1,4-diazepane-1-sulfonamide hydrochloride (Compound 029)

A stirred solution of tert-butyl ((4-(6,7-dimethoxyquinazolin-4-yl)-6,6-difluoro-1,4-diazepan-1-yl)sulfonyl)carbamate 5 (170 mg, 0.338 mmol) and 4M HCl in dioxane (10 mL) was stirred at room temperature for 16 h. The progress of the reaction was monitored by TLC. After completion of the reaction, organic solvents completely distilled off under reduced pressure. Crude was purified by trituration with 5% methanol in dichloromethane (5 mL) to afford 4-(6,7-dimethoxyquinazolin-4-yl)-6,6-difluoro-1,4-diazepane-1-sulfonamide hydrochloride Compound 029 (20 mg, 0.045 mmol, 13% yield) as an off white solid.

Analytical Data: ¹H NMR (400 MHz, DMSO) δ 8.558 (s, 1H), 7.251 (s, 1H), 7.181 (s, 1H), 7.098 (s, 2H), 4.388-4.456 (t, 2H), 3.935 (s, 6H), 3.878-3.903 (t, 3H), 3.789-3.822 (d, 2H), 3.720-3.755 (m, 2H).

LCMS: (M+H⁺): m/Z: 404.22

Synthetic Scheme for Compound 030

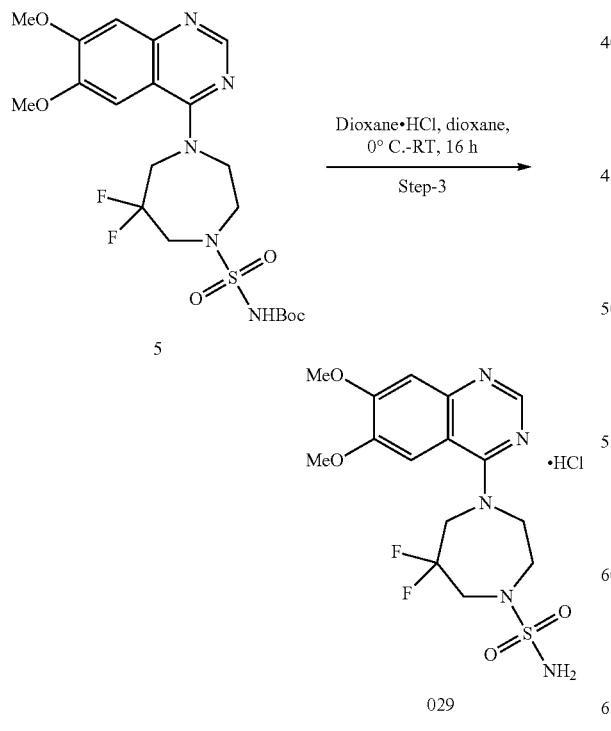

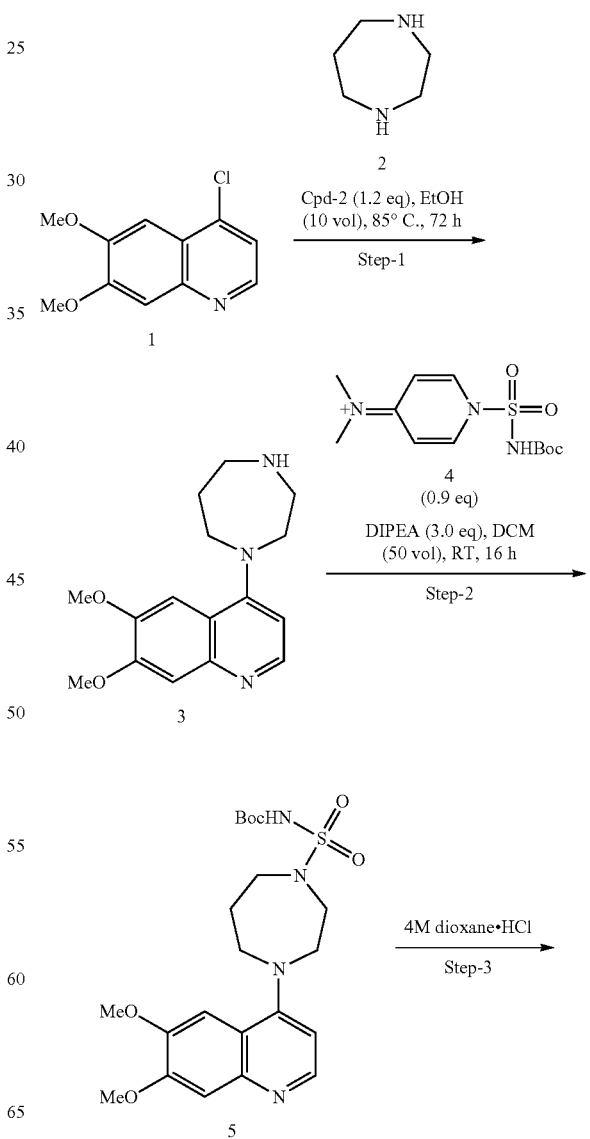

Synthesis of 4-(1,4-diazepan-1-yl)-6,7-dimethoxyquinoline (3)

Synthesis of Tert-butyl ((4-(6,7-dimethoxyquinolin-4-yl)-1,4-diazepan-1-yl)sulfonyl)carbamate (5)

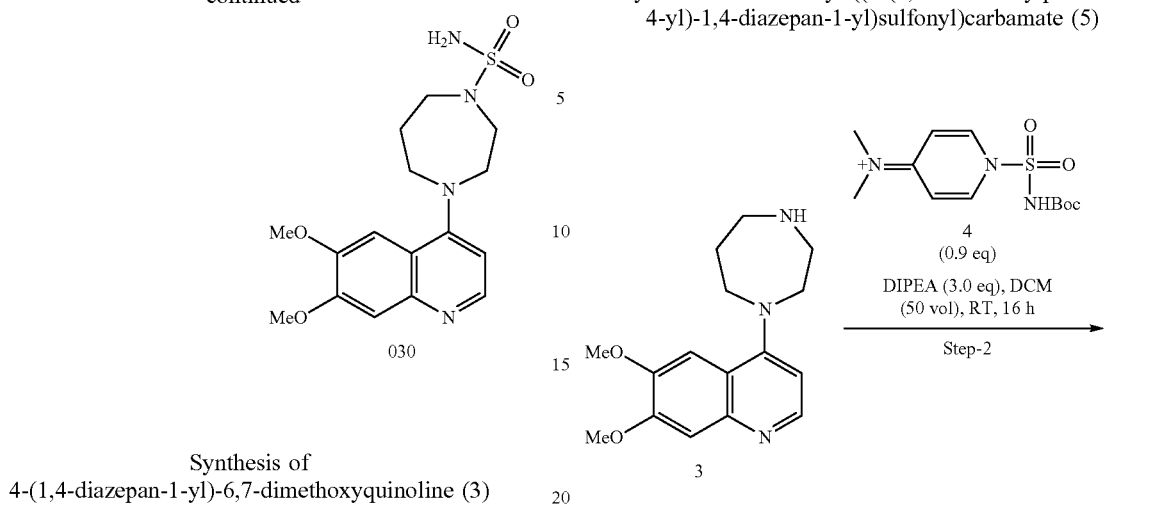

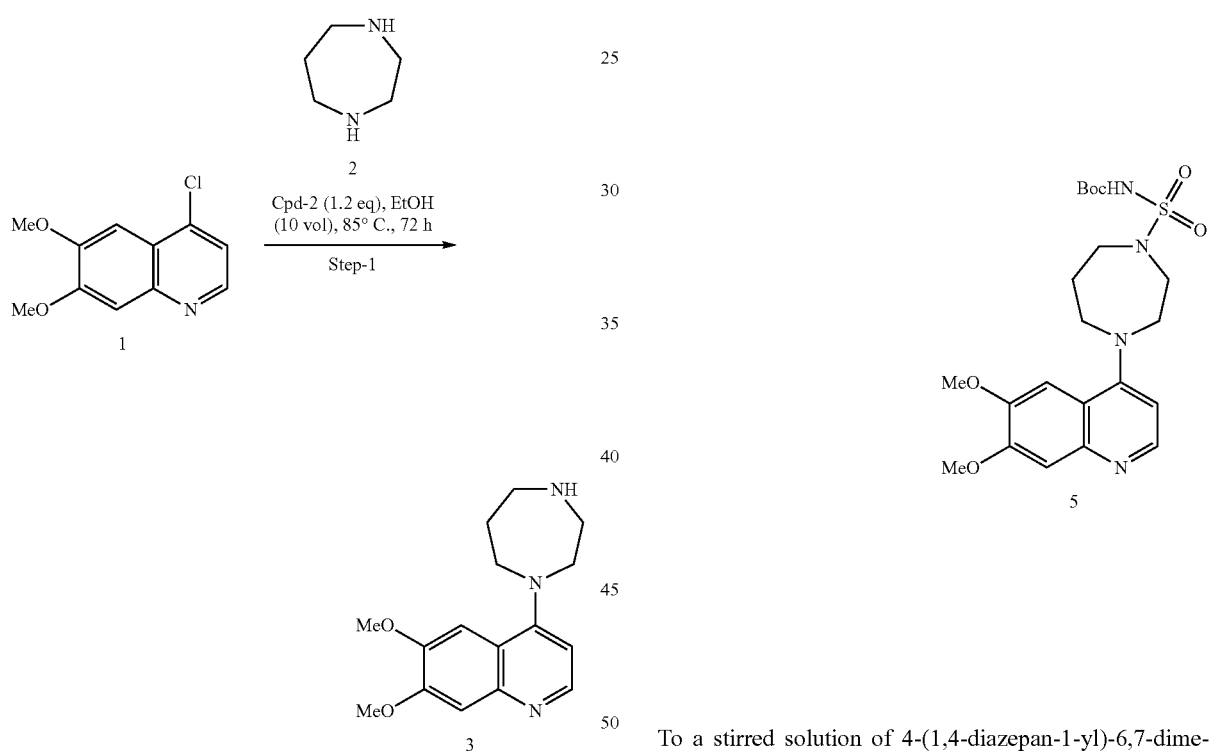

To a stirred solution of 4-chloro-6,7-dimethoxyquinoline 1 (2 g, 8.9686 mmol) in ethanol (20 ml) were added potassium carbonate (2.4 g, 17.9372 mmol) and 1,4-diazepane 2 (2.7 g, 26.9058 mmol) then stirred at 90° C. temperature for 4 days. The progress of the reaction was monitored by TLC. After completion of the reaction, the reaction mixture completely distilled off under reduced pressure. To the crude added 10% methanol in dichloromethane and filtered. Filtrate was concentrated under reduced pressure to afford 4-(1,4-diazepan-1-yl)-6,7-dimethoxyquinoline (3) (1 g) as an off white solid.

Analytical Data:

LCMS: (M+H$^+$): m/Z: 288.2.

To a stirred solution of 4-(1,4-diazepan-1-yl)-6,7-dimethoxyquinoline (3) (150 mg, 0.0522 mmol) in dichloromethane (5 mL) were added diisopropylethylamine (0.13 mL, 0.7839 mmol) and N-(1-(N-(tert-butoxycarbonyl)sulfamoyl)pyridin-4(1H)-ylidene)-N-methylmethanaminium 4 (176 mg, 0.0522 mmol) at 0° C. then stirred at room temperature for 16 h. The progress of the reaction was monitored by TLC. After completion of the reaction, reaction mixture completely distilled off under reduced pressure to afford crude compound. Crude was purified through 100-200 combi-flash chromatography by eluting 3% methanol in dichloromethane to afford Tert-butyl ((4-(6,7-dimethoxyquinolin-4-yl)-1,4-diazepan-1-yl)sulfonyl)carbamate (5) (100 mg, 41% yield) as an off white solid.

Analytical Data:

LCMS: (M+H$^+$): m/Z: 466.13

Synthesis of 4-(6,7-dimethoxyquinolin-4-yl)-1,4-diazepane-1-sulfonamide (Compound 030)

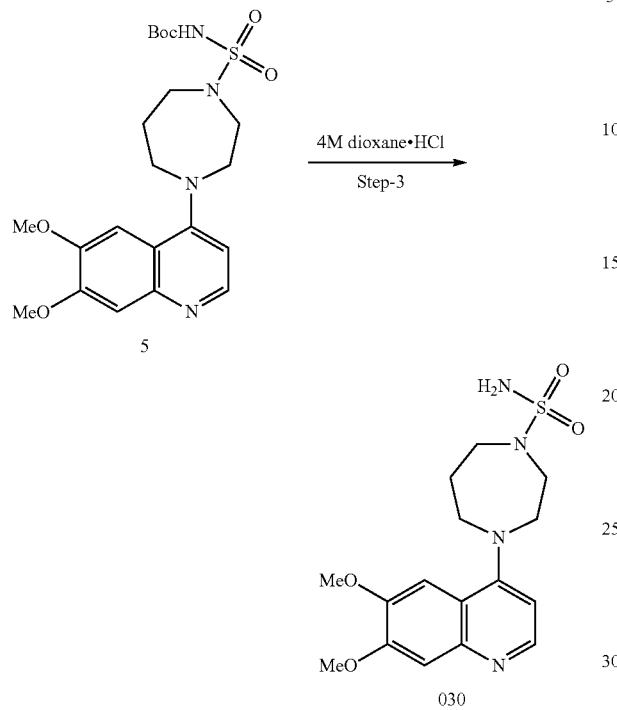

A stirred solution of Tert-butyl ((4-(6,7-dimethoxyquinolin-4-yl)-1,4-diazepan-1-yl)sulfonyl)carbamate 5 (90 mg, 0.1931 mmol) and 4M HCl in dioxane (5 mL) was stirred at room temperature for 16 h. The progress of the reaction was monitored by TLC. After completion of the reaction, organic solvents completely distilled off under reduced pressure. Crude was purified by trituration with 5% methanol in dichloromethane (5 mL) to afford 4-(6,7-dimethoxyquinolin-4-yl)-1,4-diazepane-1-sulfonamide Compound 030 (40 mg, 57% yield) as an off white solid.

Analytical Data: $^1$H NMR (400 MHz, DMSO) δ 8.42 (d, 1H), 7.40 (s, 1H), 7.35 (s, 1H), 6.98 (d, 1H), 6.86 (s, 2H), 3.94-3.99 (m, 10H), 3.56 (t, 2H), 2.13 (s, 2H).

LCMS: (M+H$^+$): m/Z: 367.28

Synthetic Scheme of Compound 031

Synthesis of 4-(1,4-diazepan-1-yl)-6,7-dimethoxy-2-(trifluoromethyl)quinazoline (3)

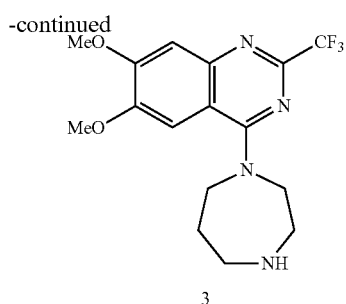

3

To a stirred solution of 4-chloro-6,7-dimethoxy-2-(trifluoromethyl)quinazoline 1 (150 mg, 0.512 mmol) in t-butanol (10 ml) were added potassium carbonate (71 mg, 0.512 mmol) and 1,4-diazepane 2 (102 mg, 1.025 mmol) then stirred at room temperature for 16 h. The progress of the reaction was monitored by TLC. After completion of the reaction, the reaction mixture completely distilled off under reduced pressure. To the crude added 10% methanol in dichloromethane and filtered. Filtrate was concentrated under reduced pressure to afford 4-(1,4-diazepan-1-yl)-6,7-dimethoxy-2-(trifluoromethyl)quinazoline (3) (170 mg, crude) as an off white solid.

Analytical Data: $^1$H NMR (400 MHz, DMSO) δ 7.380 (s, 1H), 7.312 (s, 1H), 3.903-3.969 (m, 10H), 3.044-3.069 (t, 2H), 2.793-2.820 (t, 2H), 1.947 (bs, 2H).

Synthesis of Tert-butyl ((4-(6,7-dimethoxy-2-(trifluoromethyl)quinazolin-4-yl)-1,4-diazepan-1-yl)sulfonyl)carbamate (5)

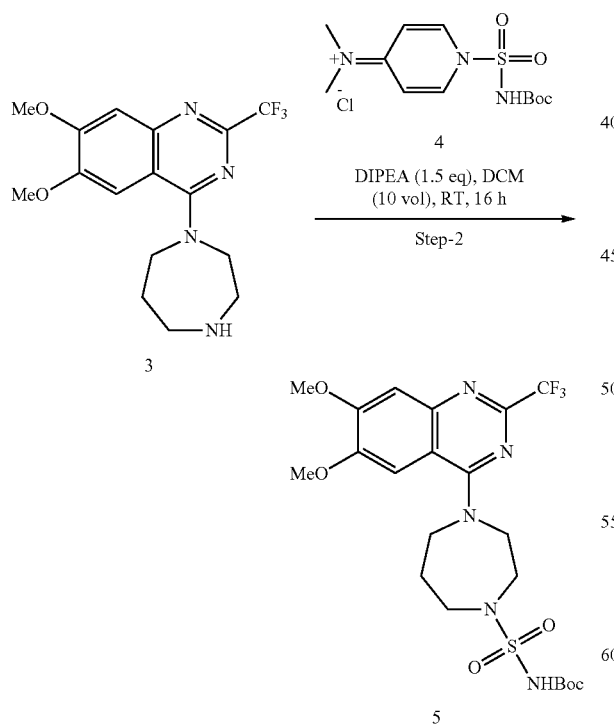

To a stirred solution of 4-(1,4-diazepan-1-yl)-6,7-dimethoxy-2-(trifluoromethyl)quinazoline (3) (150 mg, 0.421 mmol) in dichloromethane (5 ml) were added diisopropyl-ethylamine (81 mg, 0.632 mmol) and N-(1-(N-(tert-butoxycarbonyl)sulfamoyl)pyridin-4(1H)-ylidene)-N-methylmethanaminium 4 (142 mg, 0.421 mmol) at 0° C. then stirred at room temperature for 16 h. The progress of the reaction was monitored by TLC. After completion of the reaction, reaction mixture completely distilled off under reduced pressure to afford crude compound. Crude was purified through 100-200 combi-flash chromatography by eluting 3% methanol in dichloromethane to afford tert-butyl ((4-(6, 7-dimethoxy-2-(trifluoro methyl) quinazolin-4-yl)-1, 4-diazepan-1-yl) sulfonyl) carbamate (5) (190 mg, 0.355 mmol, 84% yield) as an off white solid.

Analytical Data: $^1$H NMR (400 MHz, DMSO) δ 11.094 (bs, 1H), 7.330 (d, 2H), 4.009-4.019 (m, 4H), 3.940 (s, 3H), 3.924 (s, 3H), 3.699-3.712 (t, 3H), 3.435 (t, 2H), 2.072 (bs, 2H), 1.343 (s, 9H).

Synthesis of 4-(6,7-dimethoxy-2-(trifluoromethyl) quinazolin-4-yl)-1,4-diazepane-1-sulfonamide hydrochloride (Compound 031)

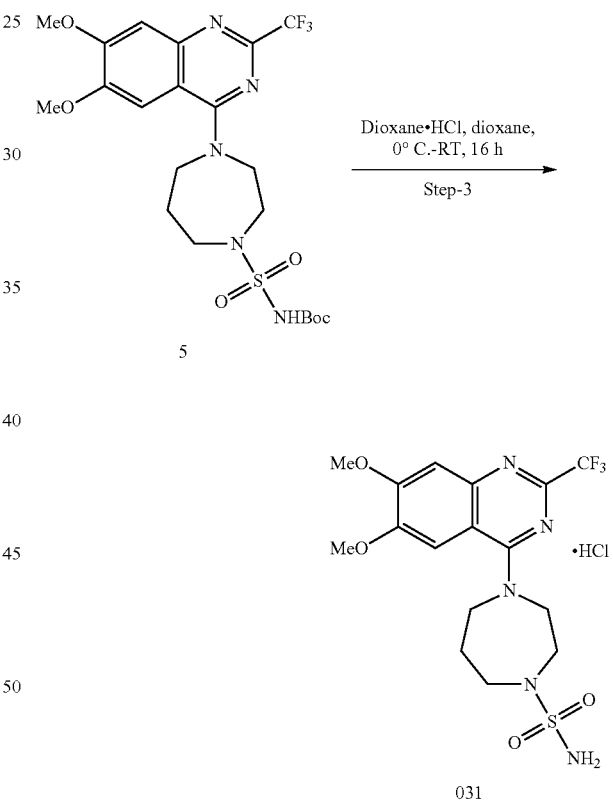

A stirred solution of tert-butyl ((4-(6,7-dimethoxy-2-(trifluoromethyl)quinazolin-4-yl)-1,4-diazepan-1-yl)sulfonyl) carbamate 5 (160 mg, 0.299 mmol) and 4M HCl in dioxane (10 mL) was stirred at room temperature for 16 h. The progress of the reaction was monitored by TLC. After completion of the reaction, organic solvents completely distilled off under reduced pressure. Crude was purified by trituration with 5% methanol in dichloromethane (5 mL) to afford 4-(6,7-dimethoxy-2-(trifluoromethyl)quinazolin-4-yl)-1,4-diazepane-1-sulfonamide hydrochloride Compound 031 (100 mg, 0.212 mmol, 71% yield) as an off white solid.

Analytical Data: ¹H NMR (400 MHz, DMSO) δ 7.340 (s, 1H), 6.802 (bs, 2H), 3.992-4.040 (m, 4H), 3.939 (s, 3H), 3.924 (s, 3H), 3.516-3.556 (t, 2H), 3.261-3.289 (t, 2H), 2.063-2.090 (m, 2H).

LCMS: (M+H⁺): m/Z: 436.33

General Scheme 6:

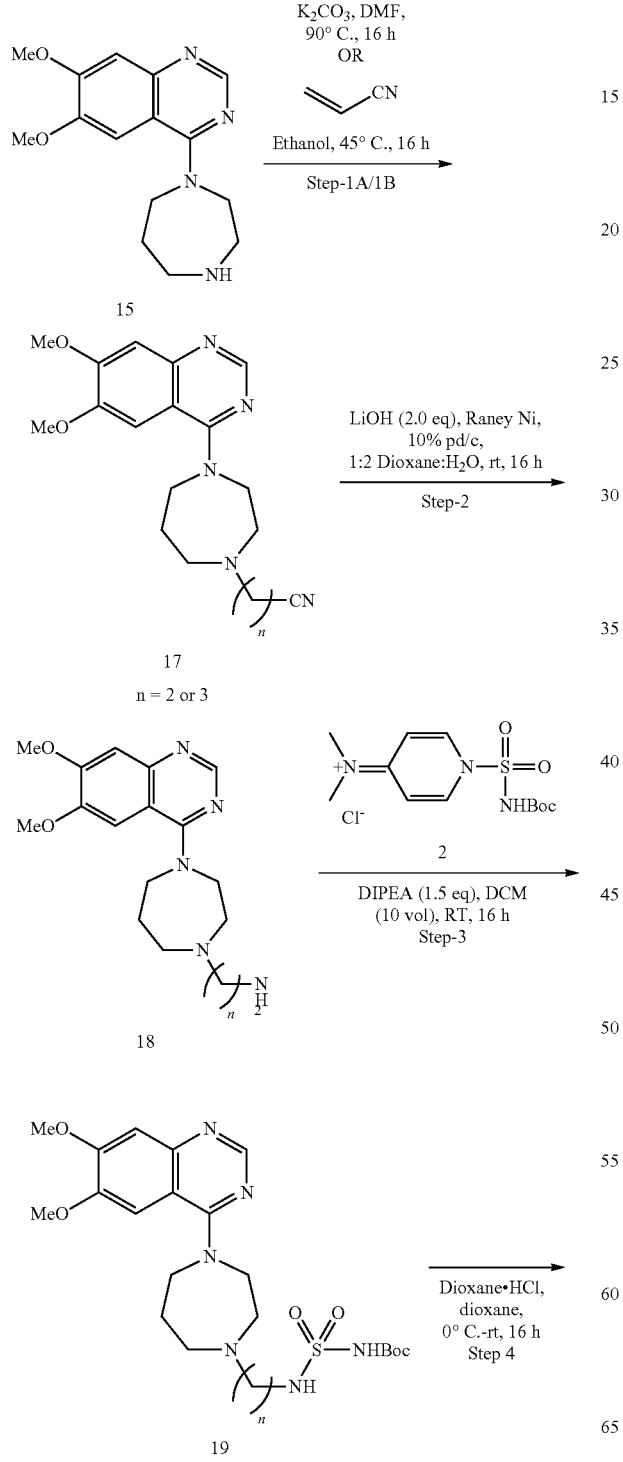

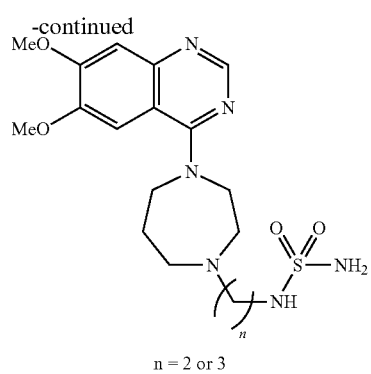

n = 2 or 3

Example 6: (N-(2-(4-(6, 7-dimethoxyquinazolin-4-yl)-1, 4-diazepan-1-yl) ethyl) sulfamide hydrochloride Step-IA: 2-(4-(6, 7-dimethoxyquinazolin-4-yl)-1, 4-diazepan-1-yl) acetonitrile To a stirred solution of 4-(1,4-diazepan-1-yl)-6,7-dimethoxyquinazoline 1 (1 g, 3.472 mmol) in N,N'-dimethylformamide (10 ml) were added potassium carbonate (1.4 g, 10.416 mmol) and 2-bromoacetonitrile (0.83 g, 6.944 mmol) then stirred at 90° C. for 16 h. The progress of the reaction was monitored by TLC. After completion of the reaction, reaction mixture completely distilled off under reduced pressure. Crude was purified through combi-flash chromatography by eluting 80% ethyl acetate in pet ether to afford 2-(4-(6, 7-dimethoxyquinazolin-4-yl)-1, 4-diazepan-1-yl) acetonitrile 2 (0.93 g, 2.844 mmol, 68% yield) as a pale brown solid.

Analytical Data: 1H NMR (400 MHz, DMSO) δ 8.40 (s, 1H), 7.27 (s, 1H), 7.14 (s, 1H), 3.87 (s, 3H), 3.90 (s, 3H), 3.94-3.92 (m, 4H), 3.79 (s, 2H), 2.93 (t, 2H), 2.69-2.66 (m, 2H), 2.05-2.04 (m, 2H). LCMS: (M+H+): m/Z: 328.2

Step-1B: 3-(4-(6, 7-dimethoxyquinazolin-4-yl)-1, 4-diazepan-1-yl) propanenitrile

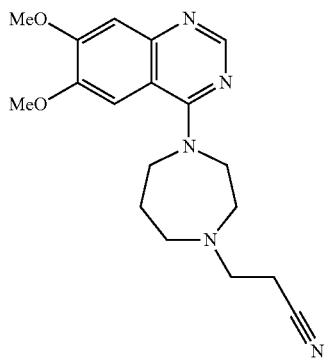 [SMILES: COc1cc2ncnc(N3CCCN(CCC#N)CC3)c2cc1OC]

To a stirred solution of 4-(1,4-diazepan-1-yl)-6,7-dimethoxyquinazoline 1 (1 g, 3.472 mmol) in ethanol (15 ml) was added acrylonitrile (0.68 mL, 10.416 mmol) then stirred at 45° C. for 16 h. The progress of the reaction was monitored by TLC. After completion of the reaction, reaction mixture completely distilled off under reduced pressure. Crude was purified through combi-flash chromatography by eluting 5% methanol in dichloromethane to afford 3-(4-(6, 7-dimethoxyquinazolin-4-yl)-1, 4-diazepan-1-yl) propanenitrile 3 (1 g, 2.932 mmol, 85% yield) as a reddish colored gummy liquid.

Analytical Data: 1H NMR (400 MHz, DMSO) δ 8.36 (s, 1H), 7.26 (s, 1H), 7.13 (t, 2H), 3.89-3.85 (m, 10H), 2.96-2.94 (m, 2H), 2.74-2.69 (m, 4H), 2.65-2.62 (m, 2H), 2.00 (m, 2H).

LCMS: (M+H)+: m/Z: 342.2

Step-2: 2-(4-(6, 7-dimethoxyquinazolin-4-yl)-1, 4-diazepan-1-yl) ethan-1-amine

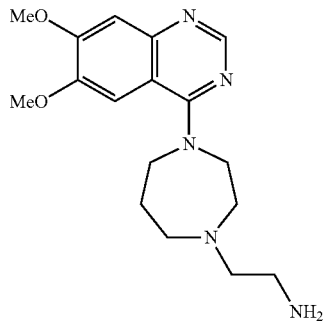 [SMILES: COc1cc2ncnc(N3CCCN(CCN)CC3)c2cc1OC]

To a stirred solution of 2-(4-(6,7-dimethoxyquinazolin-4-yl)-1,4-diazepan-1-yl)acetonitrile 2 (900 mg, 2.752 mmol) in 1,4-dioxane (18 mL) and water (10 ml) were added lithium hydroxide monohydrate (231 mg, 5.504 mmol), Raney Ni (936 mg) and 10% Pd/C (295 mg) and stirred the reaction mixture under balloon hydrogen atmosphere at room temperature for 16 h. The progress of the reaction was monitored by TLC. After completion of the reaction, reaction mixture filtered through celite and washed the celite bed with 10% methanol in dichloromethane (100 mL). Filtrate was concentrated under reduced pressure to afford crude compound. Crude was purified through Grace reverse phase column chromatography by eluting 20% acetonitrile in 0.1% formic acid in water to afford 2-(4-(6, 7-dimethoxyquinazolin-4-yl)-1, 4-diazepan-1-yl) ethan-1-amine 3 (100 mg, 0.302, 11%) as a reddish brown gummy liquid.

Analytical Data: LCMS: (M+H+): m/Z: 332.24

The following compound was synthesized by the above general procedure:

| Structure | 1HNMR |
|---|---|
| 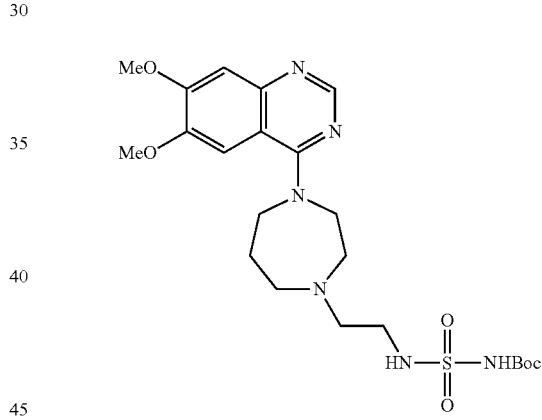 | 1H NMR (400 MHz, DMSO) δ 8.36 (s, 1H), 8.23 (brs, 2H), 7.26 (s, 1H), 7.13 (s, 1H), 3.89-3.87 (m, 10H), 2.87 (m, 2H), 2.82-2.78 (t, 2H), 2.66-2.61 (m, 2H), 2.00 (m, 2H), 1.68-1.65 (m, 2H). MS 346.2 |

Step-3: Tert-butyl (N-(2-(4-(6, 7-dimethoxyquinazolin-4-yl)-1, 4-diazepan-1-yl) ethyl) sulfamoyl) carbamate To a stirred solution of 2-(4-(6,7-dimethoxyquinazolin-4-yl)-1,4-diazepan-1-yl)ethan-1-amine 3 (100 mg, 0.302 mmol) in dichloromethane (5 ml) were added diisopropylethylamine (60 mg, 0.453 mmol) and N-(1-(N-(tert-butoxycarbonyl)sulfamoyl)pyridin-4(1H)-ylidene)-N-methylmethanaminium chloride 4 (102 mg, 0.302 mmol) at 0° C. then stirred at room temperature for 16 h. The progress of the reaction was monitored by TLC. After completion of the reaction, reaction mixture completely distilled off under reduced pressure to afford crude compound. Crude was purified through combi-flash column chromatography by eluting 5% methanol in dichloromethane to afford tert-butyl (N-(2-(4-(6, 7-dimethoxyquinazolin-4-yl)-1, 4-diazepan-1-yl) ethyl) sulfamoyl) carbamate 5 (90 mg, 0.176 mmol, 58% yield) as a brown solid.

Analytical Data: 1H NMR (400 MHz, DMSO) δ 8.37 (s, 1H), 7.26 (s, 1H), 7.18 (m, 1H), 7.14 (s, 1H), 3.89-3.87 (d, 10H), 3.00-2.97 (m, 4H), 2.75-2.68 (m, 2H), 2.66-2.62 (m, 2H), 2.04-2.01 (m, 2H), 1.39 (s, 9H). LCMS: (M+H+): m/Z: 511.21

The following compound was synthesized by the above general procedure

| Structure | 1HNMR |
|---|---|
| 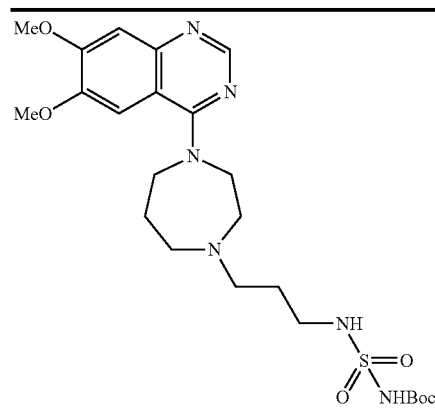 | 1HNMR (400 MHz, DMSO) δ 8.37 (s, 1H), 7.60 (brs, 1H), 7.26 (s, 1H), 7.13 (s, 1H), 3.89-3.87 (m, 10H), 2.90-2.89 (m, 4H), 2.66 (m, 2H), 2.01 (m, 2H), 1.63-1.60 (t, 2H), 1.39 (s, 9H). MS 525.3 |

Step-4: (N-(2-(4-(6, 7-dimethoxyquinazolin-4-yl)-1, 4-diazepan-1-yl) ethyl) sulfamide hydrochloride (Compound 063)

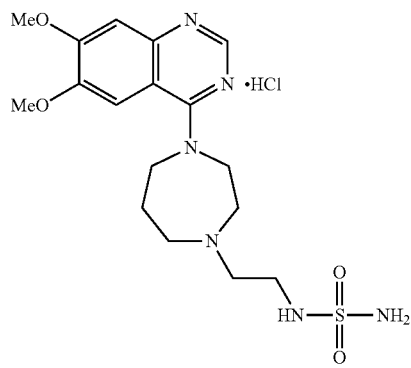

To a stirred solution of tert-butyl (N-(2-(4-(6,7-dimethoxyquinazolin-4-yl)-1,4-diazepan-1-yl)ethyl)sulfamoyl) carbamate 5 (90 mg, 0.176 mmol) in dioxane (2 ml) was added 4M HCl in dioxane (8 mL) at 0° C. then stirred at room temperature for 6 h. The progress of the reaction was monitored by TLC. After completion of the reaction, organic solvents completely distilled off under reduced pressure. Crude was purified through prep HPLC method to afford (N-(2-(4-(6, 7-dimethoxyquinazolin-4-yl)-1, 4-diazepan-1-yl) ethyl) sulfamide hydrochloride (15 mg, 0.036 mmol, 72% yield) as an off white solid.

Analytical Data: 1H NMR (400 MHz, DMSO) δ 8.38 (s, 1H), 7.26 (s, 1H), 7.14 (s, 1H), 6.56 (brs, 2H), 6.26-6.27 (brs, 1H), 3.90-3.87 (m, 10H), 2.99-96 (m, 4H), 2.03 (m, 2H). LCMS: (M+H+): m/Z: 411.2

| Compound Number | Structure | 1HNMR |
|---|---|---|
| 063 | 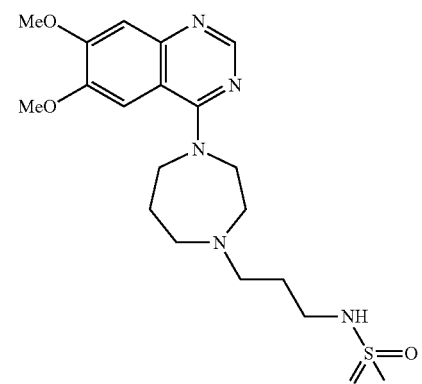 | 1H NMR (400 MHz, DMSO) δ 8.37 (s, 1H), 7.26 (s, 1H), 7.13 (s, 1H), 6.44 (m, 3H), 3.89-3.87 (m, 10H), 2.89-2.87 (m, 4H), 2.62-2.60 (m, 2H), 1.99 (m, 2H), 1.62-1.58 (t,2H). MS 425.2 |

Compound 062 was also prepared based on the general procedure described above:
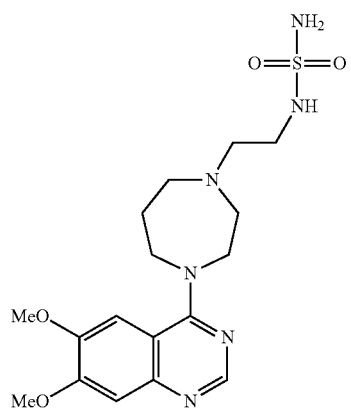
1H NMR (400 MHz, DMSO) δ 8.38 (s, 1H), 7.26 (s, 1H), 7.14 (s, 1H), 6.56 (brs, 2H), 6.26-6.27 (brs, 1H), 3.90-3.87 (m, 10H), 2.99-96 (m, 4H), 2.03 (m, 2H). LCMS 411.2. MW 446.95.
Synthetic Scheme of Compound 032
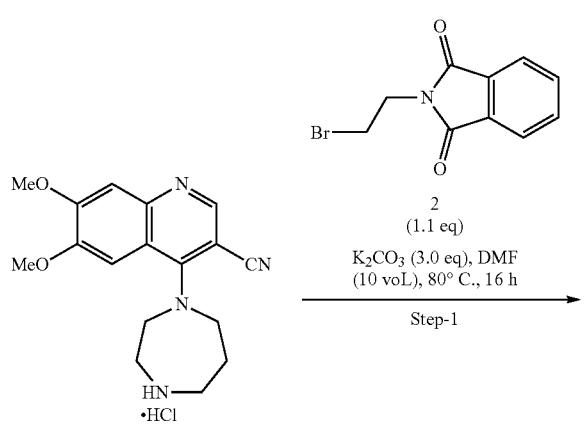
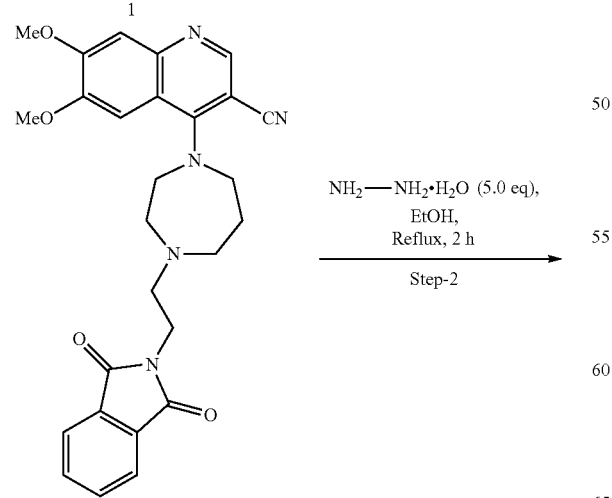
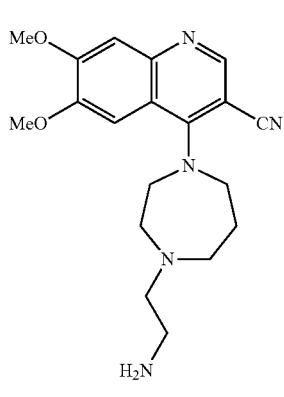
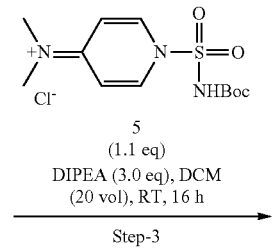
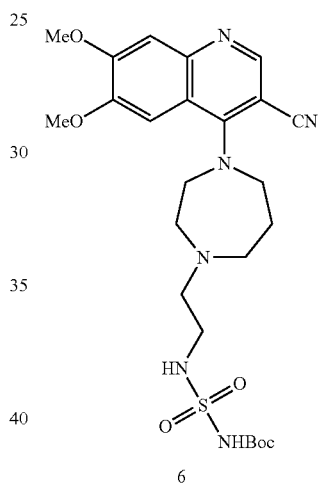
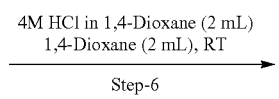
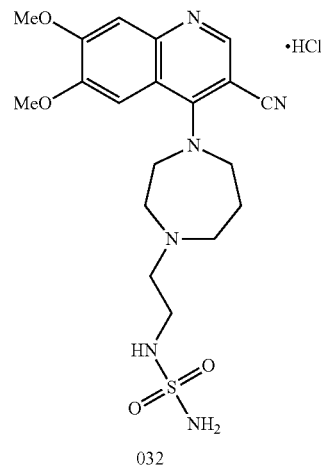

187

Synthesis of 4-(4-(2-(1,3-dioxoisoindolin-2-yl)ethyl)-1,4-diazepan-1-yl)-6,7-dimethoxyquinoline-3-carbonitrile (3)

188

Synthesis of 4-(4-(2-aminoethyl)-1,4-diazepan-1-yl)-6,7-dimethoxyquinoline-3-carbonitrile (4)

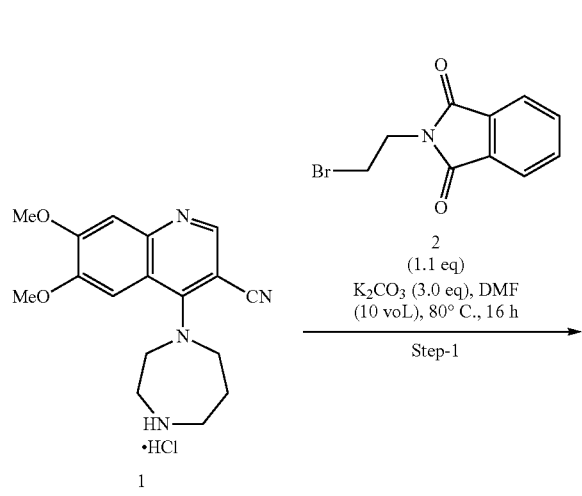

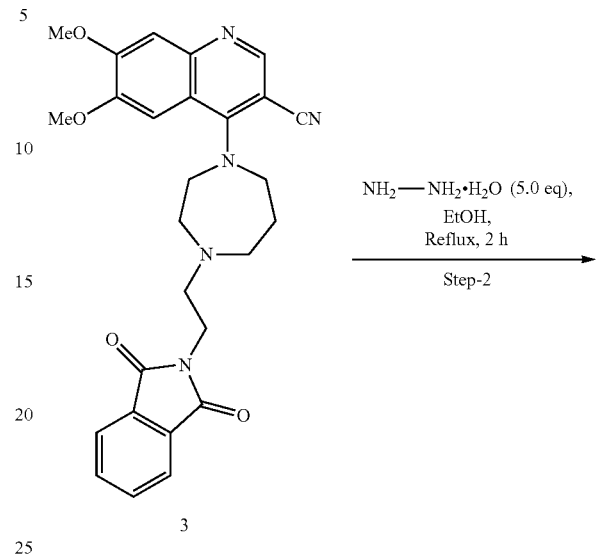

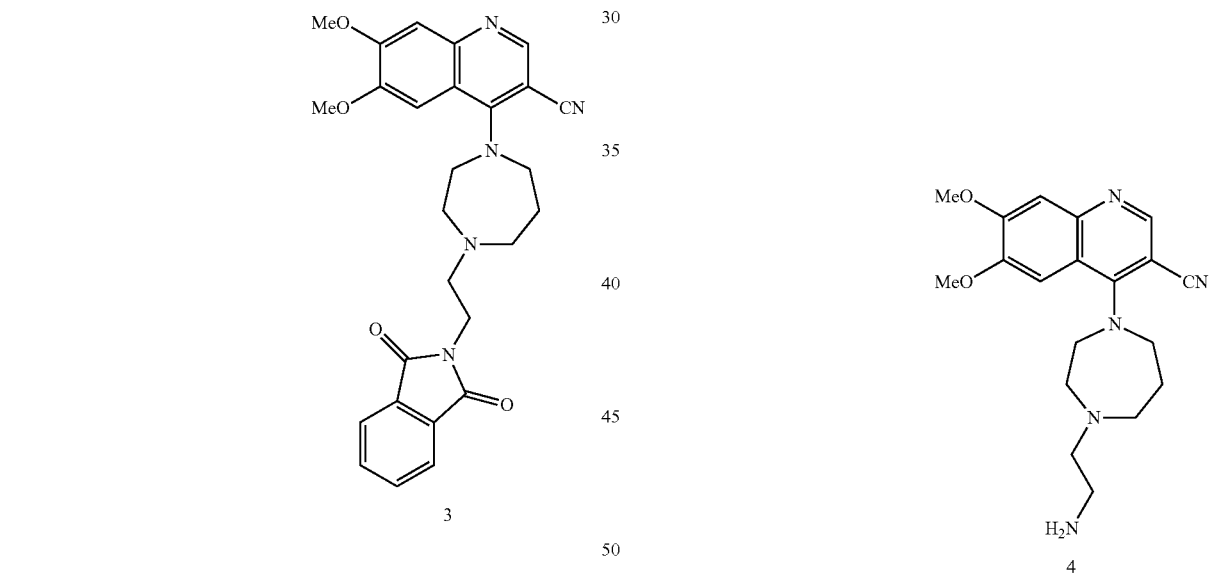

To a stirred solution of 4-(1,4-diazepan-1-yl)-6,7-dimethoxyquinoline-3-carbonitrile hydrochloride 1 (500 mg, 1.6 mmol) in DMF (5 ml) was added potassium carbonate (662 mg, 4.8 mmol) and 2-(2-bromoethyl)isoindoline-1,3-dione 2 (610 mg, 1.76 mmol) then stirred at 90° C. for 16 h. The progress of the reaction was monitored by TLC. After completion of the reaction, reaction mixture was poured on water and extracted with ethyl acetate. Organic layer was separated and washed with water, then organic layer was concentrated under reduced pressure to obtained crude. Crude residue was purified by combi-flash chromatography to afforded pure compound of 4-(4-(2-(1,3-dioxoisoindolin-2-yl)ethyl)-1,4-diazepan-1-yl)-6,7-dimethoxyquinoline-3-carbonitrile (3) (300 mg, 0.618 mmol, 38% yield) as a brown syrup.

LCMS: (M+H)$^+$: m/Z: 486.2

To a stirred solution of 4-(4-(2-aminoethyl)-1,4-diazepan-1-yl)-6,7-dimethoxyquinoline-3-carbonitrile 3 (300 mg, 0.61 mmol) in EtOH (6 mL) was added 90% of hydrazine hydrate (0.06 mL, 1.23 mmol) at RT, then reaction mixture was stirred at reflux for 2 h. The progress of the reaction was monitored by TLC. After completion of the reaction, reaction mixture was poured on water and extracted with ethyl acetate. Organic layer was separated and washed with water, Organic layer was concentrated under reduced pressure to obtain crude. Crude compound was purified by combi-flash chromatography to afford pure compound of 4-(4-(2-aminoethyl)-1,4-diazepan-1-yl)-6,7-dimethoxyquinoline-3-carbonitrile (4) (100 mg, 0.281 mmol, 45% yield) as a brown syrup.

LCMS: (M+H)$^+$: m/Z: 356.3

189
Synthesis of Tert-butyl (N-(2-(4-(3-cyano-6,7-dimethoxyquinolin-4-yl)-1,4-diazepan-1-l)ethyl)sulfamoyl)carbamate (6)

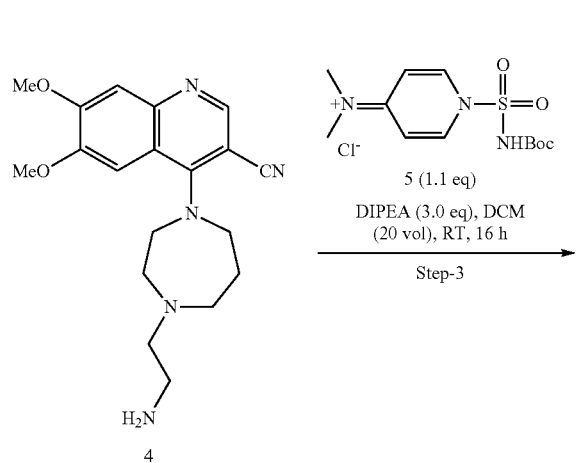

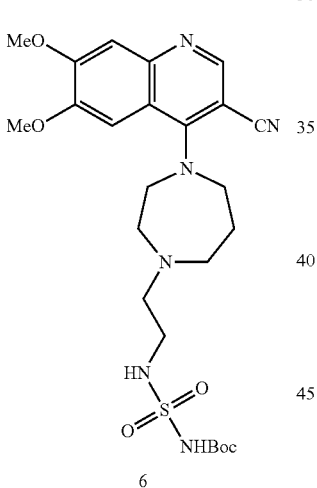

To a stirred solution of 4-(4-(2-aminoethyl)-1,4-diazepan-1-yl)-6,7-dimethoxyquinoline-3-carbonitrile (4) (100 mg, 0.28 mmol) in dichloromethane (2 mL) were added diisopropylethylamine (0.146 mL, 0.84 mmol) and N-(1-(N-(tert-butoxycarbonyl)sulfamoyl)pyridin-4(1H)-ylidene)-N-methylmethanaminium 5 (95 mg, 0.28 mmol) at RT, then stirred at room temperature for 16 h. The progress of the reaction was monitored by TLC. After completion of the reaction, organic solvents completely distilled off under reduced pressure to afford crude compound. Crude compound was purified combi flash column chromatography by eluting 5% MeOH in DCM to afford tert-butyl (N-(2-(4-(3-cyano-6,7-dimethoxyquinolin-4-yl)-1,4-diazepan-1-yl)ethyl)sulfamoyl)carbamate (6) (80 mg, 0.225 mmol, 53% yield) as a brown thick syrup.

LCMS: (M+H)$^+$: m/Z: 535.19

190
Synthesis of Compound 032

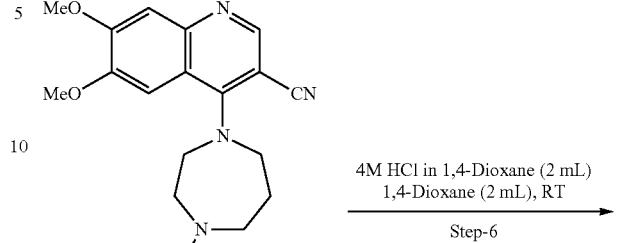

To a stirred solution of tert-butyl (N-(2-(4-(3-cyano-6,7-dimethoxyquinolin-4-yl)-1,4-diazepan-1-yl)ethyl)sulfamoyl)carbamate (6) (80 mg, 0.182 mmol) in 1,4-dioxane (1.0 mL) was added 4M HCl in dioxane (2 mL) at RT. Reaction mixture was stirred at RT for 6 h. The progress of the reaction was monitored by TLC. After completion of the reaction, organic solvents completely distilled off under reduced pressure to afford crude compound. Crude compound was purified through prep HPLC method to afford pure compound of Compound 032 (15 mg, 0.034 mmol, 23% yield) as an off white solid Analytical Data: $^1$H NMR (400 MHz, DMSO) δ 8.62 (s, 1H), 8.17 (s, 1H), 7.37 (s, 2H), 6.57 (brs, 2H), 6.30 (t, 1H), 3.94 (d, 6H), 3.71-3.7 (m, 4H), 3.0-3.05 (m, 2H), 2.84-2.89 (m, 4H), 2.67-2.71 (m, 2H), 1.98-2.01 (m, 2H).

LCMS: (M+H)$^+$: m/Z: 435.2

Synthetic Scheme for Compound 033
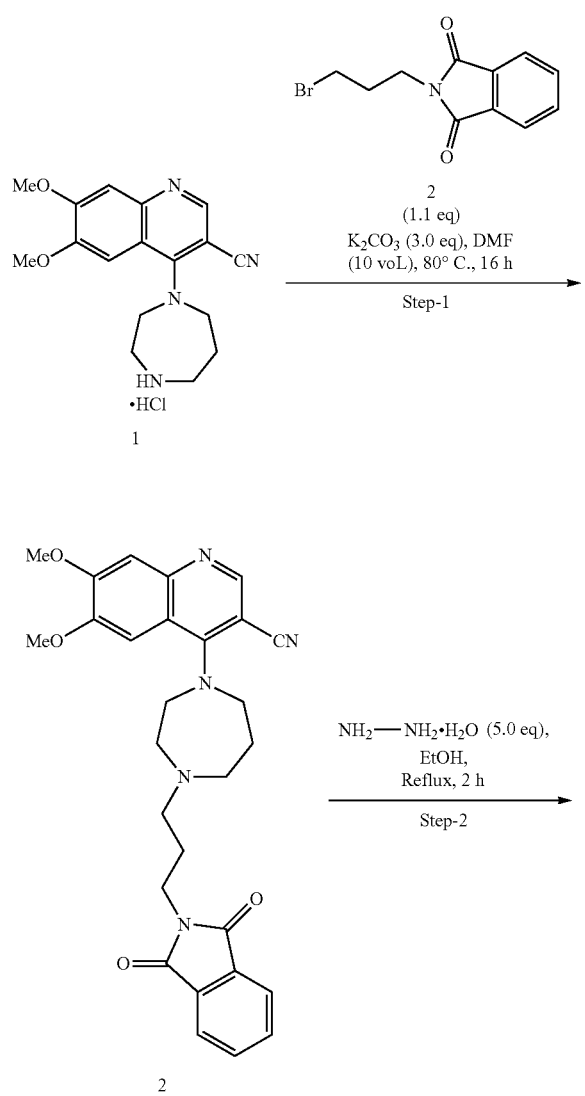
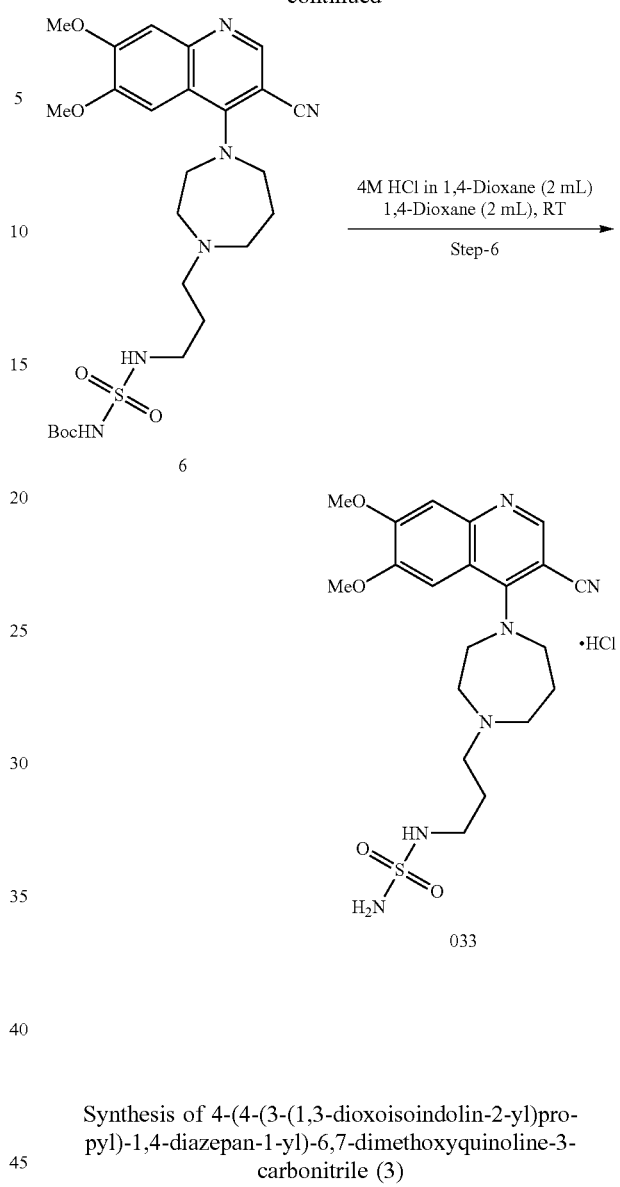
Synthesis of 4-(4-(3-(1,3-dioxoisoindolin-2-yl)propyl)-1,4-diazepan-1-yl)-6,7-dimethoxyquinoline-3-carbonitrile (3)
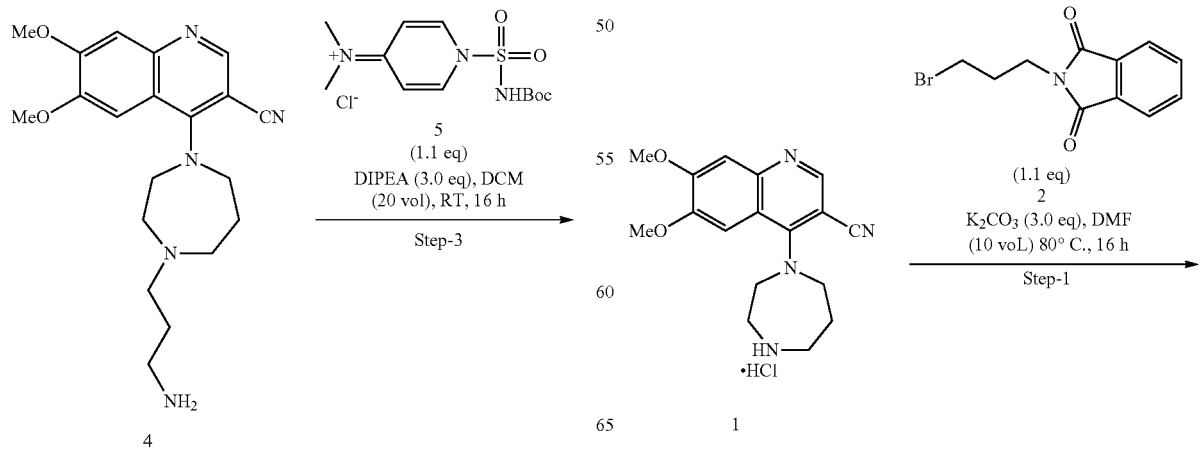

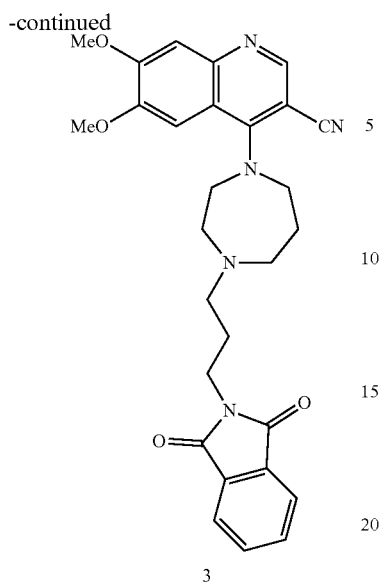

3

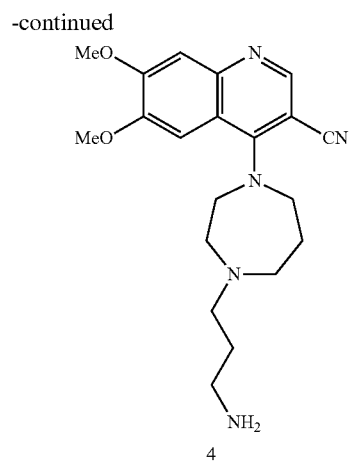

4

To a stirred solution of 4-(1,4-diazepan-1-yl)-6,7-dimethoxyquinoline-3-carbonitrile hydrochloride 1 (500 mg, 1.6 mmol) in DMF (5 mL) were added potassium carbonate (662 mg, 4.8 mmol) and 2-(3-bromopropyl)isoindoline-1,3-dione 2 (515 mg, 1.9 mmol) then stirred at 90° C. for 16 h. The progress of the reaction was monitored by TLC. After completion of the reaction, reaction mixture was poured on water and extracted with ethyl acetate. Organic layer was separated and washed with water, then organic layer was concentrated under reduced pressure to obtained crude. Crude residue was purified by combi-flash chromatography to afforded pure compound of 4-(4-(3-(1,3-dioxoisoindolin-2-yl)propyl)-1,4-diazepan-1-yl)-6,7-dimethoxyquinoline-3-carbonitrile 3 (150 mg, 0.30 mmol, 19% yield) as a brown syrup.

LCMS: (M+H)$^+$: m/Z: 500.34

Synthesis of 4-(4-(3-aminopropyl)-1,4-diazepan-1-yl)-6,7-dimethoxyquinoline-3-carbonitrile (4)

To a stirred solution of 4-(4-(3-(1,3-dioxoisoindolin-2-yl)propyl)-1,4-diazepan-1-yl)-6,7-dimethoxyquinoline-3-carbonitrile 3 (150 mg, 0.3 mmol) in EtOH (3 mL) were added 90% of hydrazine hydrate (0.03 mL, 0.6 mmol) at RT, then reaction mixture was stirred at reflux for 4 h. The progress of the reaction was monitored by TLC. After completion of the reaction, reaction mixture was poured on water and extracted with ethyl acetate. Organic layer was separated and washed with water, Organic layer was concentrated under reduced pressure to obtain crude. Crude compound was purified by combi-flash chromatography to afford pure compound of 4-(4-(3-aminopropyl)-1,4-diazepan-1-yl)-6,7-dimethoxyquinoline-3-carbonitrile (4) (100 mg, 0.271 mmol, 90% yield) as a brown syrup.

LCMS: (M+H)$^+$: m/Z: 370.2

Synthesis of Tert-butyl (N-(3-(4-(3-cyano-6,7-dimethoxyquinolin-4-yl)-1,4-diazepan-1-yl)propyl)sulfamoyl)carbamate (6)

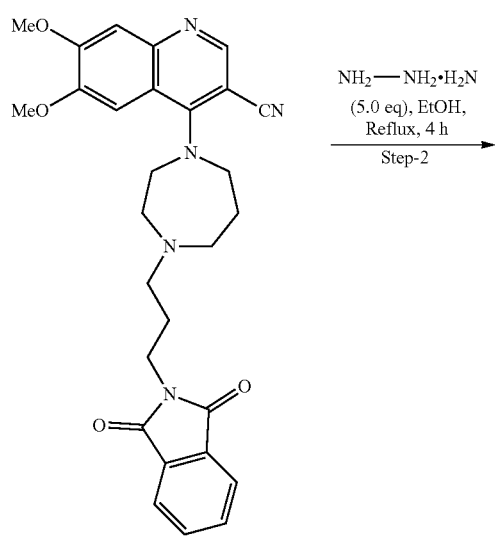

3

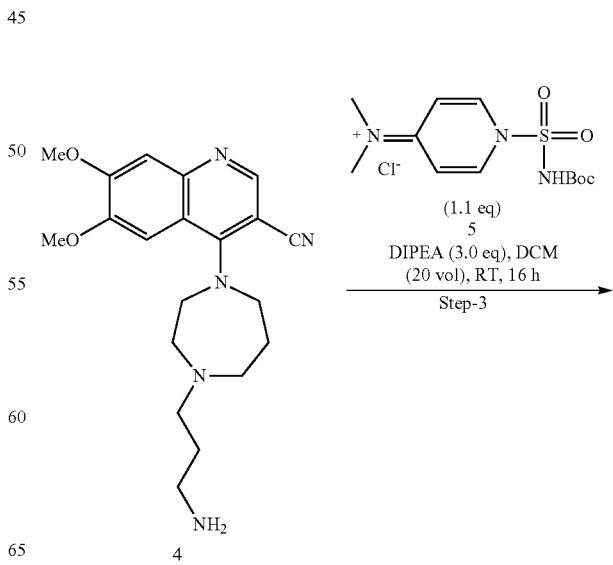

4

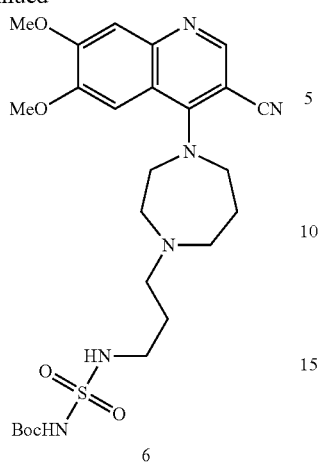

6

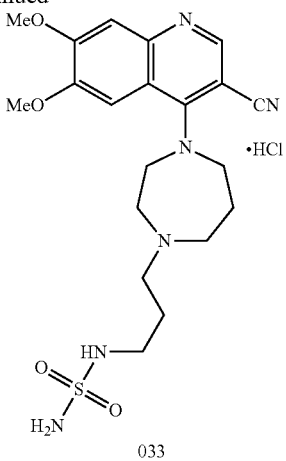

033

To a stirred solution of 4-(4-(3-aminopropyl)-1,4-diazepan-1-yl)-6,7-dimethoxyquinoline-3-carbonitrile (4) (100 mg, 0.27 mmol) in dichloromethane (2 ml) were added diisopropylethylamine (0.14 mL, 0.81 mmol) and N-(1-(N-(tert-butoxycarbonyl)sulfamoyl)pyridin-4(1H)-ylidene)-N-methylmethanaminium 5 (91 mg, 0.27 mmol) at RT, then stirred at room temperature for 16 h. The progress of the reaction was monitored by TLC. After completion of the reaction, organic solvents completely distilled off under reduced pressure to afford crude compound. Crude compound was purified combi flash column chromatography by eluting 5% MeOH in DCM to afford tert-butyl (N-(3-(4-(3-cyano-6,7-dimethoxyquinolin-4-yl)-1,4-diazepan-1-yl)propyl)sulfamoyl)carbamate (6) (100 mg, 0.182 mmol, 67% yield) as a brown solid.

LCMS: (M+H)+: m/Z: 549.31

To a stirred solution of afford tert-butyl (N-(3-(4-(3-cyano-6,7-dimethoxyquinolin-4-yl)-1,4-diazepan-1-yl)propyl)sulfamoyl)carbamate (6) (100 mg, 0.182 mmol) in 1,4-dioxane (2.0 ml) was added 4M HCl in dioxane (2 mL) at RT. Reaction mixture was stirred at RT for 6 h. The progress of the reaction was monitored by TLC. After completion of the reaction, organic solvents completely distilled off under reduced pressure to afford crude compound. Crude compound was purified through prep HPLC method to afford pure compound of Compound 033 (10 mg, 0.022 mmol, 12% yield) as an off white solid. Analytical Data: $^1$H NMR (400 MHz, DMSO) δ 8.60 (s, 1H), 7.30 (s, 1H), 7.36 (s, 2H), 6.47-6.53 (m, 3H), 3.90 (d, 6H), 3.70-3.72 (m, 4H), 2.90-2.95 (m, 2H), 2.78-2.81 (m, 4H), 2.54-2.57 (m, 2H), 1.98 (m, 2H), 1.61-1.68 (m, 2H).

LCMS: (M+H)+: m/Z: 449.2

Synthesis of Compound 033

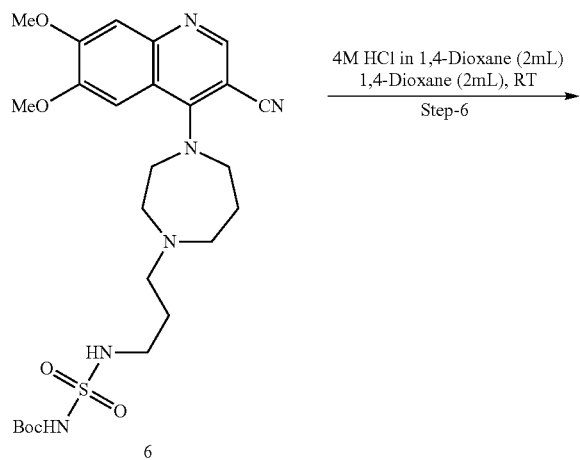

General scheme 7

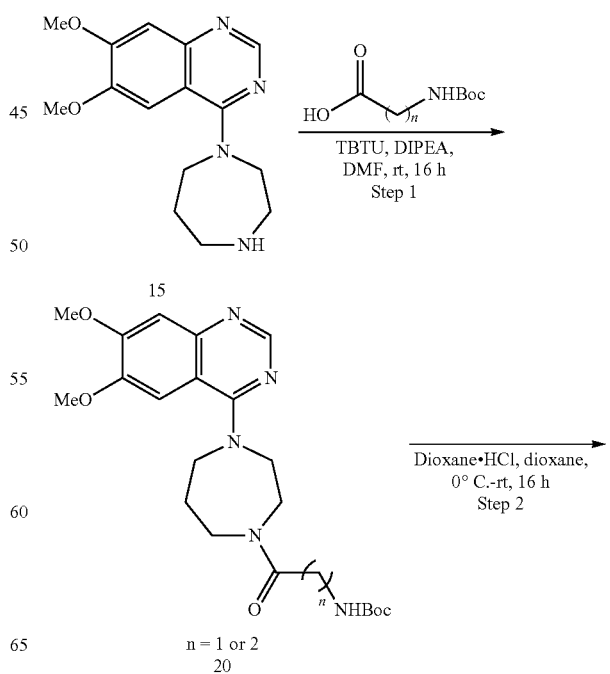

n = 1 or 2
20

-continued

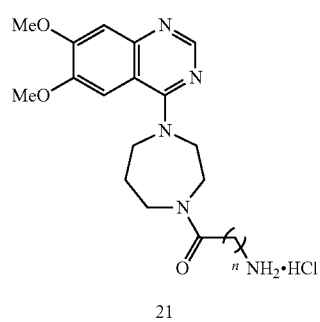 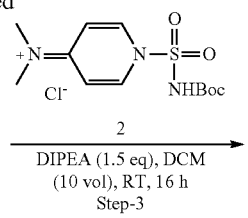

DIPEA (1.5 eq), DCM
(10 vol), RT, 16 h
Step-3

21

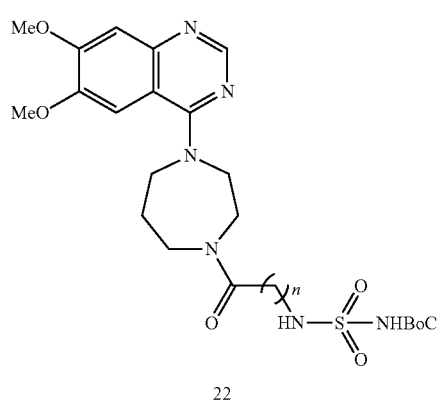

Dioxane,
HCl,
dioxane,
0° C.-RT,
16 h
Step 4

22

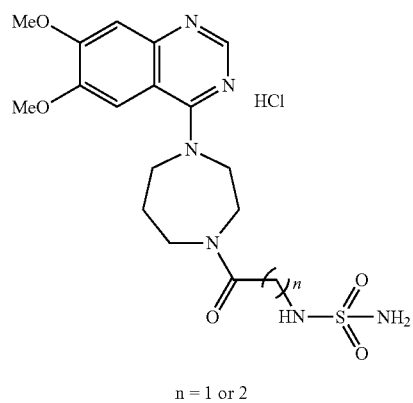

n = 1 or 2

Example 7: (N-(2-(4-(6, 7-dimethoxyquinazolin-4-yl)-1, 4-diazepan-1-yl)-2-oxoethyl) sulfamide hydrochloride

Step 1: Synthesis of tert-butyl (2-(4-(6,7-dimethoxyquinazolin-4-yl)-1,4-diazepan-1-yl)-2-oxoethyl)carbamate

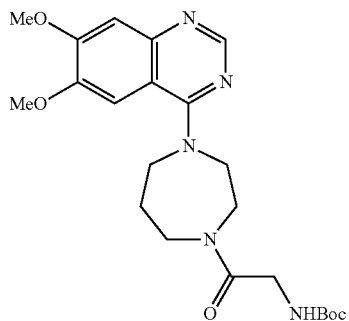 [SMILES: COc1cc2ncnc(N3CCCN(C(=O)CNC(=O)OC(C)(C)C)CC3)c2cc1OC]

To a stirred solution of 4-(1,4-diazepan-1-yl)-6,7-dimethoxyquinazoline (400 mg, 1.38 mmol) in DMF (5 ml) was added DIPEA (0.85 mL, 4.83 mmol), TBTU (531 mg, 1.65 mmol) and (tert-butoxy carbonyl)glycine (267 mg, 1.52 mmol) at room temperature. Reaction mixture was stirred at for 16 h. After completion of the reaction, reaction mixture was poured on water and extracted with ethyl acetate. Organic layer was separated and washed with water, Then organic layer was concentrated under reduced pressure to afford pure compound of tert-butyl (2-(4-(6,7-dimethoxyquinazolin-4-yl)-1,4-diazepan-1-yl)-2-oxoethyl)carbamate 20 (410 mg, 0.921 mmol, 66% yield) as a brown solid. 1H NMR (400 MHz, DMSO) δ 8.41 (d, 1H), 7.21 (d, 1H), 7.16 (d, 1H), 6.72-6.69 (m, 1H), 3.96-3.87 (m, 10H), 3.80-3.76 (m, 4H), 3.56-3.55 (m, 2H), 2.05-1.93 (m, 2H), 1.36-1.33 (m, 9H). LCMS: (M+H)+: m/Z: 446.26

The following compound was synthesized by the above general procedure:

| Structure | 1HNMR |
|---|---|
| 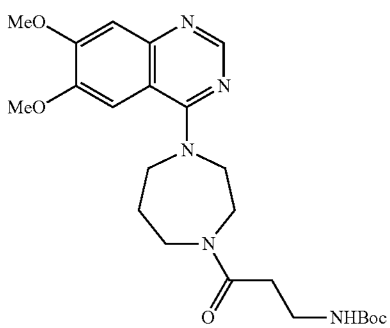 [SMILES: COc1cc2ncnc(N3CCCN(C(=O)CCNC(=O)OC(C)(C)C)CC3)c2cc1OC] | (400 MHz, DMSO) δ 8.40 (d, 1H), 7.22-7.21 (m, 1H), 7.16-7.15 (m, 1H), 6.63-6.64 (m, 1H), 3.95-3.84 (m, 10H), 3.77-3.75 (m, 2H), 3.56-3.53 (m, 2H), 3.08-3.06 (m, 2H), 2.45-2.43 (m, 2H), 2.02-1.92 (m, 2H), 1.33 (s, 9H). MS 460.26 |

Step-2: 2-amino-1-(4-(6, 7-dimethoxyquinazolin-4-yl)-1, 4-diazepan-1-yl) ethan-1-one hydrochloride

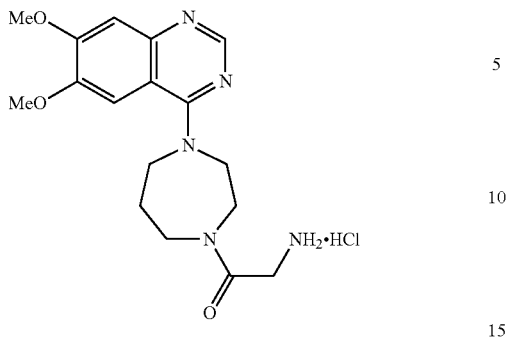

To a stirred solution of tert-butyl (2-(4-(6,7-dimethoxy-quinazolin-4-yl)-1,4-diazepan-1-yl)-2-oxoethyl)carbamate (3) (300 mg, 0.674 mmol) in dioxane (1 ml) was added 4M HCl in dioxane (3 mL) at RT, then stirred at room temperature for 16 h. The progress of the reaction was monitored by TLC. After completion of the reaction, organic solvents completely distilled off under reduced pressure to afford 2-amino-1-(4-(6, 7-dimethoxyquinazolin-4-yl)-1, 4-diazepan-1-yl) ethan-1-one hydrochloride (4) (250 mg, 0.656 mmol, 91% yield) as a brown solid.

Analytical data: 1H NMR (400 MHz, DMSO) δ 15.07 (brs, 1H), 8.77-8.78 (d, 1H), 8.10 (brs, 3H), 7.47-7.41 (m, 2H), 4.28-4.19 (m, 4H), 4.00-3.84 (m, 13H), 3.66-3.64 (m, 1H), 2.00-2.10 (m, 2H).

| Structure | 1HNMR |
|---|---|
| 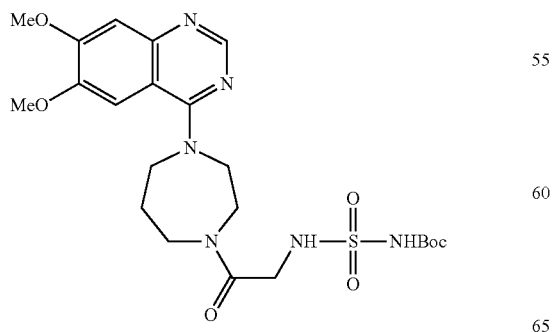 | 1H NMR (400 MHz, DMSO) δ 8.79-8.76 (d, 1H), 7.94-7.89 (m, 4H), 7.43-7.41 (m, 2H), 4.27-4.20 (m, 4H), 3.96 (s, 6H), 3.88 (bs, 4H), 3.56-3.63 (m, 2H), 2.93-2.87 (m, 1H), 2.67-2.65 (m, 1H), 2.08-2.00 (m, 2H). MS 360.2 |

Step-3: Tert-butyl (N-(2-(4-(6, 7-dimethoxyquinazolin-4-yl)-1, 4-diazepan-1-yl)-2-oxoethyl) sulfamoyl) carbamate To a stirred solution of 2-amino-1-(4-(6,7-dimethoxyquinazolin-4-yl)-1,4-diazepan-1-yl)ethan-1-one hydrochloride (4) (250 mg, 0.724 mmol) in dichloromethane (20 ml) were added diisopropylethylamine (0.631 mL, 3.62 mmol) and N-(1-(N-(tert-butoxycarbonyl)sulfamoyl)pyridin-4(1H)-ylidene)-N-methylmethanaminium chloride 4 (293 mg, 0.869 mmol) at RT, then stirred at room temperature for 16 h. The progress of the reaction was monitored by TLC. After completion of the reaction, organic solvents completely distilled off under reduced pressure to afford crude compound. Crude compound was purified combi flash column chromatography by eluting 5% methanol in DCM to afford tert-butyl (N-(2-(4-(6, 7-dimethoxyquinazolin-4-yl)-1, 4-diazepan-1-yl)-2-oxoethyl) sulfamoyl) carbamate 6 (200 mg, 0.381 mmol, 52% yield) as a brown solid. LCMS: (M+H)+: m/Z: 525.2

| Structure | 1HNMR |
|---|---|
| 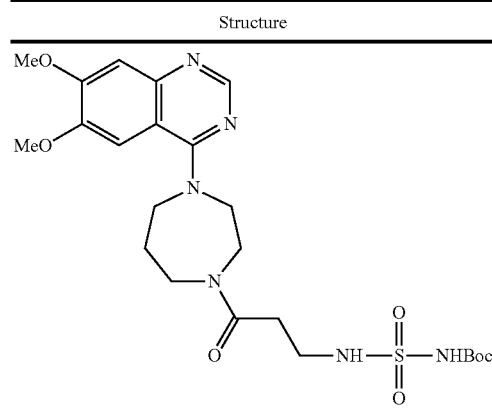 | 1H NMR (400 MHz, DMSO) δ 10.79 (bs, 1H), 8.46-8.39 (m, 2H), 7.26-7.25 (m, 1H), 7.21 (d, 1H), 7.16 (d, 1H), 6.96 (d, 1H), 3.90-3.88 (m, 10H), 3.77-3.74 (m, 2H), 3.54 (t, 2H), 3.06-3.03 (m, 2H), 2.58-2.54 (m, 2H), 2.09-1.90 (m, 2H), 1.39 (s, 9H). MS 539.3 |

Step-4: (N-(2-(4-(6, 7-dimethoxyquinazolin-4-yl)-1, 4-diazepan-1-yl)-2-oxoethyl) sulfamide hydrochloride (Compound 064)

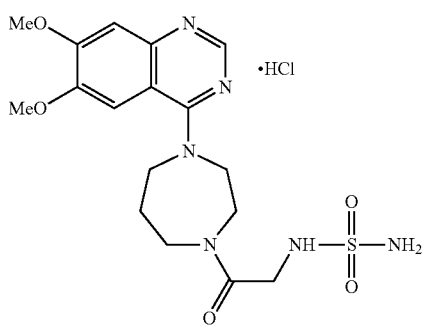 [SMILES: COc1cc2ncnc(N3CCCN(C(=O)CNS(N)(=O)=O)CC3)c2cc1OC ; Cl]

To a stirred solution of tert-butyl (N-(2-(4-(6,7-dimethoxyquinazolin-4-yl)-1,4-diazepan-1-yl)-2-oxoethyl)sulfamoyl)carbamate 6 (200 mg, 0.381 mmol) in 1,4-dioxane (1.0 ml) was added 4M HCl in dioxane (3 mL) at RT. Reaction mixture was stirred at RT for 16 h. The progress of the reaction was monitored by TLC. After completion of the reaction, organic solvents completely distilled off under reduced pressure to afford crude compound. Crude compound was purified through prep HPLC method to afford pure compound of (N-(2-(4-(6, 7-dimethoxyquinazolin-4-yl)-1, 4-diazepan-1-yl)-2-oxoethyl) sulfamide hydrochloride (50 mg, 0.117 mmol, 31% yield) as an off white solid.

Analytical Data: 1H NMR (400 MHz, DMSO) δ 8.42 (d, 1H), 7.22-7.21 (d, 1H), 7.16 (d, 1H), 6.59-6.55 (m, 2H), 6.15-6.14 (m, 1H), 3.98-3.97 (m, 1H), 3.90-3.88 (m, 10H), 3.82-3.78 (m, 3H), 3.76-3.75 (m, 1H), 3.57-3.56 (m, 2H), 2.10-1.95 (m, 2H). LCMS: (M+H)+: m/Z: 425.2

| Compound Number | Structure | 1HNMR |
|---|---|---|
| 064 | 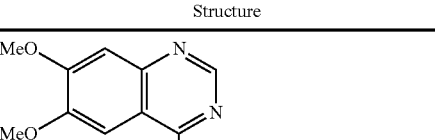 | 1H NMR (400 MHz, DMSO) δ 8.41 (d, 1H), 7.21 (d, 1H), 7.16 (d, 1H), 6.53 (s, 2H), 6.32-6.31 (m, 1H), 3.97-3.94 (m, 1H), 3.90-3.88 (m, 9H), 3.78-3.74 (m, 2H), 3.06-3.03 (m, 2H), 2.59-2.52 (m, 2H), 2.04-1.94 (m, 2H). MS 439.2 |
Compound 065 was also prepared based on the general synthesis above:
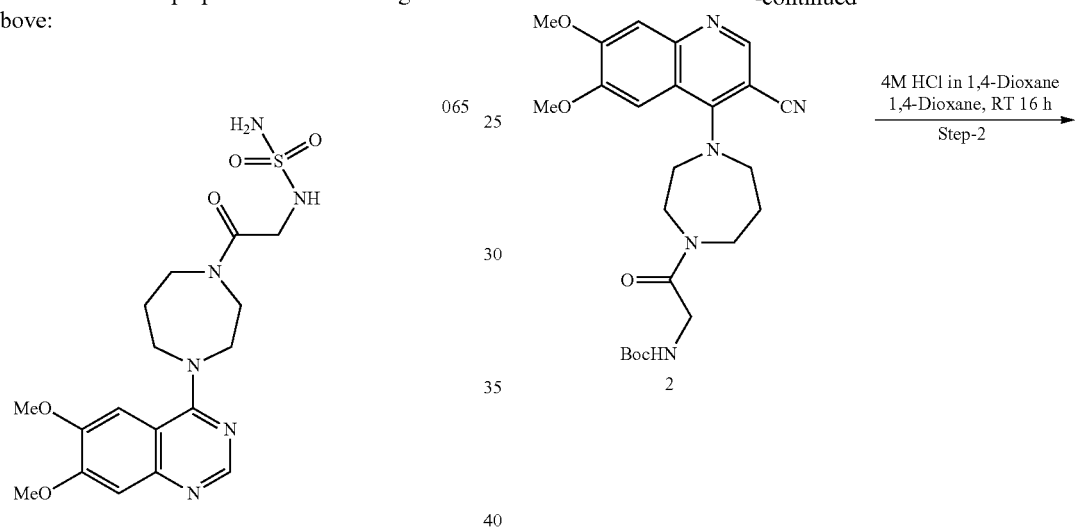
1H NMR (400 MHz, DMSO) δ 15.07 (brs, 1H), 8.77-8.78 (d, 1H), 8.10 (brs, 3H), 7.47-7.41 (m, 2H), 4.28-4.19 (m, 4H), 4.00-3.84 (m, 13H), 3.66-3.64 (m, 1H), 2.00-2.10 (m, 2H). LCMS 425.2. MW. 460.93
Synthetic Scheme for Compound 034
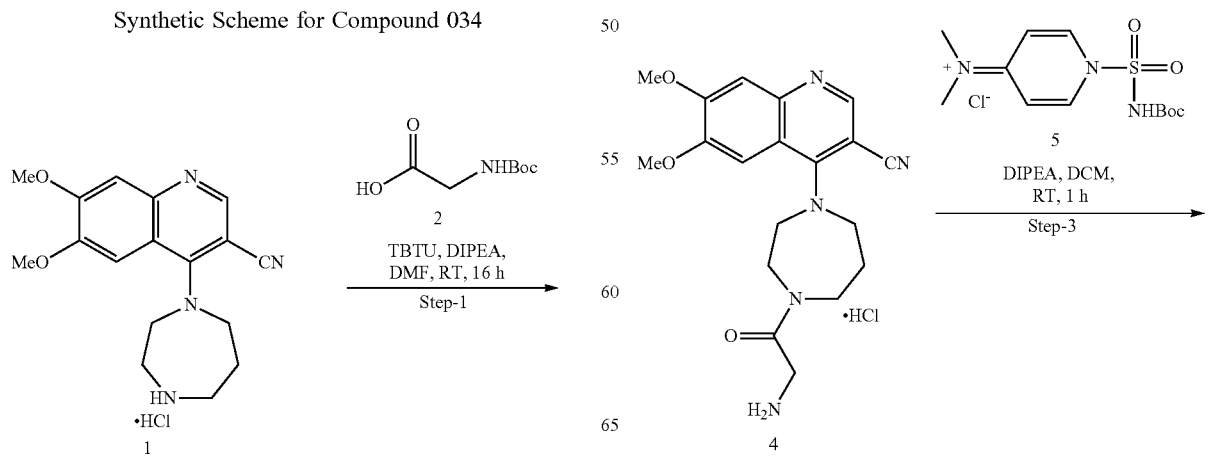

-continued

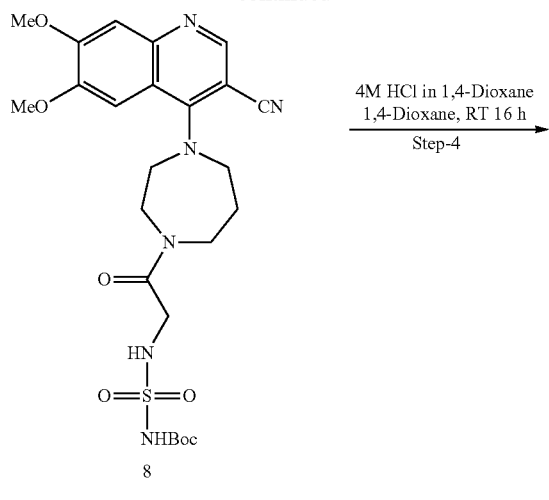

8

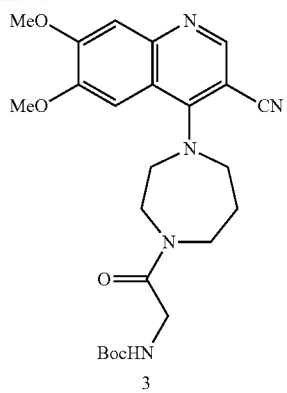

3

To a stirred solution of 4-(1,4-diazepan-1-yl)-6,7-dimethoxyquinoline-3-carbonitrile hydrochloride 1 (200 mg, 0.641 mmol) in DMF (4 mL) was added DIPEA (0.335 mL, 1.923 mmol), TBTU (247 mg, 0.769 mmol) and (tert-butoxycarbonyl)glycine (123 mg, 0.705 mmol) at room temperature. Reaction mixture was stirred at for 16 h. After completion of the reaction, reaction mixture was poured on water and extracted with ethyl acetate. Organic layer was separated and washed with water, then organic layer was concentrated under reduced pressure to obtain crude. Crude compound was purified by combi-flash chromatography to afford tert-butyl (2-(4-(3-cyano-6,7-dimethoxyquinolin-4-yl)-1,4-diazepan-1-yl)-2-oxoethyl)carbamate (3) (200 mg, 0.426 mmol, 66% yield) as a yellow solid.

Analytical Data: 1H NMR (400 MHz, DMSO) δ 8.69 (s, 1H), 7.94 (s, 1H), 7.4 (d, 1H), 7.26 (s, 1H), 6.73-6.77 (m, 1H), 4.02-4.00 (m, 8H), 3.80-3.81 (m, 2H), 3.71 (m, 2H), 3.57 (m, 2H), 3.47-3.48 (m, 1H), 2.8 (s, 2H), 2.1 (m, 2H), 1.38 (s, 9H).

Synthesis of 4-(4-glycyl-1,4-diazepan-1-yl)-6,7-dimethoxyquinoline-3-carbonitrile hydrochloride (4)

034

Synthesis of Tert-butyl (2-(4-(3-cyano-6,7-dimethoxyquinolin-4-yl)-1,4-diazepan-1-yl)-2-oxoethyl)carbamate (3)

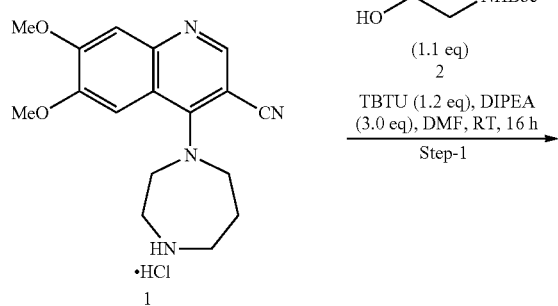

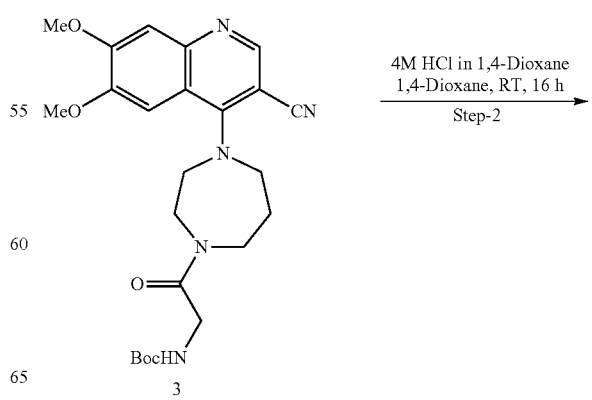

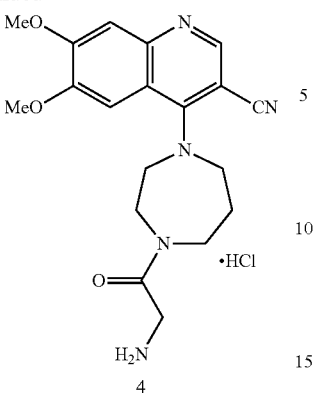

4

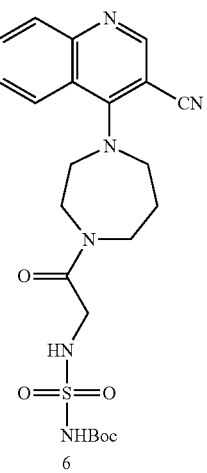

6

To a stirred solution of tert-butyl (2-(4-(3-cyano-6,7-dimethoxyquinolin-4-yl)-1,4-diazepan-1-yl)-2-oxoethyl)carbamate 3 (300 mg, 0.639 mmol) in dioxane (2 ml) was added 4M HCl in dioxane (3 mL) at 0° C. then stirred at room temperature for 6 h. The progress of the reaction was monitored by TLC. After completion of the reaction, organic solvents completely distilled off under reduced pressure. To the crude residue was washed with ether to afford 4-(4-glycyl-1,4-diazepan-1-yl)-6,7-dimethoxyquinoline-3-carbonitrile hydrochloride 4 (250 mg, 0.677 mmol, 96% yield) as a yellow solid.

LCMS: (M+H)$^+$: m/Z: 370.2

Synthesis of Tert-butyl (N-(2-(4-(3-cyano-6,7-dimethoxyquinolin-4-yl)-1,4-diazepan-1-yl)-2-oxoethyl)sulfamoyl)carbamate (6)

To a stirred solution of 4-(4-glycyl-1,4-diazepan-1-yl)-6,7-dimethoxyquinoline-3-carbonitrile hydrochloride (4) (250 mg, 0.677 mmol) in dichloromethane (20 voL) was added diisopropylethylamine (0.354 mL, 2.03 mmol) and N-(1-(N-(tert-butoxycarbonyl)sulfamoyl)pyridin-4(1H)-ylidene)-N-methylmethanaminium 5 (251 mg, 0.745 mmol) at RT, then stirred at room temperature for 16 h. The progress of the reaction was monitored by TLC. After completion of the reaction, organic solvents completely distilled off under reduced pressure to afford crude compound. Crude compound was purified combi flash column chromatography by eluting 60% ethyl acetate in pet-ether to afford tert-butyl (N-(2-(4-(3-cyano-6,7-dimethoxyquinolin-4-yl)-1,4-diazepan-1-yl)-2-oxoethyl)sulfamoyl)carbamate (6) (200 mg, 0.364 mmol, 54% yield) as a pale yellow solid.

LCMS: (M+H)$^+$: m/Z: 549.34

Preparation of Compound 034

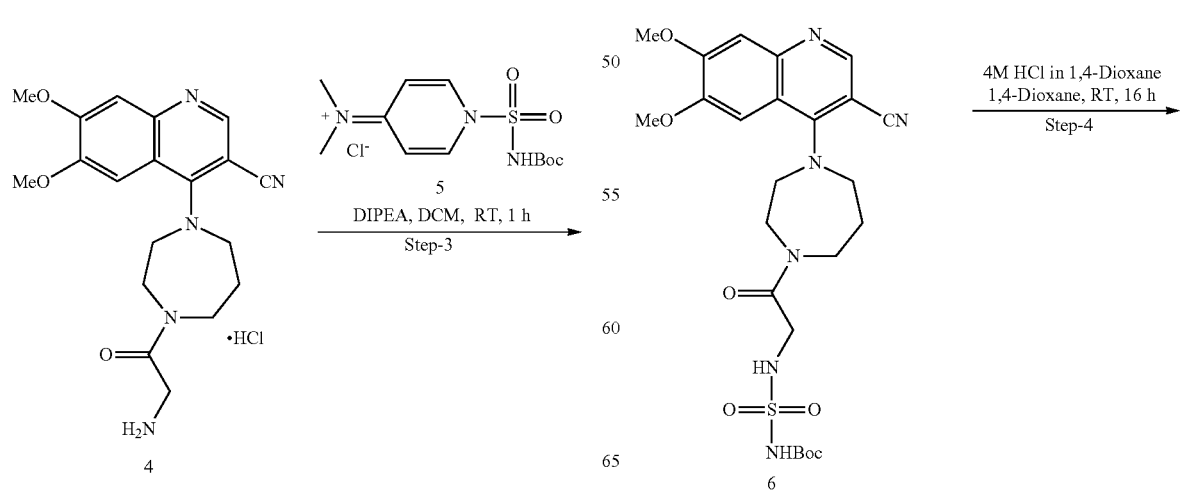

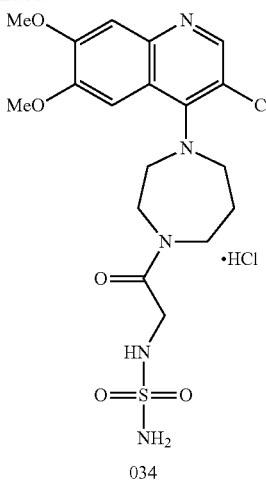

034

To a stirred solution of tert-butyl ((4-(3-cyano-6,7-dimethoxyquinolin-4-yl)-1,4-diazepan-1-yl)sulfonyl)carbamate (6) (100 mg, 0.203 mmol) in 1,4-dioxane (2.0 mL) was added 4M HCl in dioxane (2.0 mL) at RT. Reaction mixture was stirred at RT for 16 h. The progress of the reaction was monitored by TLC. After completion of the reaction, organic solvents completely distilled off under reduced pressure to afford crude compound. Crude compound was purified through prep HPLC method to afford pure compound 034 (35 mg, 0.089 mmol, 41% yield) as a pale yellow solid.

Analytical Data: 1H NMR (400 MHz, DMSO) δ 8.67-8.7 (d, 1H), 7.39-7.40 (d, 1H), 7.26 (s, 1H), 6.62 (d, 2H), 6.14-6.15 (m, 1H), 3.92-3.94 (s, 6H), 3.83 (m, 2H), 3.67-3.77 (m, 3H), 3.50-3.59 (m, 3H), 2.06-2.08 (m, 2H).

LCMS: (M+H)$^+$: m/Z: 449.2

Synthetic Scheme for Compound 035

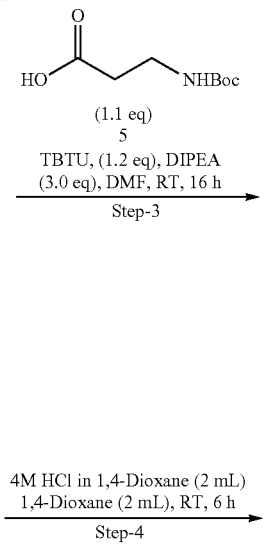

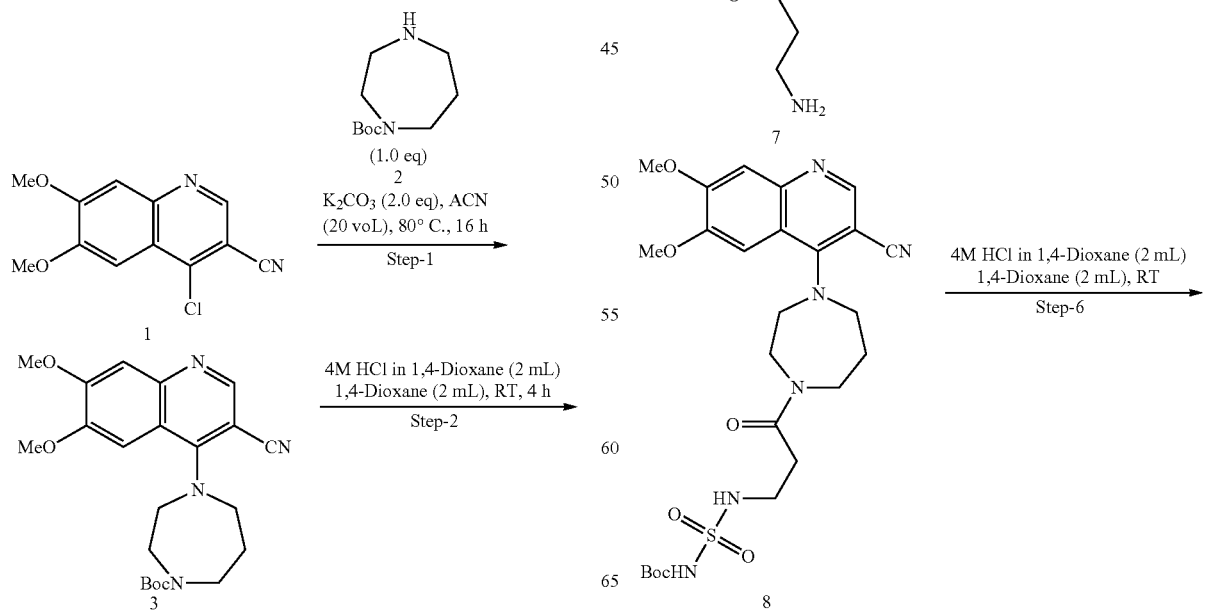

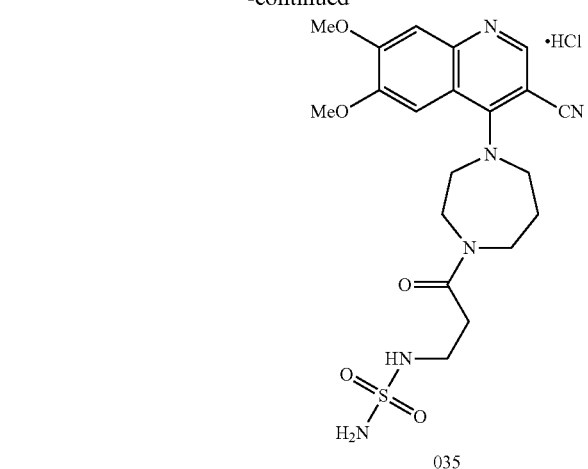

Synthesis of Tert-butyl 4-(3-cyano-6,7-dimethoxy-quinolin-4-yl)-1,4-diazepane-1-carboxylate (3)

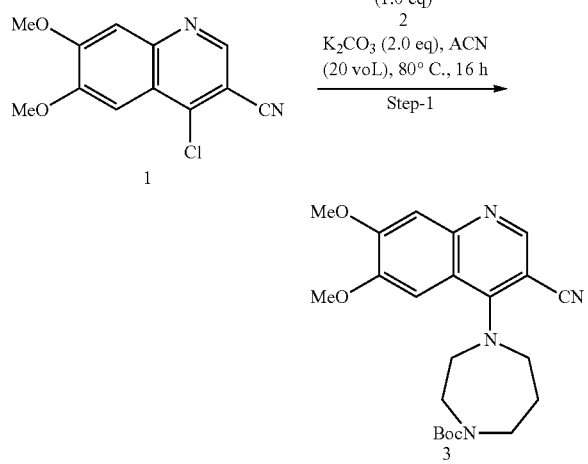

To a stirred solution of 4-chloro-6,7-dimethoxyquinoline-3-carbonitrile 1 (1.3 g, 5.22 mmol) in DMF (26 mL) were added potassium carbonate (1.45 g, 10.44 mmol) and tert-butyl 1,4-diazepane-1-carboxylate 2 (1.57 g, 7.84 mmol) then stirred at 80° C. for 16 h. The progress of the reaction was monitored by TLC. After completion of the reaction, to the reaction mixture added water (100 mL) and extracted with ethyl acetate (2×100 mL). Combined organic layers were washed with brine solution (100 mL), dried over sodium sulfate and concentrated under reduced pressure to afford pure compound of tert-butyl 4-(3-cyano-6,7-dimethoxyquinolin-4-yl)-1,4-diazepane-1-carboxylate (1.5 g, 3.64 mmol, 69% yield) as a white solid.

LCMS: (M+H)+: m/Z: 413.2

Synthesis of 4-(1,4-diazepan-1-yl)-6,7-dimethoxy-quinoline-3-carbonitrile hydrochloride (4)

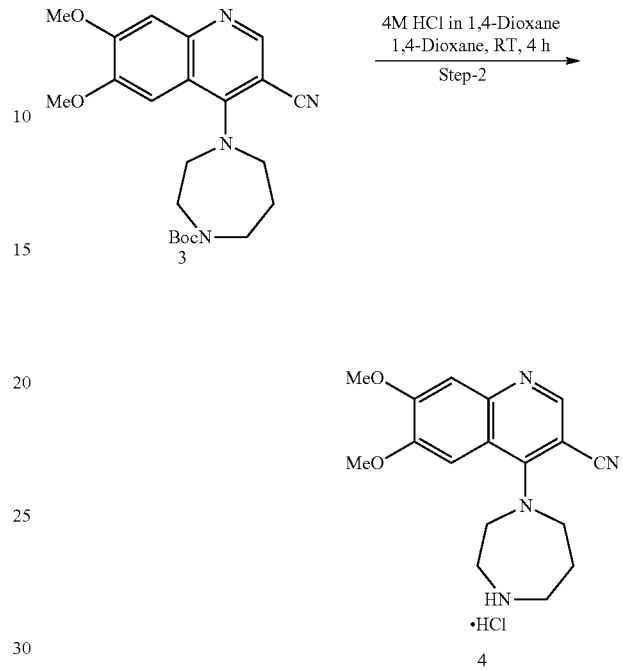

To a stirred solution of tert-butyl 4-(3-cyano-6,7-dimethoxyquinolin-4-yl)-1,4-diazepane-1-carboxylate 3 (450 mg, 1.09 mmol) in dioxane (2 mL) was added 4M HCl in dioxane (3 mL) at 0° C. then stirred at room temperature for 4 h. The progress of the reaction was monitored by TLC. After completion of the reaction, organic solvents completely distilled off under reduced pressure. To the crude residue was washed with ether to afford 4-(1,4-diazepan-1-yl)-6,7-dimethoxyquinoline-3-carbonitrile hydrochloride 4 (400 mg, 1.28 mmol, 92% yield) as a yellow solid.

LCMS: (M+H)+: m/Z: 313.31

Synthesis of Tert-butyl (3-(4-(3-cyano-6,7-dimethoxyquinolin-4-yl)-1,4-diazepan-1-yl)-3-oxopropyl)carbamate (6)

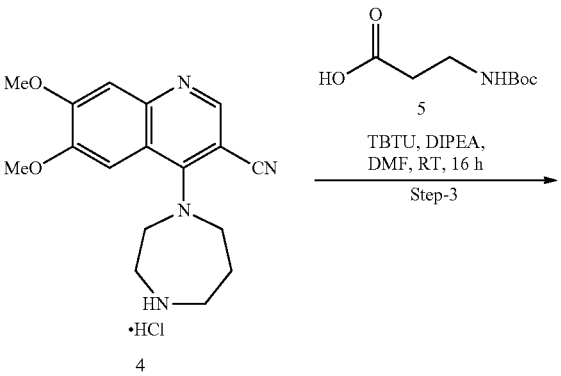

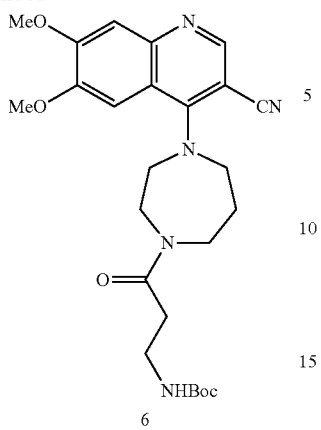

6

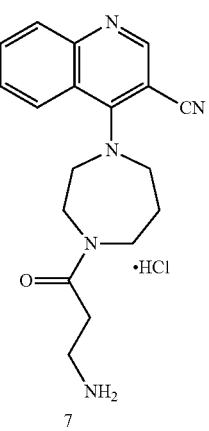

7

To a stirred solution of 4-(1,4-diazepan-1-yl)-6,7-dimethoxyquinoline-3-carbonitrile hydrochloride 4 (100 mg, 0.32 mmol) in DMF (2 ml) was added DIPEA (0.16 mL, 0.96 mmol), TBTU (124 mg, 0.38 mmol) and 3-((tert-butoxycarbonyl)amino)propanoic acid (66 mg, 0.35 mmol) at room temperature. Reaction mixture was stirred at for 16 h. After completion of the reaction, reaction mixture was poured on water and extracted with ethyl acetate. Organic layer was separated and washed with water, then organic layer was concentrated under reduced pressure to obtain crude. Crude compound was purified by combi-flash chromatography to afford tert-butyl (3-(4-(3-cyano-6,7-dimethoxyquinolin-4-yl)-1,4-diazepan-1-yl)-3-oxopropyl)carbamate (6) (100 mg, 0.154 mmol, 66% yield) as a light brown solid.

LCMS: (M+H)⁺: m/Z: 484.3

Synthesis of 4-(4-(3-aminopropanoyl)-1,4-diazepan-1-yl)-6,7-dimethoxyquinoline-3-carbonitrile hydrochloride (7)

To a stirred solution of tert-butyl (3-(4-(3-cyano-6,7-dimethoxyquinolin-4-yl)-1,4-diazepan-1-yl)-3-oxopropyl)carbamate 7 (200 mg, 0.308 mmol) in dioxane (1 mL) was added 4M HCl in dioxane (2 mL) at 0° C. then stirred at room temperature for 4 h. The progress of the reaction was monitored by TLC. After completion of the reaction, organic solvents completely distilled off under reduced pressure. To the crude residue was washed with ether to afford 4-(4-(3-aminopropanoyl)-1,4-diazepan-1-yl)-6,7-dimethoxyquinoline-3-carbonitrile hydrochloride 7 (150 mg, 0.391 mmol, 91% yield) as a brown solid.

LCMS: (M+H)⁺: m/Z: 384.2

Synthesis of Tert-butyl (N-(3-(4-(3-cyano-6,7-dimethoxyquinolin-4-yl)-1,4-diazepan-1-yl)-3-oxopropyl)sulfamoyl)carbamate (8)

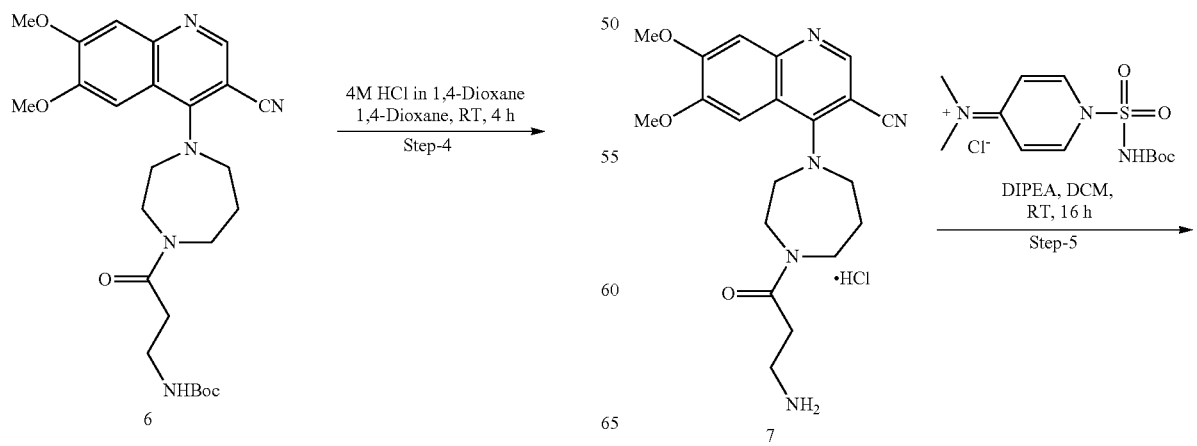

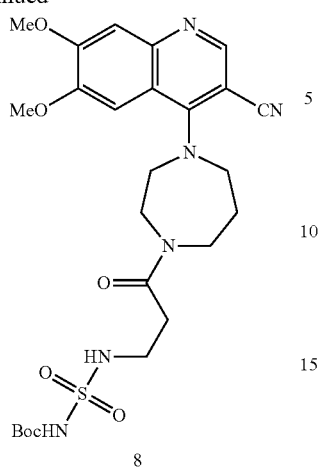

8

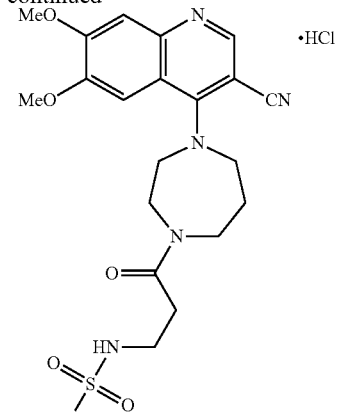

Target-98

To a stirred solution of tert-butyl (N-(3-(4-(3-cyano-6,7-dimethoxyquinolin-4-yl)-1,4-diazepan-1-yl)-3-oxopropyl)sulfamoyl)carbamate (8) (150 mg, 0.266 mmol) in 1,4-dioxane (1.0 mL) was added 4M HCl in dioxane (2.0 mL) at RT. Reaction mixture was stirred at RT for 16 h. The progress of the reaction was monitored by TLC. After completion of the reaction, organic solvents completely distilled off under reduced pressure to afford crude compound. Crude compound was purified through prep HPLC method to afford pure compound of Compound 035 (30 mg, 0.064 mmol, 24% yield) as a Off-white solid.

Analytical Data: 1H NMR (400 MHz, DMSO) δ 8.71 (d, 1H), 7.41 (d, 2H), 7.27 (s, 1H), 6.56 (d, 2H), 6.34-6.40 (m, 1H), 3.92-3.94 (m, 6H), 3.78-3.81 (m, 1H), 3.67-3.70 (m, 4H), 3.50-3.59 (m, 4H), 3.10-3.17 (m, 2H), 2.65-2.70 (m, 2H), 2.06-2.07 (m, 2H). LCMS: (M+H)+: m/Z: 463.2

To a stirred solution of 4-(4-(3-aminopropanoyl)-1,4-diazepan-1-yl)-6,7-dimethoxyquinoline-3-carbonitrile hydrochloride (7) (150 mg, 0.39 mmol) in dichloromethane (3 mL) were added diisopropylethylamine (0.2 mL, 1.17 mmol) and N-(1-(N-(tert-butoxycarbonyl)sulfamoyl)pyridin-4(1H)-ylidene)-N-methylmethanaminium (145 mg, 0.43 mmol) at RT, then stirred at room temperature for 16 h. The progress of the reaction was monitored by TLC. After completion of the reaction, organic solvents completely distilled off under reduced pressure to afford crude compound. Crude compound was purified combi flash column chromatography by eluting 5% methanol in DCM to afforded tert-butyl (N-(3-(4-(3-cyano-6,7-dimethoxyquinolin-4-yl)-1,4-diazepan-1-yl)-3-oxopropyl)sulfamoyl)carbamate (8) (150 mg, 0.266 mmol, 68% yield) as a brown solid.

LCMS: (M+H)+: m/Z: 563.3

Synthesis of Compound 035

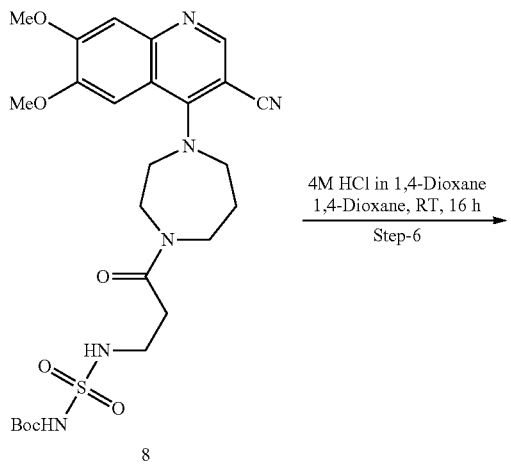

8

General scheme 8

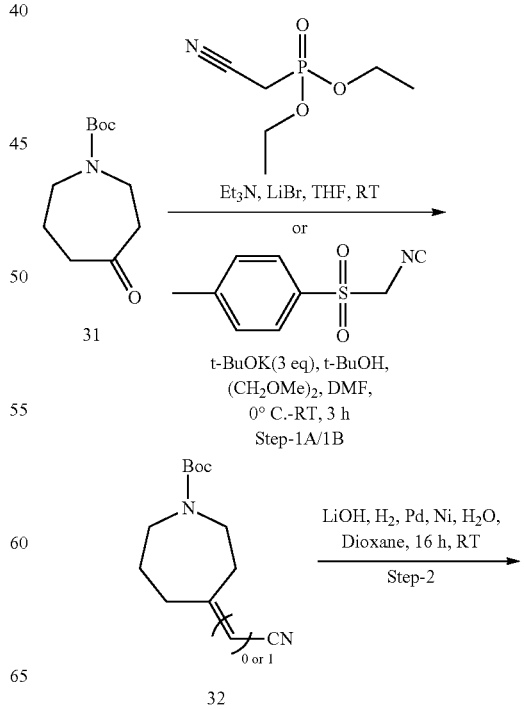

217
-continued

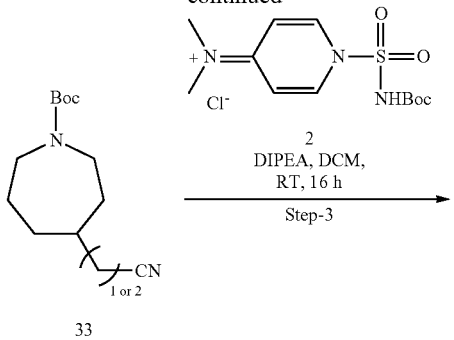

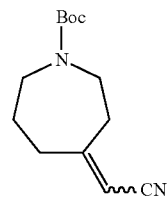

2
DIPEA, DCM,
RT, 16 h
Step-3

33

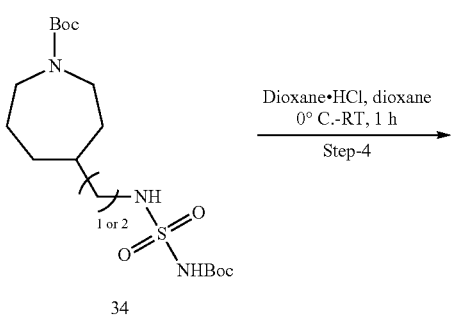

Dioxane·HCl, dioxane
0° C.-RT, 1 h
Step-4

34

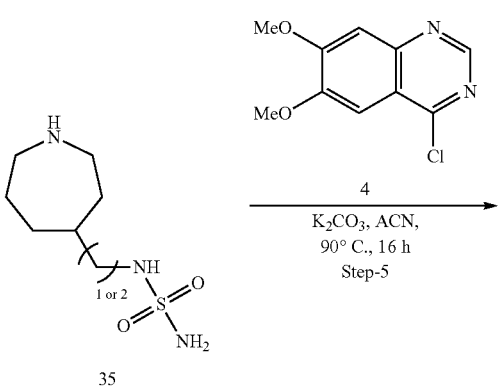

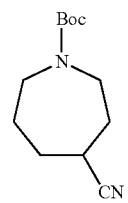

4
K₂CO₃, ACN,
90° C., 16 h
Step-5

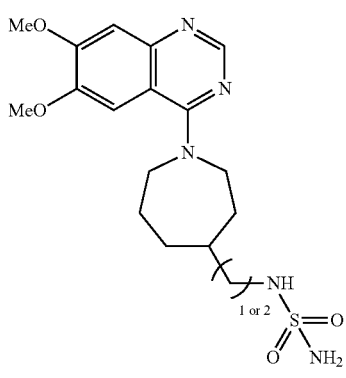

35

218

Example 8: N-(2-(1-(6,7-dimethoxyquinazolin-4-yl)azepan-4-yl)ethyl)sulfamide

Step-1A: tert-butyl 4-(cyanomethylene)azepane-1-carboxylate

To a stirred solution of tert-butyl 4-oxoazepane-1-carboxylate (500 mg, 2.347 mmol) in tetrahydrofuran (10 mL) and triethylamine (475 mg, 4.694 mmol) were added diethyl (cyanomethyl)phosphonate (436 mg, 2.464 mmol) and lithium bromide (245 mg, 2.816 mmol) at 0° C. Then stirred the reaction mixture at room temperature for 16 h. The progress of the reaction was monitored by TLC. After completion, reaction mixture was poured into ice cold water (100 mL) and extracted with ethyl acetate (2×100 mL). Combined organic layers were washed with brine solution (100 mL), dried over sodium sulfate and concentrated under reduced pressure. Crude was purified through 100-200 silica gel column chromatography by eluting 15% ethyl acetate in pet ether to afford tert-butyl 4-(cyanomethylene)azepane-1-carboxylate (510 mg, 2.161 mmol, 92% yield) as a colorless oily liquid. 1HNMR (400 MHz, DMSO) δ 5.57-5.42 (m, 1H), 3.43 (m, 2H), 3.32 (m, 1H), 3.29 (m, 1H), 2.72 (m, 1H), 2.59-2.50 (m, 2H), 2.40 (d, 1H), 1.61 (m, 2H), 1.38 (s, 9H).

Step-1B: Tert-butyl 4-cyanoazepane-1-carboxylate

To a stirred solution of tert-butyl 4-oxoazepane-1-carboxylate 1 (250 g, 1.173 mmol) in N, N'-dimethylformamide (1 ml) was added 1-((isocyanomethyl) sulfonyl)-4-methylbenzene 2 (286 mg, 1.467 mmol) at 0° C. To the reaction mixture was added the solution of potassium tert-butoxide (262 mg, 2.346 mmol) in t-butanol (1 mL) and 1, 2-dimethoxy ethane (1 mL) at 0° C. and stirred the reaction mixture at room temperature for 3 h. The progress of the reaction was monitored by TLC. After completion, reaction mixture was poured into ice cold water (50 mL) and extracted with ethyl acetate (2×30 mL). Combined organic layers were washed with brine solution (50 mL), dried over sodium sulfate and concentrated under reduced pressure. Crude was purified through 100-200 silica gel column chromatography by eluting 15% ethyl acetate in pet ether to afford tert-butyl 4-cyanoazepane-1-carboxylate 3 (150 mg, 0.669 mmol, 57% yield) as a pale blue gummy liquid.

Analytical Data: 1H NMR (400 MHz, DMSO) δ 3.43-3.37 (m, 2H), 3.27-3.16 (m, 2H), 3.07 (brs, 1H), 1.88-1.85 (m, 2H), 1.73 (brs, 4H), 1.38 (s, 9H).

Step-2: Tert-butyl 4-(2-aminoethyl) azepane-1-carboxylate

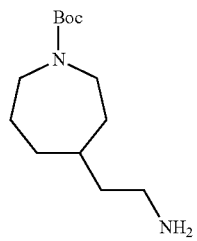

To a stirred solution of tert-butyl 4-(cyanomethylene) azepane-1-carboxylate 3 (510 mg, 2.161 mmol) in 1,4-dioxane (15 mL) and water (5 ml) were added lithium hydroxide monohydrate (200 mg, 4.754 mmol), Raney Ni (500 mg) and 10% Pd/C (150 mg) and stirred the reaction mixture under balloon hydrogen atmosphere at room temperature for 16 h. The progress of the reaction was monitored by TLC. After completion, reaction mixture filtered through celite and washed the celite bed with 5% methanol in dichloromethane (100 mL). Filtrate was concentrated under reduced pressure to afford semi pure compound of tert-butyl 4-(2-aminoethyl) azepane-1-carboxylate 4 (500 mg, crude) as a colorless gummy liquid.

Analytical Data: 1H NMR (400 MHz, DMSO) δ 3.46-3.07 (m, 8H), 2.55-2.50 (m, 2H), 1.76-1.66 (m, 3H), 1.60 (m, 1H), 1.43 (m, 3H), 1.27-1.14 (m, 4H), 1.30-1.01 (m, 1H).

| Structure | 1HNMR |
|---|---|
| 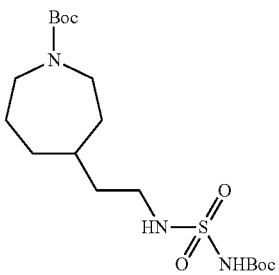 [SMILES: CC(C)(C)OC(=O)NS(=O)(=O)NCCC1CCCN(C(=O)OC(C)(C)C)CC1] | 1H NMR (400 MHz, DMSO) δ 3.42-3.33 (m, 4H), 3.21-3.10 (m, 3H), 2.37-2.31 (m, 2H), 1.81-1.73 (m, 4H), 1.42-1.37 (m, 12H), 1.22-1.15 (m, 1H), 1.01-0.96 (m, 1H). |

Step-3: Tert-butyl 4-(2-((N-(tert-butoxycarbonyl) sulfamoyl) amino) ethyl) azepane-1-carboxylate To a stirred solution of tert-butyl 4-(2-aminoethyl) azepane-1-carboxylate 4 (500 mg, 2.066 mmol) in dichloromethane (10 ml) were added diisopropylethylamine (400 mg, 3.099 mmol) and N-(1-(N-(tert-butoxycarbonyl)sulfamoyl)pyridin-4(1H)-ylidene)-N-methylmethanaminium 5 (696 mg, 2.066 mmol) at 0° C. then stirred at room temperature for 16 h. The progress of the reaction was monitored by TLC. After completion, to the reaction mixture added water (100 mL) and extracted with dichloromethane (2×100 mL). Combined organic layers were washed with brine solution (100 mL), dried over sodium sulfate and concentrated under reduced pressure to afford crude compound. Crude was purified through 100-200 silica gel column chromatography by eluting 2% methanol in dichloromethane to afford semi pure compound. This semi pure was washed with 50% ethyl acetate in pet ether to afford tert-butyl 4-(2-((N-(tert-butoxycarbonyl) sulfamoyl) amino) ethyl) azepane-1-carboxylate 6 (600 mg, 1.425 mmol, 69% yield) as a colorless gummy liquid.

Analytical Data: 1H NMR (400 MHz, DMSO) δ 10.76 (s, 1H), 7.50-7.45 (m, 1H), 3.41 (m, 1H), 3.24-3.19 (m, 2H), 3.12-3.03 (m, 1H), 2.87 (d, 2H), 1.70 (m, 2H), 1.57 (m, 1H), 1.39 (m, 25H).

| Structure | 1HNMR |
|---|---|
| 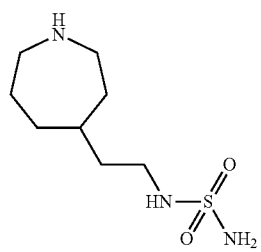 [SMILES: NS(=O)(=O)NCCC1CCCNCC1] | 1H NMR (400 MHz, DMSO) δ 10.79 (s, 1H), 7.64 (bs, 1H), 3.41-3.36 (m, 2H), 3.09-3.20 (m, 2H), 2.66-2.72 (m, 2H), 1.71-1.74 (m, 3H), 1.52 (m, 1H), 1.38 (s, 9H), 1.41 (s, 9H), 1.14 (t, 2H), 0.98 (d, 1H). |

Step-4: (N-(2-(azepan-4-yl)ethyl)sulfamide

To a stirred solution of tert-butyl 4-(2-((N-(tert-butoxycarbonyl)sulfamoyl)amino)ethyl)azepane-1-carboxylate 6 (600 mg, 1.425 mmol) in dioxane (5 ml) was added 4M HCl in dioxane (15 mL) at 0° C. then stirred at room temperature for 3 h. The progress of the reaction was monitored by TLC. After completion, organic solvents completely distilled off under reduced pressure to afford crude (N-(2-(azepan-4-yl) ethyl)sulfamide (420 mg, crude) as a pale brown gummy solid.

Analytical Data: 1H NMR (400 MHz, DMSO) δ 8.94 (d, 2H), 6.34 (broad s, 2H), 3.07 (m, 2H), 2.96 (m, 2H), 2.86 (t, 2H), 1.76 (m, 3H), 1.64 (m, 2H), 1.52-1.44 (m, 1H), 1.41-1.32 (m, 2H), 1.22 (m, 1H).

| Structure | 1HNMR |
|---|---|
| [structure: azepane with CH2-NH-S(=O)(=O)-NH2, HCl salt] | 1H NMR (400 MHz, DMSO) δ 8.94 (s, 2H), 6.48 (bs, 1H), 6.61 (bs, 1H), 3.17-3.15 (m, 1H), 3.06 (m, 1H), 2.96-2.94 (m, 2H), 2.76-2.65 (m, 2H), 1.93-1.58 (m, 5H), 1.50-1.42 (m, 1H), 1.20-1.17 (m, 1H). | added potassium carbonate (263 mg, 1.909 mmol) and compound-7 (360 mg, 1.4 mmol) then stirred at 90° C. for 16 h. The progress of the reaction was monitored by TLC. After completion of the reaction, added water (100 mL) and extracted with ethyl acetate (2×100 mL). Combined organic layers were washed with brine solution (100 mL), dried over sodium sulfate and concentrated under reduced pressure. Crude was purified through preparative HPLC method to afford N-(2-(1-(6,7-dimethoxyquinazolin-4-yl)azepan-4-yl)ethyl)sulfamide (52 mg, 0.127 mmol, 10% yield) as a pale orange solid.

Analytical Data: 1H NMR (400 MHz, DMSO) δ 8.35 (s, 1H), 7.29 (s, 1H), 7.12 (s, 1H), 6.43 (m, 3H), 3.97 (d, 2H), 3.88 (m, 6H), 3.68 (m, 2H), 2.89 (m, 2H), 1.98 (m, 2H), 1.87 (m, 1H), 1.74 (m, 1H), 1.63 (m, 2H), 1.44 (m, 2H), 1.22 (m, 1H).

| Compound Number | Structure | 1HNMR |
|---|---|---|
| 060 | [structure: 6,7-dimethoxyquinazoline-4-yl azepane with CH2-NH-S(=O)(=O)-NH2] | 1HNMR (400 MHz, DMSO) δ: 8.36 (s, 1H), 7.29 (s, 1H), 7.12 (s, 1H), 6.56 (t, 1H), 6.45 (s, 2H), 4.00-3.98 (m, 2H), 3.87 (s, 3H), 3.89 (s, 3H), 3.68-3.64 (m, 2H), 2.74 (t, 2H), 2.03 (t, 2H), 1.83-1.82 (m, 2H), 1.69-1.59 (m, 2H), 1.22-1.17 (m, 1H). MS 396.2 |

Step-5: N-(2-(1-(6,7-dimethoxyquinazolin-4-yl)azepan-4-yl)ethyl)sulfamide (Compound 060)

Compound 049 was prepared based on the general procedure described above:

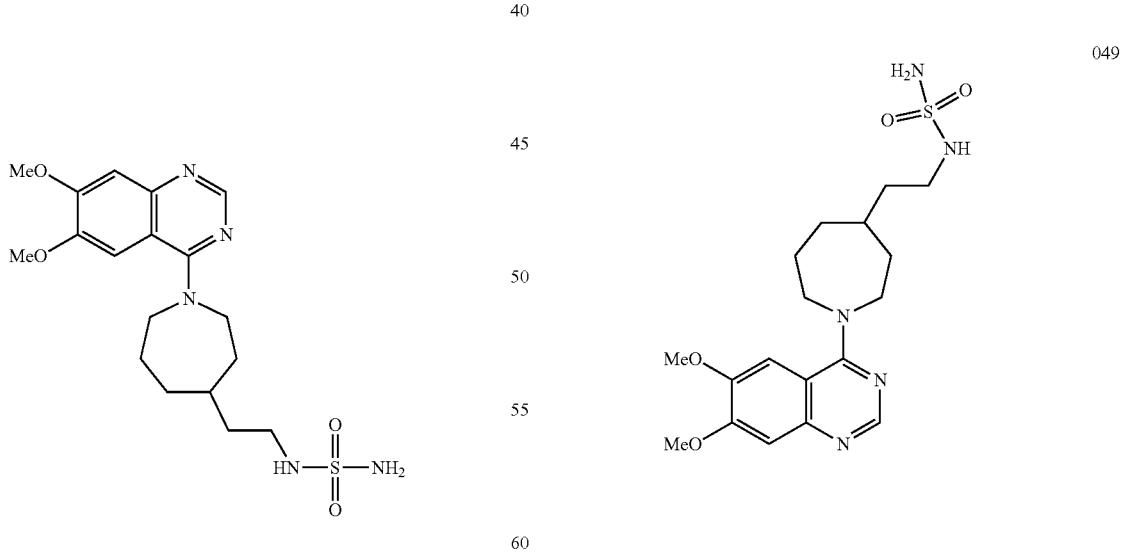

049

M.W. 409.51

1H NMR (400 MHz, DMSO) δ 8.35 (s, 1H), 7.29 (s, 1H), 7.12 (s, 1H), 6.43 (m, 3H), 3.97 (d, 2H), 3.88 (m, 6H), 3.68 (m, 2H), 2.89 (m, 2H), 1.98 (m, 2H), 1.87 (m, 1H), 1.74 (m, 1H), 1.63 (m, 2H), 1.44 (m, 2H), 1.22 (m, 1H). LCMS 409.9

To a stirred solution of 4-chloro-6,7-dimethoxyquinazoline 8 (285 mg, 1.273 mmol) in acetonitrile (15 ml) were

Synthetic Scheme of Compound 036

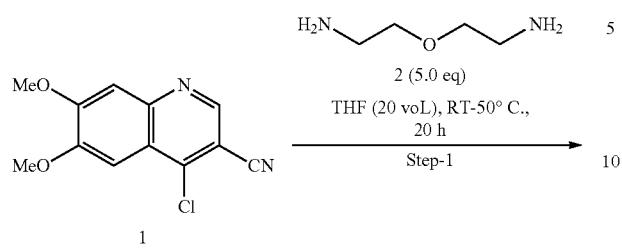

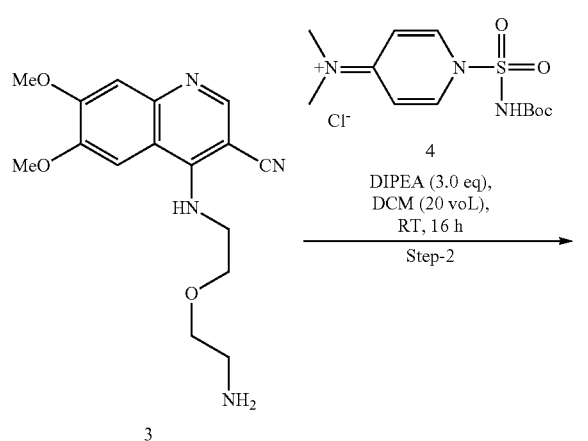

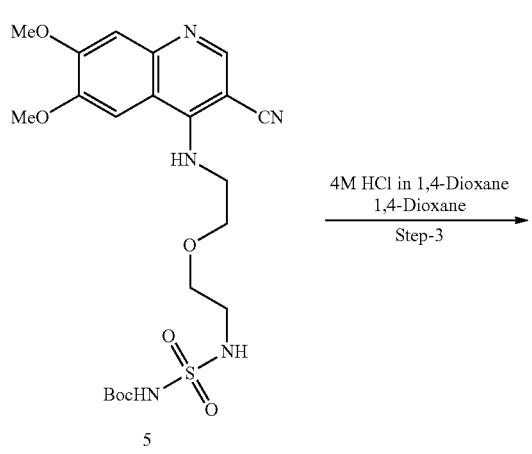

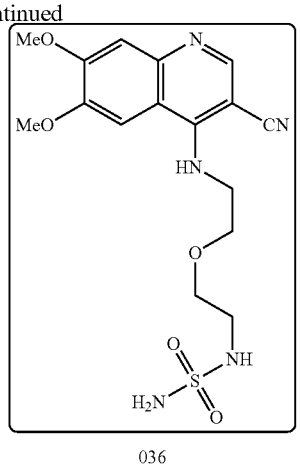

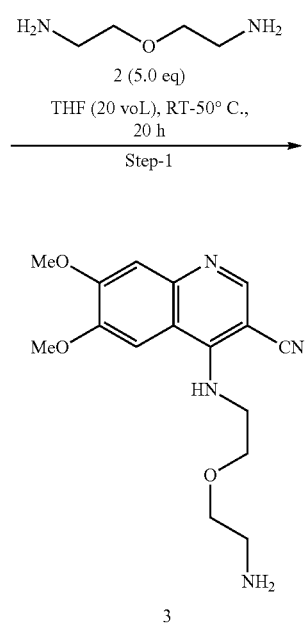

Step-1: Synthesis of 4-((2-(2-aminoethoxy)ethyl)amino)-6,7-dimethoxyquinoline-3-carbonitrile 3

To a stirred solution of 4-chloro-6,7-dimethoxyquinoline-3-carbonitrile 1 (150 mg, 0.68 mmol) in THF (15 mL) was added 2,2'-oxybis(ethan-1-amine) 2 (314 mg, 3.4 mmol) then stirred the reaction mixture at 50° C. for 20 h. The progress of the reaction was monitored by TLC. After completion of the reaction, reaction mixture completely distilled off and absorbed onto celite and reverse phase grace performed using AC N/Water system to afford 4-((2-(2-aminoethoxy)ethyl)amino)-6,7-dimethoxyquinoline-3-carbonitrile (170 mg) as a white solid.

Analytical Data: 1H NMR (400 MHz, DMSO): δ 8.36-8.33 (m, 3H), 8.09 (brs, 1H), 7.75 (s, 1H), 7.21 (s, 1H), 3.95-3.94 (m, 2H), 3.90 (s, 6H), 3.75 (t, 2H), 3.60 (t, 2H), 2.89 (t, 2H).

LCMS: (M+H)+: m/Z: 317.2

Step-2: Synthesis of tert-butyl (N-(2-(2-((3-cyano-6,7-dimethoxyquinolin-4-yl)amino)ethoxy)ethyl)sulfamoyl) carbamate 5

Step-3: Synthesis of Compound 036

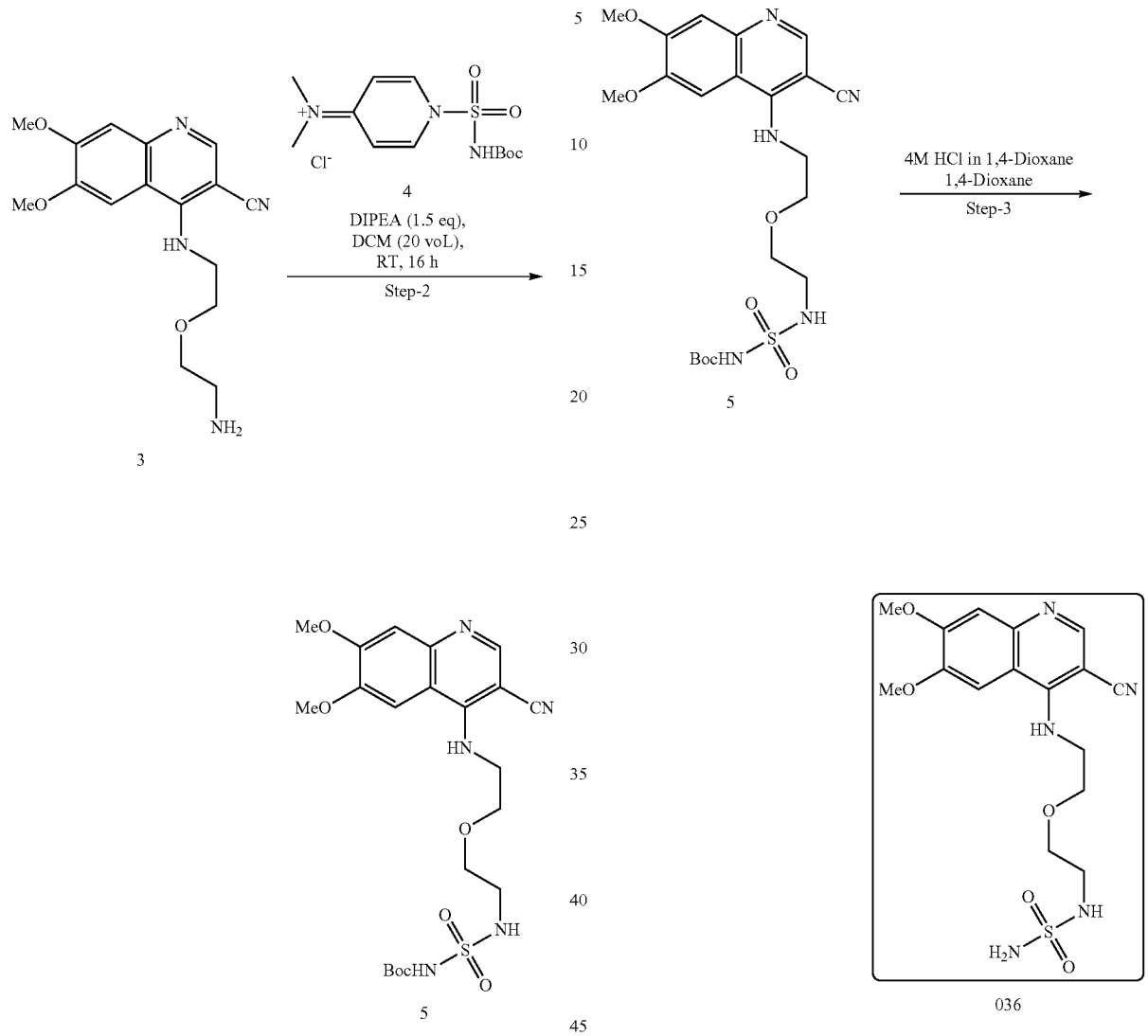

To a stirred solution of 4-((2-(2-aminoethoxy)ethyl)amino)-6,7-dimethoxyquinoline-3-carbonitrile 3 (170 mg, 0.54 mmol) in DCM (10 mL) was added N-(1-(N-(tert-butoxycarbonyl)sulfamoyl)pyridin-4(1H)-ylidene)-N-methylmethanaminium chloride 4 (163 mg, 0.48 mmol) slowly and then added DIPEA (0.3 ml, 1.6 mmol) at same temperature. Then stirred the reaction mixture at room temperature for 16 h. The progress of the reaction was monitored by TLC. Reaction mixture was directly absorbed on to silica and converted into slurry. Crude was purified through combi-flash chromatography by eluting 2-3% MeOH in DCM to afford tert-butyl (N-(2-(2-((3-cyano-6,7-dimethoxyquinolin-4-yl)amino)ethoxy)ethyl)sulfamoyl)carbamate 5 (90 mg) as a white solid.

Analytical Data: 1H NMR (400 MHz, DMSO) δ:10.84 (s, 1H), 8.34 (s, 1H), 7.81 (brs, 1H), 7.64 (s, 1H), 7.51 (t, 1H), 7.21 (s, 1H), 3.93-3.89 (m, 8H), 3.72 (t, 2H), 3.51 (t, 2H), 3.06-3.01 (m, 2H), 1.35 (s, 9H).

LCMS: (M+H)+: m/Z: 396

To a stirred solution of tert-butyl (N-(2-(2-((3-cyano-6,7-dimethoxyquinolin-4-yl)amino)ethoxy)ethyl)sulfamoyl)carbamate 5 (90 mg, 0.18 mmol) in dioxane (3 ml) was added 4M HCl in dioxane (1 mL) at 0° C. then stirred at room temperature for 16 h. The progress of the reaction was monitored by TLC. After completion of reaction, organic solvents completely distilled off under reduced pressure. Crude compound was purified by prep-HPLC to give Compound 036 (10 mg) as white solid.

Analytical Data: 1H NMR (400 MHz, DMSO) δ: 8.34 (s, 1H), 7.84 (t, 1H), 7.64 (s, 1H), 7.22 (s, 1H), 6.52 (brs, 2H), 6.45 (t, 1H) 3.94-3.89 (m, 8H), 3.72 (t, 2H), 3.54 (t, 2H), 3.06 (q, 2H).

LCMS: (M+H)+: m/Z: 396.25.

227
Synthetic Scheme for Compound 037

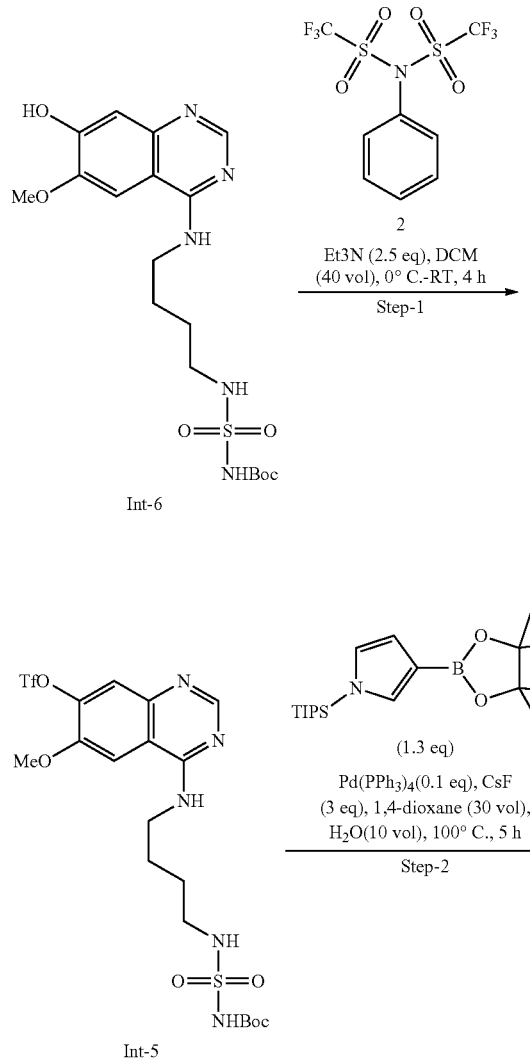

228
Synthesis of 4-((4-((N-(tert-butoxycarbonyl)sulfamoyl)amino)butyl)amino)-6-methoxyquinazolin-7-yl trifluoromethanesulfonate (Int-5)

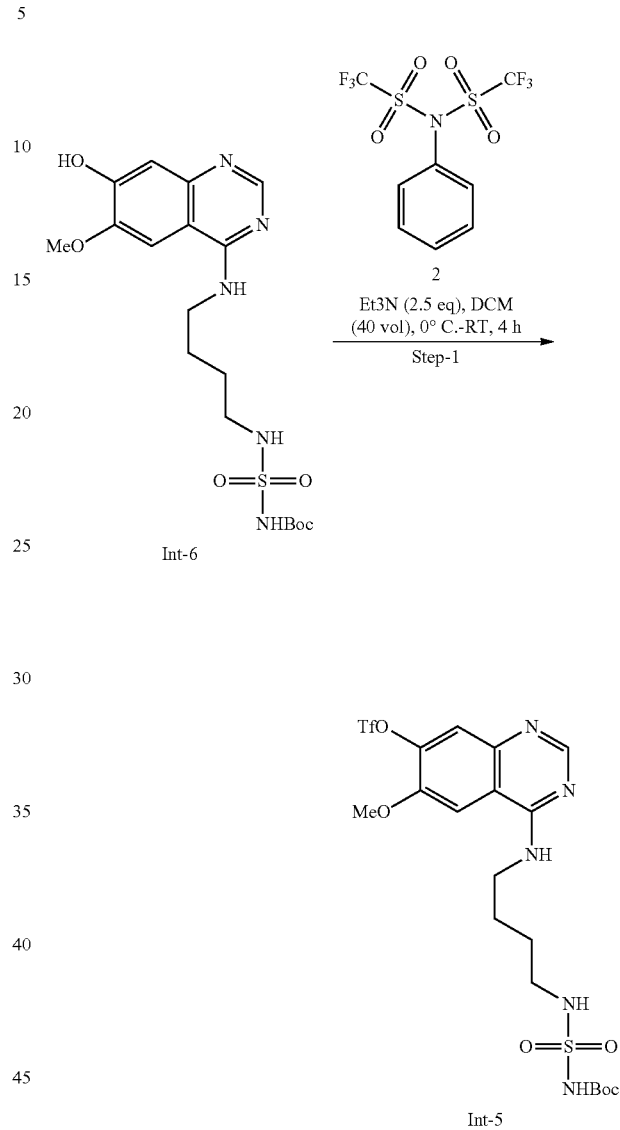

To a stirred solution of Int-6 (500 mg, 1.13 mmol) in dichloromethane (20 ml) were added triethylamine (0.475 mL, 3.39 mmol) and 1,1,1-trifluoro-N-phenyl-N-((trifluoromethyl)sulfonyl)methanesulfonamide 2 (445 mg, 1.24 mmol) at 0° C. then stirred at room temperature 4 h. The progress of the reaction was monitored by TLC. After completion of the reaction, organic solvents completely distilled off under reduced pressure and water (200 mL) was added to the crude and partitioned with dichloromethane (2×200 mL). Combined organic layers were washed with brine solution (200 mL), dried over sodium sulfate and concentrated under reduced pressure. Crude was purified by combi-flash chromatography by eluting 70% ethyl acetate in pet ether to afford 4-((4-((N-(tert-butoxycarbonyl)sulfamoyl)amino)butyl)amino)-6-methoxyquinazolin-7-yl trifluoromethanesulfonate Int-5 (450 mg, 0.785 mmol, 69% yield over two steps) as a pale yellow solid.

LCMS: (M+H$^+$): m/Z: 574.

Preparation of Compound 037

Synthetic Scheme for Compound 038

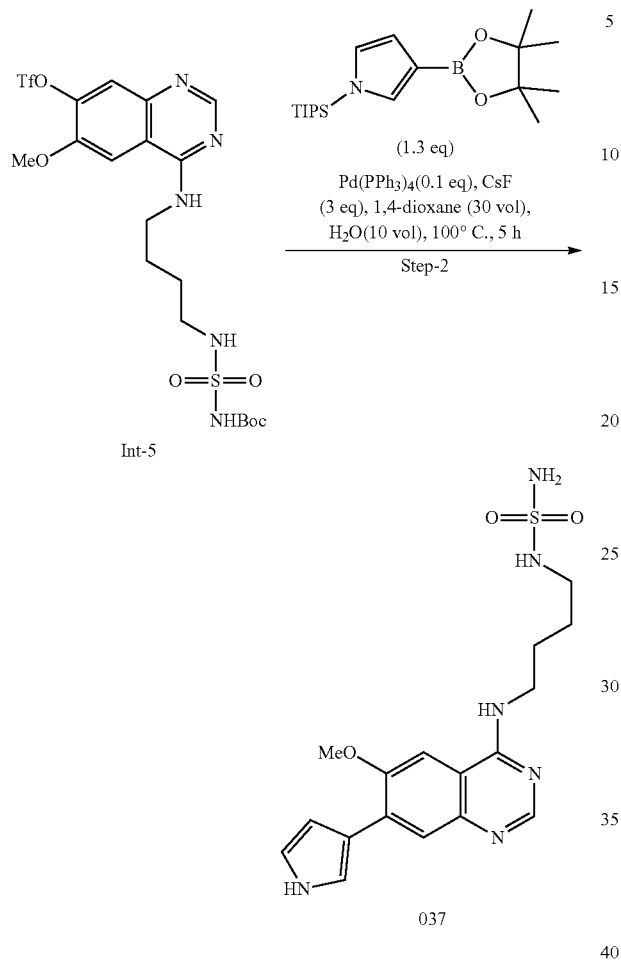

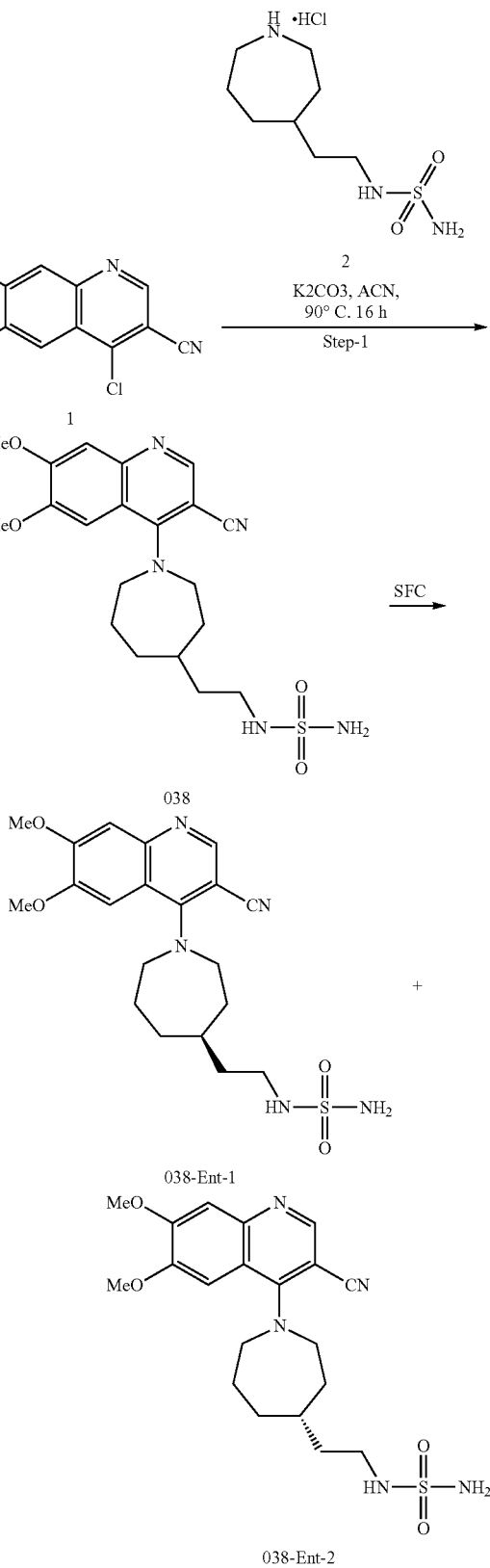

In a sealed tube, to the stirred solution of 4-((4-((N-(tert-butoxycarbonyl)sulfamoyl)amino)butyl)amino)-6-methoxyquinazolin-7-yl trifluoromethanesulfonate Int-5 (200 mg, 0.349 mmol) in dioxane (8 mL) and water (2 mL) were added 3-(4,4,5,5-tetramethyl-1,3,2-dioxaborolan-2-yl)-1-(triisopropylsilyl)-1H-pyrrole (121 mg, 0.453 mmol) and cesium fluoride (159 mg, 1.047 mmol) was then degassed the reaction mixture for 30 minutes. Then tetrakis(triphenylphosphine)palladium(0) (40 mg, 0.034 mmol) was added again degassed for 5 minutes and stirred the reaction mixture at 100° C. for 5 h. The progress of the reaction was monitored by TLC. After completion of the reaction, reaction mixture was poured into water (100 mL) and filtered through celite. Washed the celite bed with 10% methanol in dichloromethane (100 mL) and separated the two layers. Organic layer washed with brine solution (200 mL), dried over sodium sulfate and concentrated under reduced pressure. Crude was purified prep HPLC method to afford (Compound 037) (30 mg, 0.052 mmol, 23%) as a pale yellow solid.

Analytical Data: 1HNMR (400 MHz, DMSO) δ 11.13 (s, 1H), 8.625 (brs, 1 h), 8.49 (s, 1H), 7.8 (s, 1H), 7.7 (s, 1H), 7.51 (s, 1H), 6.86-6.87 (m, 1H), 6.62-63 (m, 1H), 6.46-6.52 (m, 3H), 4.0 (s, 3H), 3.59-3.61 (q, 2H), 2.92-2.95 (q, 2H), 1.55-1.72 (m, 4H).

LCMS: (M+H$^+$): m/Z: 391.1

To a stirred solution of 4-chloro-6,7-dimethoxyquinoline-3-carbonitrile 1 (100 mg, 0.403 mmol) in N,N'-dimethylformamide (5 ml) was added potassium carbonate (83 mg, 0.443 mmol) and compound-2 (114 mg, 0.443 mmol) then stirred at 90° C. for 3 h. The progress of the reaction was monitored by TLC. After completion of the reaction, added water (100 mL) and extracted with ethyl acetate (2×100 mL). Combined organic layers were washed with brine solution (100 mL), dried over sodium sulfate and concentrated under reduced pressure. Crude was purified through preparative HPLC method to afford Compound 038 (29 mg, 0.067 mmol, 16% yield) as an off white solid.

Analytical Data: 1H NMR (400 MHz, DMSO) δ 8.618 (s, 1H), 7.365 (s, 1H), 7.330 (s, 1H), 6.450-6.467 (d, 3H), 3.94 (s, 3H), 3.931 (s, 3H), 3.671-3.689 (m, 2H), 3.554-3.587 (m, 2H), 2.903-2.953 (m, 2H), 1.820-1.926 (m, 5H), 1.437-1.582 (m, 4H).

LCMS: (M+H+): m/Z: 434.2

Compound 038 was submitted for SFC and separated into two enantiomers to afford 038-Ent-1 (17 mg, 0.039 mmol) & 038-Ent-2 (17 mg, 0.039 mmol).

Analytical Data of 038-Ent-1: 1H NMR (400 MHz, DMSO) δ 8.628 (s, 1H), 7.376 (s, 1H), 7.343 (s, 1H), 6.456 (bs, 3H), 3.951 (s, 3H), 3.942 (s, 3H), 3.679-3.722 (t, 2H), 3.580-3.624 (m, 2H), 2.925-2.958 (t, 2H), 1.835-1.935 (m, 5H), 1.423-1.591 (m, 4H).

LCMS: (M+H+): m/Z: 434.2

Analytical Data of 038-Ent-2: 1H NMR (400 MHz, DMSO) δ 8.627 (s, 1H), 7.376 (s, 1H), 7.342 (s, 1H), 6.462 (bs, 3H), 3.950 (s, 3H), 3.941 (s, 3H), 3.665-3.678 (m, 2H), 3.596-3.615 (m, 2H), 2.940-2.957 (t, 2H), 1.836-2.060 (m, 5H), 1.507-1.523 (m, 4H).

LCMS: (M+H+): m/Z: 434.2

Synthetic Scheme for Compound 039

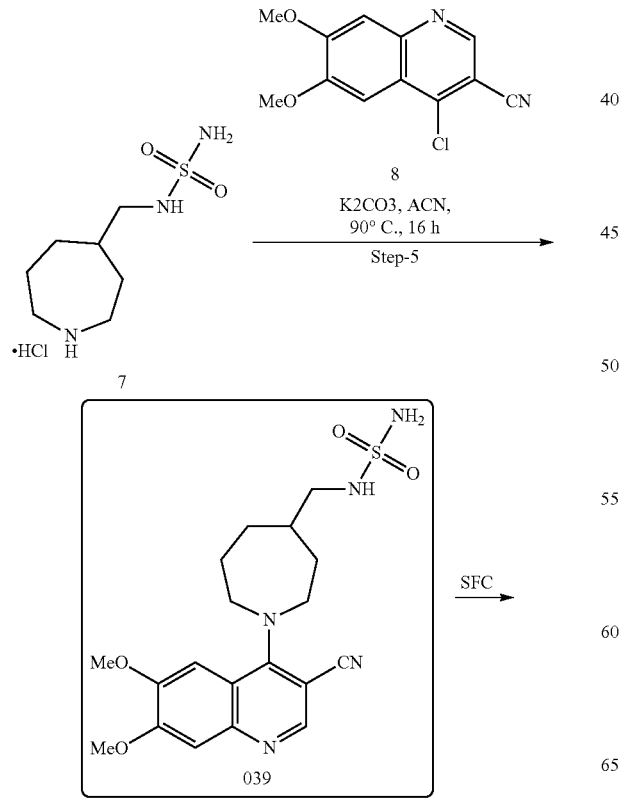

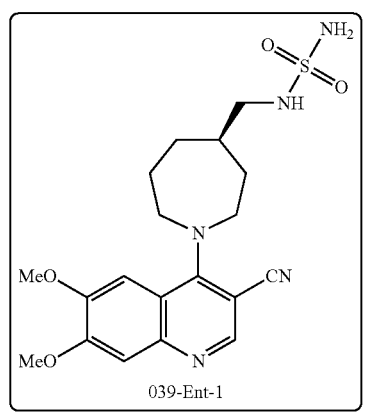

039-Ent-1

+

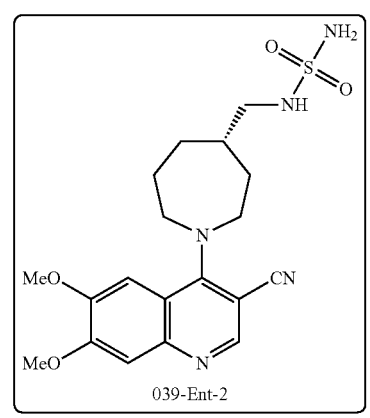

039-Ent-2

Synthesis of Preparation of Compound 039

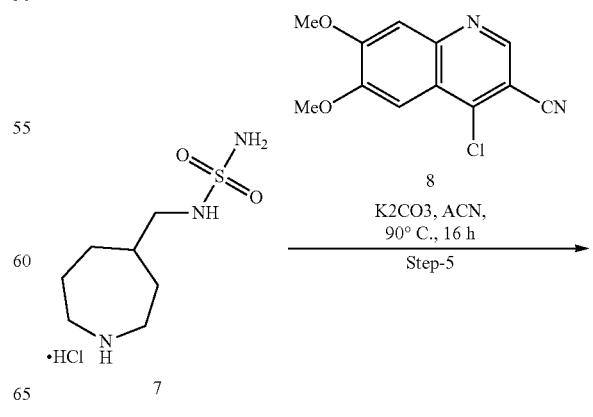

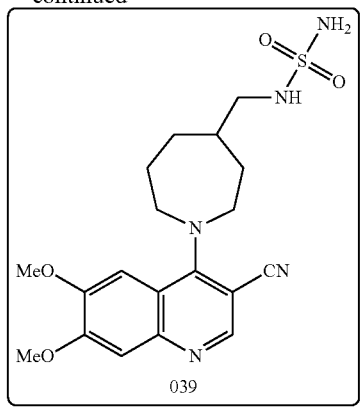

039

To a stirred solution of 4-chloro-6,7-dimethoxyquinoline-3-carbonitrile 8 (150 mg, 0.605 mmol) in N,N'-dimethylformamide (3 ml) was added potassium carbonate (250 mg, 1.814 mmol) and compound-7 (220 mg, 0.907 mmol) then stirred at 90° C. for 6 h. The progress of the reaction was monitored by TLC. After completion of the reaction, added water (100 mL) and extracted with ethyl acetate (2×100 mL). Combined organic layers were washed with brine solution (100 mL), dried over sodium sulfate and concentrated under reduced pressure. Crude was purified through preparative HPLC method to afford Compound 039 (170 mg, 0.405 mmol, 67% yield) as an off white solid.

Analytical Data: 1H NMR (400 MHz, DMSO) δ 8.625 (s, 1H), 7.368 (s, 1H), 7.331 (s, 1H), 6.613-6.644 (t, 1H), 6.483 (s, 2H), 3.94 (s, 3H), 3.931 (s, 3H), 3.544-3.3.688 (m, 4H), 2.788-2.848 (m, 2H), 1.937-2.045 (m, 4H), 1.740-1.793 (m, 1H), 1.511-1.589 (m, 1H), 1.368-1.424 (m, 1H).

LCMS: (M+H+): m/Z: 420.2

Compound 039 was submitted for SFC and separated into two enantiomers to afford 039-Ent-1 (25 mg, 0.059 mmol) & 039-Ent-2 (17 mg, 0.04 mmol).

Analytical Data of 039-Ent-1: 1H NMR (400 MHz, DMSO) δ 8.635 (s, 1H), 7.379 (s, 1H), 7.343 (s, 1H), 6.618-6.644 (t, 1H), 6.487 (s, 2H), 3.941 (s, 3H), 3.951 (s, 3H), 3.645-3.672 (m, 4H), 2.801-2.843 (m, 2H), 1.952-2.053 (m, 4H), 1.785-1.825 (m, 1H), 1.551-1.593 (m, 1H), 1.390-1.456 (m, 1H).

LCMS: (M+H+): m/Z: 420.2

Analytical Data of 039-Ent-2: 1H NMR (400 MHz, DMSO) δ 8.636 (s, 1H), 7.379 (s, 1H), 7.343 (s, 1H), 6.634 (bs, 1H), 6.488 (t, 1H), 6.487 (s, 2H), 3.941 (s, 3H), 3.951 (s, 3H), 3.645-3.672 (m, 4H), 2.801-2.843 (m, 2H), 1.952-2.055 (m, 4H), 1.765-1.825 (m, 1H), 1.553-1.573 (m, 1H), 1.386-1.456 (m, 1H).

LCMS: (M+H$^+$): m/Z: 420

Synthetic Scheme of Compound 040-Ent-1

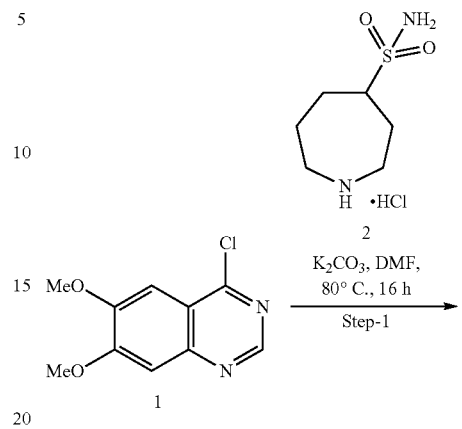

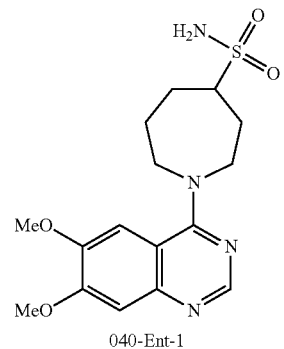

040-Ent-1

Synthesis of 1-(6,7-dimethoxyquinazolin-4-yl)azepane-4-sulfonamide (Compound 040-Ent-1)

To a stirred solution of 4-chloro-6,7-dimethoxyquinazoline 1 (120 mg, 0.5357 mmol) in ACN (2 mL) and K2CO3 (222 mg, 1.6071 mmol), then stirred at 90° C. for 16 h. After completion of the reaction the crude residue added water (10 mL). Then extracted with 10% methanol in dichloromethane (30 mL) and concentrated under reduced pressure to afford crude compound. Crude compound was purified through Prep HPLC method to afford pure compound 1-(6,7-dimethoxyquinazolin-4-yl)azepane-4-sulfonamide (T-116-Ent-1) (10 mg, 5% yield) as an off white solid.

Analytical Data: 1H NMR (400 MHz, DMSO) δ 8.40 (s, 1H), 7.26 (s, 1H), 7.15 (s, 1H), 6.74 (s, 2H), 4.09 (m, 2H), 3.90 (s, 3H), 3.88 (s, 3H), 3.69-3.80 (m, 2H), 3.69 (m, 1H), 3.01 (p, 2H), 2.30 (m, 1H), 2.08 (p, 2H), 1.91 (m, 1H), 1.60 (m, 1H).

LCMS: (M+H$^+$): m/Z: 367.1

Synthetic Scheme for Compound 040-Ent-2

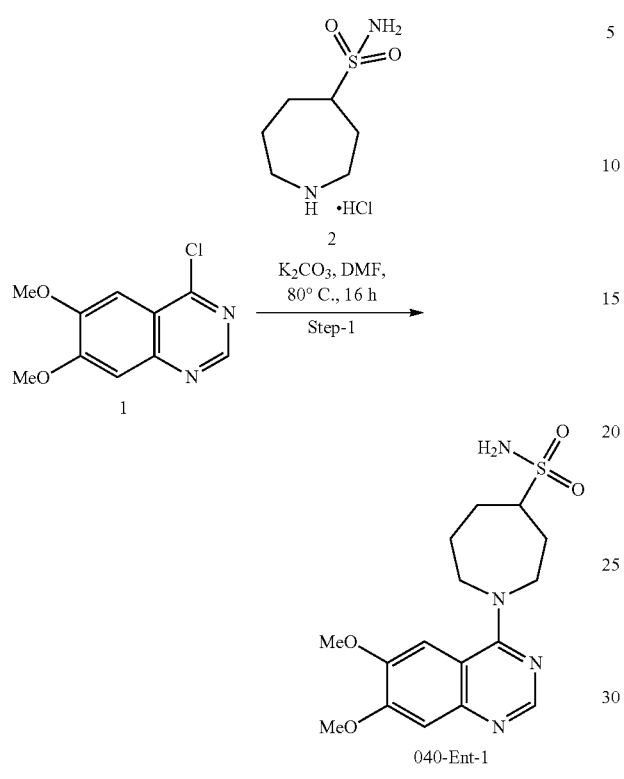

Synthesis of 1-(6,7-dimethoxyquinazolin-4-yl) azepane-4-sulfonamide (Compound 040-Ent-2)

To a stirred solution of 4-chloro-6,7-dimethoxyquinazoline 1 (120 mg, 0.5357 mmol) in ACN (2 mL) and K2CO3 (222 mg, 1.6071 mmol), then stirred at 90° C. for 16 h. After completion of the reaction the crude residue added water (10 mL). Then extracted with 10% methanol in dichloromethane (30 mL) and concentrated under reduced pressure to afford crude compound. Crude compound was purified through Prep HPLC method to afford pure compound 1-(6,7-dimethoxyquinazolin-4-yl)azepane-4-sulfonamide (T-116-Ent-2) (10 mg, 5% yield) as an off white solid.

Analytical Data: Analytical Data: 1H NMR (400 MHz, DMSO) δ 8.50 (s, 1H), 7.34 (s, 1H), 7.18 (s, 1H), 6.78 (s, 2H), 4.18 (m, 2H), 3.93 (s, 3H), 3.91 (s, 3H), 3.76-3.84 (m, 2H), 3.04 (m, 1H), 3.01 (p, 2H), 2.92 (m, 1H), 2.13 (m, 1H), 1.98 (m, 1H), 1.60 (m, 1H). LCMS: (M+H+): m/Z: 367.1

Synthetic Scheme for Compound 041

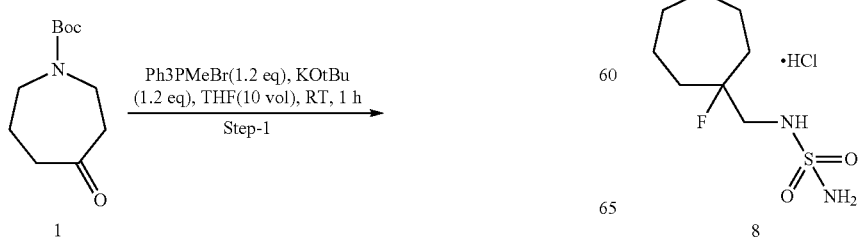

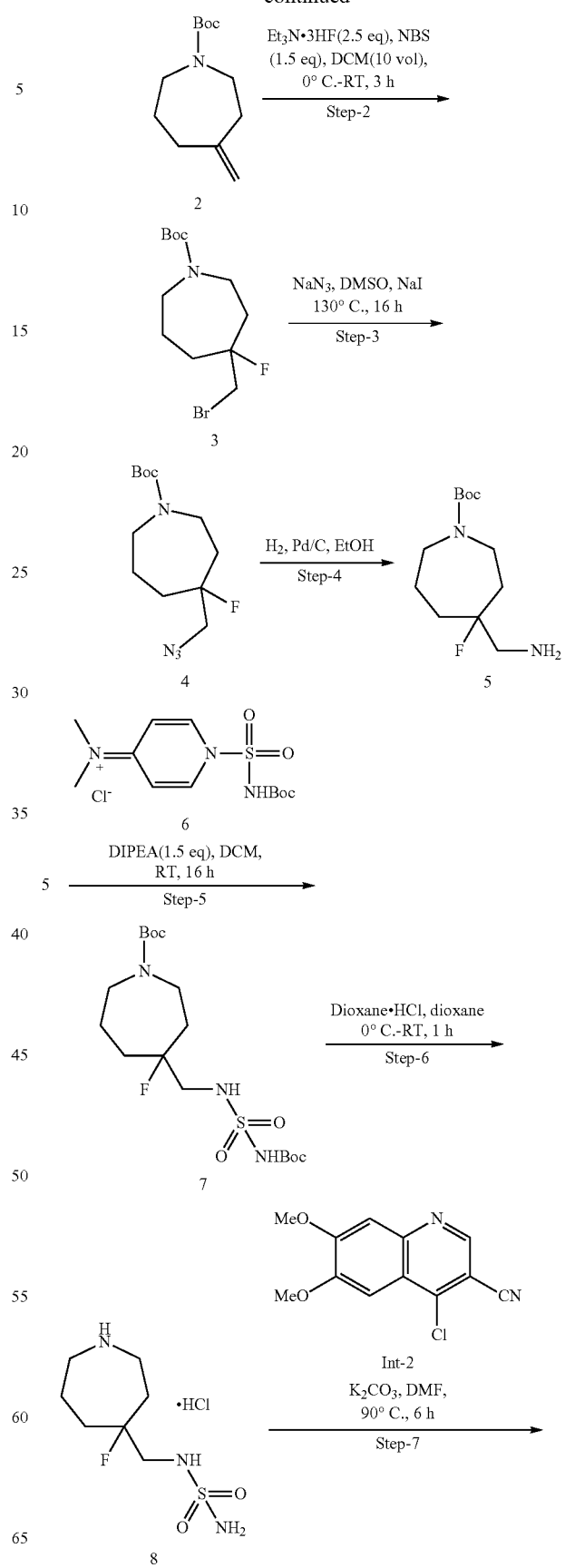

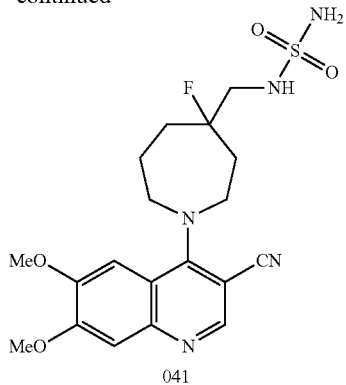

041

Synthesis of tert-butyl 4-methyleneazepane-1-carboxylate (2)

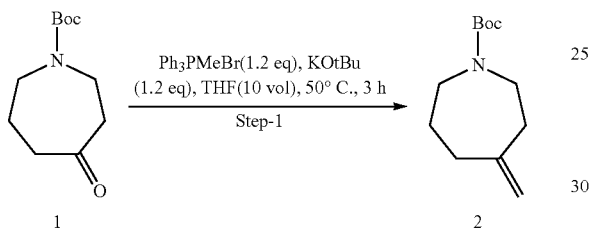

To a stirred solution of methyltriphenylphosphonium-brimide 2 (227 mg, 0.563 mmol) in diethyl ether (5 mL) was added 1M of potassium tert-butoxide in t-butanol (63 mg, 0.563 mmol), reaction turns to yellow. Then added tert-butyl 4-oxoazepane-1-carboxylate 1 (100 mg, 0.469 mmol) and stirred at 50° C. for 3 h. The progress of the reaction was monitored by TLC. After completion of the reaction, to the reaction mixture added water (30 mL) and extracted with ethyl acetate (2×20 mL). Combined organic layers were washed with brine solution (40 mL), dried over sodium sulfate and concentrated under reduced pressure. Crude compound was purified through 100-200 silica gel column chromatography by eluting 5% ethyl acetate in pet ether to afford tert-butyl 4-methyleneazepane-1-carboxylate 2 (60 mg, 0.284 mmol) as a colorless oily liquid.

Analytical Data: 1H NMR (400 MHz, DMSO) δ 4.732-4.786 (m, 4H), 2.404-2.433 (m, 2H), 2.209-2.239 (t, 2H), 1.655-1.706 (m, 2H), 1.448 (s, 9H).

Synthesis of tert-butyl 4-(bromomethyl)-4-fluoroazepane-1-carboxylate (3)

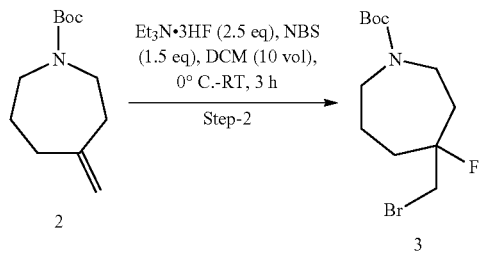 [SMILES: C=C1CCCN(C(=O)OC(C)(C)C)CC1 ; CC(C)(C)OC(=O)N1CCCC(F)(CBr)CC1]

To a stirred solution of tert-butyl 4-methyleneazepane-1-carboxylate 2 (1.9 g, 9.005 mmol) in dichloromethane (50 mL) were added triethylamine trihydrofluoride (3.6 g, 22.52 mmol) and N-bromo succinimide (2.4 g, 13.507 mmol) at 0° C. then stirred at room temperature for 2 h. The progress of the reaction was monitored by TLC. After completion of the reaction, reaction mixture quenched with saturated NaHCO3 solution (100 mL) and extracted with excess dichloromethane (2×150 mL). Combined organic layers were washed with brine solution (150 mL), dried over Na2SO4 and concentrated under reduced pressure to afford crude compound. Crude was purified through 100-200 combi-flash chromatography by eluting 5% ethyl acetate in pet ether to afford tert-butyl 4-(bromomethyl)-4-fluoroazepane-1-carboxylate 3 (1.7 g, 5.5 mmol, 61% yield) as a colorless oily liquid.

Analytical Data: 1H NMR (400 MHz, DMSO) δ 3.500-3.673 (m, 2H), 3.434-3.477 (d, 2H), 3.162-3.269 (m, 4H), 1.980-2.114 (m, 4H), 1.652-1.913 (m, 2H), 1.465 (s, 9H).

Synthesis of Tert-butyl 4-(azido methyl)-4-fluoroazepane-1-carboxylate (4)

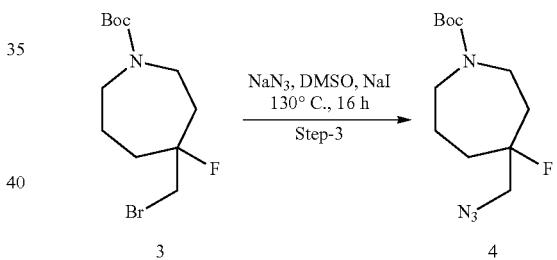

To a stirred solution of tert-butyl 4-(bromo methyl)-4-fluoroazepane-1-carboxylate 3 (1.5 g, 4.854 mmol) in dimethyl sulfoxide (20 mL) were added sodium azide (473 mg, 7.281 mmol) and sodium iodide (1 g, 7.281 mmol) then stirred at 130° C. for 16 h. The progress of the reaction was monitored by TLC. After completion of the reaction, to the reaction mixture added water (200 mL) and extracted with ethyl acetate (2×150 mL). Combined organic layers were washed with brine solution (200 mL), dried over sodium sulfate and concentrated under reduced pressure to afford crude compound. Crude was purified through combi-flash chromatography by eluting 20% ethyl acetate in pet ether to afford tert-butyl 4-(azido methyl)-4-fluoroazepane-1-carboxylate 4 (600 mg, 2.205 mmol, 45% yield) as a colorless oily liquid.

Analytical Data: 1H NMR (400 MHz, DMSO) δ 3.508-3.797 (m, 2H), 3.148-3.387 (m, 4H), 1.952-2.158 (m, 3H), 1.648-1.790 (m, 2H), 1.442 (s, 9H).

Synthesis of tert-butyl 4-(aminomethyl)-4-fluoroazepane-1-carboxylate (5)

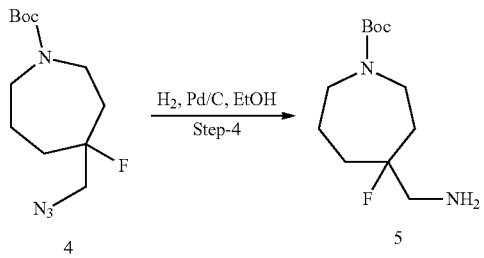 [SMILES: CC(C)(C)OC(=O)N1CCCC(F)(CN=[N+]=[N-])CC1 ; CC(C)(C)OC(=O)N1CCCC(F)(CN)CC1]

A stirred solution of tert-butyl 4-(azidomethyl)-4-fluoroazepane-1-carboxylate 5 (600 mg, 2.206 mmol) in methanol (20 mL) was added 10% Pd/C (60 mg, 10% w/w) and then stirred under balloon hydrogen atmosphere for 16 h. The progress of the reaction was monitored by TLC. After completion of the reaction, reaction mixture filtered through celite, washed the celite bed with 10% methanol in dichloromethane (50 mL). Filtrate was concentrated under reduced pressure to afford crude compound. Crude was purified through combi-flash chromatography by eluting 30% ethyl acetate in pet ether to afford tert-butyl 4-(aminomethyl)-4-fluoroazepane-1-carboxylate 5 (400 mg, 1.626 mmol, 74% yield) as a colorless oily liquid.

Analytical Data: 1HNMR (400 MHz, DMSO) δ 3.106-3.503 (m, 6H), 2.618-2.625 (d, 2H), 2.570-2.576 (d, 1H), 1.490-1.912 (m, 6H), 1.380 (s, 9H).

Synthesis of Tert-butyl 4-(((N-(tert-butoxycarbonyl) sulfamoyl) amino) methyl)-4-fluoroazepane-1-carboxylate (7)

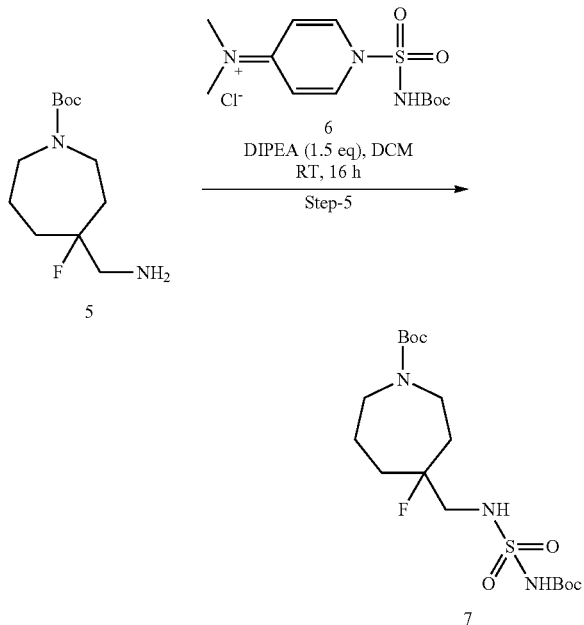

To a stirred solution of tert-butyl 4-(aminomethyl)-4-fluoroazepane-1-carboxylate 5 (400 mg, 1.626 mmol) in dichloromethane (10 mL) were added diisopropylethylamine (315 mg, 2.439 mmol) and N-(1-(N-(tert-butoxycarbonyl)sulfamoyl)pyridin-4(1H)-ylidene)-N-methylmethanaminium 6 (548 mg, 1.626 mmol) at 0° C. then stirred at room temperature for 16 h. The progress of the reaction was monitored by TLC. After completion of the reaction, reaction mixture completely distilled off under reduced pressure to afford crude compound. Crude was purified through 100-200 combi-flash chromatography by eluting 3% methanol in dichloromethane to afford tert-butyl 4-(((N-(tert-butoxycarbonyl) sulfamoyl) amino) methyl)-4-fluoroazepane-1-carboxylate 7 (350 mg, 0.823 mmol, 50% yield) as an brown solid.

Analytical Data: 1H NMR (400 MHz, DMSO) δ 10.827 (s, 1H), 7.858 (bs, 1H), 3.031-3.515 (m, 4H), 1.506-1.977 (m, 6H), 1.381 (s, 9H), 1.406 (s, 9H), 1.218-1.234 (m, 1H).

Synthesis of Compound-8

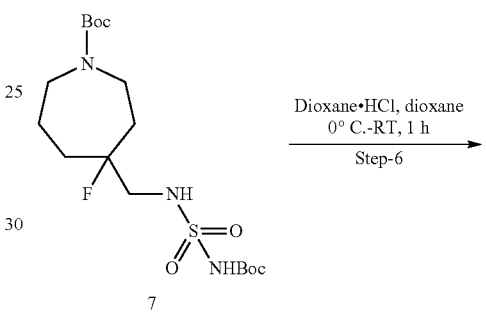

A stirred solution of tert-butyl 4-(((N-(tert-butoxycarbonyl) sulfamoyl) amino) methyl)-4-fluoroazepane-1-carboxylate 7 (350 mg, 0.823 mmol) and 4M HCl in dioxane (10 mL) was stirred at room temperature for 16 h. The progress of the reaction was monitored by TLC. After completion of the reaction, organic solvents completely distilled off under reduced pressure to afford compound-8 (250 mg, 0.958 mmol, quantitative yield) as a brown gummy liquid.

Analytical Data: 1H NMR (400 MHz, DMSO) δ 9.088 (bs, 2H), 7.147 (t, 1H), 6.880 (bs, 1H), 6.583 (bs, 1H), 2.994-3.151 (m, 6H), 2.077-2.163 (m, 2H), 1.689-1.945 (m, 4H).

Synthesis of Compound 041

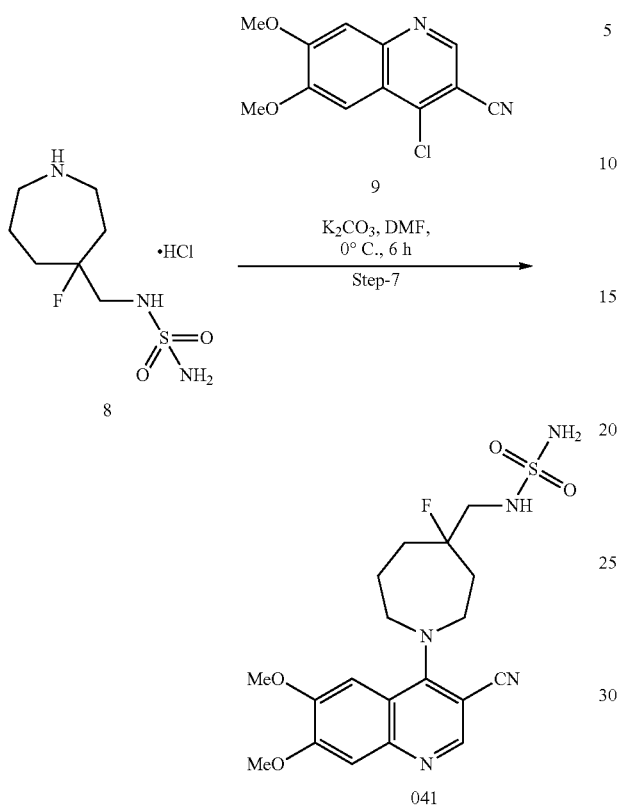

To a stirred solution of 4-chloro-6,7-dimethoxyquinoline-3-carbonitrile 9 (80 mg, 0.332 mmol) in N,N'-dimethylformamide (5 ml) were added potassium carbonate (137 mg, 0.996 mmol) and compound-8 (130 mg, 0.498 mmol) then stirred at 90° C. for 6 h. The progress of the reaction was monitored by TLC. After completion of the reaction, added water (100 mL) and extracted with ethyl acetate (2×100 mL). Combined organic layers were washed with brine solution (100 mL), dried over sodium sulfate and concentrated under reduced pressure. Crude was purified through preparative HPLC method to afford Compound 041 (30 mg, 0.068 mmol, 21% yield) as an off white solid.

Analytical Data: 1H NMR (400 MHz, DMSO) δ 8.651 (s, 1H), 7.377 (s, 1H), 7.319 (s, 1H), 6.860-6.895 (t, 1H), 6.567 (s, 2H), 3.945 (s, 3H), 3.937 (s, 3H), 3.811-3.856 (m, 1H), 3.549-3.639 (m, 2H), 3.462-3.500 (m, 1H), 3.073-3.3.137 (dd, 2H), 2.030-2.217 (m, 5H), 1.831-1.862 (bs, 1H).

Synthetic Scheme for Compounds 042 and 043

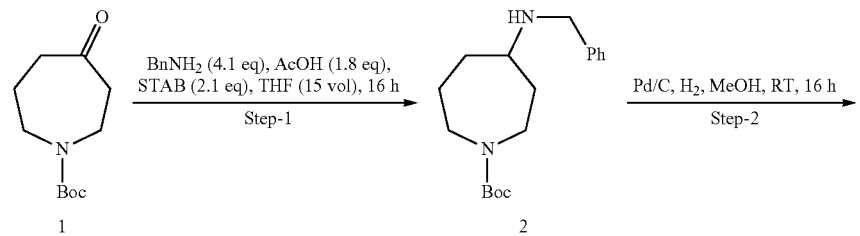

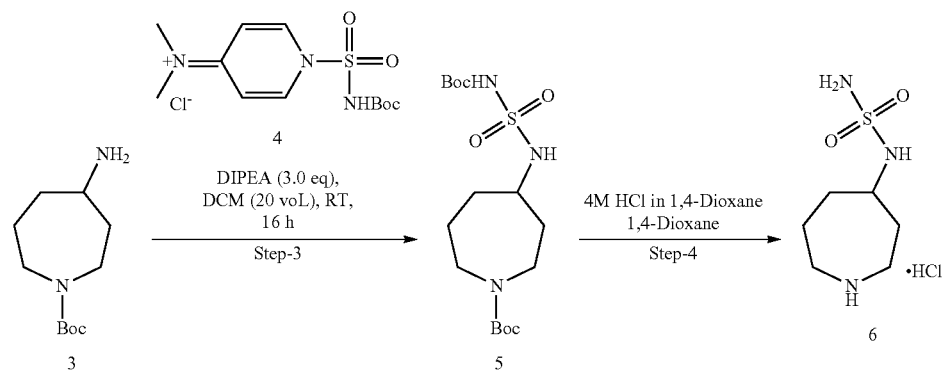

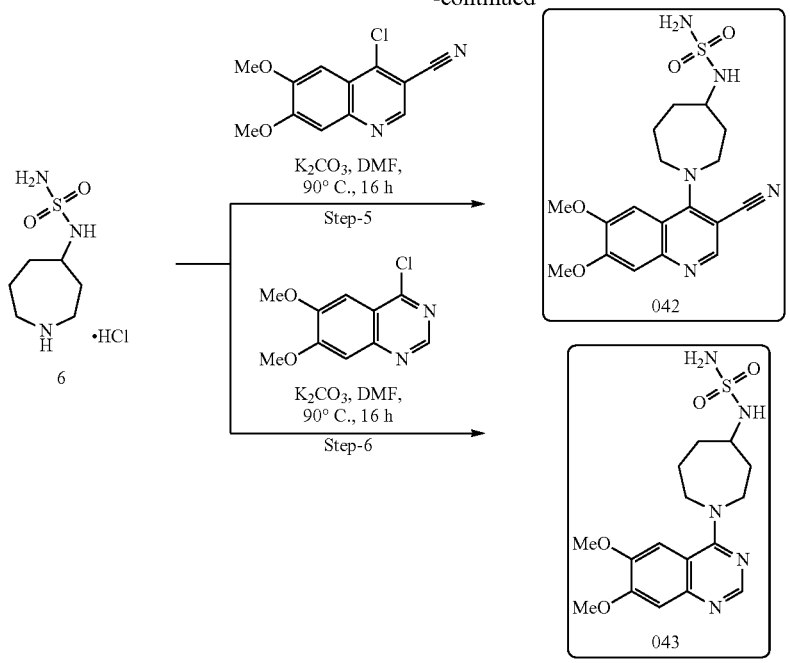

Step-1: Synthesis of tert-butyl 4-(benzyl amino) azepane-1-carboxylate (2)

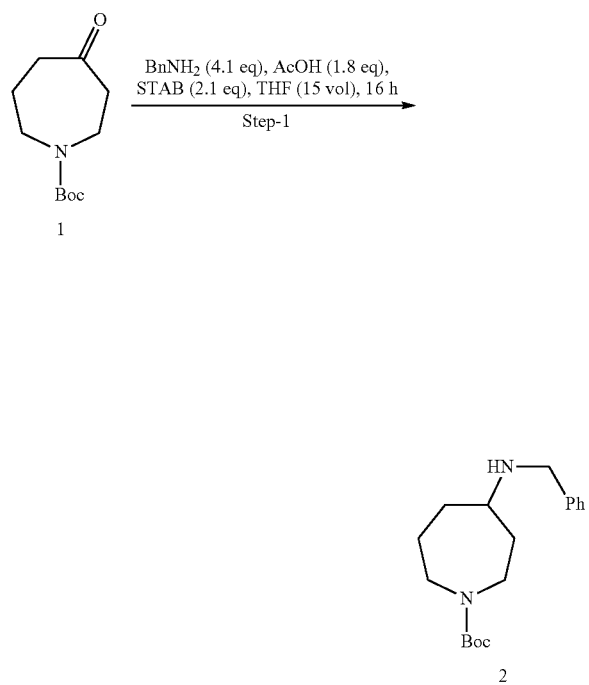

To a stirred solution of tert-butyl 4-oxoazepane-1-carboxylate 1 (1 g, 4.69 mmol) in DMF (7.5 mL) was added Benzyl amine (2.1 ml, 19.2 mmol) and STAB (2.1 g, 9.9 mmol) at 0° C. followed by AcOH (0.5 ml). Then the reaction mixture was allowed to stir at RT for 16 h. The progress of the reaction was monitored by TLC. After completion of reaction, reaction mixture was directly poured on to ice cold water and stirred. Organics were extracted with EtOAc thrice and combined organics were washed with brine, dried and concentrated. Compound was directly absorbed on silica and combi-flash chromatography to afford tert-butyl 4-(benzyl amino) azepane-1-carboxylate 2 (1.2 g, 3.947 mmol, 85% yield)

Analytical Data: LCMS: (M+H)+: m/Z: 305.2

Step-2: Synthesis of tert-butyl 4-aminoazepane-1-carboxylate (3)

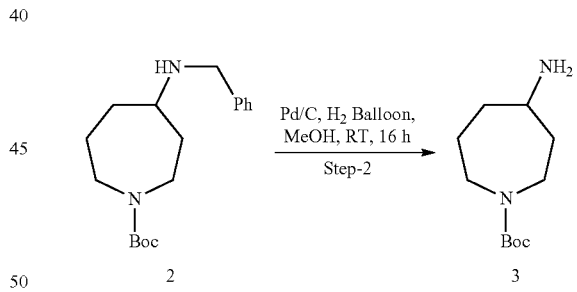

To a stirred solution of tert-butyl 4-(benzyl amino) azepane-1-carboxylate 2 (1.1 g, 3.6 mmol) in MeOH (20 mL) was added Pd/C (100 mg) and stirred at RT for 16 h. After completion of reaction, reaction mixture was filtered through a pad of celite. The filtrate was concentrated under reduced pressure to afford light yellowish liquid of tert-butyl 4-aminoazepane-1-carboxylate 3 (600 mg, 2.803 mmol, 71% yield)

Analytical Data: 1H NMR (400 MHz, DMSO): 3.48-3.41 (m, 2H), 3.29-3.27 (m, 1H), 3.10-3.05 (m, 1H), 2.97-2.94 (m, 1H), 1.93-1.89 (m, 1H), 1.85-1.77 (m, 3H), 1.53-1.48 (m, 2H), 1.39 (s, 9H).

Step-3: tert-butyl 4-((N-(tert-butoxycarbonyl)sulfamoyl)amino)azepane-1-carboxylate 5

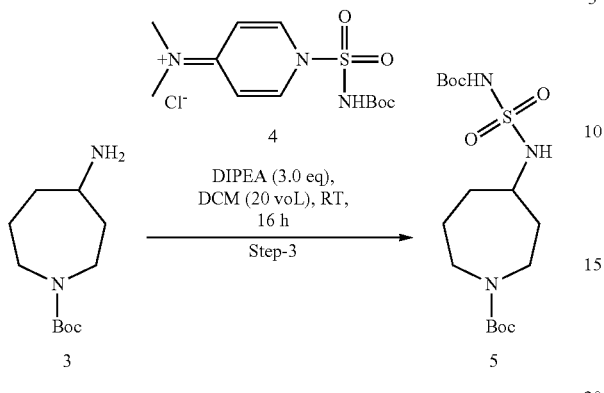

To a stirred solution of tert-butyl 4-aminoazepane-1-carboxylate 3 (600 mg, 2.8 mmol) in DCM (30 mL) was added N-(1-(N-(tert-butoxycarbonyl)sulfamoyl)pyridin-4(1H)-ylidene)-N-methylmethanaminium chloride 4 (1.4 g, 3.08 mmol) slowly and then added DIPEA (1.5 ml, 8.4 mmol) at same temperature. Then stirred the reaction mixture at room temperature for 16 h. The progress of the reaction was monitored by TLC. Reaction mixture was directly absorbed on to silica, crude was purified through combi-flash chromatography by eluting 80% EtOAc in Hexane to afford tert-butyl 4-((N-(tert-butoxycarbonyl)sulfamoyl)amino)azepane-1-carboxylate 5 (650 mg, 1.65 mmol, 59% yield) as a white solid.

Analytical Data: 1H NMR (400 MHz, DMSO): 10.77 (s, 1H), 7.68-7.63 (m, 1H), 3.32-3.30 (m, 1H), 3.20-3.10 (m, 4H), 1.89-1.74 (m, 3H), 1.58-1.48 (m, 3H), 1.41-1.38 (m, 18H).

LCMS: (M−H)+: m/Z: 392.1

Step-4: Synthesis of 4-((N-sulfamoyl)amino)azepane-hydrochloride (6)

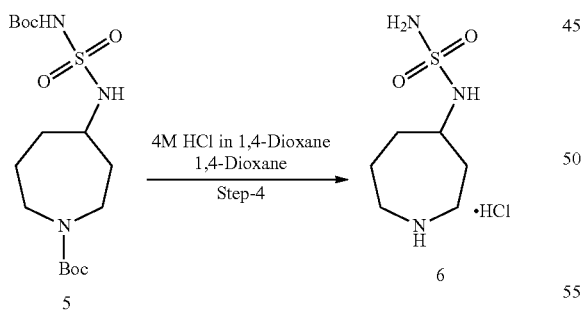

To a stirred solution of tert-butyl 4-((N-(tert-butoxycarbonyl)sulfamoyl)amino)azepane-1-carboxylate 5 (650 mg, 1.6 mmol) in dichloromethane (10 ml) was added 4M HCl in dioxane (0.6 mL) at 0° C. then stirred at room temperature for 16 h. The progress of the reaction was monitored by TLC. After completion of reaction, organic solvents completely distilled off under reduced pressure. Crude compound was triturated with diethyl ether to give 4-((N-sulfamoyl)amino)azepane-hydrochloride (310 mg) as white solid.

Analytical Data: 1H NMR (400 MHz, DMSO) δ: 8.92 (brs, 2H), 6.72-6.70 (brs, 1H), 6.53 (brs, 1H), 3.39-3.37 (s, 1H), 3.16-3.14 (m, 1H), 3.16-3.14 (m, 1H), 3.08-3.05 (m, 1H), 3.05-2.98 (m, 2H), 2.06-2.04 (m, 1H), 1.95-1.90 (m, 1H), 1.87-1.81 (m, 2H), 1.67-1.54 (m, 2H)

Step-5: Synthesis of N-(1-(3-cyano-6,7-dimethoxyquinolin-4-yl)azepan-4-yl)sulfamoylamine (Compound 042)

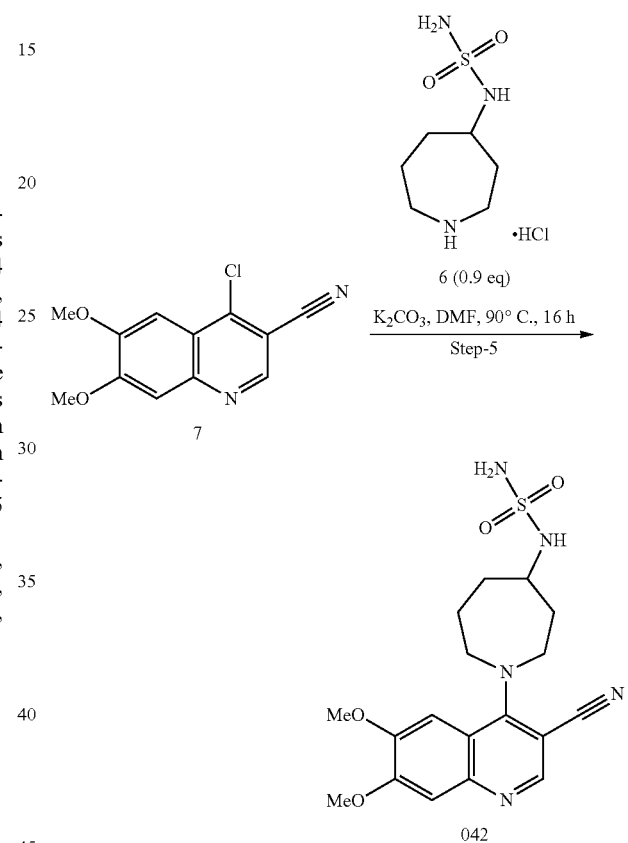

To a stirred solution of 4-chloro-6,7-dimethoxyquinoline-3-carbonitrile 7 (146 mg, 0.65 mmol) in DMF (5 ml) was added 4-((N-sulfamoyl)amino)azepane-hydrochloride (135 mg, 0.58 mmol) followed by K2CO3 (0.270 mg, 1.96 mmol) at RT. After addition, the reaction mixture was heated to 90° C. stirred for 16 h. The progress of the reaction was monitored by TLC. After completion of reaction, quenched with water and organics were extracted with EtOAc thrice and combined organics was washed with brine, dried and concentrate under reduced pressure to get crude. Crude compound was purified through prep-HPLC to afford N-(1-(3-cyano-6,7-dimethoxyquinolin-4-yl)azepan-4-yl)sulfamoylamine (Compound 042) (22 mg, 0.054 mmol, 9% yield) was obtained as a pale yellow fluffy solid.

Analytical Data: 1H NMR (400 MHz, DMSO) δ: 8.62 (s, 1H), 7.36 (s, 1H), 7.32 (s, 1H), 6.72 (d, 1H), 6.51 (s, 2H), 3.94 (s, 6H), 3.62-3.61 (m, 3H), 3.54-3.51 (m, 2H), 2.21-2.10 (m, 2H), 1.93-1.91 (m, 1H), 1.87-1.74 (m, 3H)

LCMS: (M+H)+: m/Z: 406.31

Step-6: Synthesis of N-(1-(6, 7-dimethoxyquinazolin-4-yl) azepan-4-yl)sulfamoylamine (Compound 043)

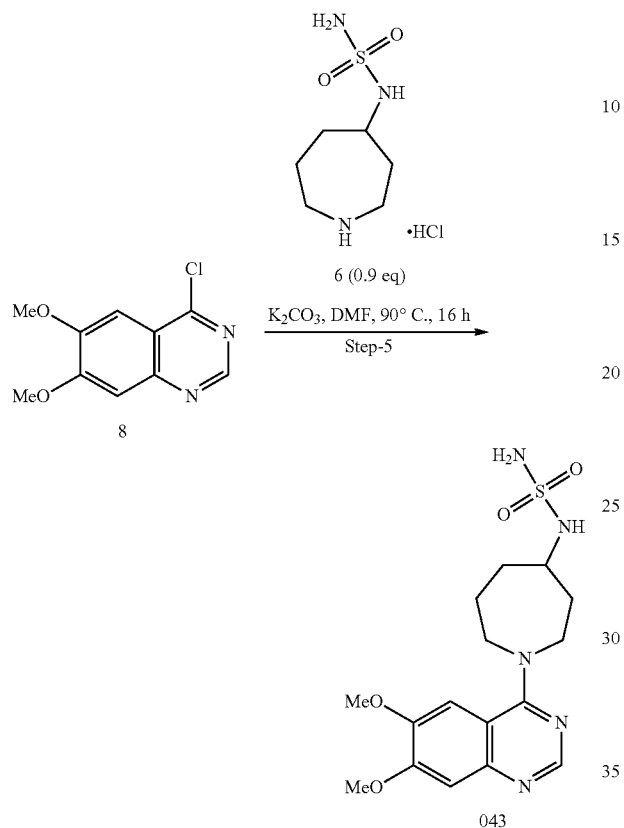

To a stirred solution of 4-chloro-6, 7-dimethoxyquinazoline 8 (146 mg, 0.65 mmol) in DMF (5 ml) was added 4-((N-sulfamoyl) amino) azepane-hydrochloride (135 mg, 0.589 mmol) followed by K2CO3 (0.270 mg, 1.96 mmol) at RT. After addition, the reaction mixture was heated to 90° C. stirred for 16 h. The progress of the reaction was monitored by TLC. After completion of the reaction, reaction mixture was poured on water and extracted with EtOAc thrice and combined organic layer was washed with brine, dried under reduced pressure to get crude. Crude compound was purified through prep-HPLC to afford N-(1-(6, 7-dimethoxyquinazolin-4-yl)azepan-4-yl) sulfamoylamine Compound 043 (24 mg, 0.062 mmol, 9.6% yield) was obtained as an off-white solid.

Analytical Data: 1H NMR (400 MHz, DMSO) δ: 8.36 (s, 1H), 7.27 (s, 1H), 7.13 (s, 1H), 6.62 (d, 1H), 6.49 (s, 2H), 3.87-3.96 (m, 8H), 3.63-3.71 (m, 2H), 3.31-3.37 (m, 1H), 2.2-2.25 (m, 1H), 1.95-2.01 (m, 3H), 1.82-1.85 (m, 1H), 1.50-1.58 (m, 1H)

LCMS: (M+H)$^+$: m/Z: 382.19

Synthetic Scheme of Compounds 044 and 045

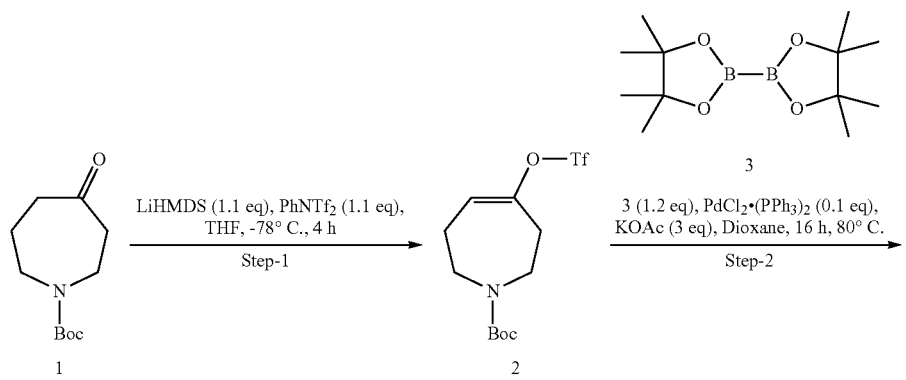

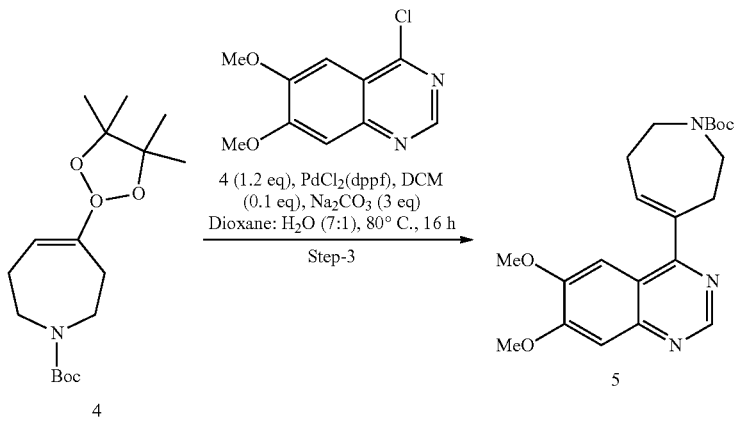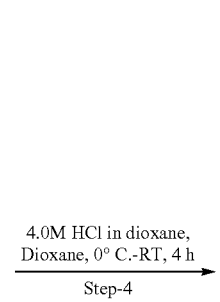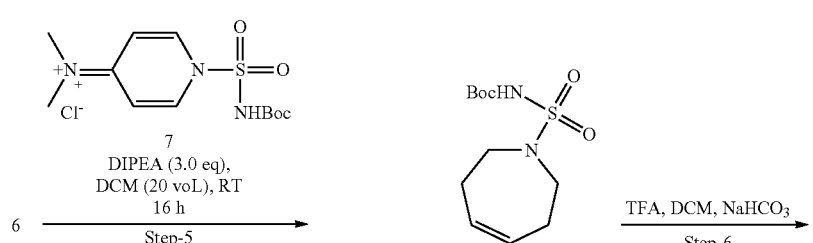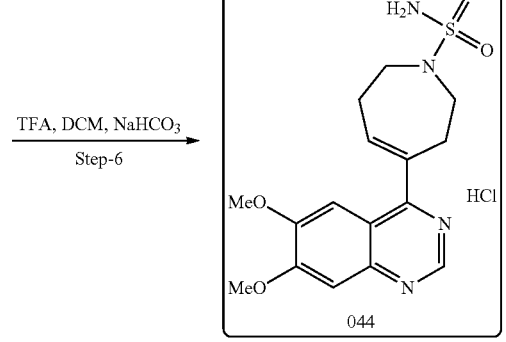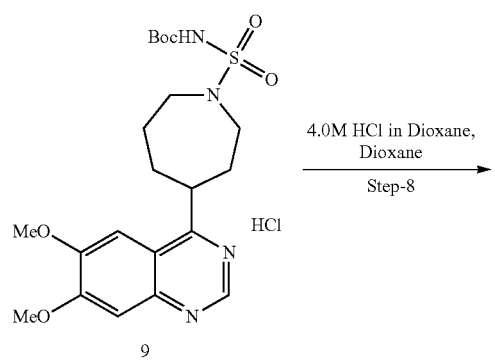

Step-1: Synthesis of tert-butyl 4-(((trifluoromethyl)sulfonyl)oxy)-2,3,6,7-tetrahydro-1H-azepine-1-carboxylate (2)

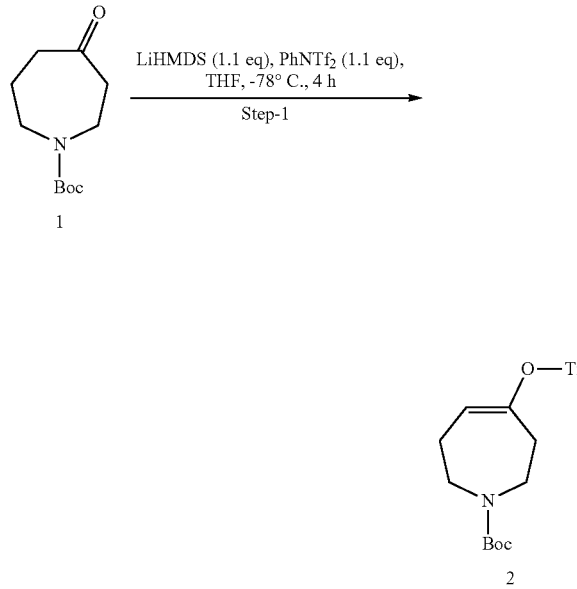

To a solution of tert-butyl 4-oxoazepane-1-carboxylate (1.5 g, 7.04 mmol, 1 eq.) in THF (20 mL) at −78° C., was added a 1N solution of LiHMDS (7.7 mL, 7.74 mmol) dropwise under nitrogen. The mixture was stirred for 20 minutes, then a solution of PhNTf2 (2.75 g, 7.71 mmol) in THF (10 mL) was added. The mixture was warmed to 0° C. and stirred for 3 hours. The reaction was concentrated and diluted with DCM, filtered through neutral alumina and the product was eluted with 9:1 Hexanes/EtOAc to afford tert-butyl 4-(((trifluoromethyl)sulfonyl)oxy)-2,3,6,7-tetrahydro-1H-azepine-1-carboxylate (2.1 g, 6.08 mmol, 87% yield).

Analytical Data: 1H NMR (400 MHz, CDCl3): 5.90 (m, 1H), 3.90-3.99 (m, 2H), 3.51-3.60 (m, 2H), 2.56 (m, 1H), 1.92-1.97 (m, 2H), 1.45 (s, 9H)

Step-2: Synthesis of tert-butyl 4-(4,4,5,5-tetramethyl-1,3,2-dioxaborolan-2-yl)-2,3,6,7-tetrahydro-1H-azepine-1-carboxylate (4)

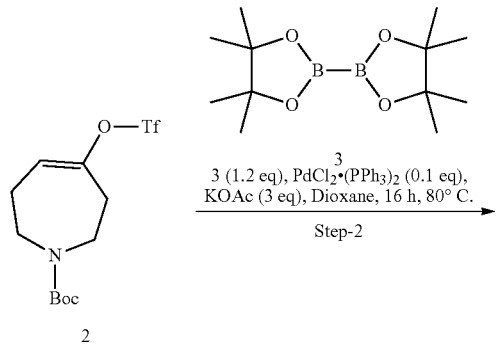

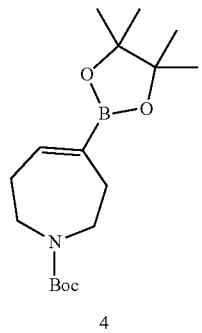

To a stirred solution of tert-butyl 4-(((trifluoromethyl)sulfonyl)oxy)-2,3,6,7-tetrahydro-1H-azepine-1-carboxylate 2 (1.5 g, 4.34 mmol) in dioxane was added bis(pinacolato)diboron 3 (1.3 g, 4.9 mmol) and potassium acetate (1.28 g, 12.9 mmol) at RT. The mixture was degassed under nitrogen for 15 minutes, then added PdCl2(PPh3)2 (300 mg, 0.43 mmol) at RT and the mixture was degassed for an additional 5 minutes. The reaction was stirred at 80° C. overnight, concentrated, diluted with ethyl acetate and filtered through celite pad, filtrate was concentrated under reduced pressure to get crude (3 gm) was used as such for the next step.

Step-3: tert-butyl 4-(6,7-dimethoxyquinazolin-4-yl)-2,3,6,7-tetrahydro-1H-azepine-1-carboxylate (5)

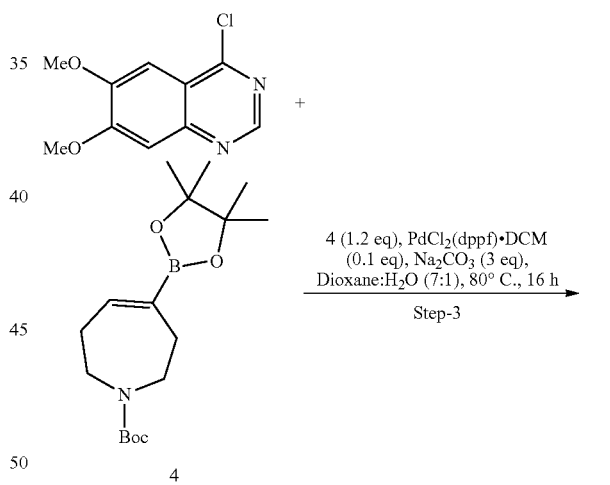

To the stirred solution of 4-chloro-6,7-dimethoxyquinazoline (208 mg, 0.9 mmol) in Dioxane (7 mL) and water (1 ml) was added tert-butyl 4-(4,4,5,5-tetramethyl-1,3,2-dioxaborolan-2-yl)-2,3,6,7-tetrahydro-1H-azepine-1-carboxylate 4 (600 mg crude, 1.8 mmol) followed by Na2CO3 (300 mg, 2.7 mmol) and degassed with Argon for 30 min. Then added PdCl2(dppf).DCM (76 mg, 0.09 mmol) was added and purged again for 5 min with Argon. The reaction mixture was heated to 80° C. for 16 h. The progress of the reaction was monitored by TLC. Reaction mixture was filtered through celite pad and filtrate was quenched with water and extracted with EtOAc thrice and combined organic layer was washed with brine & water. Organic layer was concentrated under reduced pressure to get crude. Crude compound was purified through combi-flash chromatography by eluting 90% EtOAc in Hexane to afford tert-butyl 4-(6,7-dimethoxyquinazolin-4-yl)-2,3,6,7-tetrahydro-1H-azepine-1-carboxylate 5 (250 mg, 0.649 mmol, 70% yield) as a Light brown solid.

Analytical Data: 1H NMR (400 MHz, DMSO): 9.06 (s, 1H), 7.55 (s, 1H), 7.30-7.30 (m, 1H), 6.19 (t, 1H), 4.11-4.44 (m, 2H), 4.00-4.05 (m, 6H), 3.69-3.74 (m, 2H), 2.81-2.83 (m, 2H), 2.07-2.10 (m, 2H), 1.48 (s, 9H)

LCMS: (M–H)+: m/Z: 386.2

Step-4: 6,7-dimethoxy-4-(2,3,6,7-tetrahydro-1H-azepin-4-yl)quinazoline hydrochloride (6)

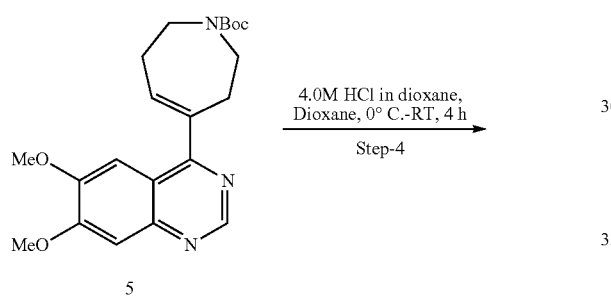

To the stirred solution of tert-butyl 4-(6,7-dimethoxyquinazolin-4-yl)-2,3,6,7-tetrahydro-1H-azepine-1-carboxylate 5 (100 mg, 0.83 mmol) in 1,4 Dioxane (10 mL) was added 4.0M HCl in 1,4-Dioxane (1 ml) slowly at 0° C. and slowly allowed to RT and stirred for 2 h. After completion of reaction, volatile organics were removed under reduced pressure, co-distilled thrice with DCM and triturated with ether to give off-white solid 6,7-dimethoxy-4-(2,3,6,7-tetrahydro-1H-azepin-4-yl)quinazoline hydrochloride 6 (88 mg, 0.24 mmol, 95% yield)

Analytical Data: LCMS: (M–H)+: m/Z: 286.2

Step-5: tert-butyl ((4-(6,7-dimethoxyquinazolin-4-yl)-2,3,6,7-tetrahydro-1H-azepin-1-yl) sulfonyl) carbamate (8)

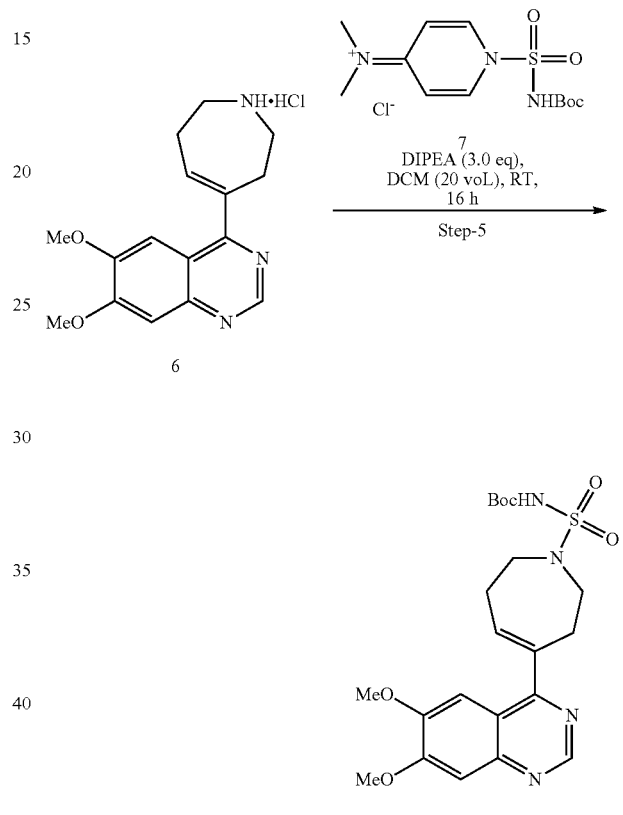

To the stirred solution of 6,7-dimethoxy-4-(2,3,6,7-tetrahydro-1H-azepin-4-yl)quinazoline hydrochloride 6 (90 mg, 0.28 mmol) in DCM was added N-(1-(N-(tert-butoxycarbonyl)sulfamoyl)pyridin-4(1H)-ylidene)-N-methylmethanaminium chloride 4 (95 mg, 0.28 mmol) and DIPEA (0.146 ml, 0.841 mmol) at room temperature. Then stirred the reaction mixture at room temperature for 16 h. The progress of the reaction was monitored by TLC. Reaction mixture was directly absorbed on to silica and converted into slurry. Crude was purified through combi-flash chromatography by eluting 90% EtOAc in Hexane to afford tert-butyl ((4-(6,7-dimethoxyquinazolin-4-yl)-2,3,6,7-tetrahydro-1H-azepin-1-yl)sulfonyl)carbamate 8 (120 mg, 0258 mmol, 92% yield) as an off-white solid.

Analytical Data: 1H NMR (400 MHz, DMSO): 11.03 (s, 1H), 8.98 (s, 1H), 7.47 (s, 1H), 7.34 (s, 1H), 6.15 (t, 1H), 4.17-4.16 (m, 2H), 3.96 (s, 3H), 3.90 (s, 3H), 3.57 (t, 2H), 2.78-2.80 (m, 2H), 2.01-2.03 (m, 2H), 1.38 (s, 9H)

LCMS: (M–H)+: m/Z: 465.2

Step-6: Synthesis of 4-(6,7-dimethoxyquinazolin-4-yl)-2,3,6,7-tetrahydro-1H-azepine-1-sulfonamide (Compound 044)

Step-7: tert-butyl ((4-(6,7-dimethoxyquinazolin-4-yl)azepan-1-yl)sulfonyl)carbamate (9)

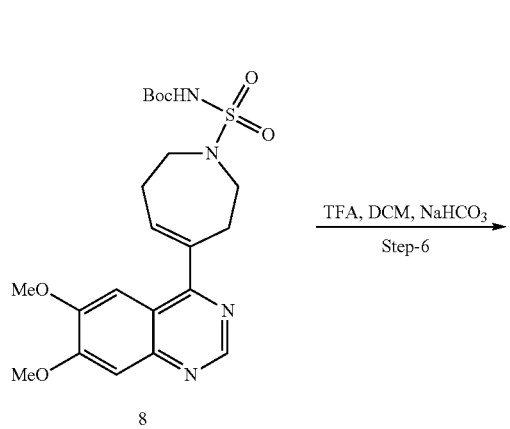

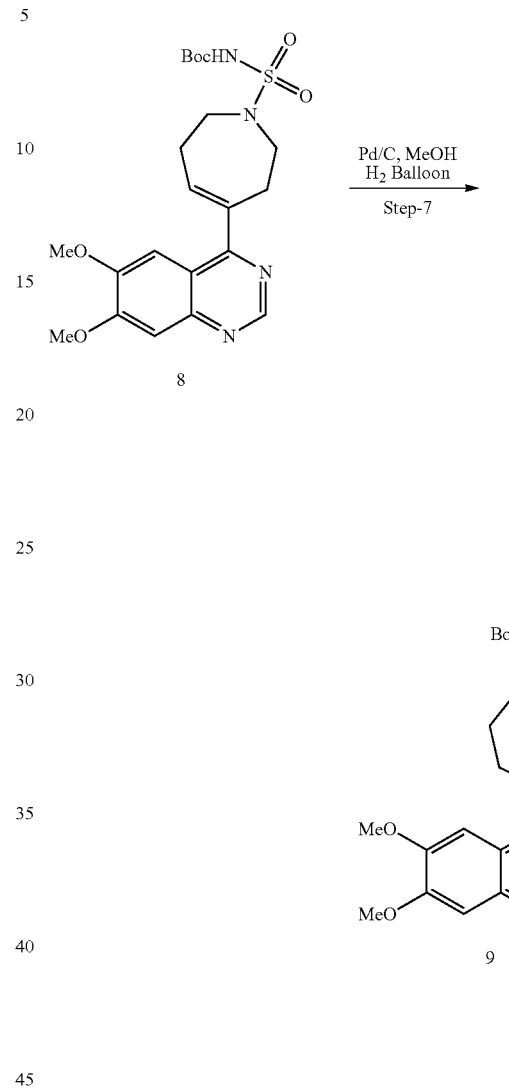

To a stirred solution of tert-butyl ((4-(6,7-dimethoxyquinazolin-4-yl)-2,3,6,7-tetrahydro-1H-azepin-1-yl)sulfonyl)carbamate 8 (125 mg, 0.26 mmol) in dichloromethane (5 ml) was added was added TFA (1.2 mL) at 0° C., then stirred at same temperature for 4 h. The progress of the reaction was monitored by TLC. After completion of reaction, TFA was neutralized by using aq.NaHCO3, and extracted with 10% MeOH/DCM and dried and concentrated under reduced pressure to get crude. Crude compound was submitted to prep-HPLC to afford 4-(6,7-dimethoxyquinazolin-4-yl)-2,3,6,7-tetrahydro-1H-azepine-1-sulfonamide Compound 044 (70 mg, 0.192 mmol, 70% yield) as an off-white solid.

Analytical Data: 1H NMR (400 MHz, DMSO): 8.97 (s, 1H), 7.52 (s, 1H), 7.32 (s, 1H), 6.82 (s, 2H), 6.16 (t, 1H), 4.02-4.00 (m, 2H), 3.96 (s, 3H), 3.98 (s, 6H), 3.51 (t, 2H), 2.82-2.79 (m, 2H), 2.02-1.98 (m, 2H)

LCMS: (M−H)+: m/Z: 365.1

To a stirred solution of tert-butyl ((4-(6,7-dimethoxyquinazolin-4-yl)-2,3,6,7-tetrahydro-1H-azepin-1-yl)sulfonyl)carbamate 8 (250 mg, 0.53 mmol) in MeOH (3 mL) was added 10% Pd/C (25 mg) and stirred at RT for 16 h. After completion of reaction, reaction mixture was filtered through a celite pad. Filtrate was concentrated under reduced pressure to give light yellowish liquid of tert-butyl ((4-(6,7-dimethoxyquinazolin-4-yl)azepan-1-yl)sulfonyl)carbamate 9 (220 mg, 0.472 mmol, 87% yield)

Analytical Data: 1HNMR (400 MHz, DMSO) δ: 11.13 (s, 1H), 8.96 (s, 1H), 7.45 (s, 1H), 7.32 (s, 1H), 6.97 (d, 2H), 3.96-3.95 (m, 6H), 3.89-3.81 (m, 1H), 3.79-3.64 (m, 1H), 3.58-3.32 (m, 3H), 2.04-1.85 (m, 6H).

LCMS: (M+H)+: m/Z: 467.11

Step-8: Synthesis of 4-(6, 7-dimethoxyquinazolin-4-yl)azepane-1-sulfonamide hydrochloride (Compound 045)

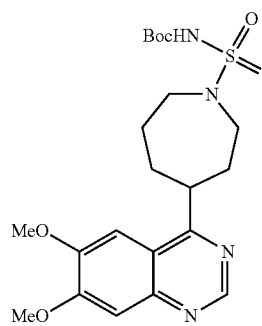

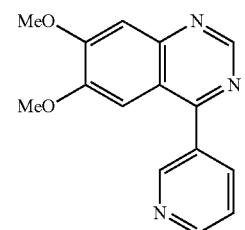

To a stirred solution of tert-butyl ((4-(6,7-dimethoxyquinazolin-4-yl)azepan-1-yl)sulfonyl)carbamate 9 (250 mg, 0.53 mmol) in dichloromethane (2.5 mL) was added 4M HCl in dioxane (2.5 mL) at 0° C. then stirred at room temperature for 16 h. The progress of the reaction was monitored by TLC. Crude reaction mixture was purified through prep-HPLC to afford 4-(6,7-dimethoxyquinazolin-4-yl)azepane-1-sulfonamide hydrochloride Compound 045 (25 mg, 0.062 mmol, 11% yield) was obtained as an off-white solid.

Analytical Data: 1H NMR (400 MHz, DMSO) δ: 8.96 (s, 1H), 7.44 (s, 1H), 7.32 (s, 1H), 6.71 (s, 2H), 3.95-3.96 (m, 6H), 3.81-3.83 (m, 1H), 3.47-3.53 (m, 2H), 3.17-3.23 (m, 1H), 2.00-2.04 (m, 2H), 1.85-1.95 (m, 4H)

LCMS: (M+H)+: m/Z: 367.3

General scheme 9

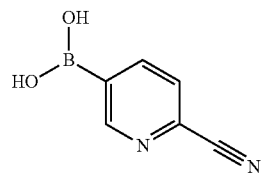

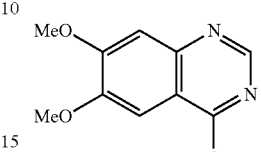

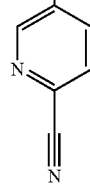

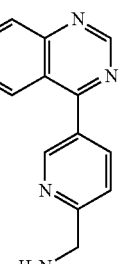

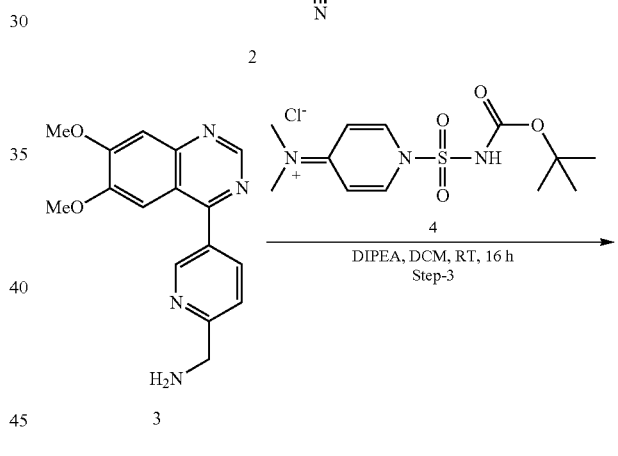

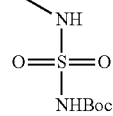

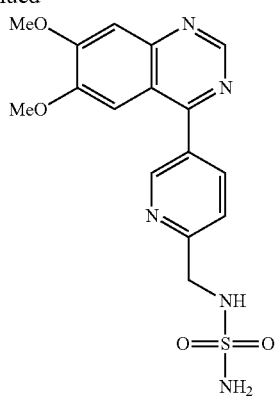

Example 9: N-((5-(6, 7-dimethoxyquinazolin-4-yl) pyridin-2-yl) methyl) sulfamide

Step-1: 5-(6, 7-dimethoxyquinazolin-4-yl) picolinonitrile

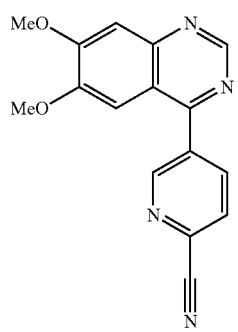 [SMILES: COc1cc2ncnc(-c3ccc(C#N)nc3)c2cc1OC]

In a sealed tube, to the stirred solution of 4-chloro-6,7-dimethoxyquinazoline 1 (1.5 g, 6.67 mmol) in dioxane (50 mL) and water (20 mL) were added (6-cyanopyridin-3-yl) boronic acid (1.08 g, 0.72 mmol) and sodium carbonate (2.12 g, 20.0 mmol) was then degassed the reaction mixture for 30 minutes. Then, [1, 1'-Bis (diphenylphosphino) ferrocene] dichloropalladium (II) dichloromethane complex (544 mg, 0.66 mmol) was added again degassed for 5 minutes and stirred the reaction mixture at 100° C. for 16 h. The progress of the reaction was monitored by TLC. After completion of the reaction, reaction mixture was poured into water (100 mL) and filtered through celite. Washed the celite bed with 10% methanol in dichloromethane (100 mL) and separated the two layers. Organic layer washed with brine solution (200 mL), dried over sodium sulfate and concentrated under reduced pressure. Crude was purified using combi-flash column chromatography by eluting 3% methanol in dichloromethane to afford 5-(6, 7-dimethoxyquinazolin-4-yl) picolinonitrile 2 (700 mg, 2.39 mmol, 37%) as a brown solid.

Analytical Data: 1H NMR (400 MHz, DMSO) 9.18 (d, 2H), 8.51 (d, 1H), 8.27 (d, 1H), 7.48 (s, 1H), 7.23 (s, 1H), 4.01 (s, 3H), 3.86 (s, 3H). LCMS: (M+H+): m/Z: 292.9

Step-2: (5-(6, 7-dimethoxyquinazolin-4-yl) pyridin-2-yl) methanamine

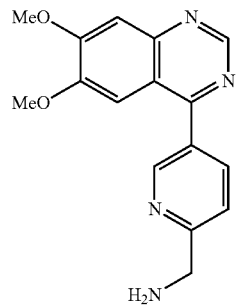 [SMILES: COc1cc2ncnc(-c3ccc(CN)nc3)c2cc1OC]

To a stirred solution of 5-(6, 7-dimethoxyquinazolin-4-yl) picolinonitrile 2 (500 mg, 1.7 mmol) in acetic acid (30 mL) was added 10% Pd/C (300 mg) and stirred under balloon hydrogen atmosphere at room temperature for 16 h. The progress of the reaction was monitored by TLC. After completion of the reaction, reaction mixture was passed through celite and washed the celite bed with 5% methanol in dichloromethane (100 mL). Filtrate was concentrated under reduced pressure to afforded (5-(6, 7-dimethoxyquinazolin-4-yl) pyridin-2-yl) methanamine 3 (500 mg, 1.689 mmol, 98% yield) as a yellow solid.

Analytical Data: 1H NMR (400 MHz, DMSO) 9.15 (s, 1H), 8.97 (s, 1H), 8.29 (d, 1H), 7.70 (d, 1H), 7.45 (s, 1H), 7.25 (s, 1H), 4.11 (brs, 2H), 4.00 (s, 3H), 3.87 (s, 3H). LCMS: (M+H+): m/Z: 297.0

Step-3: Tert-butyl (N-((5-(6, 7-dimethoxyquinazolin-4-yl) pyridin-2-yl) methyl) sulfamoyl) carbamate (Int-5)

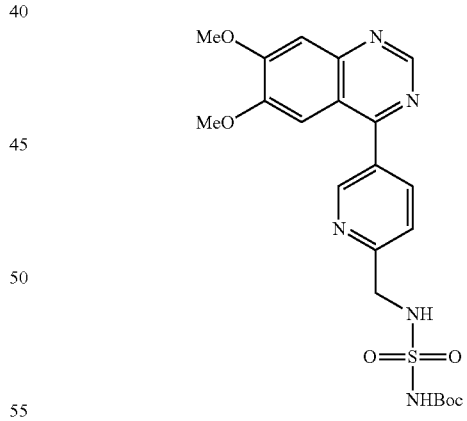

To a stirred solution of (5-(6,7-dimethoxyquinazolin-4-yl)pyridin-2-yl) methanamine 3 (500 mg, 1.689 mmol) in dichloromethane (40 ml) were added diisopropylethylamine (1.65 mL, 10.134 mmol) and N-(1-(N-(tert-butoxycarbonyl) sulfamoyl)pyridin-4(1H)-ylidene)-N-methylmethanaminium chloride 4 (569 mg, 1.689 mmol) at RT allowed to stir at room temperature for 16 h. The progress of the reaction was monitored by TLC. After completion of reaction, organic solvents completely distilled off under reduced pressure to afford crude compound. Crude compound was purified over combi flash column chromatography by eluting 2% methanol in dichloromethane to afforded tert-butyl (N-((5-(6, 7-dimethoxyquinazolin-4-yl) pyridin-2-yl) methyl) sulfamoyl) carbamate (300 mg, 0.631 mmol, 37% yield) as a yellow solid.

Analytical Data: 1H NMR (400 MHz, DMSO) 9.15 (s, 1H), 8.37 (s, 1H), 8.29 (d, 1H), 7.67 (d, 1H), 7.46 (s, 1H), 7.26 (s, 1H), 4.37 (d, 2H), 4.01 (s, 3H), 3.59 (s, 3H), 1.39 (s, 9H).

LCMS: (M+H+): m/Z: 475.9

Step-4: N-((5-(6, 7-dimethoxyquinazolin-4-yl) pyridin-2-yl) methyl) sulfamide (Compound 047)

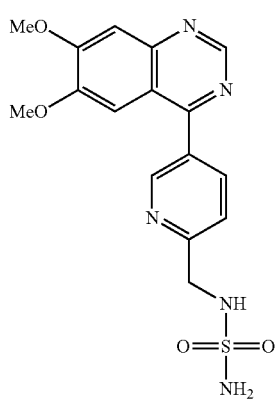 [SMILES: COc1cc2ncnc(-c3ccc(CNS(N)(=O)=O)nc3)c2cc1OC]

To a stirred solution of tert-butyl (N-((5-(6,7-dimethoxyquinazolin-4-yl)pyridin-2-yl)methyl)sulfamoyl)carbamate Int-5 (100 mg, 0.210 mmol) in 1,4-dioxane (1.0 ml) was added 4M HCl in dioxane (2.5 mL) at RT, then stirred at RT for 16 h. The progress of the reaction was monitored by TLC. After completion of the reaction, organic solvents completely distilled off under reduced pressure to afford crude compound. Crude compound was purified through prep. HPLC to afford pure compound of N-((5-(6, 7-dimethoxyquinazolin-4-yl) pyridin-2-yl) methyl) sulfamide 30 mg, 0.08 mmol, 38% yield) (Compound 47) as an off white solid.

Analytical Data: 1H NMR (400 MHz, DMSO) 9.15 (s, 1H), 8.93 (s, 1H), 8.28 (d, 1H), 7.73 (d, 1H), 7.46 (s, 1H), 7.30-7.27 (m, 2H), 6.75 (s, 2H), 4.32 (d, 2H), 4.01 (s, 3H), 3.85 (s, 3H). LCMS: (M+H+): m/Z: 375.9; M.W. 411.86.

Synthetic Scheme for Compound 046

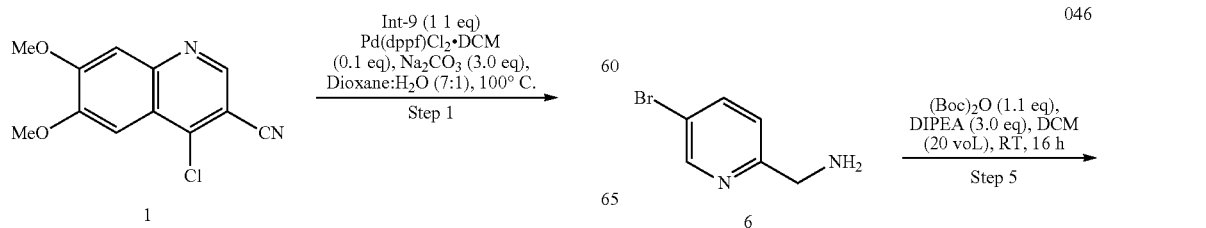

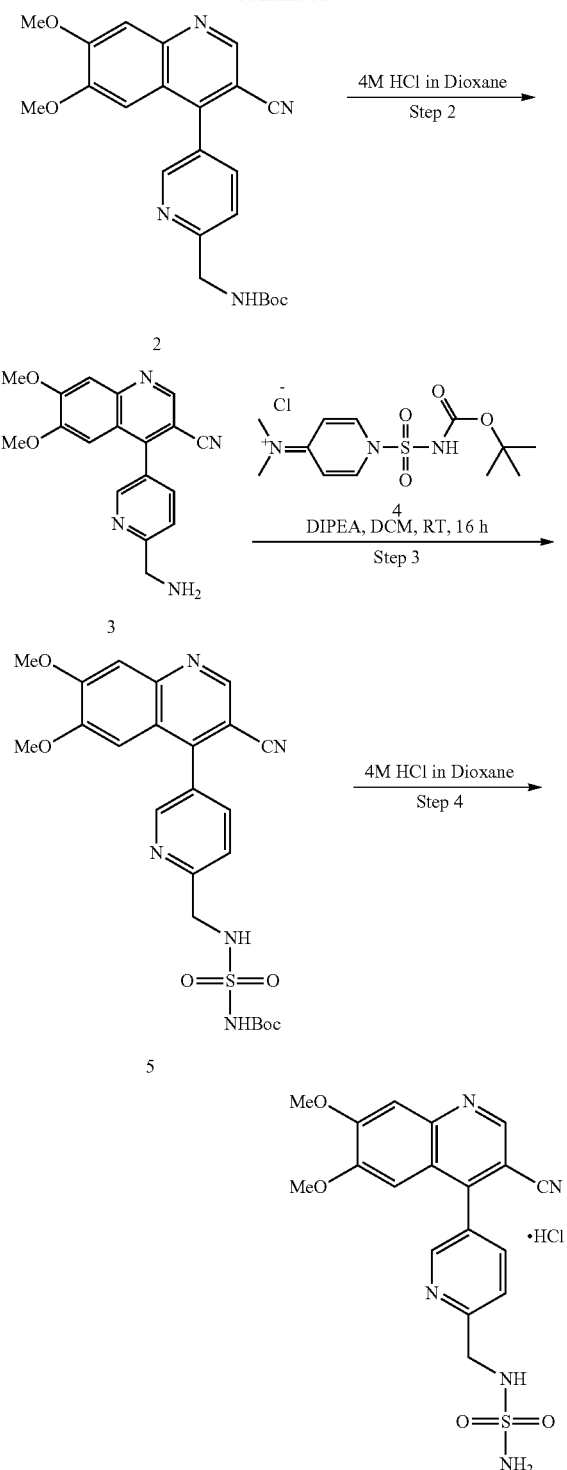

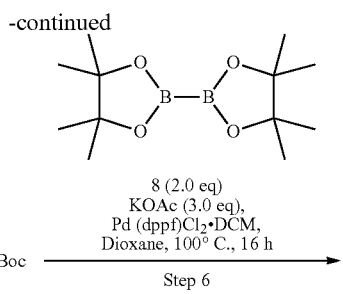

Step 6: 8 (2.0 eq), KOAc (3.0 eq), Pd(dppf)Cl₂·DCM, Dioxane, 100° C., 16 h

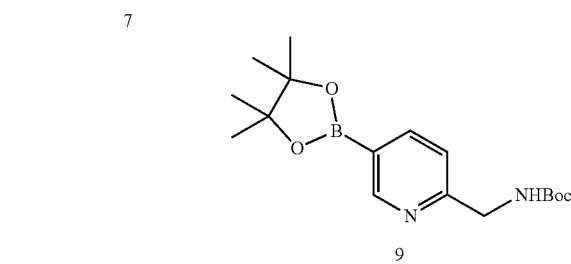

9

Synthesis of Tert-butyl ((5-(3-cyano-6,7-dimethoxy-quinolin-4-yl)pyridin-2-yl)methyl)carbamate (2)

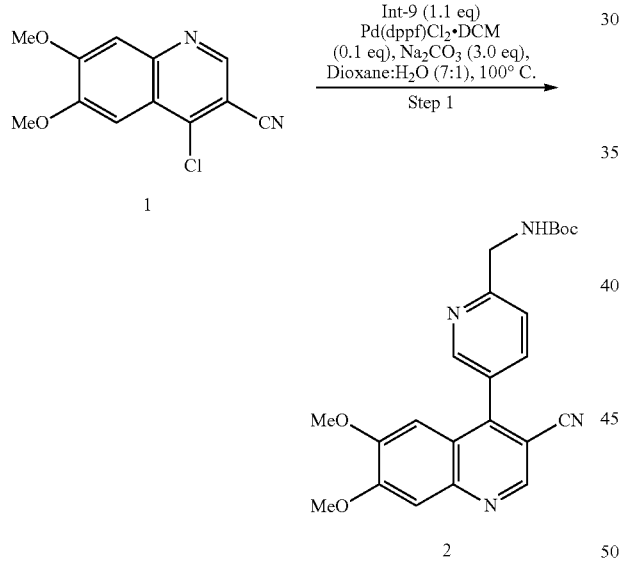

Step 1: Int-9 (1.1 eq), Pd(dppf)Cl₂·DCM (0.1 eq), Na₂CO₃ (3.0 eq), Dioxane:H₂O (7:1), 100° C.

To a stirred solution of 4-chloro-6,7-dimethoxyquinoline-3-carbonitrile (500 mg, 2.01 mmol) in 3:1 dioxane:H₂O (20 mL) were added Na₂CO₃ (641 mg, 6.04 mmol) and tert-butyl ((5-(4,4,5,5-tetramethyl-1,3,2-dioxaborolan-2-yl)pyridin-2-yl)methyl)carbamate Int-9 (1.3 g, 4.03 mmol) at RT, was then degassed the reaction mixture for 30 minutes. Then [1,1'-Bis(diphenylphosphino)ferrocene]dichloropalladium (II) (165 mg, 0.2 mmol) was added again degassed for 5 minutes and stirred the reaction mixture at 100° C. for 16 h. The progress of the reaction was monitored by TLC. After completion of the reaction, reaction mixture was poured into water (100 mL) and filtered through celite. Washed the celite bed with 10% methanol in dichloromethane (100 mL) and separated the two layers. Organic layer washed with brine solution (200 mL), dried over sodium sulfate and concentrated under reduced pressure. Crude was purified prep HPLC method to afford tert-butyl ((5-(3-cyano-6,7-dimethoxyquinolin-4-yl)pyridin-2-yl)methyl)carbamate (2) (250 mg, 0.127 mmol, 30%) as a yellow solid.

Analytical Data: ¹H NMR (400 MHz, DMSO) δ 9.066 (s, 1H), 8.72 (s, 1H), 8.07-8.09 (dd, 1H), 7.52-7.59 (m, 4H), 6.86 (s, 1H), 4.38-4.41 (m, 2H), 4.01 (s, 3H), 3.74 (s, 3H), 1.43 (s, 9H).

LCMS: (M+H⁺): m/Z: 421.2

Synthesis of 4-(6-(aminomethyl)pyridin-3-yl)-6,7-dimethoxyquinoline-3-carbonitrile (3)

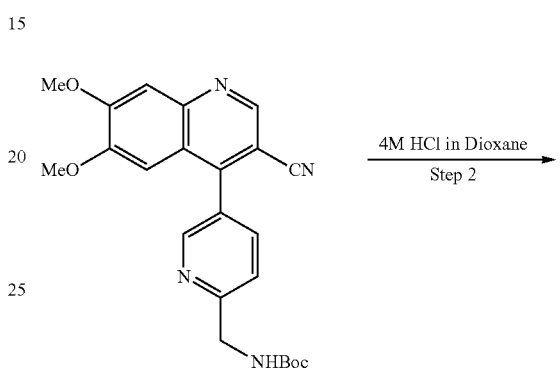

Step 2: 4M HCl in Dioxane

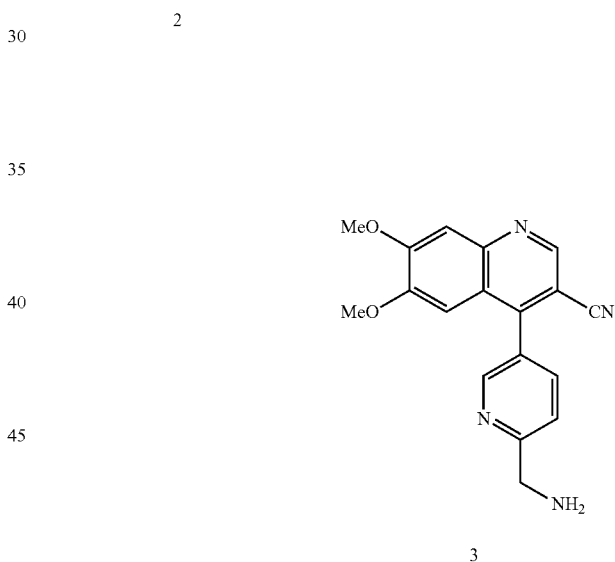

3

To a stirred solution of tert-butyl ((5-(3-cyano-6,7-dimethoxyquinolin-4-yl)pyridin-2-yl)methyl)carbamate 2 (250 mg, 0.127 mmol) in dioxane (2 mL) was added 4M HCl in dioxane (4 mL) at 0° C. then stirred at room temperature for 6 h. The progress of the reaction was monitored by TLC. After completion of the reaction, organic solvents completely distilled off under reduced pressure. To the crude residue was washed with ether to afford 4-(6-(aminomethyl)pyridin-3-yl)-6,7-dimethoxyquinoline-3-carbonitrile (3) (150 mg, 0.451 mmol, 88% yield) as a pale brown solid.

Analytical Data: ¹H NMR (400 MHz, DMSO) δ 9.1 (s, 1H), 8.89 (s, 1H), 8.45 (brs, 2H), 8.19-8.22 (dd, 1H), 7.76-7.79 (dd, 1H), 7.61 (s, 1H), 6.82 (s, 1H), 4.39-4.41 (m, 2H), 4.02 (s, 3H), 3.74 (s, 3H).

LCMS: (M+H⁺): m/Z: 321.1

265

Synthesis of tert-butyl (N-((5-(3-cyano-6,7-dimethoxyquinolin-4-yl)pyridin-2-yl)methyl)sulfamoyl)carbamate (5)

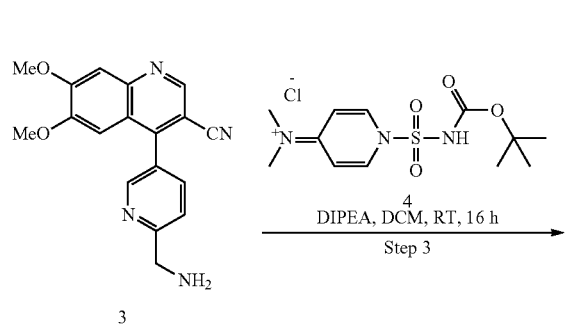

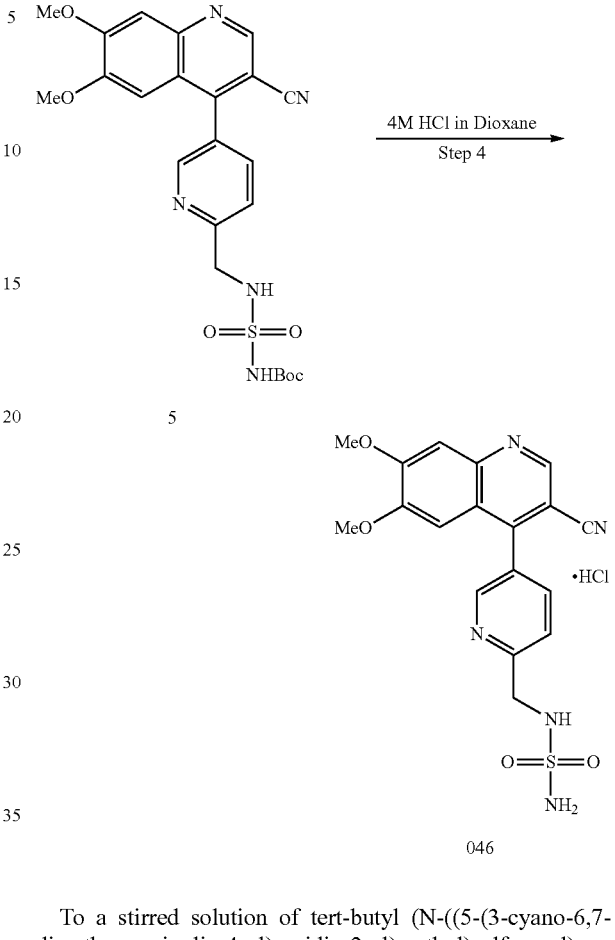

To a stirred solution of 4-(6-(aminomethyl)pyridin-3-yl)-6,7-dimethoxyquinoline-3-carbonitrile (3) (200 mg, 0.625 mmol) in dichloromethane (4 mL) were added diisopropylethylamine (0.326 mL, 1.87 mmol) and N-(1-(N-(tert-butoxycarbonyl)sulfamoyl)pyridin-4(1H)-ylidene)-N-methylmethanaminium 4 (210 mg, 0.625 mmol) at RT, then stirred at room temperature for 16 h. The progress of the reaction was monitored by TLC. After completion of the reaction, organic solvents completely distilled off under reduced pressure to afford crude compound. Crude compound was purified combi flash column chromatography by eluting 60% ethyl acetate in pet-ether to afford tert-butyl (N-((5-(3-cyano-6,7-dimethoxyquinolin-4-yl)pyridin-2-yl)methyl)sulfamoyl)carbamate (5) (150 mg, 0.30 mmol, 48% yield) as a yellow solid.

LCMS: (M+H)$^+$: m/Z: 499.97

266

Preparation of Compound 046

To a stirred solution of tert-butyl (N-((5-(3-cyano-6,7-dimethoxyquinolin-4-yl)pyridin-2-yl)methyl)sulfamoyl)carbamate (5) (150 mg, 0.294 mmol) in 1,4-dioxane (1.0 mL) was added 4M HCl in dioxane (2.0 mL) at RT. Reaction mixture was stirred at RT for 16 h. The progress of the reaction was monitored by TLC. After completion of the reaction, organic solvents completely distilled off under reduced pressure to afford crude compound. Crude compound was purified through prep HPLC method to afford pure compound of Compound 046 (85 mg, 0.213 mmol, 66% yield) as an Off-white solid.

Analytical Data: $^1$H NMR (400 MHz, DMSO) δ 9.06 (s, 1H), 8.71-8.72 (d, 1H), 8.08-8.11 (dd, 1H), 7.76-7.78 (dd, 1H), 7.58 (s, 1H), 7.29-7.31 (t, 1H), 6.85 (s, 1H), 6.77 (s, 1H), 4.35 (d, 2H), 4.0 (s, 3H), 3.73 (s, 3H).

LCMS: (M+H)$^+$: m/Z: 400.0

Synthesis of tert-butyl ((5-bromopyridin-2-yl)methyl)carbamate (6)

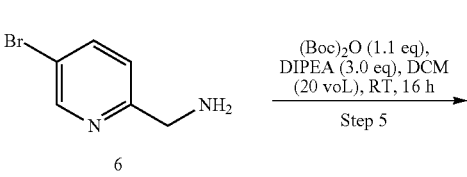

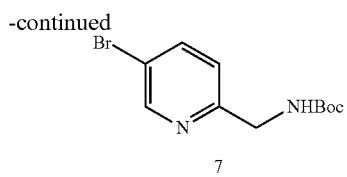

To a stirred solution of (5-bromopyridin-2-yl)methanamine 6 (1 g, 5.34 mmol) in dichloromethane (20 mL) was added diisopropylethylamine (2.8 mL, 16.04 mmol), and di-tert-butyl dicarbonate (1.28 mL, 5.88 mmol) at 0° C. Then stirred the reaction mixture at room temperature for 16 h. The progress of the reaction was monitored by TLC. After completion, reaction mixture was poured into ice cold water (500 mL) and extracted with DCM (2×100 mL). Combined organic layers were washed with brine solution (200 mL), dried over sodium sulfate and concentrated under reduced pressure to afford tert-butyl ((5-bromopyridin-2-yl)methyl) carbamate 6 (1.0 g, 3.49 mmol, 66% yield) as a brown solid.

Analytical Data: $^1$H NMR (400 MHz, CDCl$_3$) δ 8.6 (d, 1H), 8.00-8.03 (dd, 1H), 7.45 (t, 1H), 7.23 (d, 1H), 4.17 (d, 1H), 1.39 (s, 9H).
LCMS: (M−Boc)$^+$: m/Z: 287.0

Preparation of Intermediate-9

To a stirred solution of tert-butyl ((5-bromopyridin-2-yl) methyl)carbamate 6 (1 g, 3.49 mmol) in dioxane (15 ml) was added KOAc (1.02 g, 10.48 mmol) and 4,4,4',4',5,5,5',5'-octamethyl-2,2'-bi(1,3,2-dioxaborolane) (1.77 g, 6.99 mmol) at RT, was then degassed the reaction mixture for 30 minutes. Then [1,1'-Bis(diphenylphosphino)ferrocene]dichloropalladium (II) (285 mg, 0.34 mmol) was added again degassed for 5 minutes and stirred the reaction mixture at 100° C. for 16 h. The progress of the reaction was monitored by TLC. After completion of the reaction, reaction mixture was poured into water (100 mL) and filtered through celite. Washed the celite bed with ethyl acetate (100 mL) and separated the two layers. Organic layer washed with brine solution (200 mL), dried over sodium sulfate and concentrated under reduced pressure. Crude was use as without purification as such as next step to afford Int-9 (1.1 g, crude) as a white solid.

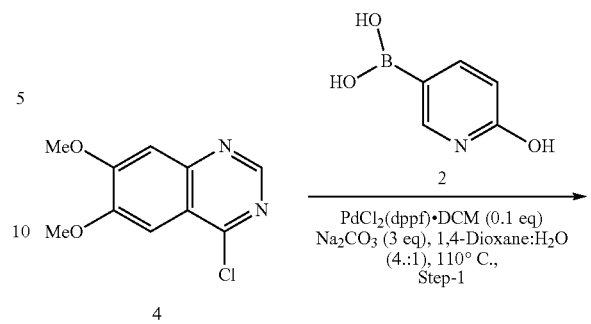

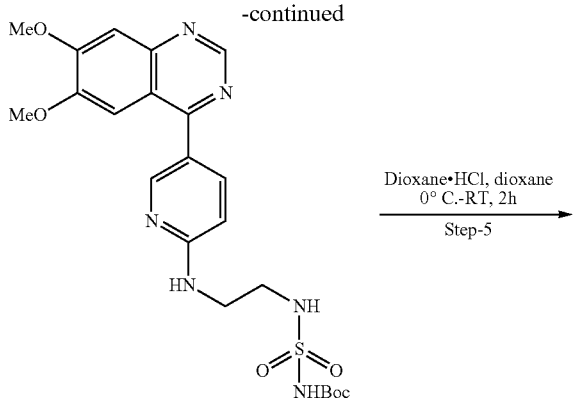

Example 10: (N-(2-((5-(6, 7-dimethoxyquinazolin-4-yl) pyridin-2-yl) amino) ethyl) sulfamide hydrochloride salt Step-1: 5-(6, 7-dimethoxyquinazolin-4-yl) pyridin-2-ol

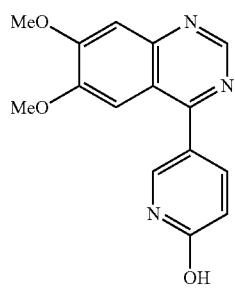 [SMILES: COc1cc2ncnc(-c3ccc(O)nc3)c2cc1OC]

To a stirred solution of 4-chloro-6, 7-dimethoxyquinazoline 1 (107 mg, 0.48 mmol) in dioxane (7 mL) and water (3 mL) were added (6-hydroxypyridin-3-yl) boronic acid 2 (100 mg, 0.72 mmol) and sodium carbonate (0.15 g, 1.44 mmol). Reaction mixture was then degassed for 30 minutes. Then chloro [1, 1'-Bis (diphenylphosphino) ferrocene] dichloropalladium (II) dichloromethane complex (38 mg, 0.048 mmol) was added, degassed again the reaction mixture for 5 minutes and stirred the reaction mixture at 110° C. for 16 h. The progress of the reaction was monitored by TLC. After completion of the reaction, reaction mixture was poured into water (100 mL) and filtered through celite. Washed the celite bed with 10% methanol in dichloromethane (100 mL) and separated the two layers. Organic layer washed with brine solution (100 mL), dried over sodium sulfate and concentrated under reduced pressure. Crude was purified through 100-200 silica gel column chromatography by eluting 100% ethyl acetate to afford 5-(6, 7-dimethoxyquinazolin-4-yl) pyridin-2-ol 3 (57 mg, 0.201 mmol, 45%) as a yellow solid.

Analytical Data: 1H NMR (400 MHz, DMSO) δ 11.98 (brs, 1H), 9.02 (s, 1H), 7.97 (s, 1H), 7.35 (s, 1H), 7.38 (d, 2H), 6.52 (d, 1H), 3.90 (s, 3H), 3.98 (s, 3H). LCMS: (M+H+): m/Z: 283.9

Step-2: 4-(6-chloropyridin-3-yl)-6, 7-dimethoxyquinazoline

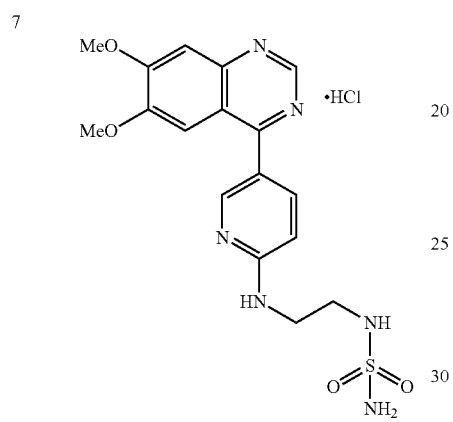

A solution of 5-(6, 7-dimethoxyquinazolin-4-yl) pyridin-2-ol 3 (500 mg, 1.766 mmol) and phosphorous oxychloride (16 mL) was stirred at 110° C. for 2 h. The progress of the reaction was monitored by TLC. After completion of the reaction, reaction mixture was poured into saturated NaHCO3 solution (100 mL) slowly under cooling and extracted with 5% methanol in dichloromethane (2×50 mL). Combined organic layers were washed with brine solution (100 mL), dried over sodium sulfate and concentrated under reduced pressure to afford 4-(6-chloropyridin-3-yl)-6,7-dimethoxyquinazoline 4 (430 mg, 0.305 mmol, 86%) as an off white solid.

Analytical Data: LCMS: (M+H+): m/Z: 301.9

Step-3: N1-(5-(6, 7-dimethoxyquinazolin-4-yl) pyridin-2-yl) ethane-1,2-diamine

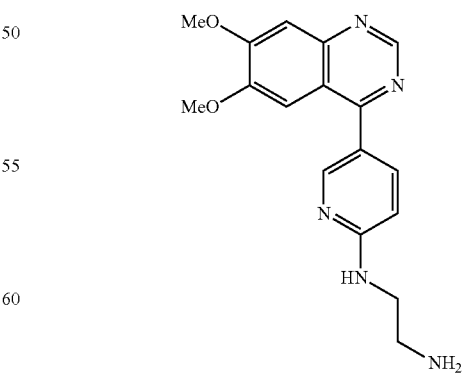

A solution of 4-(6-chloropyridin-3-yl)-6, 7-dimethoxyquinazoline 4 (300 mg, 0.996 mmol) and ethylenediamine (5 mL) was stirred at 100° C. for 5 h. The progress of the reaction was monitored by TLC. After completion of the reaction, to the reaction mixture completely distilled off under reduced pressure to afford crude compound. Crude compound was purified through combi-flash chromatography by eluting 10% methanol in dichloromethane to afford pure compound of N1-(5-(6, 7-dimethoxyquinazolin-4-yl)pyridin-2-yl) ethane-1, 2-diamine 5 (130 mg, 0.4 mmol, 40% yield) as a pale brown solid.

Analytical Data: 1H NMR (400 MHz, DMSO) δ 9.01 (s, 1H), 8.51 (s, 1H), 7.91 (d, 1H), 7.37 (s, 1H), 7.38 (s, 1H), 6.65 (d, 1H), 3.87 (s, 3H), 3.98 (s, 3H), 2.69-2.72 (m, 4H). LCMS: (M+H+): m/Z: 326.0

Step-4: Tert-butyl (N-(2-((5-(6, 7-dimethoxyquinazolin-4-yl) pyridin-2-yl) amino) ethyl) sulfamoyl) carbamate

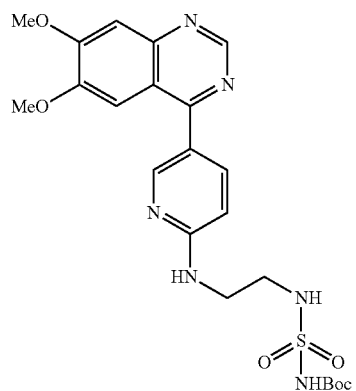 [SMILES: COc1cc2ncnc(-c3ccc(NCCNS(=O)(=O)NC(=O)OC(C)(C)C)nc3)c2cc1OC]

To a stirred solution of N1-(5-(6,7-dimethoxyquinazolin-4-yl)pyridin-2-yl)ethane-1,2-diamine 5 (100 mg, 0.307 mmol) in dichloromethane (8 ml) were added diisopropylethylamine (0.1 mL, 0.461 mmol) and N-(1-(N-(tert-butoxycarbonyl)sulfamoyl)pyridin-4(1H)-ylidene)-N-methylmethanaminium chloride 6 (156 mg, 0.461 mmol) at 0° C. then stirred at room temperature for 16 h. The progress of the reaction was monitored by TLC. After completion of the reaction, reaction mixture completely distilled off under reduced pressure to afford crude compound. Crude was purified through 100-200 silica gel column chromatography by eluting 3% methanol in dichloromethane to afford tert-butyl (N-(2-((5-(6, 7-dimethoxyquinazolin-4-yl) pyridin-2-yl) amino) ethyl) sulfamoyl) carbamate 7 (140 mg, 0.277 mmol, 90% yield) as a pale yellow solid.

Analytical Data: 1H NMR (400 MHz, DMSO) δ 10.92 (bs, 1H), 9.02 (s, 1H), 8.52 (s, 1H), 7.94 (d, 1H), 7.70 (t, 1H), 7.38 (s, 2H), 7.19 (t, 1H), 6.65 (d, 1H), 3.87 (s, 3H), 3.98 (s, 3H), 3.48-3.46 (m, 2H), 3.09-3.08 (m, 2H), 1.38 (s, 9H). LCMS: (M+H+): m/Z: 504.9

Step-5: (N-(2-((5-(6, 7-dimethoxyquinazolin-4-yl) pyridin-2-yl) amino) ethyl) sulfamide hydrochloride Salt (Compound 048)

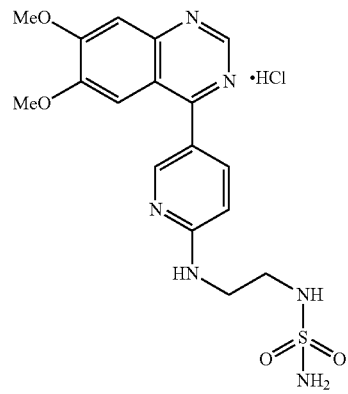 [SMILES: COc1cc2ncnc(-c3ccc(NCCNS(N)(=O)=O)nc3)c2cc1OC ; Cl]

To a stirred solution of tert-butyl (N-(2-((5-(6,7-dimethoxyquinazolin-4-yl)pyridin-2-yl)amino)ethyl)sulfamoyl) carbamate 7 (110 mg, 0.216 mmol) in dioxane (2 ml) was added 4M HCl in dioxane (8 mL) at 0° C. then stirred at room temperature for 6 h. The progress of the reaction was monitored by TLC. After completion of the reaction, organic solvents completely distilled off under reduced pressure. Crude was purified through prep HPLC method to afford (N-(2-((5-(6, 7-dimethoxyquinazolin-4-yl) pyridin-2-yl) amino) ethyl) sulfamide hydrochloride salt (Compound 048).

(41 mg, 0.101 mmol, 46% yield) as a yellow solid.

Analytical Data: 1H NMR (400 MHz, DMSO) δ 9.02 (s, 1H), 8.53 (s, 1H), 7.94 (d, 1H), 7.38 (s, 2H), 7.18-7.10 (m, 1H), 6.67-6.63 (m, 2H), 6.57 (s, 2H), 3.98 (s, 3H), 3.88 (s, 3H), 3.48-3.51 (m, 2H), 3.11-3.06 (m, 2H). LCMS: (M+H+): m/Z: 405.1

Compound 050 was prepared based on the general procedure of Example 10.

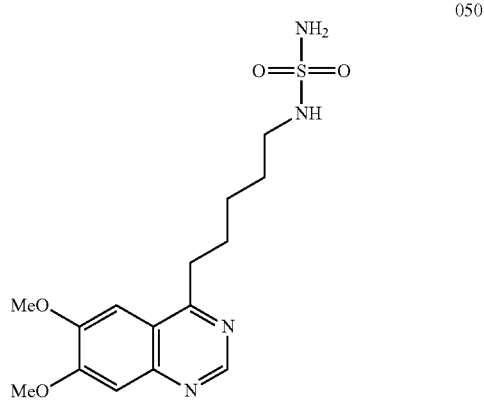 [SMILES: COc1cc2ncnc(CCCCCNS(N)(=O)=O)c2cc1OC]

(400 MHz, DMSO) δ 8.94 (s, 1H), 7.43 (s, 1H), 7.31 (s, 1H), 6.44 (s, 3H), 3.96 (d, 6H), 3.18 (t, 2H), 2.85 (dd, 2H), 1.85-1.73 (m, 2H), 1.56-1.46 (m, 2H), 1.42 (d, 2H). LCMS 355.1. MW 390.88

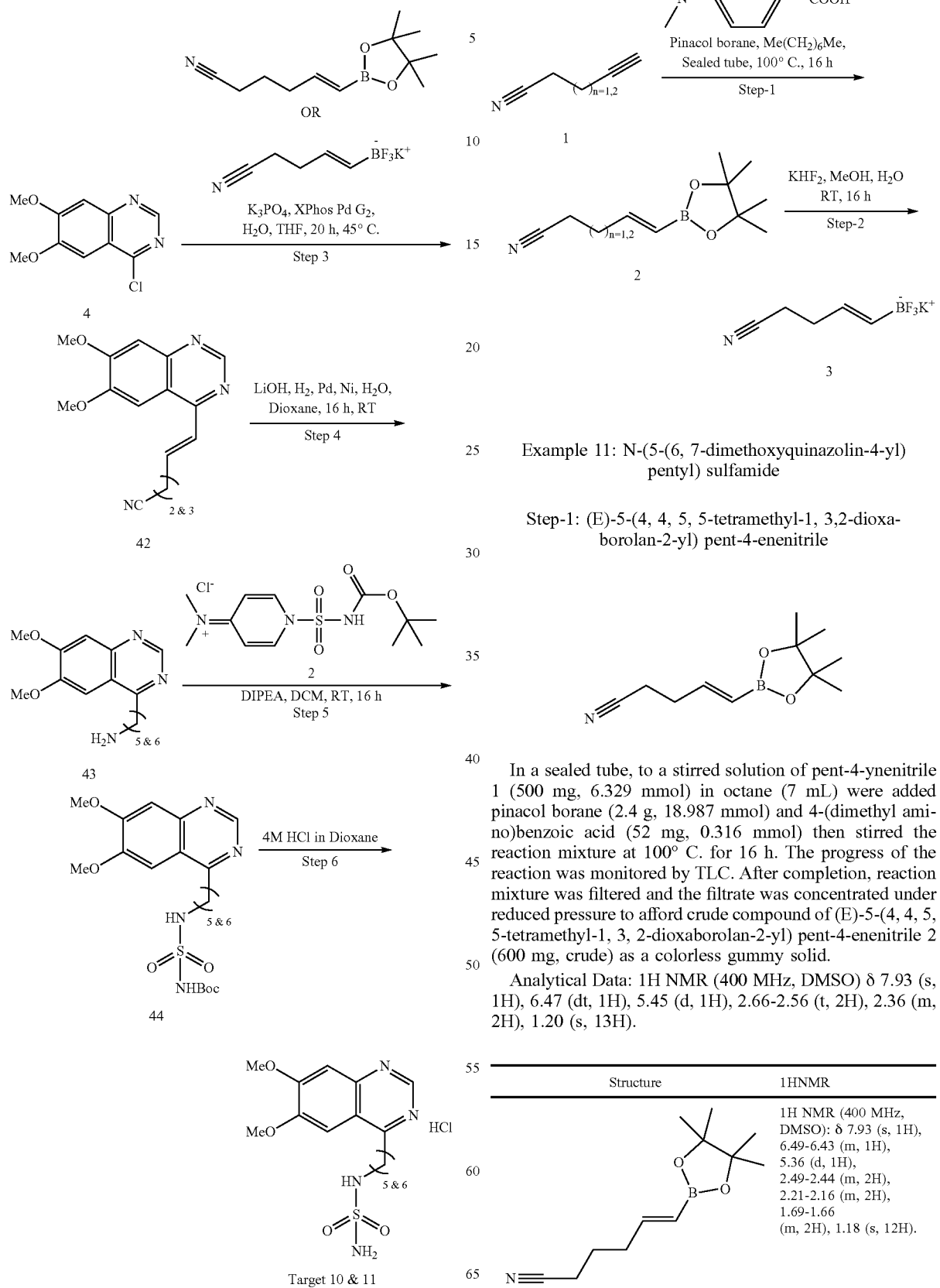

Example 11: N-(5-(6, 7-dimethoxyquinazolin-4-yl) pentyl) sulfamide

Step-1: (E)-5-(4, 4, 5, 5-tetramethyl-1, 3,2-dioxaborolan-2-yl) pent-4-enenitrile In a sealed tube, to a stirred solution of pent-4-ynenitrile 1 (500 mg, 6.329 mmol) in octane (7 mL) were added pinacol borane (2.4 g, 18.987 mmol) and 4-(dimethyl amino)benzoic acid (52 mg, 0.316 mmol) then stirred the reaction mixture at 100° C. for 16 h. The progress of the reaction was monitored by TLC. After completion, reaction mixture was filtered and the filtrate was concentrated under reduced pressure to afford crude compound of (E)-5-(4, 4, 5, 5-tetramethyl-1, 3, 2-dioxaborolan-2-yl) pent-4-enenitrile 2 (600 mg, crude) as a colorless gummy solid.

Analytical Data: 1H NMR (400 MHz, DMSO) δ 7.93 (s, 1H), 6.47 (dt, 1H), 5.45 (d, 1H), 2.66-2.56 (t, 2H), 2.36 (m, 2H), 1.20 (s, 13H).

| Structure | 1HNMR |
|---|---|
| 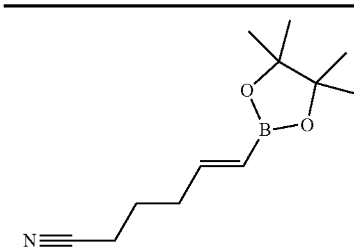 | 1H NMR (400 MHz, DMSO): δ 7.93 (s, 1H), 6.49-6.43 (m, 1H), 5.36 (d, 1H), 2.49-2.44 (m, 2H), 2.21-2.16 (m, 2H), 1.69-1.66 (m, 2H), 1.18 (s, 12H). |

Step-2: Potassium (E)-(4-cyanobut-1-en-1-yl) trifluoroborate

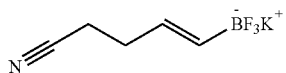

To a stirred solution of (E)-5-(4, 4, 5, 5-tetramethyl-1, 3, 2-dioxaborolan-2-yl) pent-4-enenitrile 2 (600 mg, 2.898 mmol) in methanol (6 mL) and water (6 mL) was added potassium hydrogen fluoride (1.35 g, 17.391 mmol) and stirred the reaction mixture at room temperature for 16 h. The progress of the reaction was monitored by TLC. After completion of the reaction, reaction mixture completely distilled off under reduced pressure, to the crude residue was added acetone (10 mL) and unwanted solids were filtered off. Filtrate was concentrated under reduced pressured to afford crude compound. Crude was purified by trituration with diethyl ether (50 mL) to afford potassium (E)-(4-cyanobut-1-en-1-yl) trifluoroborate 3 (200 mg, crude) as an off white solid.

Analytical Data: 1H NMR (400 MHz, DMSO) δ 5.47 (dt, 1H), 5.34 (ds, 1H), 2.43 (t, 2H), 2.13 (d, 2H).

Step-3: (E)-5-(6, 7-dimethoxyquinazolin-4-yl) pent-4-enenitrile

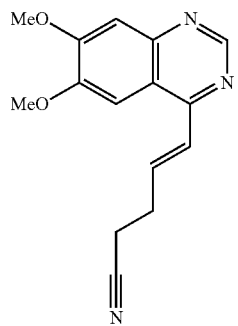 [SMILES: COc1cc2ncnc(/C=C/CCC#N)c2cc1OC]

To a stirred solution of 4-chloro-6, 7-dimethoxyquinazoline 4 (200 mg, 0.893 mmol) in tetrahydrofuran (2.2 mL) and water (1.5 mL) were added potassium (E)-(4-cyanobut-1-en-1-yl) trifluoroborate 3 (183 mg, 0.982 mmol) and potassium phosphate (946 mg, 4.465 mmol) then degassed the reaction mixture for 30 minutes. Then added chloro (2-dicyclohexylphosphino-2', 4', 6'-triisopropyl-1, 1'-biphenyl) [2-(2'-amino-1, 1'-biphenyl)] palladium (II) (35 mg, 0.044 mmol) again degassed the reaction mixture for 5 minutes and stirred the reaction mixture at 50° C. for 16 h. The progress of the reaction was monitored by TLC. After completion of the reaction, reaction mixture was poured into water (100 mL) and filtered through celite. Washed the celite bed with 10% methanol in dichloromethane (100 mL) and separated the two layers. Organic layer washed with brine solution (100 mL), dried over sodium sulfate and concentrated under reduced pressure. Crude was purified through 100-200 silica gel column chromatography by eluting 2% methanol in dichloromethane to afford (E)-5-(6, 7-dimethoxyquinazolin-4-yl) pent-4-enenitrile 5 (150 mg, 0.557 mmol, 62%) as a brown solid.

Analytical Data: 1H NMR (400 MHz, DMSO) δ 8.97 (s, 1H), 7.61 (d, 2H), 7.32-7.22 (m, 2H), 3.98 (d, 6H), 2.83 (t, 2H), 2.72-2.63 (m, 2H).

Same reaction was performed with corresponding pinacol boronate to obtain the following intermediate

| Structure | 1HNMR |
|---|---|
| 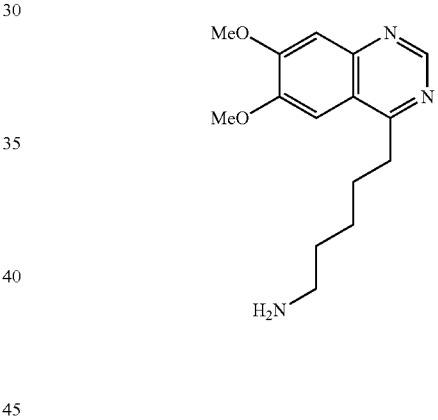 | 1H NMR (400 MHz, DMSO) δ 8.94 (s, 1H), 7.62 (s, 1H), 7.55-7.51 (d, 1H), 7.29 (s, 1H), 7.28-7.26 (m, 1H), 3.98- 3.96 (m, 6H), 3.89-3.82 (m, 2H), 2.55-2.60 (t, 2H), 1.89-1.82 (m, 2H). MS 284.2 |

Step-4: 5-(6, 7-dimethoxyquinazolin-4-yl) pentan-1-amine

To a stirred solution of (E)-5-(6,7-dimethoxyquinazolin-4-yl)pent-4-enenitrile 5 (670 mg, 2.49 mmol) in 1,4-dioxane (25 mL) and water (10 ml) were added lithium hydroxide monohydrate (230 mg, 5.48 mmol), Raney Ni (700 mg) and 10% Pd/C (220 mg) and stirred the reaction mixture under balloon hydrogen atmosphere at room temperature for 16 h. The progress of the reaction was monitored by TLC. After completion of the reaction, reaction mixture filtered through celite and washed the celite bed with 5% methanol in dichloromethane (100 mL). Filtrate was concentrated under reduced pressure. Crude compound was purified through Grace reverse phase method by eluting 40% acetonitrile in 0.1% formic acid in water to afford 5-(6, 7-dimethoxyquinazolin-4-yl) pentan-1-amine 4 (200 mg, 0.727 mmol, 29% yield) as a reddish brown gummy liquid.

Analytical Data: 1H NMR (400 MHz, DMSO) δ 8.94 (s, 1H), 8.46 (s, 1H), 7.43 (s, 1H), 7.31 (s, 1H), 3.95 (s, 7H), 3.23-3.17 (t, 2H), 2.64 (t, 2H), 1.79 (m, 2H), 1.51 (m, 2H), 1.40 (m, 2H).

| Structure | 1HNMR |
|---|---|
| (structure: 6,7-dimethoxyquinazoline with pentylamine chain, NH2 terminus) | 1HNMR (400 MHz, DMSO) δ 8.93 (s, 1H), 7.43 (s, 1H), 7.31 (s, 1H), 3.95 (s, 6H), 3.20-3.6 (m, 2H), 1.81-1.77 (m, 2H), 1.34 (m, 6H). MS 290.3 |

Step-5: Tert-butyl (N-(5-(6, 7-dimethoxyquinazolin-4-yl) pentyl) sulfamoyl) carbamate

| Structure | 1HNMR |
|---|---|
| (structure: 6,7-dimethoxyquinazoline with pentyl-NH-SO2-NH-Boc) | 1H NMR (400 MHz, DMSO) δ 10.76 (bs, 1H), 8.93 (s, 1H), 7.50-7.53 (m, 1H), 7.43 (s, 1H), 7.31 (s, 1H), 3.96 (s, 6H), 3.16-3.20 (m, 2H), 2.84-2.87 (m, 2H), 1.76-1.80 (m, 2H), 1.41-1.45 (m, 2H), 1.38 (s, 9H), 1.32-1.34 (m, 2H), 1.14-1.22 (m, 2H). MS 469.15 |

Step-6: N-(5-(6, 7-dimethoxyquinazolin-4-yl) pentyl) sulfamide (Compound 051)

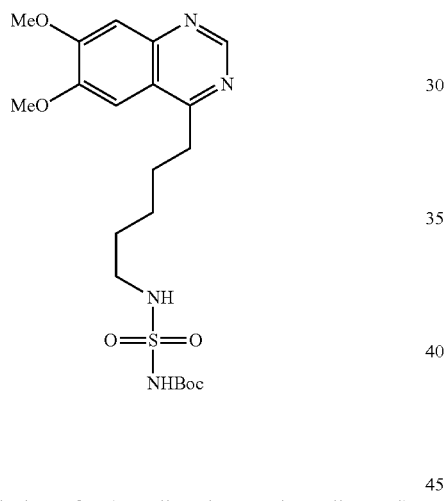

To a stirred solution of 5-(6,7-dimethoxyquinazolin-4-yl) pentan-1-amine 6 (200 mg, 0.727 mmol) in dichloromethane (5 ml) were added diisopropylethylamine (140 mg, 1.091 mmol) and N-(1-(N-(tert-butoxycarbonyl)sulfamoyl)pyridin-4(1H)-ylidene)-N-methylmethanaminium 7 (269 mg, 0.8 mmol) at 0° C. then stirred at room temperature for 16 h. The progress of the reaction was monitored by TLC. After completion, to the reaction mixture added water (50 mL) and extracted with dichloromethane (2×50 mL). Combined organic layers were washed with brine solution (50 mL), dried over sodium sulfate and concentrated under reduced pressure to afford crude compound. Crude was purified through 100-200 silica gel column chromatography by eluting 2% methanol in dichloromethane to afford tert-butyl (N-(5-(6, 7-dimethoxyquinazolin-4-yl) pentyl) sulfamoyl) carbamate (200 mg, 0.44 mmol, 60% yield) as a pale brown solid.

Analytical Data: 1H NMR (400 MHz, DMSO) δ 10.76 (s, 1H), 8.93 (s, 1H), 7.53 (bs, 1H), 7.42 (s, 1H), 7.31 (s, 1H), 3.96 (s, 6H), 3.18 (t, 2H), 2.89-2.81 (m, 2H), 1.83-1.72 (m, 2H), 1.51 (m, 2H), 1.39 (m, 11H), To a stirred solution of tert-butyl (N-(5-(6,7-dimethoxyquinazolin-4-yl)pentyl)sulfamoyl)carbamate Int-5 (200 mg, 0.44 mmol) in dioxane (2 ml) was added 4M HCl in dioxane (7 mL) at 0° C. then stirred at room temperature for 16 h. The progress of the reaction was monitored by TLC. After completion of the reaction, organic solvents completely distilled off under reduced pressure. Crude was purified through prep HPLC method to afford N-(5-(6, 7-dimethoxyquinazolin-4-yl) pentyl) sulfamide (50 mg, 0.141 mmol, 29% yield) as a pale yellow solid.

Analytical Data: 1H NMR (400 MHz, DMSO) δ 8.94 (s, 1H), 7.43 (s, 1H), 7.31 (s, 1H), 6.44 (s, 3H), 3.96 (d, 6H), 3.18 (t, 2H), 2.85 (dd, 2H), 1.85-1.73 (m, 2H), 1.56-1.46 (m, 2H), 1.42 (d, 2H)

| Compound Number | Structure | 1HNMR |
|---|---|---|
| 051 | 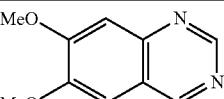 | 1 H NMR (400 MHz, DMSO): δ 8.93 (s, 1H), 7.43 (s,1H), 7.31 (s, 1H), 6.44-6.41 (m, 3H), 3.96 (s, 6H), 3.19 (t, 2H), 2.84-2.82 (m, 2H), 1.81-1.74 (m, 2H), 1.48-1.42 (m, 2H), 1.37-1.36 (m, 4H). MS 369.3 |

In Vitro Biology

Example 1: ENPP1 Assay (TMP)

Materials:
Assay Buffer: 1 mM $CaCl_2$, 0.2 mM $ZnCl_2$, 50 mM Tris, pH 9.0
Substrate: 1.5 mM Thymidine 5'-monophosphate disodium salt hydrate (Sigma: T4510)—Assay Conc.: 150 μM
Enzyme: 1 ng/μL Recombinant Human ENPP-1 Protein (purified in-house)—Assay Conc.: 5 ng/well
DMSO
96-well clear assay plates Protocol:
A ten point serial dilution of drugs was prepared in 10× in assay buffer with the final assay concentrations starting at 10 μM, 3 μM, 1 μM, 0.3 μM . . . 0 μM. A dilution of DMSO was included as a control. The assay plate was set up as follows with each well in duplicate: 75 μL assay buffer+10 μL ENPP1 inhibitor or DMSO Dilutions+10 μL Substrate+5 μL Enzyme (5 ng). Both the enzyme and substrate were added to opposite sides of the well to ensure that there was no interaction until all wells had both components. The plate was then centrifuged gently for 10 seconds, followed by an incubation at 37° C. for 45 minutes. The reaction was quantified by measuring absorbance at 405 nm using the Envision Plate Reader. Data was analyzed using GraphPad Prism 8.0.

The results are shown below in Table 1:

TABLE 1

| Compound Number | IC50 (nM) |
|---|---|
| 053 | 3.60 |
| 056 | 6.87 |
| 057 | 46.57 |
| 005 | 36.45 |
| 006 | 36.72 |
| 007 | 4.37 |
| 008 | 8.11 |
| 013 | 17.05 |
| 015 | 32.38 |
| 018 | 4.23 |
| 020 | 99.71 |
| 022 | 116.20 |
| 026 | 117.8 |
| 027 | 20.96 |
| 028 | 35.74 |
| 029 | 1.21 |
| 032 | 4.80 |
| 033 | 80.66 |
| 034 | 81.14 |
| 036 | 18.12 |
| 038 | 0.94 |
| 038-E1 | 4.95 |
| 038-E2 | 18.0 |
| 039 | 0.87 |
| 039-E1 | 0.50 |
| 039-E2 | 0.22 |
| 040-E1 | 67.38 |
| 040-E2 | 41.71 |
| 041 | 10.23 |
| 042 | 40.52 |
| 043 | 3.92 |
| 046 | 9.8 |
| 047 | 67.11 |
| 048 | 60.36 |
| 049 | 1.79 |
| 050 | 20.12 |
| 063 | 68.1 |
| 054 | 23.81 |
| 058 | 3.06 |
| 060 | 4.34 |
| 061 | 28.88 |
| 015-MES | 6.38 |
| 015-HCl | 5.97 |
| 065 | 7.74 |
| 064 | 71.99 |

Example 2: ENPP1 Thermal Shift Assay

Materials:
Recombinant Human ENPP-1 Protein (Purified In-House)
Assay Buffer (1 mM $CaCl_2$, 0.2 mM $ZnCl_2$, 50 mM Tris, pH 9.0)
5000×SYPRO Orange (ThermoFisher cat #S6651)
384-well PCR Plates Protocol:
Each drug was prepared as a 10× solution in the assay buffer and SYPRO Orange was diluted to 10× concentration in water. Wells were set up in duplicate in a 384-well PCR plate as follows: 14 μL assay buffer, 2 μL ENPP1 Inhibitor or DMSO, 2 μL (0.5 μg) ENPP1 protein. Each well was mixed and incubated on ice for 5 minutes. Post incubation, 2 μL of SYPRO Orange was mixed into each well and followed by a gentle centrifugation. The protein melt reaction was run using ViiA7 software with temperatures beginning at 25° C. and increasing by 0.05° C./s to the maximum temperature of 99° C.

| Compd# | Thermal Shift @10 uM(dTm(o C.)^ |
|---|---|
| 047 | $$ |
| 048 | $$ |
| 049 | $$$ |
| 050 | $$ |
| 051 | NC |
| 052 | NC |
| 053 | $$$ |
| 054 | $$ |
| 055 | $$ |
| 056 | $$ |
| 057 | $$ |
| 058 | $$$ |
| 059 | NC |
| 060 | $$$ |
| 061 | $$ |
| 062 | $$ |
| 015-HCl | $$$ |
| 005 | $$ |
| 063 | $$ |
| 065 | $$$ |
| 064 | $$ |

^$$ <3o C.;
$$$ >3o C.;
NC, Not Calculated

Example 3: ENPP2 Assay

Materials:

Assay Buffer: 50 mM Tris, 10 mM CaCl$_2$, 5 mM MgCl$_2$, 0.02% Brij-35 (v/v), pH 8.5

Substrate: 20 mM Bis(p-Nitrophenyl) Phosphate Sodium Salt (BPNPP) (Sigma, Catalog #N3002)

Enzyme: 0.01 ng/µL Recombinant Human ENPP-2/Autotaxin (rhENPP-2) (R&D Catalog #5255-EN)

DMSO

PF8380 (Selleck S8218)

96-well clear assay plates

Protocol:

An eight point serial dilution of drugs was prepared in 10× in assay buffer with the final assay concentrations starting at 10 µM, 3 µM, 1 µM, 0.3 µM . . . 0 µM. A dilution of DMSO was included as a control. The assay plate was set up as follows with each well in duplicate: 81 µL assay buffer+10 µL ENPP1 inhibitor or DMSO+5 µL Substrate+5 µL Enzyme (0.05 ng). Both the enzyme and substrate were added to opposite sides of the well to ensure that there was no interaction until all wells had both components. The plate was then centrifuged gently for 10 seconds, followed by an incubation at 37° C. for 10 minutes. The reaction was quantified by measuring absorbance at 400 nm using the Envision. PF8380 was used as a positive control for the assay. Data was analyzed using GraphPad Prism 8.0.

| Compd# | ENPP2 Activity^ |
|---|---|
| 047 | ** |
| 048 | ** |
| 049 | ** |
| 050 | ** |
| 051 | NC |
| 052 | NC |
| 053 | NC |
| 054 | NC |
| 055 | NC |
| 056 | ** |
| 057 | NC |
| 058 | NC |
| 059 | NC |
| 060 | ** |
| 061 | NC |
| 062 | ** |
| 015-HCl | ** |
| 005 | NC |
| 063 | ** |
| 065 | ** |
| 064 | NC |

^** >1 µM;
*** <1 µM;
NC, Not Calculated

Example 4: Cell-Based ENPP Selectivity Assay (TMP)

Materials:

HEK293T cells

Media: 89% DMEM, 10% FBS, 1% Penicillin/Streptomycin

Transfection Reagent: Polyethylenimine Branched, 1 mg/mL (Sigma: 408719)

Transfection Media: Opti-MEM Reduced Serum Medium (ThermoFisher: 31985088)

Plasmid Constructs:

pCMV6 empty construct (Origene: PS100001)

hENPP1 (Origene: RC209222)

hENPP3 (Genscript: OHu19400D)

mENPP1 (Origene: MR227498)

Assay Buffer: 1 mM CaCl2, 0.2 mM ZnCl2, 50 mM Tris, pH 9.0

Substrate: 8 mM Thymidine 5'-monophosphate disodium salt hydrate (Sigma Cat #T7004-1G)

6-well tissue culture treated plates 96-well clear assay plates

Protocol:

HEK293T cells were seeded in a 6 well tissue culture treated plate at 5×10$^5$ cells per well. Transfection mixtures containing 7 µL of transfection reagent, 2 µg of plasmid construct, and 200 µL of transfection media were incubated for 20 minutes at room temperature. Transfection mixtures were added dropwise to each well and incubated at 37° C./5% CO$_2$ for 48 hours. Transfected cells were collected by trypsinization, lysed, and protein concentrations were determined. Drugs were prepared at 10× in assay buffer and tested at a final assay concentration of 1 µM. Lysate (3 µg) was incubated with 10 µL ENPP1 inhibitor and 81 µL assay buffer for 2 hours at 4° C. prior to the addition of 5 µL of substrate. The final reaction was incubated at 37° C. for 45 minutes and quantified by measuring absorbance at 405 nm using the Envision plate reader. The data were normalized to empty construct controls.

The results are shown in FIG. 1.

Example 5: Solubility and Stability Assay

Materials:

PBS pH 7.4 (Catalog #10010-031; from Thermo Fisher Scientific),

FaSSIF (pH 6.5), FeSSIF (pH 5.0) and FaSSGF (pH 1.6) aqueous buffers (Catalog #FFF01, #FASBUF01, #FESBUF01, #FASGBUF01 from biorelevant.com)

Protocol:

1 mg of powder for each compound was combined with 1 mL of buffer to make a 1 mg/mL mixture. These samples were stirred in magnetic stirrer with beads for overnight at room temperature. The samples were then passed through a 0.45μ PTFE syringe filter. The filtrates were diluted with the corresponding buffer before analysis. All samples were assayed by UV-VIS spectrophotometry (Thermo scientific, Nanodrop 8000) against standards. Samples were kept at RT (room temperature) and at corresponding time points aliquots were subjected to UV-VIS spectrophotometry analysis to measure stability.

Example 6: Immune Infiltration Assay

Materials:
HP AC (ATCC Catalog #: CRL-2119)
Matrigel Matrix Growth Factor Reduced (Corning Catalog #: 354230)
96-well Spheroid Microplates: ULA, Round Bottom, black walled plates (Corning Catalog #: 10185-094)
Corning HTS Transwell 96 well permeable supports, 5 μm (Corning Catalog #: 3387)
DMEM, high glucose, HEPES, no phenol red (ThermoFisher Scientific Catalog #: 21063045)
Human PBMC Peripheral Blood Mono, cryo amp (Lonza Catalog #: CC-2702)
Molecular Probes CellTracker CM Dil Dye (ThermoFisher Scientific Catalog #: C7000)
10× Drug
Protocol:

HP AC cells were cultured according to the ATCC guidelines. On the initial day of the experiment, 5,000 cells were plated in the 96-well spheroid microplates in 50 μL of media containing 1.5% matrigel. The cells were centrifuged at 1800 RPM for 2 minutes and then incubated on a plate shaker at low speed at 37° C./5% $CO_2$ for 72 hours to allow formation of a single spheroid per well. After incubation, 150 μL of media containing either vehicle (DMSO) or drug was added to each corresponding well and incubated for 1 hour at 37° C./5% $CO_2$. During incubation, human PBMCS were counted and fluorescently stained with Molecular Probes CellTracker CM Dil Dye using the manufacturer's protocol. After the 1-hour incubation with drug, a transwell plate was gently placed into the spheroid plate. The PBMCs were then washed and added to each corresponding well at 400,000 cells/100 μL of media. The experiment was incubated at 37° C./5% $CO_2$ for 48 hours to allow for infiltration of the immune cells into the spheroids. Following incubation, the transwell was removed and RFP fluorescence and bright field Z-stack images were taken for each spheroid using the Biotek Cytation5. The images were compressed and the total RFP expression was assessed. The data was analyzed using GraphPad Prism 8.0.

Prophetic Pharmaceutical Composition Examples

"Active ingredient" as used throughout these examples relates to one or more of the compounds of the invention, or a pharmaceutically acceptable salt, solvate, polymorph, hydrate and the stereochemically isomeric form thereof. The following examples of the formulation of the compounds of the present invention in tablets, suspension, injectables and ointments are prophetic.

Typical examples of recipes for the formulation of the invention are as given below. Various other dosage forms can be applied herein such as a filled gelatin capsule, liquid emulsion/suspension, ointments, suppositories or chewable tablet form employing the disclosed compounds in desired dosage amounts in accordance with the present invention. Various conventional techniques for preparing suitable dosage forms can be used to prepare the prophetic pharmaceutical compositions, such as those disclosed herein and in standard reference texts, for example the British and US Pharmacopoeias, Remington's Pharmaceutical Sciences (Mack Publishing Co.) and Martindale The Extra Pharmacopoeia (London The Pharmaceutical Press). The disclosure of this reference is hereby incorporated herein by reference.

a. Pharmaceutical Composition for Oral Administration

A tablet can be prepared as follows:

| Component | Amount |
| --- | --- |
| Active ingredient | 10 to 500 mg |
| Lactose | 100 mg |
| Crystalline cellulose | 60 mg |
| Magnesium stearate | 5 |
| Starch (e.g. potato starch) | Amount necessary to yield total weight indicated below |
| Total (per capsule) | 1000 mg |

Alternatively, about 100 mg of a disclosed compound, 50 mg of lactose (monohydrate), 50 mg of maize starch (native), 10 mg of polyvinylpyrrolidone (PVP 25) (e.g. from BASF, Ludwigshafen, Germany) and 2 mg of magnesium stearate are used per tablet. The mixture of active component, lactose and starch is granulated with a 5% solution (m/m) of the PVP in water. After drying, the granules are mixed with magnesium stearate for 5 min. This mixture is moulded using a customary tablet press (e.g. tablet format: diameter 8 mm, curvature radius 12 mm). The moulding force applied is typically about 15 kN.

Alternatively, a disclosed compound can be administered in a suspension formulated for oral use. For example, about 100-5000 mg of the desired disclosed compound, 1000 mg of ethanol (96%), 400 mg of xanthan gum, and 99 g of water are combined with stirring. A single dose of about 10-500 mg of the desired disclosed compound according can be provided by 10 ml of oral suspension.

In these Examples, active ingredient can be replaced with the same amount of any of the compounds according to the present invention, in particular by the same amount of any of the exemplified compounds. In some circumstances it may be desirable to use a capsule, e.g. a filled gelatin capsule, instead of a tablet form. The choice of tablet or capsule will depend, in part, upon physicochemical characteristics of the particular disclosed compound used.

Examples of alternative useful carriers for making oral preparations are lactose, sucrose, starch, talc, magnesium stearate, crystalline cellulose, methyl cellulose, hydroxypropyl cellulose, hydroxypropylmethyl cellulose, carboxymethyl cellulose, glycerin, sodium alginate, gum arabic, etc. These alternative carriers can be substituted for those given above as required for desired dissolution, absorption, and manufacturing characteristics.

The amount of a disclosed compound per tablet for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

b. Pharmaceutical Composition for Injectable Use

A parenteral composition can be prepared as follows:

| Component | Amount |
|---|---|
| Active ingredient | 10 to 500 mg |
| Sodium carbonate | 560 mg* |
| Sodium hydroxide | 80 mg* |
| Distilled, sterile water | Quantity sufficient to prepare total volumen indicated below. |
| Total (per capsule) | 10 ml per ampule |

*Amount adjusted as required to maintain physiological pH in the context of the amount of active ingredient, and form of active ingredient, e.g. a particular salt form of the active ingredient.

Alternatively, a pharmaceutical composition for intravenous injection can be used, with composition comprising about 100-5000 mg of a disclosed compound, 15 g polyethyleneglycol 400 and 250 g water in saline with optionally up to about 15% Cremophor EL, and optionally up to 15% ethyl alcohol, and optionally up to 2 equivalents of a pharmaceutically suitable acid such as citric acid or hydrochloric acid are used. The preparation of such an injectable composition can be accomplished as follows: The disclosed compound and the polyethyleneglycol 400 are dissolved in the water with stirring. The solution is sterile filtered (pore size 0.22 µm) and filled into heat sterilized infusion bottles under aseptic conditions. The infusion bottles are sealed with rubber seals.

In a further example, a pharmaceutical composition for intravenous injection can be used, with composition comprising about 10-500 mg of a disclosed compound, standard saline solution, optionally with up to 15% by weight of Cremophor EL, and optionally up to 15% by weight of ethyl alcohol, and optionally up to 2 equivalents of a pharmaceutically suitable acid such as citric acid or hydrochloric acid. Preparation can be accomplished as follows: a desired disclosed compound is dissolved in the saline solution with stirring. Optionally Cremophor EL, ethyl alcohol or acid are added. The solution is sterile filtered (pore size 0.22 µm) and filled into heat sterilized infusion bottles under aseptic conditions. The infusion bottles are sealed with rubber seals.

In this Example, active ingredient can be replaced with the same amount of any of the compounds according to the present invention, in particular by the same amount of any of the exemplified compounds.

The amount of a disclosed compound per ampule for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

Carriers suitable for parenteral preparations are, for example, water, physiological saline solution, etc. which can be used with tris(hydroxymethyl)aminomethane, sodium carbonate, sodium hydroxide or the like serving as a solubilizer or pH adjusting agent. The parenteral preparations contain preferably 50 to 1000 mg of a disclosed compound per dosage unit.

Example 7

In Vivo Methods

Study I: Determination of the Bioavailability of 015-HCl Following Intravenous and Oral Administration in Male Sprague-Dawley Rats The compound 015-HCl was dosed by intravenous (IV) and oral (PO) routes of administration at 2 and 10 mg/kg, respectively. Blood samples were collected up to 24 hours post-dose, and blood concentrations of 015-HCl were determined by LC-MS/MS. Pharmacokinetic parameters were determined using Phoenix WinNonlin (v8.0) software.

Study II: Anti-Tumor Efficacy of Compound 015-HCl in PAN02 (Mouse Pancreatic Ductal Adenocarcinoma Model) Syngeneic Model of C57BL/6 Mice Experimental Design Animals: Female C57BL/6 (4-6 Week's Age from Charles River Laboratories).

The PAN02 cells were propagated in DMEM cell culture medium containing 10% Fetal Bovine Serum. Cells were harvested in logarithmic growth phase and implanted subcutaneously ($1\times10^6$) in the lower abdomen of mice. Tumor growth was monitored daily and after the tumors had reached 80 to 100 $mm^3$, mice were randomized into groups consisting of 10 animals per group and treated as shown in Table 2. Animals were euthanized when tumors reached around 2000 $mm^3$ or treatment regime completed or 20% of body weight loss, or developed ulceration and necrosis. Upon termination, tumor samples and blood was collected and analyzed for biomarkers.

TABLE 2

Study design, number of groups, route and doses

| Groups | No. of animals | Dose | Route | Dose regimen |
|---|---|---|---|---|
| Vehicle G1 | 10 | — | P.O | BID |
| Compound 015-HCl G2 | 10 | 50 mg/kg | P.O | BID |
| Compound 015-HCl G3 | 10 | 150 mg/kg | P.O | BID |
| Compound 015-HCl G4 | 10 | 300 mg/kg | P.O. | BID |
| Compound 015-HCl G5 | 10 | 150 mg/kg | P.O. | QD |

Study III: Anti-Tumor Efficacy of Compound 015-HCl in MC38 (Colon Adenocarcinoma Mouse Model) Syngeneic Model of C57BL/6 Mice Experimental Design Animals: Female C57BL/6 (4-6 week's age from Charles River Laboratories). The MC38 cells were propagated in RPMI cell culture medium containing 10% Fetal Bovine Serum. Cells were harvested in logarithmic growth phase and implanted subcutaneously ($2\times10^5$) in flank of mice. Tumor growth was monitored daily and after the tumors had reached about 100 $mm^3$, mice were randomized into groups consisting of 10 animals per group. On Day 17, mice were treated with 015-HCl compound or vehicle as shown in Table 3. On day 18, groups 2, 5, and 6 were given a single 10 Gy exposure of focal radiation to the tumor site. Animals were euthanized when tumors reached around 2000 $mm^3$ or treatment regime completed or 20% of body weight loss, or developed ulceration and necrosis. Upon termination, tumor samples and blood were collected and analyzed for biomarkers.

TABLE 3

Study design, number of groups, route and doses

| Groups | No. of animals | Dose | Route | Dose regimen |
|---|---|---|---|---|
| Vehicle G1 | 10 | — | I.P | BID |
| Radiation G2 | 10 | 10 Gy Rad | — | BID |
| Compound G3 | 10 | 50 mg/kg | I.P. | BID |
| Compound + Radiation G5 | 10 | 50 mg/kg + 10 Gy Rad | I.P. | BID |

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound of Formula II:

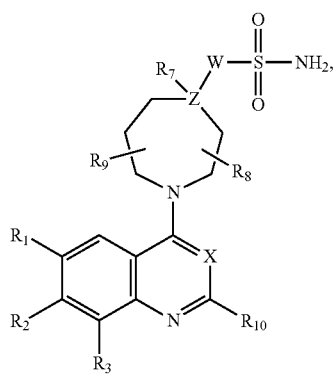

Formula II wherein

X is N or $CR_{11}$;

Z is C or N;

W is selected from the group consisting of an $C_1$-$C_5$ alkyl, —C(=O)—$(CH_2)_n$—, —($C_1$-$C_5$ alkyl)-N—;

NH, and a direct bond as follows:

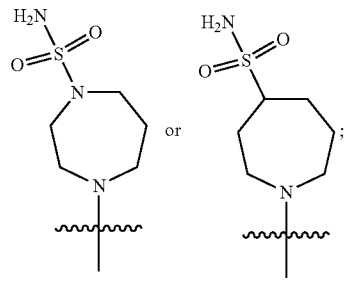 [SMILES: *N1CCCN(S(N)(=O)=O)CC1 ; *N1CCCC(S(N)(=O)=O)CC1]

each $R_1$, $R_2$ and $R_3$ are independently selected from the group consisting of hydrogen, halogen, CN, $OR^a$, —C(=O)$NR^bR^c$, —$NR^bR^c$, —C(=O)$R^d$, aryl, heteroaryl, cycloalkyl, and heterocycloalkyl;

each $R^a$ is independently selected from the group consisting of hydrogen, lower alkyl, and —$(CH_2)_n$—C(=O)$NR^bR^c$, aralkyl, aryl, heteroaryl, heterocycloalkyl, cycloalkyl;

wherein n is an integer between 1 and 3;

each $R^b$ and $R^c$ is independently selected from the group consisting of hydrogen, a lower alkyl, and lower aryl, heterocycloalkyl, or cycloalkyl;

each $R^d$ is independently selected from the group consisting of —$OR^e$ and lower alkyl;

each $R^e$ is independently selected from the group consisting of hydrogen, a lower alkyl, and a lower aryl;

$R_{11}$ is independently selected from the group consisting of hydrogen, halogen, COOEt, COOH, and CN;

$R_7$, $R_8$ and $R_9$ are independently selected from the group consisting of H, halogen and lower alkyl; and $R_8$ and $R_9$ can also form a bridge across the 7-membered ring with 1 or 2 atoms, as follows:

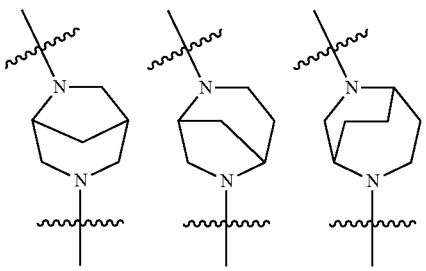

$R_{10}$ is independently selected from the group consisting of hydrogen and $CF_3$;

or an isomer, hydrate, solvate, polymorph, tautomer or a pharmaceutically acceptable salt thereof.

2. The compound of claim 1, wherein Z is N.

3. The compound of claim 1, wherein W is selected from the group consisting of -4,5-imidazole, 2-Oxazole, 3-pyrrole; pyrazole, and thiazole.

4. The compound of claim 1, wherein $R_1$, $R_2$ and $R_3$ are selected form $CH_3O$ or H.

5. The compound of claim 1, wherein X is N.

6. The compound of claim 1, wherein X is C—CN.

7. The compound of claim 1, wherein $R_7$, $R_8$ and $R_9$ are independently selected from the group consisting of H and halogen.

8. The compound of claim 1, wherein $R_7$ is a halogen.

9. The compound of claim 8, wherein the halogen is F.

10. The compound of claim 1, wherein $R_8$ and $R_9$ are both halogen.

11. The compound of claim 10, wherein the halogen is F.

12. The compound of claim 1, wherein

X is N;

Z is N;

W is selected from the group consisting of $C_1$-$C_5$ alkyl, —C(=O)—(CH$_2$)—, —($C_1$-$C_5$ alkyl)-N; and a direct bond; and $R_1$, $R_2$ and $R_3$ are selected form CH$_3$O or H.

13. A compound is selected from the group consisting of

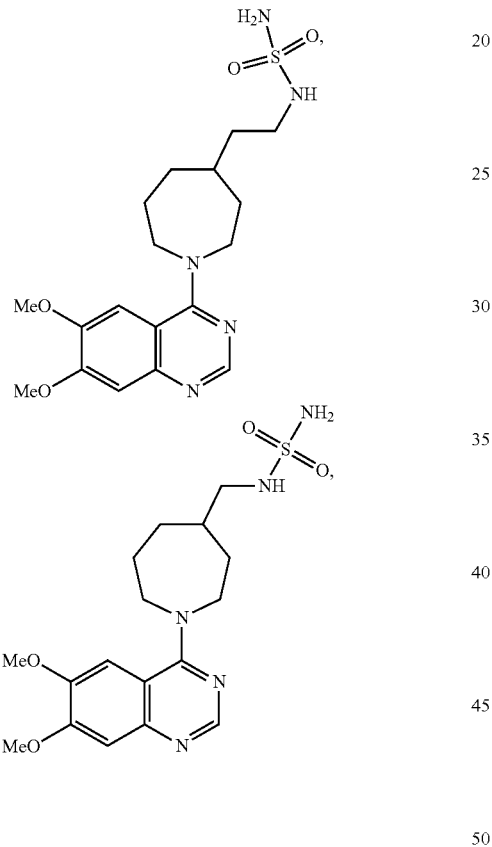

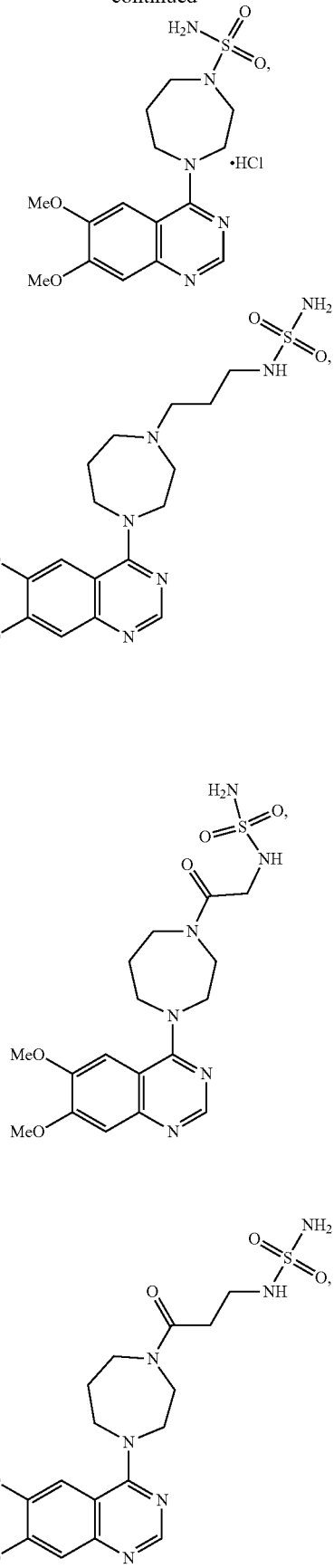

291
-continued
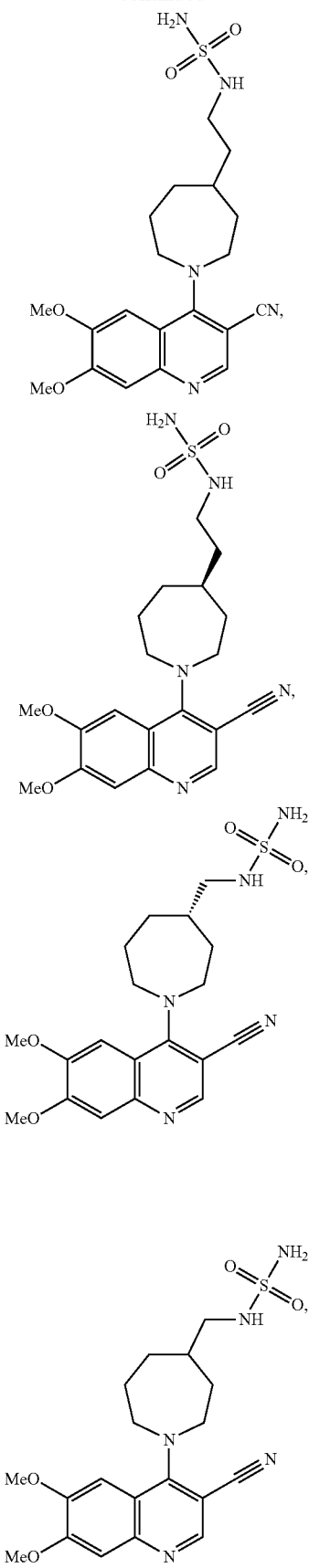
292
-continued
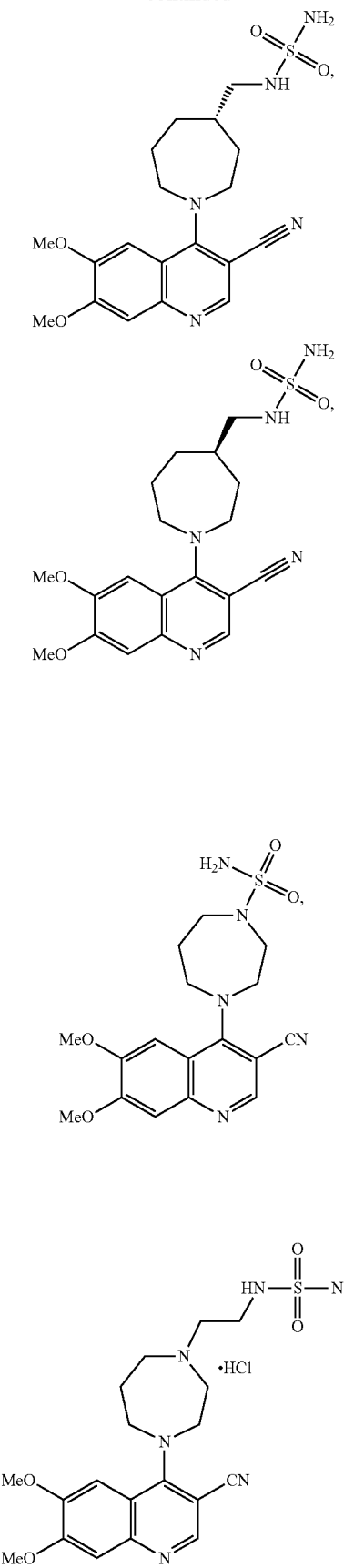

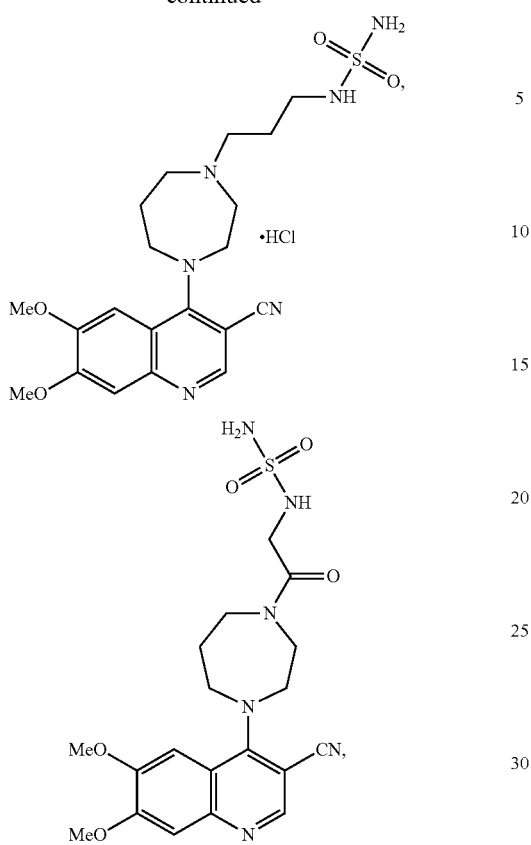
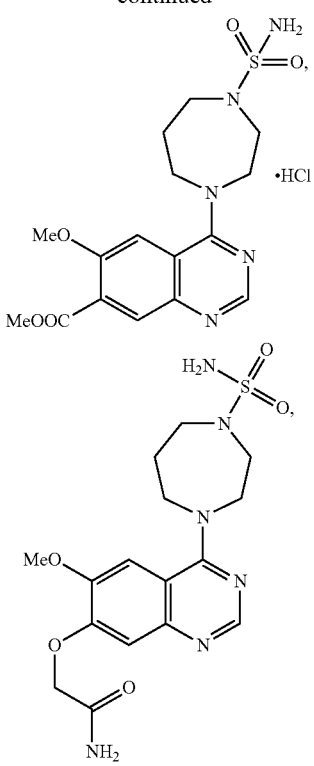

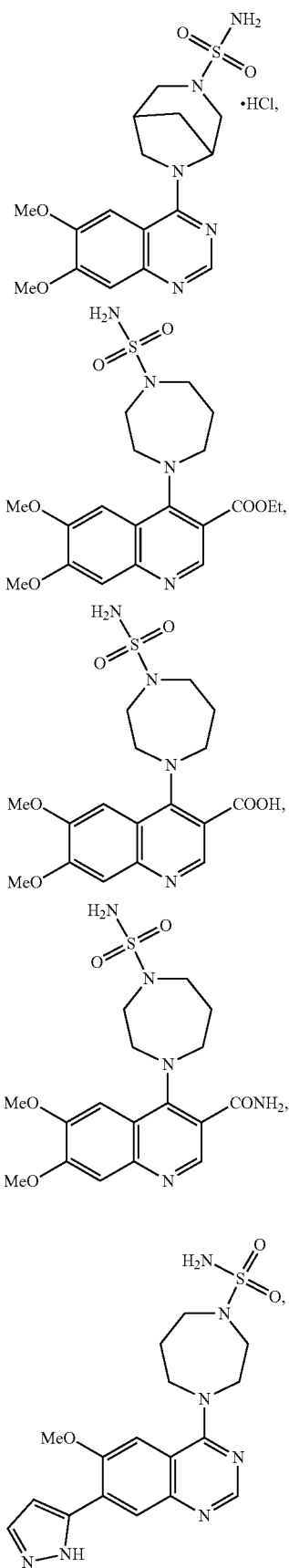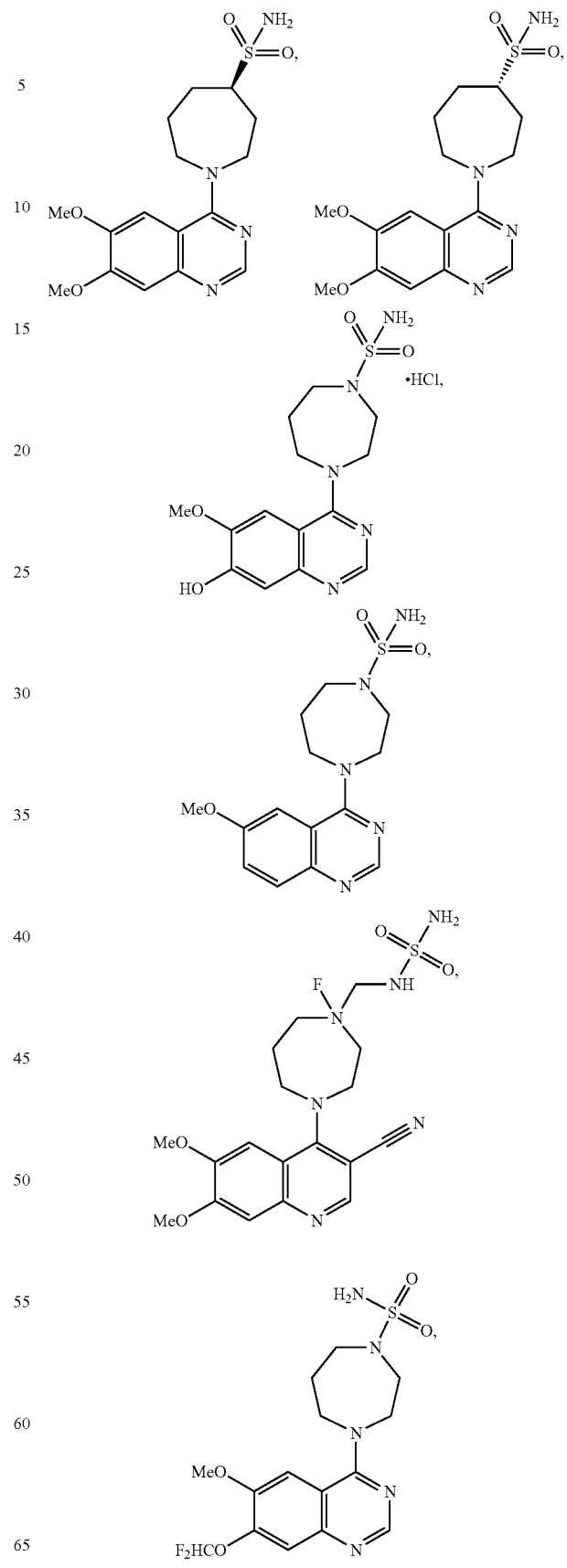

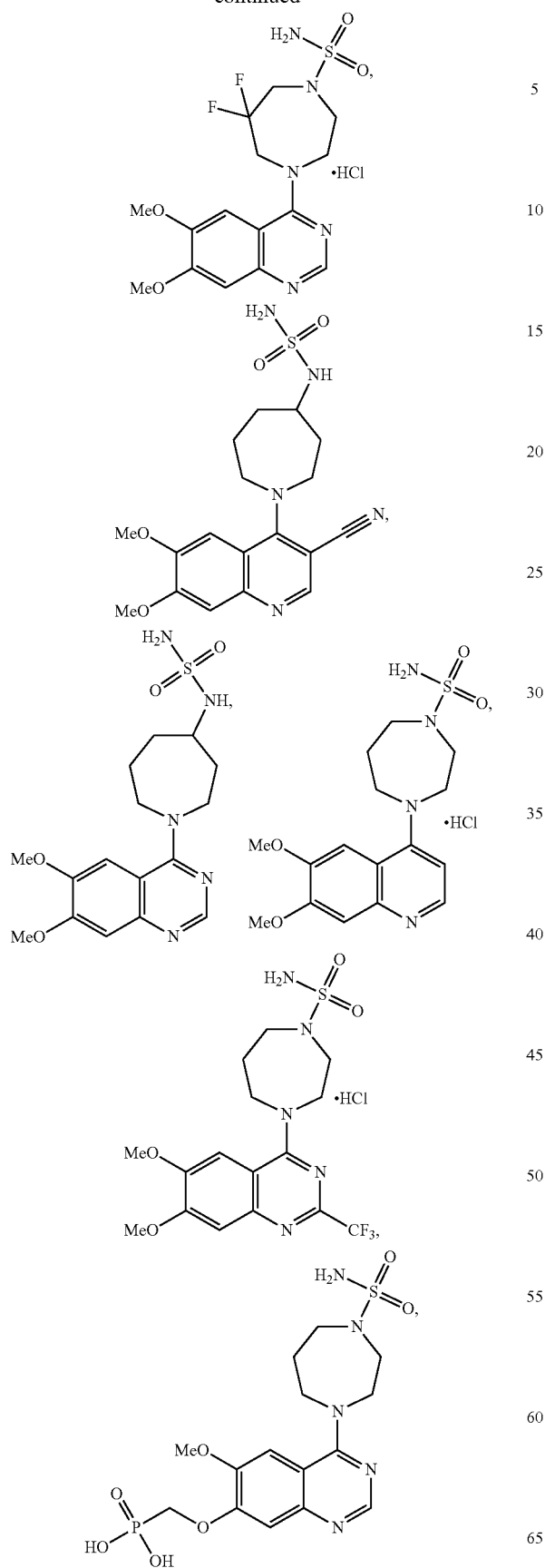
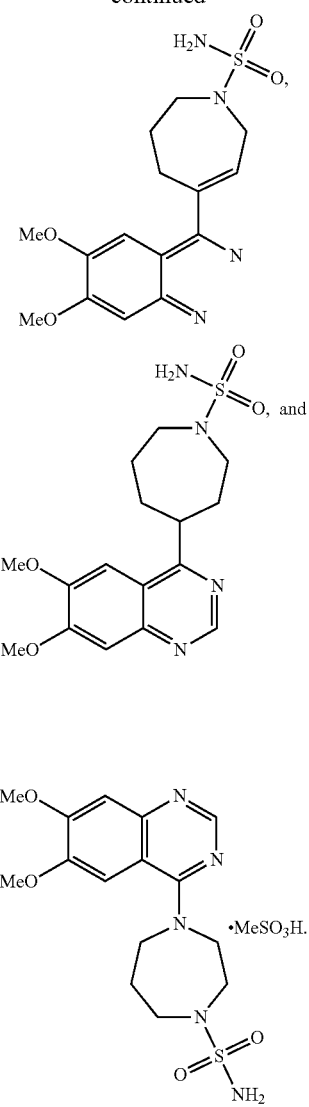
14. The compound of claim 1 having the following structure:
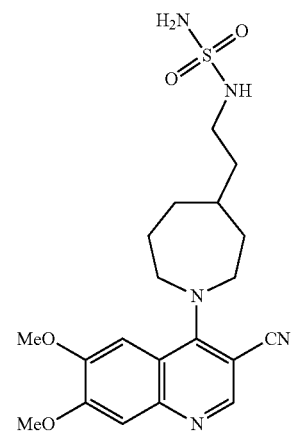 [SMILES: COc1cc2ncc(C#N)c(N3CCCC(CCNS(N)(=O)=O)CC3)c2cc1OC]
or a pharmaceutically acceptable salt thereof.

15. The compound of claim 1 having the following structure:

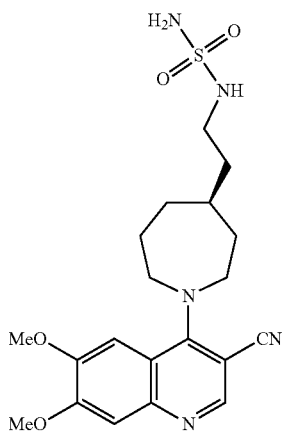 [SMILES: COc1cc2ncc(C#N)c(N3CCC[C@@H](CCNS(N)(=O)=O)CC3)c2cc1OC]

or a pharmaceutically acceptable salt thereof.

16. The compound of claim 1 having the following structure:

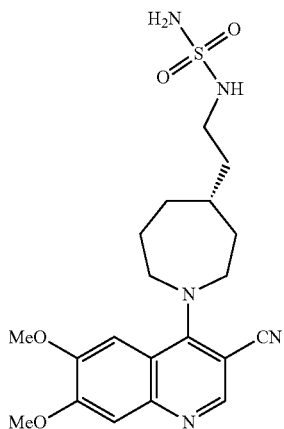 [SMILES: COc1cc2ncc(C#N)c(N3CCC[C@H](CCNS(N)(=O)=O)CC3)c2cc1OC]

or a pharmaceutically acceptable salt thereof.

17. The compound of claim 1 having the following structure:

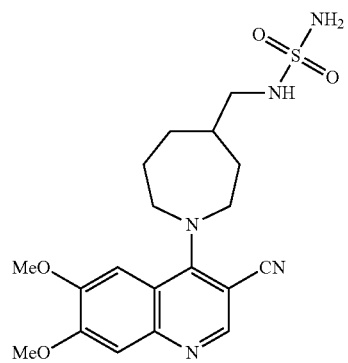 [SMILES: COc1cc2ncc(C#N)c(N3CCCC(CNS(N)(=O)=O)CC3)c2cc1OC]

or a pharmaceutically acceptable salt thereof.

18. The compound of claim 1 having the following structure:

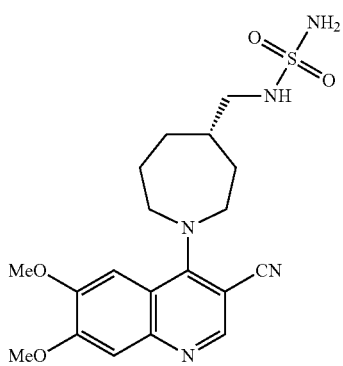 [SMILES: COc1cc2ncc(C#N)c(N3CCC[C@H](CNS(N)(=O)=O)CC3)c2cc1OC]

or a pharmaceutically acceptable salt thereof.

19. The compound of claim 1 having the following structure:

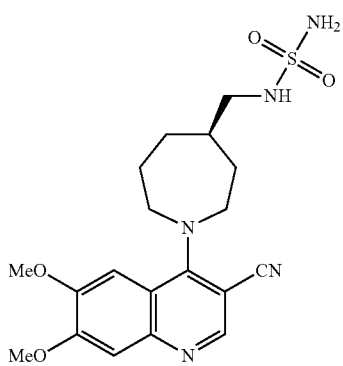 [SMILES: COc1cc2ncc(C#N)c(N3CCC[C@@H](CNS(N)(=O)=O)CC3)c2cc1OC]

or a pharmaceutically acceptable salt thereof.

20. The compound of claim 1 having the following structure:

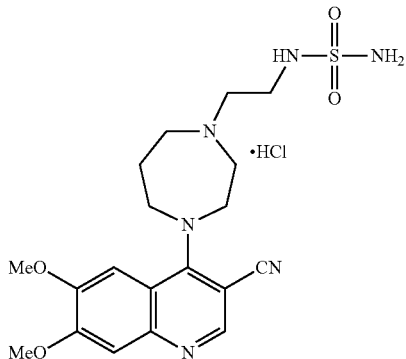 [SMILES: COc1cc2ncc(C#N)c(N3CCCN(CCNS(N)(=O)=O)CC3)c2cc1OC ; Cl]

or a pharmaceutically acceptable salt thereof.

21. The compound of claim 1 having the following structure:

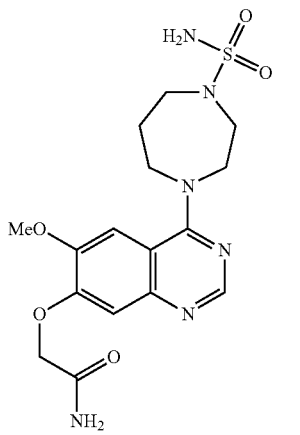 [SMILES: COc1cc2c(N3CCCN(S(N)(=O)=O)CC3)ncnc2cc1OCC(N)=O]

or a pharmaceutically acceptable salt thereof.

22. The compound of claim 1 having the following structure:

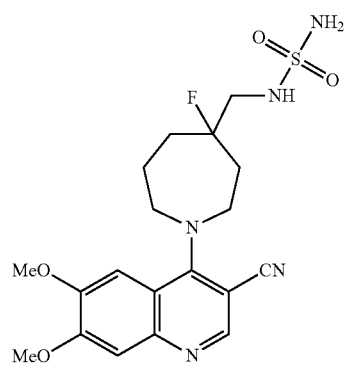 [SMILES: COc1cc2ncc(C#N)c(N3CCCC(F)(CNS(N)(=O)=O)CC3)c2cc1OC]

or a pharmaceutically acceptable salt thereof.

23. The compound of claim 1 having the following structure:

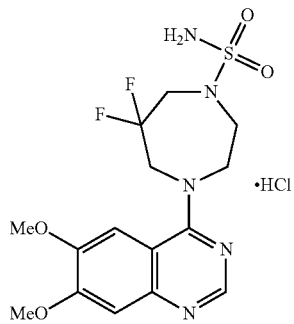 [SMILES: COc1cc2ncnc(N3CCN(S(N)(=O)=O)CC(F)(F)C3)c2cc1OC ; Cl]

or a pharmaceutically acceptable salt thereof.

24. The compound of claim 1 having the following structure:

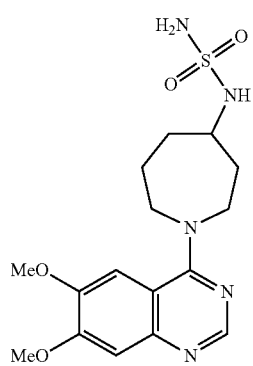 [SMILES: COc1cc2ncnc(N3CCCC(NS(N)(=O)=O)CC3)c2cc1OC]

or a pharmaceutically acceptable salt thereof.

25. The compound of claim 1 having the following structure:

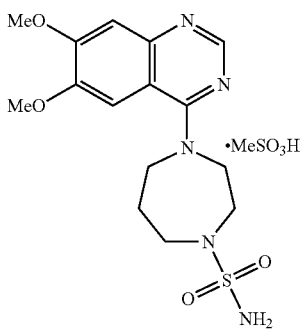 [SMILES: "·MeSO3H" ; COc1cc2ncnc(N3CCCN(S(N)(=O)=O)CC3)c2cc1OC]

or a pharmaceutically acceptable salt thereof.

26. The compound of claim 1 having the following structure:

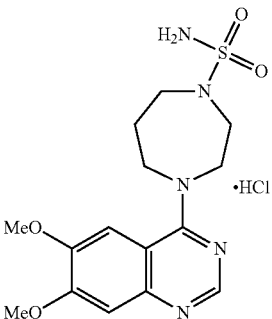 [SMILES: COc1cc2ncnc(N3CCCN(S(N)(=O)=O)CC3)c2cc1OC ; Cl]

or a pharmaceutically acceptable salt thereof.

27. The compound of claim 1 having the following structure:

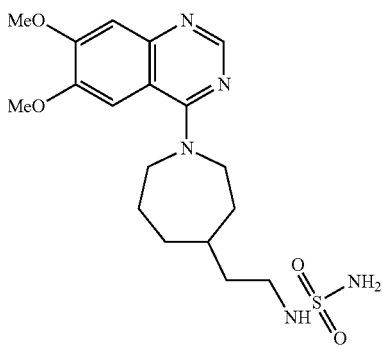

or a pharmaceutically acceptable salt thereof.

28. The compound of claim 1 having the following structure:

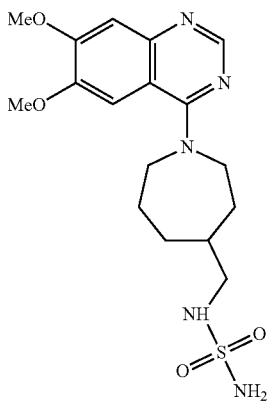 [SMILES: COc1cc2ncnc(N3CCCC(CNS(N)(=O)=O)CC3)c2cc1OC]

or a pharmaceutically acceptable salt thereof.

29. A pharmaceutical composition comprising a therapeutically effective amount of a compound of claim 1 and a pharmaceutically acceptable carrier.

30. A pharmaceutical composition comprising a therapeutically effective amount of a compound of claim 13 and a pharmaceutically acceptable carrier.

31. A pharmaceutical composition comprising a therapeutically effective amount of a compound of claim 14 and a pharmaceutically acceptable carrier.

32. A pharmaceutical composition comprising a therapeutically effective amount of a compound of claim 15 and a pharmaceutically acceptable carrier.

33. A pharmaceutical composition comprising a therapeutically effective amount of a compound of claim 16 and a pharmaceutically acceptable carrier.

34. A pharmaceutical composition comprising a therapeutically effective amount of a compound of claim 17 and a pharmaceutically acceptable carrier.

35. A pharmaceutical composition comprising a therapeutically effective amount of a compound of claim 18 and a pharmaceutically acceptable carrier.

36. A pharmaceutical composition comprising a therapeutically effective amount of a compound of claim 19 and a pharmaceutically acceptable carrier.

37. A pharmaceutical composition comprising a therapeutically effective amount of a compound of claim 20 and a pharmaceutically acceptable carrier.

38. A pharmaceutical composition comprising a therapeutically effective amount of a compound of claim 21 and a pharmaceutically acceptable carrier.

39. A pharmaceutical composition comprising a therapeutically effective amount of a compound of claim 22 and a pharmaceutically acceptable carrier.

40. A pharmaceutical composition comprising a therapeutically effective amount of a compound of claim 23 and a pharmaceutically acceptable carrier.

41. A pharmaceutical composition comprising a therapeutically effective amount of a compound of claim 24 and a pharmaceutically acceptable carrier.

42. A pharmaceutical composition comprising a therapeutically effective amount of a compound of claim 25 and a pharmaceutically acceptable carrier.

43. A pharmaceutical composition comprising a therapeutically effective amount of a compound of claim 26 and a pharmaceutically acceptable carrier.

44. A pharmaceutical composition comprising a therapeutically effective amount of a compound of claim 27 and a pharmaceutically acceptable carrier.

45. A pharmaceutical composition comprising a therapeutically effective amount of a compound of claim 28 and a pharmaceutically acceptable carrier.

* * * * *